(12) United States Patent
Grace et al.

(10) Patent No.: US 11,185,254 B2
(45) Date of Patent: Nov. 30, 2021

(54) ENTRAINMENT SONIFICATION TECHNIQUES

(71) Applicant: Muvik Labs, LLC, Locust Valley, NY (US)

(72) Inventors: Victoria A. Grace, Oyster Bay, NY (US); Paul Batchelor, Newton, MA (US)

(73) Assignee: Muvik Labs, LLC, Locust Valley, NY (US)

( * ) Notice: Subject to any disclaimer, the term of this patent is extended or adjusted under 35 U.S.C. 154(b) by 0 days.

(21) Appl. No.: 16/785,068

(22) Filed: Feb. 7, 2020

(65) Prior Publication Data

US 2021/0030308 A1 Feb. 4, 2021

Related U.S. Application Data

(63) Continuation-in-part of application No. 16/634,928, filed as application No. PCT/US2015/047375 on Aug. 21, 2018.

(Continued)

(51) Int. Cl.
*A61B 5/087* (2006.01)
*A61B 5/00* (2006.01)

(52) U.S. Cl.
CPC .............. *A61B 5/087* (2013.01); *A61B 5/486* (2013.01); *A61B 5/7415* (2013.01)

(58) Field of Classification Search
CPC ........... G10H 1/0025; G10H 2210/111; G10H 2240/081; G10H 2240/085
See application file for complete search history.

(56) References Cited

U.S. PATENT DOCUMENTS 5,730,140 A * 3/1998 Fitch .................... A61B 5/0205
600/514
5,836,302 A * 11/1998 Homuth .............. A61M 16/024
128/205.23

(Continued)

FOREIGN PATENT DOCUMENTS

WO 2019040524 A1 2/2019

OTHER PUBLICATIONS

L. Kennedy et al., "Biofeedback as a Stress Management Tool: A Systematic Review," Cognition, Technology & Work, May 2019, pp. 161-190, vol. 21, No. 2 (abstract only).

(Continued)

*Primary Examiner* — Jeffrey Donels
(74) *Attorney, Agent, or Firm* — Ryan, Mason & Lewis, LLP

(57) ABSTRACT

A processing device in one embodiment is configured to generate a first sound cue of a first type, the first sound cue comprising a primary entrainment cue for an entrainment sonification system, to generate one or more additional sound cues of a second type, each of the one or more additional sound cues comprising an auxiliary entrainment cue for the entrainment sonification system, to provide the first sound cue and the one or more additional sound cues to one or more audio devices of the entrainment sonification system for generation of sound for audible presentation to a user, to receive from one or more sensors of the entrainment sonification system one or more feedback signals, and to adjust one or more characteristics of at least one of the first sound cue and the one or more additional sound cues based at least in part on the one or more received feedback signals.

21 Claims, 44 Drawing Sheets

Related U.S. Application Data

(60) Provisional application No. 62/548,001, filed on Aug. 21, 2017, provisional application No. 62/802,521, filed on Feb. 7, 2019, provisional application No. 62/850,882, filed on May 21, 2019, provisional application No. 62/915,935, filed on Oct. 16, 2019.

(56) References Cited

U.S. PATENT DOCUMENTS

| | | | | |
|---|---|---|---|---|
| 6,449,501 | B1* | 9/2002 | Reuss | A61B 5/14551 600/322 |
| 9,968,305 | B1 | 5/2018 | Brown et al. | |
| 2004/0243016 | A1* | 12/2004 | Sanderson | A61B 5/0836 600/532 |
| 2006/0111621 | A1* | 5/2006 | Coppi | A61B 5/486 600/300 |
| 2007/0074619 | A1 | 4/2007 | Vergo | |
| 2008/0156176 | A1 | 7/2008 | Edlund | |
| 2011/0082695 | A1 | 4/2011 | Bengt | |
| 2014/0074479 | A1* | 3/2014 | Kassam | G10L 25/48 704/270 |
| 2015/0079562 | A1 | 3/2015 | Yeh et al. | |
| 2015/0081066 | A1* | 3/2015 | Yeh | A61B 5/1123 700/94 |
| 2015/0093729 | A1* | 4/2015 | Plans | A61B 5/01 434/236 |
| 2015/0127818 | A1 | 5/2015 | Bates et al. | |
| 2015/0133749 | A1* | 5/2015 | Janata | A61B 5/14551 600/301 |
| 2015/0150520 | A1* | 6/2015 | Chafe | A61B 5/349 600/483 |
| 2015/0213789 | A1 | 7/2015 | Plott et al. | |
| 2015/0286858 | A1 | 10/2015 | Shaburov et al. | |
| 2015/0356876 | A1 | 12/2015 | Wang et al. | |
| 2017/0061950 | A1* | 3/2017 | Benway | G06K 9/00892 |
| 2017/0203074 | A1* | 7/2017 | Joseph | A61B 5/486 |
| 2017/0208027 | A1* | 7/2017 | Goldstein | H04L 51/26 |
| 2017/0220316 | A1 | 8/2017 | Garmark et al. | |
| 2017/0225035 | A1 | 8/2017 | Riley et al. | |
| 2018/0216953 | A1 | 8/2018 | Suenaga | |

OTHER PUBLICATIONS

B. Yu et al., "Designing Auditory Display of Heart Rate Variability in Biofeedback Context," The 21st International Conference on Auditory Display (ICAD), Jul. 8-10, 2015, pp. 294-298.

A.L. Wheat et al., "Biofeedback of Heart Rate Variability and Related Physiology: A Critical Review," Applied Psychophysiology and Biofeedback, Sep. 2010, pp. 229-242, vol. 35, No. 3.

A. Parnandi et al., "Chill-Out: Relaxation Training Through Respiratory Biofeedback in a Mobile Casual Game," 5th International Conference on Mobile Computing, Applications, and Services (MobiCASE), Nov. 7-8, 2013, pp. 252-260.

D. Plans et al., "Use of a Biofeedback Breathing App to Augment Poststress Physiological Recovery: Randomized Pilot Study," JMIR Formative Research, Jan. 11, 2019, 8 pages, vol. 3, No. 1.

V. Grace, "About Muvik Labs," [Video], YouTube, https://www.youtube.com/watch?v=0ftLLkJhPUI, Sep. 6, 2019, 3 pages.

Actor, "Interactive Study of Timbre Semantics," https://www.actorproject.org/interactive-study-on-timbre-semantics, Accessed Jul. 1, 2021, 3 pages.

Orchestration Education, "IInteractive Study on Timbre Semantics—Demo of Interface—Muvik Labs," [Video], YouTube, https://www.youtube.com/watch?v=ICwvZe3kFzw&t=21s, Jul. 10, 2019, 3 pages.

V. Grace et al., "Sonic Anxiety," CCRMA Music 250A Project, [Video], YouTube, https://www.youtube.com/watch?v=vNvwmWxqIDo&t=2s, Jan. 4, 2015, 3 pages.

Stanford University, "CCRMA Music 250A Past Projects," https://ccrma.stanford.edu/courses/250a-fall-2014/past-projects/, Fall 2014, 16 pages.

* cited by examiner

Example of Possible Musical Expression Mappings for Generative Interface:
Demonstration of mapping 2 parameters (Pos/Neg and Intensity) to region on interface determining multiple musical attributes
** NOTE: These will vary with different applications/users

| Emotion Category/ Region | Positivity (1-10) | Negativity (1-10) | Intensity (1-100) | Musical Attributes |
|---|---|---|---|---|
| Happy | ~10 | 0 | 90-100 | Major mode, fast tempo, staccato, quick attack (note onsets) and short decay, bright timbre |
| Playful | ~9 | ~1 | 80-95 | Major mode, crescendos, flutter curvature, medium dynamics, medium timbre and note range |
| Calm | ~2 | ~8 | 0-20 | Low dynamics, slow tempo, fewer voices, lower pitches, dark timbre, long attack, smooth pitch curvature |
| Dreamy | ~5 | ~5 | 10-30 | Medium dissonance, low dynamics, slow tempo, varying pitch envelope |
| Sad | ~0 | ~10 | 0-10 | Minor mode, slow tempo, fewer voices, long attack and decay note envelope |
| Anxious | ~1 | ~9 | 90-100 | Minor mode, lower median pitch, high dissonance, high staccato, bright timbre |
| Excited | ~9 | ~1 | 90-100 | Major mode, high highest pitch, loud dynamics, high voice density, bright timbre |

Fig. 4A

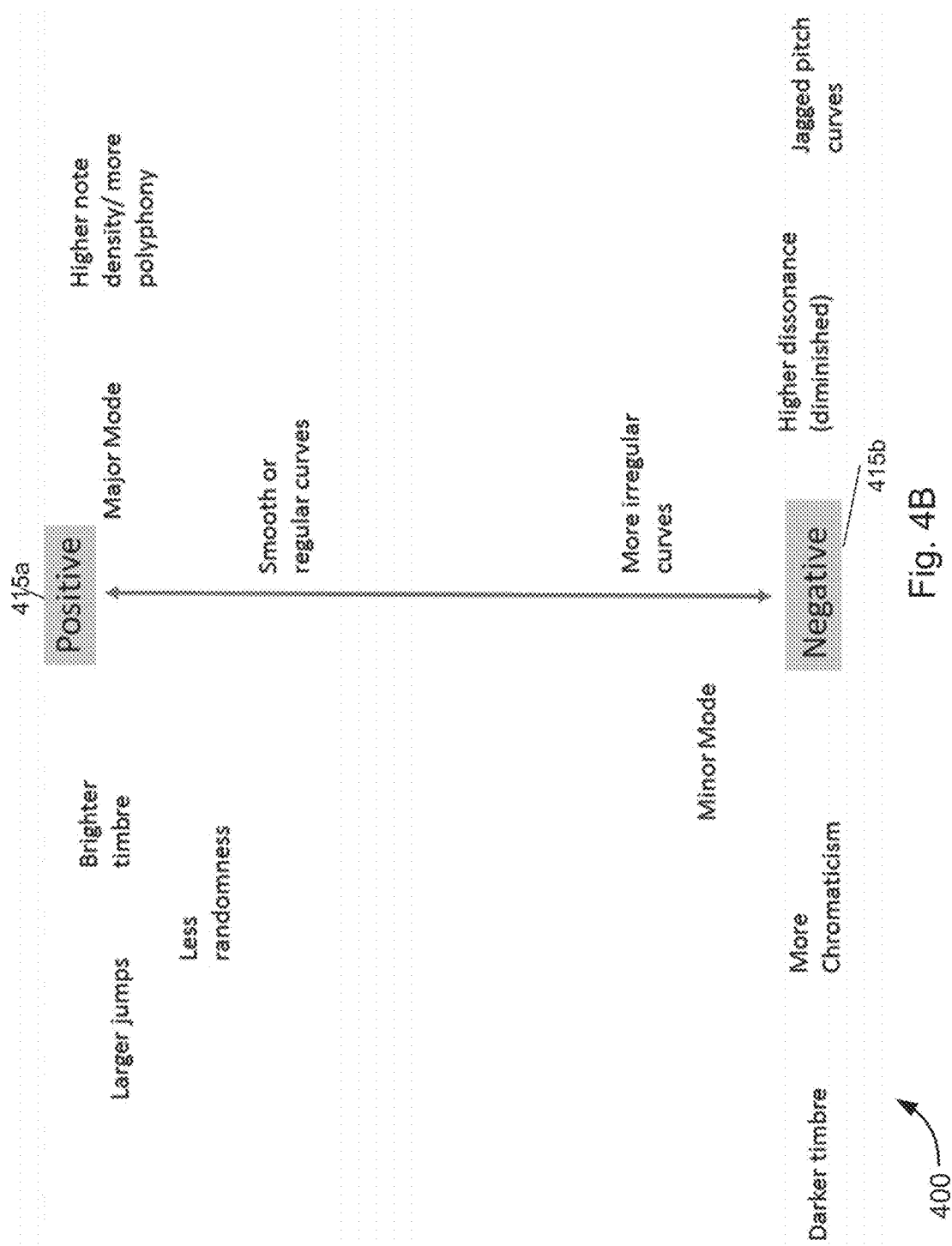

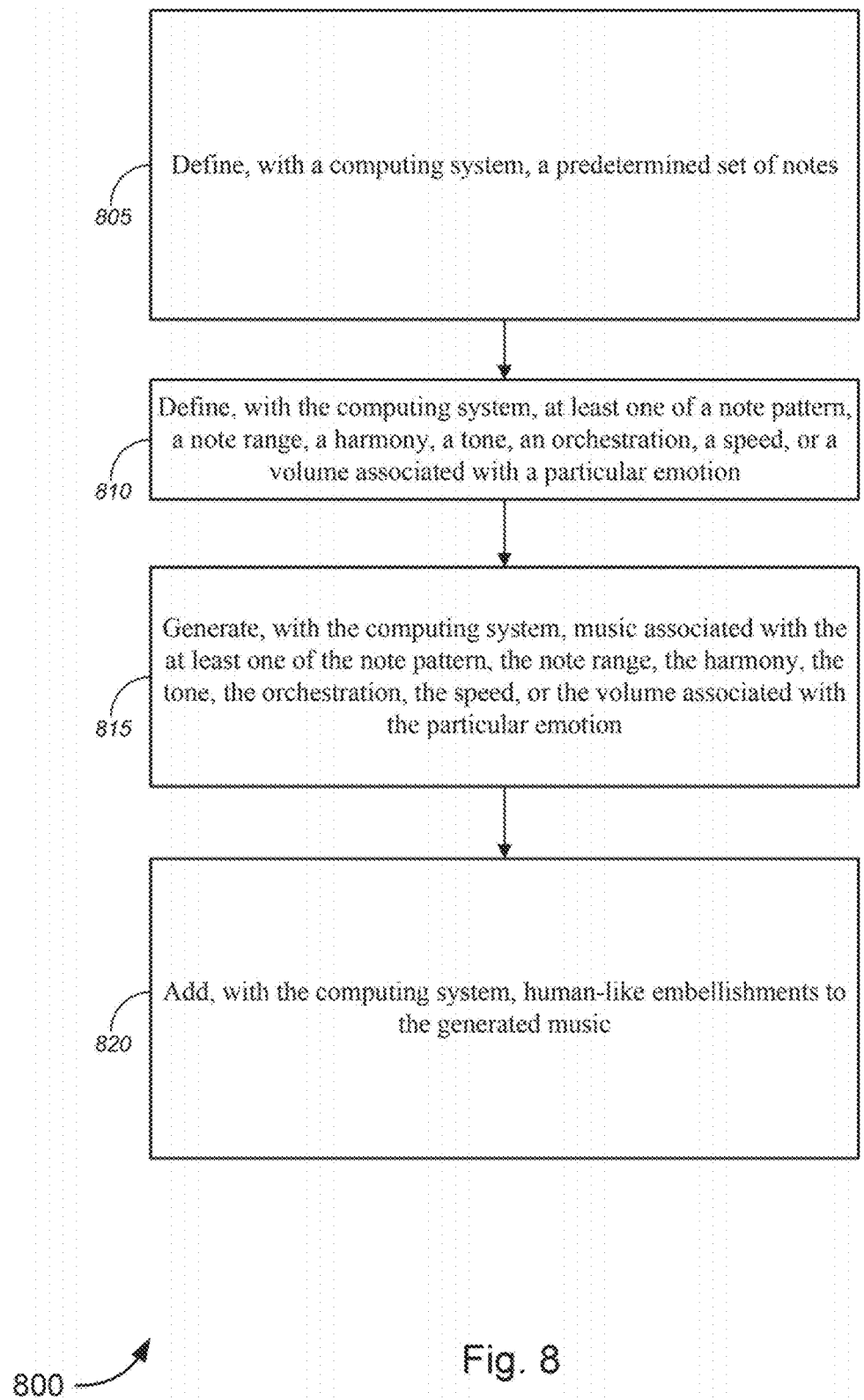

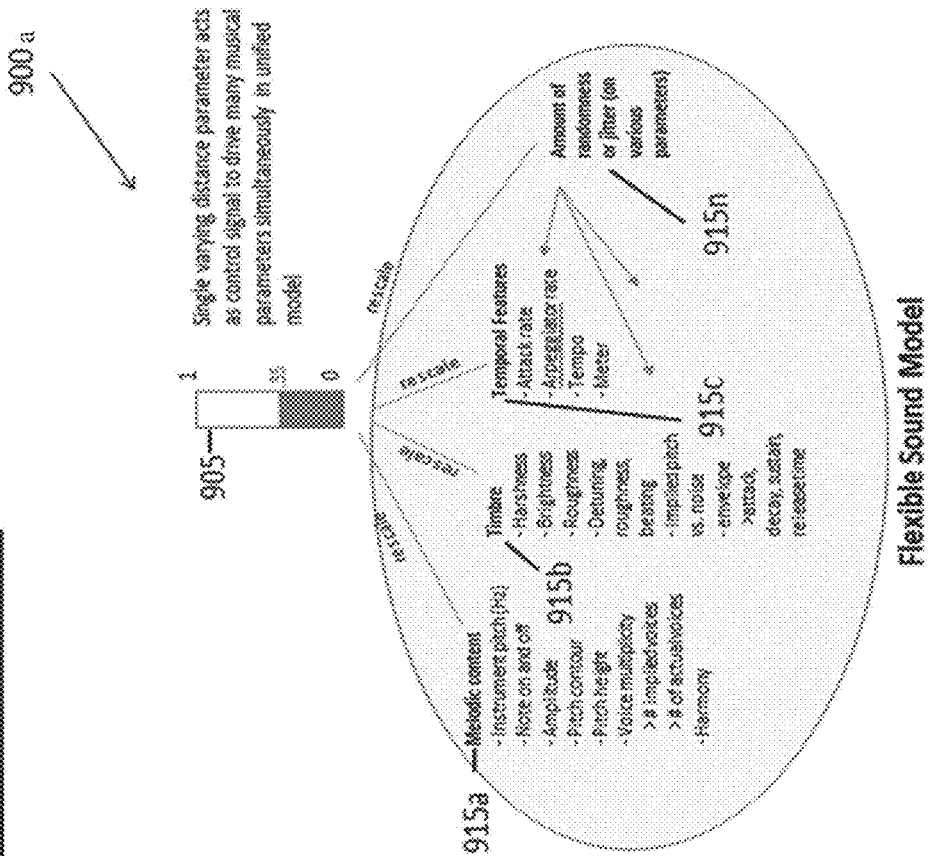
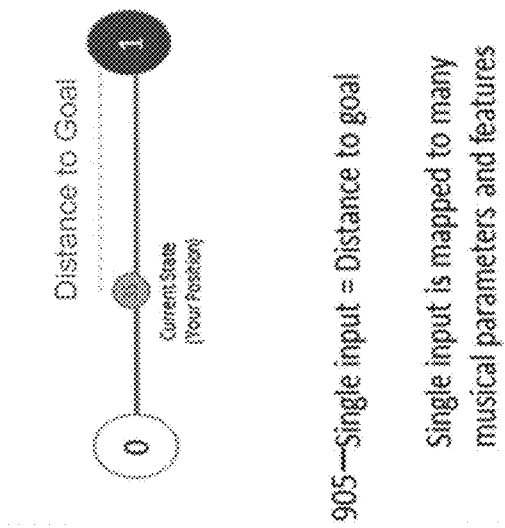
Fig. 9A

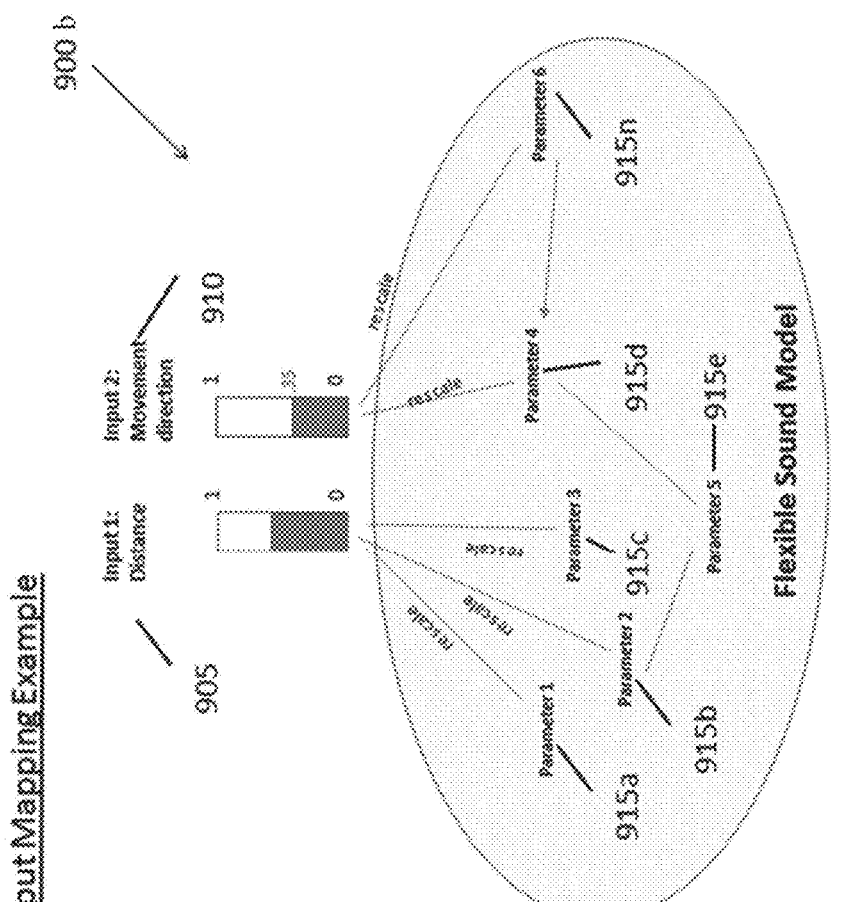
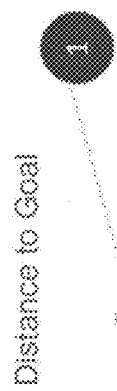
Fig. 9B

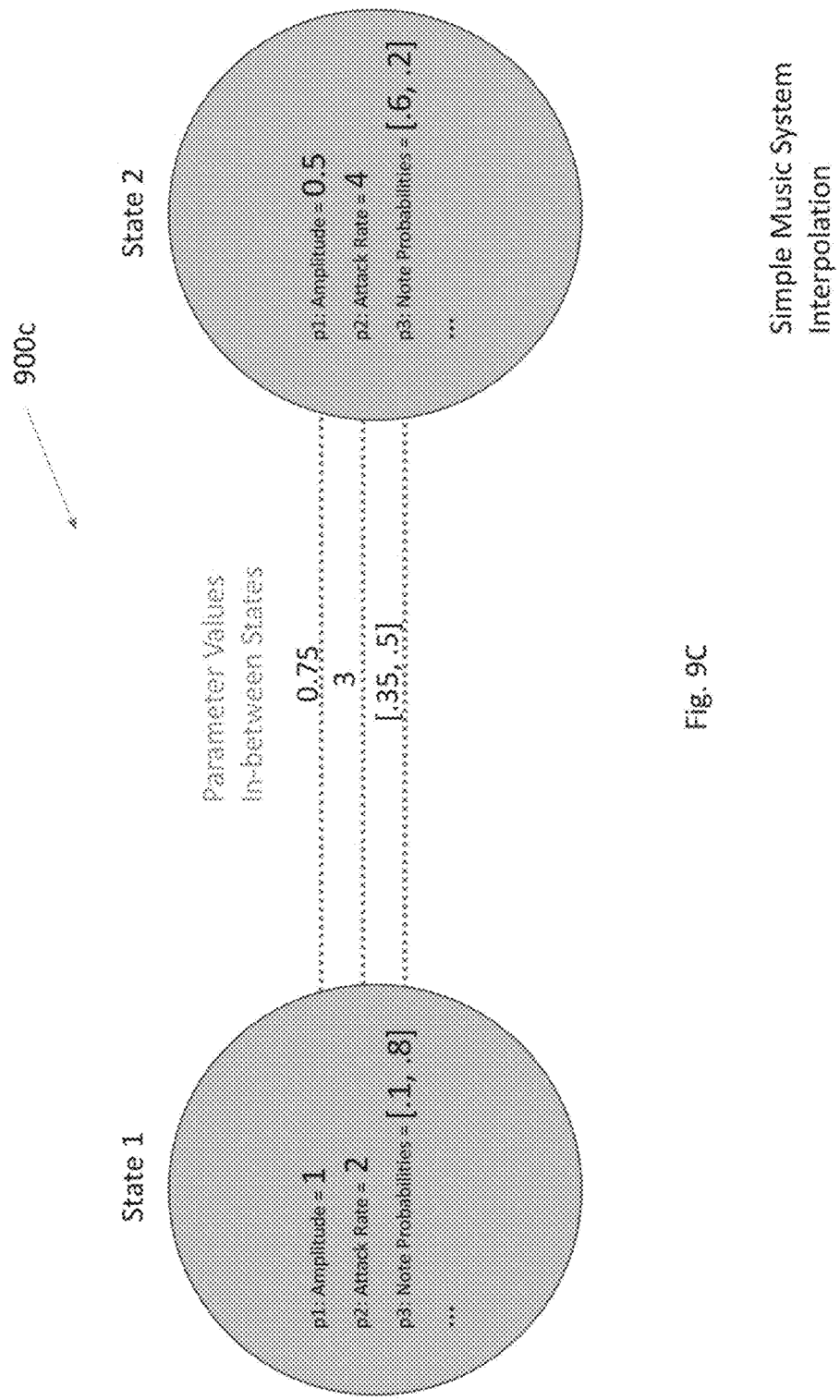

ENTRAINMENT SONIFICATION TECHNIQUES

RELATED APPLICATIONS

The present application is a continuation-in-part of U.S. patent application Ser. No. 16/634,928, filed Jan. 29, 2020 and entitled "Method and System for Musical Communication," which is a 35 U.S.C. § 371 national phase of PCT Application No. PCT/US2018/047375, entitled "Method and System for Musical Communication," which was filed on Aug. 21, 2018 claiming priority to U.S. Provisional Patent Application Ser. No. 62/548,001 filed Aug. 21, 2017, each of which is incorporated by reference herein in its entirety. The present application also claims priority to U.S. Provisional Patent Application Ser. No. 62/802,521, filed Feb. 7, 2019 and entitled "Breathing Entrainment Sonification Techniques," U.S. Provisional Patent Application Ser. No. 62/850,882, filed May 21, 2019 and entitled "Goal-Driven Auditory Display Techniques for Cardio Fitness, Aerobic Activity and other Contexts," and U.S. Provisional Patent Application Ser. No. 62/915,935, filed Oct. 16, 2019 and entitled "Applications for Musical Communication System," each of which is incorporated by reference herein in its entirety.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The field relates generally to information processing systems, and more particularly to systems that implement techniques for musical communication and/or sonification for entrainment and/or other applications.

BACKGROUND

A wide variety of different systems for musical communication and/or sonification are known to those skilled in the art. However, these and other conventional systems fail to provide suitable entrainment sonification. For example, the conventional systems are highly limited in their functionality and effectiveness. Accordingly, a need exists for improvements in the field of sonification.

SUMMARY

Illustrative embodiments provide methods, apparatus, systems and computer program products for entrainment sonification. The disclosed techniques are particularly well-suited for use in breathing entrainment sonification but are more generally applicable to numerous other contexts involving entrainment sonification.

In some embodiments, a breathing entrainment sonification system is implemented in the form of a musical communication system more particularly configured for a breathing entrainment sonification application. A wide variety of other entrainment sonification embodiments are possible utilizing the techniques disclosed herein.

For example, in some embodiments, a breathing entrainment sonification system is configured in accordance with a breathing entrainment model. The system configured in accordance with the breathing entrainment model more particularly comprises a closed-loop system featuring two different types of sound cues, namely, a sound cue of a first type to direct the user's breathing pattern (an "entrainment component") and one or more sound cues of a second type to provide feedback to the user on their current status during the exercise (one or more "auxiliary components").

Other types of closed-loop and open-loop entrainment sonification systems, each utilizing at least one entrainment component and possibly one or more auxiliary components, are provided in other embodiments. Accordingly, some embodiments disclosed herein are configured to utilize only entrainment components, and such embodiments can be implemented using closed-loop or open-loop arrangements.

One or more embodiments can be illustratively configured to provide a user with an awareness of a current state and guidance towards an optimal state, possibly with appropriate rewards for achieving and/or maintaining the optimal state, and can provide additional or alternative functionality.

These and other illustrative embodiments include but are not limited to systems, methods, apparatus, and computer program products. The illustrative embodiments are advantageously configured to address and solve one or more significant problems of conventional approaches, as outlined in more detail elsewhere herein.

BRIEF DESCRIPTION OF THE FIGURES

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

FIGS. 4A-4C are schematic diagrams illustrating systems for mapping music/audio to emotions/states, in accordance with various embodiments.

FIG. 8 is a flow diagram illustrating a method for generating music/audio, in accordance with various embodiments.

FIGS. 9A-9E are schematic diagrams illustrating systems for mapping states to music, in accordance with various embodiments.

DETAILED DESCRIPTION

Figure 1:
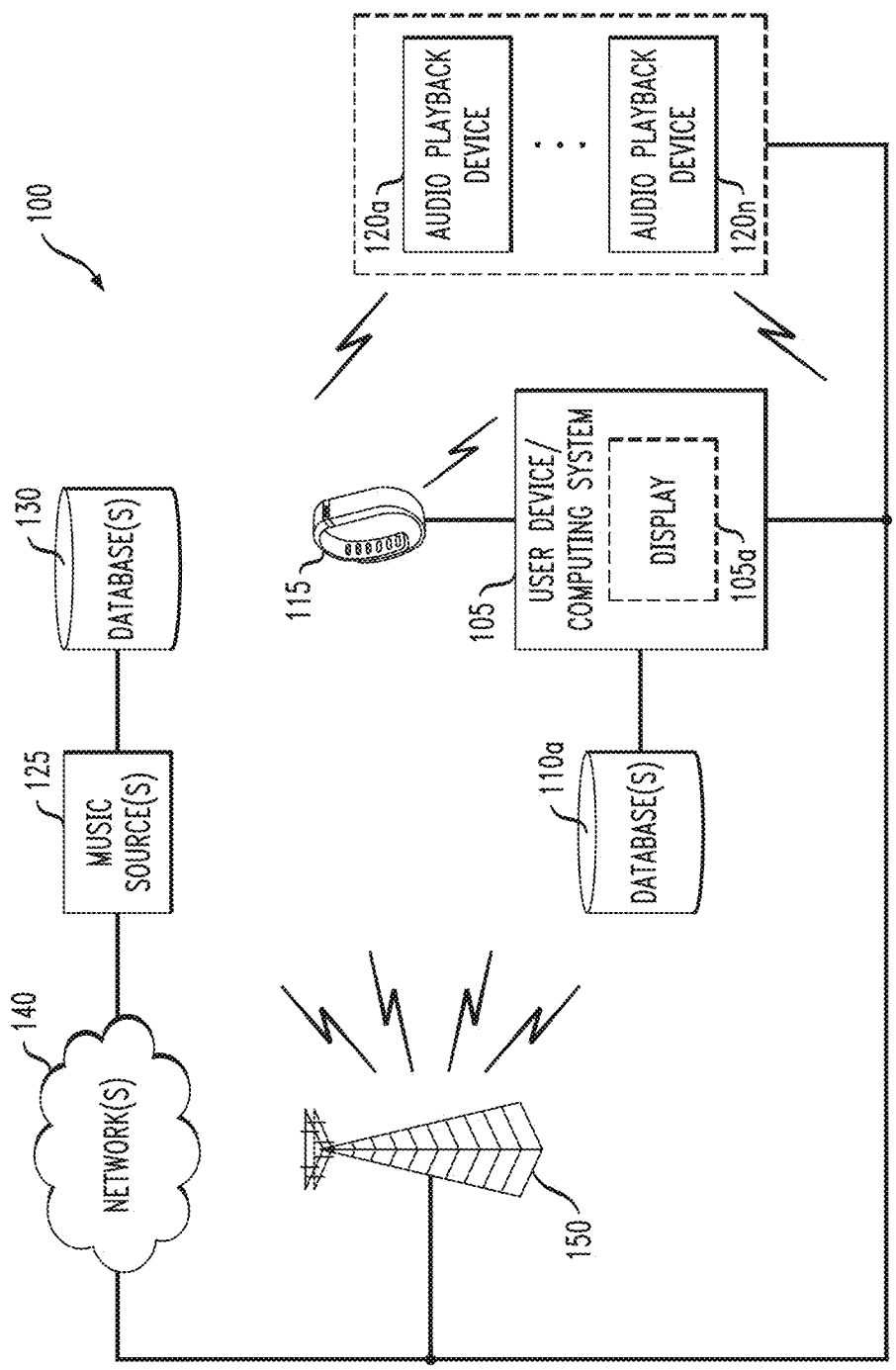
FIG. 1 is a schematic diagram illustrating a system for implementing the generation of music and audio, in accordance with various embodiments.

Some illustrative embodiments of the present disclosure relate, in general, to methods, systems, and apparatuses for implementing procedural, generative, interactive, and reactive music and audio, and, more particularly, to methods, systems, and apparatuses for generating music and audio associated with a state or an emotion contained within a communication, for a user interface for generating and controlling music and audio characteristics associated with a state or an emotion, for generating audio to inform the user of a current state, for generating audio to give the user awareness of movement between states, and for generating audio to guide a user toward a desired state or goal.

While there are several services that generate music on a computer, none of these services tailor the music and audio generated in real-time or near real-time to an emotion or a current state of a particular user/person or environment. Further, none of these services are driven by an emotion or state of a user/person contained within a communication or have an intuitive interface for a user/person to influence the audio that allows for smooth transformations between different musical states. Additionally, none of these services seek to direct and/or guide a user toward a desired state or goal.

Hence, there is a need for a more robust, and portable solution for generating music/audio, and, more particularly, for generating music/audio associated with an emotion/state contained within a communication, for a user interface for generating music/audio associated with a state, and for generating music to guide a user toward a desired state or goal.

Illustrative embodiments of methods and systems for musical communication will now be described with reference to FIGS. 1 through 12. For example, some of these embodiments provide novel tools and techniques for generating music, and, more particularly, methods, systems, and apparatuses for generating music associated with a state contained within a communication, for a user interface for generating music associated with a state, for generated music to reflect movement between states, and for generating music to guide a user toward a desired state. In various embodiments, a computing system might analyze a communication of a user to determine at least one state contained within the communication. The communication may be a sensor communication, a biometric/health communication, a voice communication, a numerical communication, a textual communication, a picture/video communication, etc. Based on the determined at least one state, the computing system might generate music associated with the state or continuously control the generation of music to guide a user toward a desired state. A user interface for generating music may also be provided.

Accordingly, various embodiments disclosed herein provide, for example, tools and techniques for generating interactive music/audio, and, more particularly, methods, systems, and apparatuses for generating music associated with an emotion/state contained within a communication, for a user interface for generating music/audio associated with an emotion, and for generating music to guide a user toward a desired state or goal or more optimally performing in an environment.

Some methods, systems, and apparatuses disclosed herein provide means for musical/audio communication. In an age of digital communication dominated by screens, text, and interactive mediums composed of static sound files (e.g., mp4 and .wav), there is a need to express information through a flexible audio feedback system. Understanding of communication through real-time adaptive music and audio can be achieved by transforming musical states which feature characteristic emotional nuance. These emotional sound qualities and changing states may be expressed through music/audio feature parameters associated with particular states and interpolating between different state parameters.

The methods, systems, and apparatuses described herein provide an audio engine with generative audio/music models and interfaces that generate or synthesize music or interactive sound in real-time based on feedback from one or more sensors and/or user interaction. These models can produce procedurally generated audio featuring infinite variation and influence from one or more sensors and/or user interactions. This approach consists of mapping detailed music content, performance and expressive features and components to input data streams and probabilistic structures.

Further, the methods, systems, and apparatuses described herein provide personalized, interactive, generative music and/or interactive audio that adapt to and convey a user's current physiological state (emotional, physical, or the like), the state of a person that the user is interacting with via text, video, voice communication, and/or the like, the state of a technology communicating to a user, and/or the state of an environment surrounding a user or a device. For example, instead of sending text/photographic emojis, users of these methods, systems, and apparatuses may send musical emojis to express how they are feeling. Additionally and/or alternatively, the music/sound that is generated may reflect a state of a technology (e.g., an amount of power, types of applications that are open, a typing speed of the user, and/or the like). In some cases, the music/audio may reflect a state of the environment (e.g., a type of weather, temperature of a room, and/or the like).

The methods, systems, and apparatuses described herein may be used to provide a soundtrack to user activities including goal-oriented tasks, communications (e.g., text, voice, video, and/or the like), user applications (e.g., games, social media applications, and/or the like), video games, a user's environment, and/or the like. Real-time data streams input into the generative music model may come from one or more sensors, user interaction with a user interface, computer software, a computer program, a virtual world, and/or the like. Additionally and/or alternatively, by interpreting the body language, tone of voice, brain waves, pulse of a user and/or person a user is interacting with and/or by detecting an environment within a room, a surrounding area, and/or the like, the methods, systems, and apparatuses described herein may generate instant audio feedback on psychological state of the user and/or a person interacting with the user, and/or an environment of a user or a person interacting with the user in the form of complex, sounds abstracting natural human expression. Thus, through the methods, systems, and apparatuses described herein, a user's mind, voice, body, environment, and/or the like may be used as input data driving the musical instrument.

Physiological states and/or environmental states are temporal in nature, therefore they can most be conveyed highly accurately through evolving music or sound. Thus, the music and audio that is generated, by methods, systems, and apparatuses described herein, is not static and may transition, transform or diverge over time as the user's state or environment changes.

These methods, systems, and apparatuses could also be embraced as an accessibility tool, facilitating blind and autistic communication. Further, these methods, systems, and apparatuses could be used in situations where text/photograph emojis fail, such as in accessibility devices for the blind or with individuals with autism. Additionally, these methods, systems, and apparatuses could be used for therapy sessions to make a patient feel at ease and to provide feedback to the therapist about the emotional state of the patient or be used for sound therapy for the patient.

Additionally and/or alternatively, the methods, systems, and apparatuses disclosed determine different emotions contained within a communication (e.g., a biometric/health communication, a voice communication, a textual communication, a picture communication, a video communication, a haptic communication and/or the like). Based on the determined emotions, the methods, systems, and apparatuses may generate and play music and/or other audio content associated with at least one determined emotion. The generated music and/or other audio content would provide a soundtrack to the communication and add emotional nuance to the communication through music to more effectively express how a person is feeling.

In other embodiments disclosed, an intuitive user interface is provided to a user such that a user may generate music associated with different emotions and smoothly transition between generating music associated with different emotions. The user interface provides for smoother and less audible jarring of music when transitioning between music associated with different emotions, and/or the like. The unique input of each user will cause the music that is generated to uniquely vary in sound and expression.

Additionally and/or alternatively, these methods, systems, and apparatuses may be used as assistive sound guides for goal-based activities. Continuous control over musical content and expression can allow for morphing between different musical states to convey to the user the direction they are moving in from their initial state. The changing characteristics in the audio can indicate to the user the direction moved in from the initial state, if they are closer or father away from their goal, how quickly they are moving in either direction. These methods, systems, and apparatus may be used to generate continuously evolving and/or changing sound characteristics over time to direct a user toward a desired state or goal. In a non-limiting example, various embodiments may be configured to exercise continuous control over musical/sound characteristics based on input from one or more sensors (e.g., one or more biometric/health sensors, motion sensors, distance sensors, GPS sensors, touch screen position, pressure sensor and/or the like). In some embodiments, the musical characteristics may also evolve or change to act as a guide to guide a user to a desired location (e.g., conveying a person's current position and/or the direction he or she is moving).

In several non-limiting examples, the musical/sound characteristics may act to guide a user from a negative state to a positive state, from a stressed state to a relaxed state, from a non-meditative state to a meditative state, from an unfocused state to a focused state, from a restful state to an exercise state, from an exercise state to a restful state, from a first location to a second location, and/or the like. Additionally and/or alternatively, the music may guide a user through increasing/decreasing an intensity of a workout, increasing/decreasing a breathing pattern, increasing/decreasing a heartrate, increasing/decreasing a number of steps per minute, and/or the like. In other embodiments, the music may act as a musical guide/navigator for the visually impaired or to enhance the experience of a visual task such as navigation in the real or virtual environment. In yet other embodiments, the evolving music may guide a user to better posture and/or balance.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Various embodiments described herein, while embodying (in some cases) software products, computer-performed methods, and/or computer systems, represent tangible, concrete improvements to existing technological areas, including, without limitation, user communication technology, music content generation technology, music content navigation or selection technology, user interface technology, audio playback technology, and/or the like. In other aspects, certain embodiments, can improve the functioning of user equipment or systems themselves (e.g., music players, music streaming or downloading systems, audio playback devices, etc.), for example, by, analyzing, with a computing system, a communication to determine at least one emotion or state contained within the communication, embodiments can determine a particular state that a user/person or technology is experiencing and generate music associated with the at least one state contained within the communication. Additionally and/or alternatively, a user interface may be provided that facilitates the generation of music and transitions between music associated with different states to convey to the user the current state musically. In particular, to the extent any abstract concepts are present in the various embodiments, those concepts can be implemented as described herein by devices, software, systems, and methods that involve specific novel functionality (e.g., steps or operations), such as, analyzing a communication to determine at least one emotion or state contained within the communication and generating music associated with the at least one emotion contained within the communication and utilizing a user interface to generate music associated with a particular emotion and to smoothly transition between music associated with different states, and/or the like, to name a few examples, that extend beyond mere conventional computer processing operations. These functionalities can produce tangible results outside of the implementation of a computer system, including, merely by way of example, optimized presentation of audio content (e.g. music associated with an emotion) to a user, generation of audio content (e.g. music associated with an emotion or state), and transitioning of audio content (e.g. music associated with an emotion or state). The presentation of audio content allows users to provide a soundtrack to their communications or function as the communication itself. The generation/transitioning of audio content provides for smoother and less audibly jarring changing of audio content, and/or the like, at least some of which may be observed or measured by customers.

Various modifications and additions can be made to the embodiments discussed without departing from the scope of the invention. For example, while the embodiments described above refer to particular features, the scope of this invention also includes embodiments having different combination of features and embodiments that do not include all of the above described features.

We now turn to the embodiments as illustrated by the drawings. FIGS. 1-12 illustrate some of the features of the method, system, and apparatus for generating music (and/or other audio/sound content), and, more particularly, to methods, systems, and apparatuses for generating music (and/or other audio/sound content) associated with an emotion contained within a communication and for a user interface for generating music associated with an emotion or state, as referred to above. Although the specification generally refers to generating music, it should be noted that other interactive audio/sound content (e.g., reactive sound, reactive audio, and/or the like) may be generated using the methods, systems, and apparatuses described below. The methods, systems, and apparatuses illustrated by FIGS. 1-12 refer to examples of different embodiments that include various components and steps, which can be considered alternatives or which can be used in conjunction with one another in the various embodiments. The description of the illustrated methods, systems, and apparatuses shown in FIGS. 1-12 is provided for purposes of illustration and should not be considered to limit the scope of the different embodiments.

With reference to the figures, FIG. 1 is a schematic diagram illustrating a system 100 for generating music, in accordance with various embodiments. Although the generation of music is often referred to throughout the specification, a person of ordinary skill in the art can understand that similar methods that generate music may be used to generate sound and/or audio.

In the non-limiting embodiment of FIG. 1, system 100 might comprise one or more user devices 105 (also referred to as "computing system 105") and a data store or database 110a that is local to the one or more user devices 105. In some cases, the database 110a might be external, yet communicatively coupled, to the one or more user devices 105. In other cases, the database 110 might be integrated within a user device 105. User device 105 might comprise a display 105a. The display 105a may be a touchscreen display that is configured to receive tactile input from a user or a display that is configured to receive input from a mouse. The database system may apply some preprocessing to the data before it is fed into the music system as an input. Additionally and/or alternatively, system 100 may further comprise one or more input devices 115 and one or more audio playback devices 120a-120n (collectively, "audio playback devices 120" or "speakers 120" or the like), and/or the like.

Each of the one or more user devices 105, the one or more input devices 115, and/or the one or more audio playback devices 120, might be communicatively coupled to each other, either via wireless connection and/or via wired connection. Additionally and/or alternatively, each of the one or more input devices 115, and/or the one or more audio playback devices 120 might be integrated within user device 105.

The one or more user devices 105 might each be configured to receive user input from a user. The user input may be received through touch input from the user, through the use of a mouse, and/or the like. The one or more user devices may further be configured to receive communications from data streams (e.g., text communications, voice communications, Internet of Things ("IoT" e.g., smart home appliance) communications, video communications, biometric/health or physiological sensor communications, and/or the like), according to some embodiments. In some cases, the user devices 105 might include, without limitation, a desktop computer, a television, a tablet computer, a laptop computer, a video game console, a smart phone, an e-reader, a smart watch, a portable fitness tracker, an electroencephalography ("EEG") device, medical equipment, fitness gym equipment, a virtual reality ("VR") device, an augmented reality ("AR") device, and/or the like. The one or more user devices 105 may further be configured to receive communications from one or more input devices 115. The one or more input devices 115 may include, without limitation, a tablet computer that has been paired, synced, or synchronized with the user device 105, a laptop computer that has been paired, synced, or synchronized with the user device 105, a smart phone that has been paired, synced, or synchronized with the user device 105, a sensor that has been paired, synced, or synchronized with the user device 105, a biometric/health or physiological sensor that has been paired, synced, or synchronized with the user device 105, a fitness tracker that has been paired, synced, or synchronized with the user device 105, an EEG device that has been paired, synced, or synchronized with the user device 105, a virtual reality ("VR") device that has been paired, synced, or synchronized with the user device 105, an augmented reality ("AR") device that has been paired, synced, or synchronized with the user device 105, a camera that has been paired, synced, or synchronized with the user device 105, a facial recognition sensor that has been paired, synced, or synchronized with the user device 105, a distance sensor that has been paired, synced, or synchronized with the user device 105, a motion sensor that has been paired, synced, or synchronized with the user device 105, a movement sensor that has been paired, synced, or synchronized with the user device 105, a skin conductance sensor that has been paired, synced, or synchronized with the user device 105, a speed or velocity sensor that has been paired, synced, or synchronized with the user device 105, an air movement sensor that has been paired, synced, or synchronized with the user device 105, a pressure sensor that has been paired, synced, or synchronized with the user device 105, an accelerometer that has been paired, synced, or synchronized with the user device 105, a gyroscope sensor that has been paired, synced, or synchronized with the user device 105, an IoT sensor that has been paired, synced, or synchronized with the user device 105, a temperature sensor that has been paired, synced, or synchronized with the user device 105, a weather sensor that has been paired, synced, or synchronized with the user device 105, a humidity sensor that has been paired, synced, or synchronized with the user device 105, one or more security sensors that has been paired, synced, or synchronized with the user device 105, a smart home interface device (e.g., echo, etc.) that has been paired, synced, or synchronized with the user device 105, and/or the like and/or combinations of the like.

Each of the one or more user devices 105 and/or input devices 115 may be located with a user, at a customer premises, in a home, in a car, at a gym, at a wellness centers, in a medical center, in a physical therapy center, at a hotel, at a retail store, and/or the like.

In some embodiments, the computing system 105 might comprise one of a processor within the user device 105 running a software application ("app"), a processor within the input device 115 running an app, a processor within one of the audio playback devices, and/or the like. In some embodiments, the audio playback devices 120 might each include, without limitation, one or more speakers external to but communicatively coupled to the user device 105 and/or input device 115, one of one or more speakers integrated within the user device 105 and/or input device 115, one or more headphones, one or more earbuds, one or more sound bars, one or more wireless speakers, or one or more stereo speakers, and/or the like.

System 100 might further comprise one or more music content sources or servers 125 or music generation sources or servers 125 and corresponding databases 130 that might communicatively couple to the computing system 105 via one or more networks 140 (and in some cases, via one or more telecommunications relay systems 150, which might include, without limitation, one or more wireless network interfaces (e.g., wireless modems, wireless access points, and the like, one or more towers, one or more satellites, and/or the like). The lightning bolt symbols are used to denote wireless communications between the one or more telecommunications relay systems 150 and each of at least one of the user devices 105, between the telecommunications relay systems 150 and each of at least one of the input devices 115, between the one or more user devices 105 and each of at least one of the input devices 115, between the user devices and each of the one or more audio playback devices 120*a*-120*n*, between the input devices 115 and each of at least one of the one or more audio playback devices 120*a*-120*n*, and/or the like.

At least one of computing system 105, input device 115, or at least one audio playback device 120 might receive a communication and/or user input, the user communication and/or user input may contain and/or indicate at least one state of a user, a person other than a user, a state of an environment, a state of a digital book, a state of a video game, and/or the like. A state of the user and/or a person other than a user might correspond to at least one of an emotion of a user and/or a person other than a user, a feeling of a user and/or a person other than a user, a location of the user and/or a person other than a user, a physical position of a user and/or a person other than a user, a level of activity of a user and/or a person other than a user, an action of a user and/or a person other than a user, and/or the like. A state of an environment might correspond to at least one of a weather situation (e.g., sunny, rainy, etc.), a temperature of an area, an amount of humidity, an amount of light, a time of day, a time of year, and/or the like. A state of a digital book might be at least one of a state of one or more characters in a book, a scene of a book (e.g., action, suspenseful, etc.), and/or the like. A state of a video game might be at least one of a state of one or more characters in a book, a scene of a book (e.g., action, suspenseful, etc.), and/or the like. A processor of the computing system 105, input device 115, or at least one audio playback device 120 may analyze the user and/or communication to determine at least one state indicated by the user input and/or at least one state contained within the communication.

In some embodiments, the communication that is analyzed to determine at least one state of a user, a person other than a user, an environment, etc. may be at least one of a sensor communication, an IoT sensor communication, a biometric/health communication, a movement-based gesture communication, a voice communication, a textual communication, a photographic communication, a video communication, a virtual reality ("VR") communication, an augmented reality ("AR") communication, a numerical communication, a vehicular communication, and/or the like. The computing system 105, input device 115, and/or at least one audio playback device 120 may receive input from the one or more communications periodically (e.g., every second, every minute, every few seconds, every few minutes and/or the like).

A sensor communication may contain feedback from one or more sensors including, but not limited to, one or more GPS sensors, one or more distance sensors, one or more motion sensors, one or more movement sensors, one or more speed or velocity sensors, one or more accelerometer sensors, one or more gyroscope sensors, one or more biometric/health sensors, one or more facial recognition sensors, one or more cameras, one or more weather sensors, one or more temperature sensors, one or more ambient light sensors, one or more humidity sensors, one or more audio sensors, and/or the like. Based on input from the one or more sensors, the computing system 105, input device 115, and/or at least one audio playback device 120 may determine a state that a person is experiencing or a state of the environment.

An IoT sensor communication may contain feedback from one or more IoT sensors contained within a home. The IoT communication may be sent by one or more smart home devices (e.g., echo, google home, etc.). For example, the one or more IoT sensors might include one of one or more thermometers in one or more rooms, one or more infrared ("IR") thermometers aimed at one or more positions in the one or more rooms, one or more air flow sensors in the one or more rooms, one or more air flow sensors in air ducts directed toward the one or more rooms, one or more indoor solar light sensors, one or more outdoor solar light sensors, one or more outdoor wind sensors, one or more neighborhood weather station sensors, one or more regional weather station sensors, one or more motion detectors detecting presence of people or animals in at least one of the one or more rooms or outside the customer premises, one or more humidity sensors in the one or more rooms, one or more smoke detectors detecting smoke in the one or more rooms, one or more gas detection sensors detecting gas in the one or more rooms, one or more biometric sensors identifying at least one person, or one or more health device with sensors detecting health information for at least one person, and/or the like. Based on input from the one or more sensors, the computing system 105, input device 115, and/or at least one audio playback device 120 may determine a state that a person is experiencing or a state of the environment. The music may be adapted to change in real-time as the state of the user, other person, or environment changes based on feedback from the one or more sensors contained in the IoT communications.

A biometric/health communication may contain biometric/health feedback from at least one of a medical device, smart phone, a smart watch, a fitness tracker, an EEG device, and/or the like. The biometric/health feedback may include at least one of a heart rate, a HRV, a breathing rate, a blood pressure, a stress level, a measure of electrical activity within a brain, pupil dilation, skin conductivity, and/or the like. Based on the at least one of a heart rate, a blood pressure, a stress level, a measure of electrical activity within a brain, and/or the like, the computing system 105, input device 115, and/or at least one audio playback device 120 may determine a state that a person or an environment is experiencing.

In a non-limiting example, if a heart rate is elevated, then the computing system 105, input device 115, and/or at least one audio playback device 120 may determine that a person is stressed. The music that the computing system 105, input device 115, and/or at least one audio playback device 120 generates may be louder and have a faster rhythm to reflect that a person is feeling stressed. Alternatively, the system may play music to compliment a person's state and play calming music when the person is stressed to guide a user from a negative state into a more positive state. Additionally and/or alternatively, in a non-limiting example, if a heart rate is low and/or skin conductivity or pupil dilation is low then the computing system 105, input device 115, and/or at least one audio playback device 120 may determine that a person is calm. The music that the computing system 105, input device 115, and/or at least one audio playback device 120 generates may reflect the person's calm state and/or the music that is generated may be designed to cause a person to become excited. The music may be adapted to change in real-time as the state of the user and/or other person changes in the biometric/health communication. Preset parameters within the music system define different states. Interpolation of the parameters defining each state allows for continuous morphing of the music between states.

Additionally and/or alternatively, multiple biometric communications may be received from multiple users. The music generated from the communications may be used to reflect how one or more users are doing in a competitive activity (e.g., a swim race, a track race, virtual race etc.). Additionally and/or alternatively, the music that is generated may be used to reflect the compatibility/connectiveness of a team.

A voice communication may be obtained from at least one of a phone call, voice input, microphone input, and/or the like. The computing system 105, input device 115, and/or at least one audio playback device 120 may parse the words contained within the voice communication to determine one or more particular states that at least one person is experiencing. Additionally and/or alternatively, the computing system 105, input device 115, and/or at least one audio playback device 120 may determine a tone of voice used in the voice communication to determine at least one state that a person is experiencing. For example, a higher, louder tone of voice might indicate happiness while a lower, quieter tone of voice might indicate sadness. The music may be adapted to change in real-time as the state of the user and/or other person changes in the voice communication.

A textual communication may be obtained from at least one of a text message, an email message, an instant message, a webpage, an e-book, and/or the like. The computing system 105, input device 115, and/or at least one audio playback device 120 may parse the words contained within the textual communication to determine one or more particular states that at least one person and/or character is experiencing. Computing system 105, input device 115, and/or at least one audio playback device 120 may perform machine translation on the text. The computing system 105, input device 115, and/or at least one audio playback device 120 may further determine whether one or more emojis are contained within the textual communication and determine one or more states associated with the one or more emojis contained within the textual communication. The music may be adapted to change in real-time as the state of the user and/or other person changes in the textual communication.

A photographic communication may be obtained from at least one of a photograph, video, and/or the like. The computing system 105, input device 115, and/or at least one audio playback device 120 may analyze the facial expression, body language, and/or the like of one or more persons in the photograph to determine one or more particular states that the at least one person or character is experiencing. The computing system 105, input device 115, and/or at least one audio playback device 120 may analyze the facial expression, body language, and/or the like of one or more persons and/or characters in the video to determine one or more particular states that the at least one person/character is experiencing. The computing system 105, input device 115, and/or at least one audio playback device 120 may also parse the dialogue of the at least one person in the video or determine a tone of voice of the at least one person in the video to determine one or more particular states that the at least one person/character is experiencing. The music may be adapted to change over time as the state of the user and/or other person changes in the photographic communication.

A VR communication and/or AR communication may be obtained from VR/AR devices (e.g., cell phones, tablets, headsets, glasses, goggles, lenses, and/or the like) or be a parameter built into the game determined by the context within the game. The computing system 105, input device 115, and/or at least one audio playback device 120 may analyze the facial expression, body language, and/or the like of the user of the AR/VR device, one or more persons interacting/communicating with the user of the AR/VR device, and/or one or more characters displayed by the AR/VR device. The computing system 105, input device 115, and/or at least one audio playback device 120 may also parse the dialogue or determine a tone of voice of the user, one or more persons interacting with the user of the AR/VR device, and/or one or more characters displayed by the AR/VR device. Additionally and/or alternatively, the computing system 105, input device 115, and/or at least one audio playback device 120 may detect how a person is performing in a game and generate music based on the person's performance. In non-limiting examples, if the user is doing well, then the music that is generated may be more upbeat, if the user is in an action scene, the music that may be generated may be more intense, if the character is performing poorly, then the music generated may become more tense, if the user's character dies in the game, then the music that is generated may contain lower tones, and/or the like. The music may be adapted to change continuously in real-time as the state of the user and/or other person changes in the VR/AR communication.

A numerical communication may be obtained from one or more trading applications, option prices, profit/loss calculations, risk calculations, etc. The audio may change continuously to convey real-time price changes, risk changes, etc.

A vehicular communication may be obtained from one or more vehicular components (e.g., one or more location sensors, one or more motion sensors, one or more speed sensors, or more velocity sensors, one or more GPS, one or more acceleration sensors, one or more pressure sensors, one or more force/impact sensors, one or more steering sensors, one or more autonomous vehicle controls, one or more self-driving controls, one or more position sensors, one or more other vehicular sensors, a horn, and/or the like). The music or audio may be adapted to change continuously in real-time as the state/action of the user, other person, environment of surrounding a vehicle, and/or the vehicle changes in the vehicular communication. For example, based on the input from the vehicular component, the system may determine the driver or passenger is distracted or stressed. Music or audio may then be generated to help the driver or passenger focus or relax. Additionally, the audio generated can be used to enhance the communication of a horn, where different states can convey information to another vehicle about why the horn signal was pressed by the driver or passenger.

Additionally and/or alternatively, the computing system 105, input device 115, and/or at least one audio playback device 120 may receive an indication from a user on a display of the computing system 105, the input device 115, and/or the at least one audio playback device 120. The indication may be received via tactile input or input via a mouse. Each state may be mapped to a position in a circular pattern (shown in FIG. 2), an XY coordinate system (shown in FIG. 9D), an XYZ coordinate system, and/or the like.

In some embodiments, the music/audio that is generated may be based on a combination of two or more of one or more sensor inputs, one or more communications, and/or one or more user indications.

Based on the at least one determined state indicated by one or more sensor inputs, contained within the communication, and/or indicated by the user input, the processor of the computing system 105, input device 115, and/or at least one audio playback device 120 may autonomously determine one or more first characteristics of a plurality of characteristics of music/audio associated with the determined at least one state indicated by one or more sensor inputs, contained within the communication, and/or indicated by the user. Additionally and/or alternatively, the computing system 105, input device 115, and/or at least one audio playback device 120 may access database 110a and/or music source 125 to determine one or more first characteristics of a plurality of characteristics of music associated with the determined at least one state contained within the communication and/or indicated by the user. The one or more first characteristics of the plurality of characteristics of music may include at least one of a note selection, a note pattern, an envelope, a harmony or combination of notes, an orchestration, a timbre quality, a filter, a speed, a rhythm, and/or a volume associated with the first state indicated by the communication.

The communication and/or indication may further indicate an age and/or sex of a user. The one or more first characteristics of a plurality of characteristics of music may further be associated with the at least one of the age or the sex contained within the communication and/or indicated by the user input. The music that is generated may further have one or more characteristics of the plurality of characteristics associated with the at least one of the age or the sex indicated by the communication and/or user input. In a non-limiting example, people associated with an older age demographic may prefer classical music rhythms and orchestrations while people associated with a younger age demographic may prefer hip-hop music rhythms and orchestrations. The demographics may determine initial position of the music system and shape the directions, (states or presets) that the system will move to.

Additionally and/or alternatively, a user may be able to indicate characteristics of music that the user prefers to have. For example, a user may prefer to listen to hip hop music. Computing system 105, input devices 115, and/or playback devices 120 may receive this input (indicating that a user prefers hip hop music) and generate music having hip hop characteristics (e.g., featuring sub bass, louder low frequencies, characteristic rhythmic attributes, and/or the like).

A user may explicitly indicate a particular preference for certain types of music and/or computing system 105 may determine types of music a user prefers. For example, computing system 105 may monitor the type of music a user buys or listens to on an application (e.g., a music application). Based on the determined music a user buys and/or listens to on the application, the computing system 105 may generate music that has similar characteristics. For example, a user may buy and listen to mostly classical music, the computing system 105 may then generate music having classical characteristics such as orchestra sounding instruments so that the music that is generated in appealing to the user.

Additionally and/or alternatively, instead of detecting states, computing system 105 may detect different types of elements and/or concepts. In a non-limiting example, computing system 105 may detect different types of scenes (e.g., action scene, adventure scene, landscape scenes, traffic scenes, and/or the like) of a book, video game, movie, and/or the like. The music that is generated may further have one or more characteristics of the plurality of characteristics associated with the at least one of the type of scene indicated by the communication and/or user input. In a non-limiting example, a particular part of a book may have a sword fight and the music that is generated may have a faster rhythm and louder volume to reflect that the scene is an action scene. Additionally and/or alternatively, computing system 105 may detect a state and/or action (e.g., running, walking, biking, sitting down, swimming, driving, etc.) of the user. For example, the computing system 105 may generate faster music when it determines a person is running and generate slower music when it determines a person is sitting down. Alternatively, a car may be stuck in traffic and the music that is generated might be designed to calm a driver. Alternatively, a driver may be falling asleep and the music generated might be designed to wake up the driver.

In additional embodiments, computing system 105 may detect a type of application that is using the music generation system. The music that is generated may be adjusted to fit the application, game, sensor system, and/or the like. For example, if the music generation system is being used to supplement a voice conversation, then the music that is generated may contain lower tones/volumes. If the music generation system is being used to supplement information received from a fitness tracker, then the music that is generated may contain higher tones/volumes or stronger rhythmic attributes. If the music is functioning as background sound in a VR/AR game, it may not only portray psychological and physical state of the player but also convey player's performance in the game.

Based on the determination of the one or more first characteristics of a plurality of characteristics of music associated with the computing system 105, input device 115, and/or at least one audio playback device 120 may generate music having the one or more first characteristics of the plurality of characteristics associated with the at least one state/element/concept contained within the communication and/or indicated by the user. The music may change as the input(s) from the one or more communications change. The music may change periodically (e.g., every second, every minute, every few seconds, every few minutes). The generated music may further contain one or more first characteristics associated with the at least one of the age or the sex indicated by the communication and/or user input. Additionally and/or alternatively, the generated music may further have one or more characteristics indicated by a preference of the user.

The music may be generated using one or more of frequency modulation, additive synthesis, subtractive synthesis, wave table synthesis, granular synthesis or sample-based synthesis and/or the like. The music may be generated from input from one or more communications (e.g., a sensor communication, an IoT sensor communication, a biometric/health communication, a movement-based gesture communication, a voice communication, a textual communication, a photographic communication, a video communication, a virtual reality ("VR") communication, an augmented reality ("AR") communication, a tactile communication, and/or the like). The music generated from two or more communications may be synthesized and harmonized together.

Additionally and/or alternatively, the music that is generated may be designed to have an opposite effect on the user listening to the music, complimenting their current state. For example, if the computing system 105, input device 115, and/or at least one audio playback device 120 determines that a user is sad based on the state detected within the communication, then the music that is generated may have one or more characteristics associated with the emotion "Happy" to uplift the user's spirits.

Each emotion, age, sex, and/or preference may have a customized algorithm for generating music that reflects the determined emotion, element/concept, scene, age, sex, and/or preference of a person. These algorithms may be inspired by soundtrack clichés, like those used in Hollywood films and/or used by composers. These algorithms may be inspired by associations of musical attributes to emotion perceived in music from psychoacoustics research. These algorithms may be contained in database 110*a*, music source 125, and/or database 130.

The music that is generated may be digital instruments which sound like real instruments (e.g., violins, violas, flutes, drums, etc.). Additionally and/or alternatively, the music that is generated may not be limited to instrumental music, but rather, synthesized electronic instruments, that may compose the sound generated to convey a human emotion. The model can be, for instance, generalized to include vocal synthesis and/or imitate human or animal sounds (e.g., birds, whales, and/or the like). Synthesized vocalizations may imitate natural human expressions and responses with associated emotions.

The generated music may be configured to evolve over time and transition between different states as the user's state changes, the one or more persons' state changes, and/or the state of the environment changes. Additionally and/or alternatively, the music may be configured to guide a user toward a desired state by continuously adapting based on at least one of the one or more sensor inputs, the one or more communications, and/or one or more indications by a user.

In yet another non-limiting example, the computing system 105, input device 115, and/or at least one audio playback device 120 may exercise continuous control over one or more musical characteristics to cause the one or more musical characteristics to evolve or change over time and guide a user from one state to another state. For example, based on feedback received from the one or more communications, the computing system 105, input device 115, and/or at least one audio playback device 120 may continuously control the one or more musical characteristics to guide a user from a first state to a second desired state. This process will be described more with respect to FIGS. 9 and 10, below.

The music that is generated by computing system 105 may further have human-like embellishments. Human performers have a natural imprecision which must be explicitly accounted for in computer generated music. To do this, irregular micro-fluctuations are added to the timing of note onsets. This kind of small random signal bias is often referred to as "timing jitter." As a result, quantized notes are gently un-quantized to provide a more pleasing and human-sounding musical aesthetic. Timing jitter provides subtle rhythmic variation that add nuance to the static note patterns.

Similar to jittered timing offsets ("timing jitter"), "frequency jitter" is utilized to modulate the frequency (pitch) of the generated music. Depending on the duration and articulation of the note, frequency jitter parameters will change. For instance, long sustained notes will be subject to more evolved jitter (gradual drift), a technique to add warmth; while shorter, more percussive notes will have little to no jitter.

Jitter may also be mapped to a number of other parameters in charge of producing timbre or the sound qualities of the notes. This is referred to as "timbral jitter." These parameters exist due in part to the real-time audio synthesis engine, which allow dynamic control and modulation of a sound over time via digital signal processing.

The generated music associated with the at least one determined state may be played through one or more playback devices 120.

In a non-limiting example, if the computing system 105, input device 115, and/or at least one audio playback device 120 determines that a communication and/or indication contains the state "Happy," the music that is generated may contain higher notes and a faster rhythm. If the computing system computing system 105, input device 115, and/or at least one audio playback device 120 determines that an indication and/or communication contains the state "Sad," the music that is generated may contain lower notes and a slower rhythm. Additionally and/or alternatively, if the computing system 105, input device 115, and/or at least one audio playback device 120 determines that a communication contains an environmental state of "Sunny" the music that is generated may contain higher notes and a faster rhythm.

The computing system 105 may detect that more than one state is contained within the communication and/or indicated by a user. If the computing system 105 detects at least two states, then the computing system may simultaneously generate, play, and/or harmonize the music that is associated with the at least two states. Additionally and/or alternatively, if the computing system detects at least two states, then the computing system may determine an order to play music associated with each of the at least two states and smoothly transition between playing music associated with each of the at least two states. Depending on the number of emotions contained within each indication and/or communication, the computing system 105 may determine an order of subsets of two or more states to simultaneously generate, play, and/or harmonize and smoothly transition between playing music associated with each subset of two or more states.

If the music associated with the at least two states are played in a particular order, the music associated with each state may be played for a predetermined amount of time (e.g., the music/sound may be played until a note is finished playing, until a sequence has ended, and/or the like) before transitioning. Additionally and/or alternatively, the music associated with each state may be transitioned based on a tracked position of a user in a communication (e.g., a book or text) or based on which person is talking in a phone call. Computing system 105 may further use a fitness tracker, an EEG device, a video communication, and/or a voice communication to track how a user's state or another person's state is changing and transition to different music based on a determined change in a user's state and/or another person's state in real-time or near real-time. In order to transition the generated music in real-time or near real-time, the computing system may introduce interpolation in different areas which enables gradual and/or abrupt transition between musical parameters associated with different emotions. There may be a mixture of interpolation including smoothed continuous control (which may feature a smoothing filter) and beat quantized transitioning. Interpolated aspects of music may include harmonic, timbre, orchestration and rhythmic content in order to transition smoothly from one musical aspect or phrase to another.

In a non-limiting example, the communication may be a book, or digital medium with a narrative and computing system 105 may track where a particular user is in the narrative. Based on one or more states contained within a particular part of the narrative, the computing system may generate music associated with those states. The music associated with these states may be harmonized and/or played in the order that each state appears on the page of book. This creates a customized soundtrack associated with the book and adds an additional element beyond merely reading the text or viewing video content in digital medium.

In an additional non-limiting example, a calling party may be having a phone conversation with called party and the computing system 105 may determine a particular state associated with both the calling party and the called party. The computing system may play music associated with each state simultaneously or play music associated with the particular person when that particular person is talking. The music may be played at a lower volume so that the music adds additional elements to the conversation without drowning out the conversation between the calling party and the called party.

In an additional non-limiting example, a fitness tracker may be used to track a user as the user is transitioning through a work out. The fitness tracker may detect that a user is cooling down from a workout and transition the music that is generated from excited/vigorous to calm/soothing.

In an additional non-limited example, a fitness tracker, handheld device or exercise machine may be used to track the cyclic nature of a work out. The tempo and rhythmic pattern of the music generated will adapt to the cyclic activity in the workout.

In an additional example, a movement detector from a handheld device may detect the amount of movement during a work-out. The amount of movement may be used to increase the energy in the music generated.

Figure 2A:
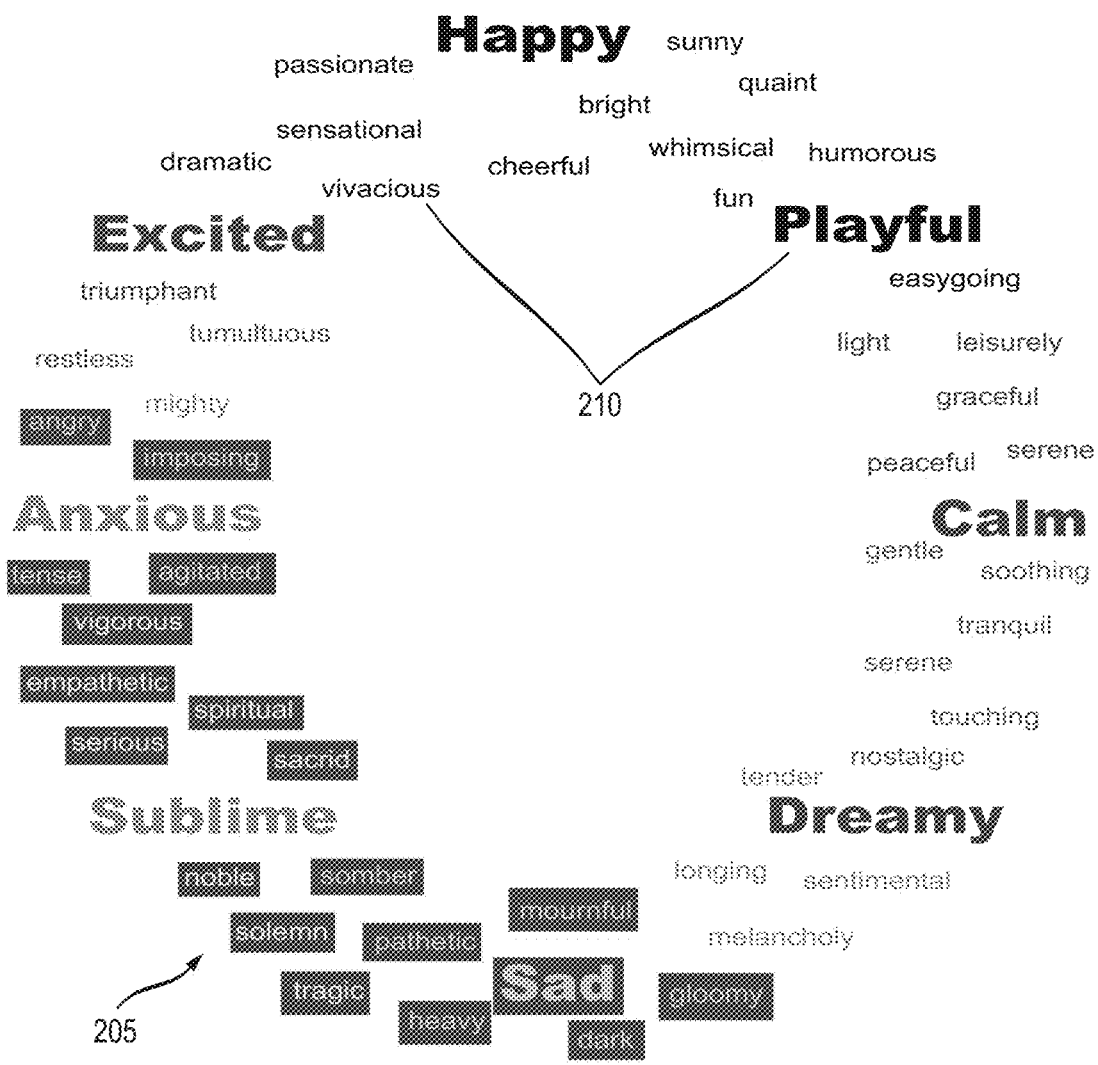
FIGS. 2A-2C illustrate user interface designs for interacting with the music/audio and music/audio generation system, in accordance with various embodiments.
Figure 2B:
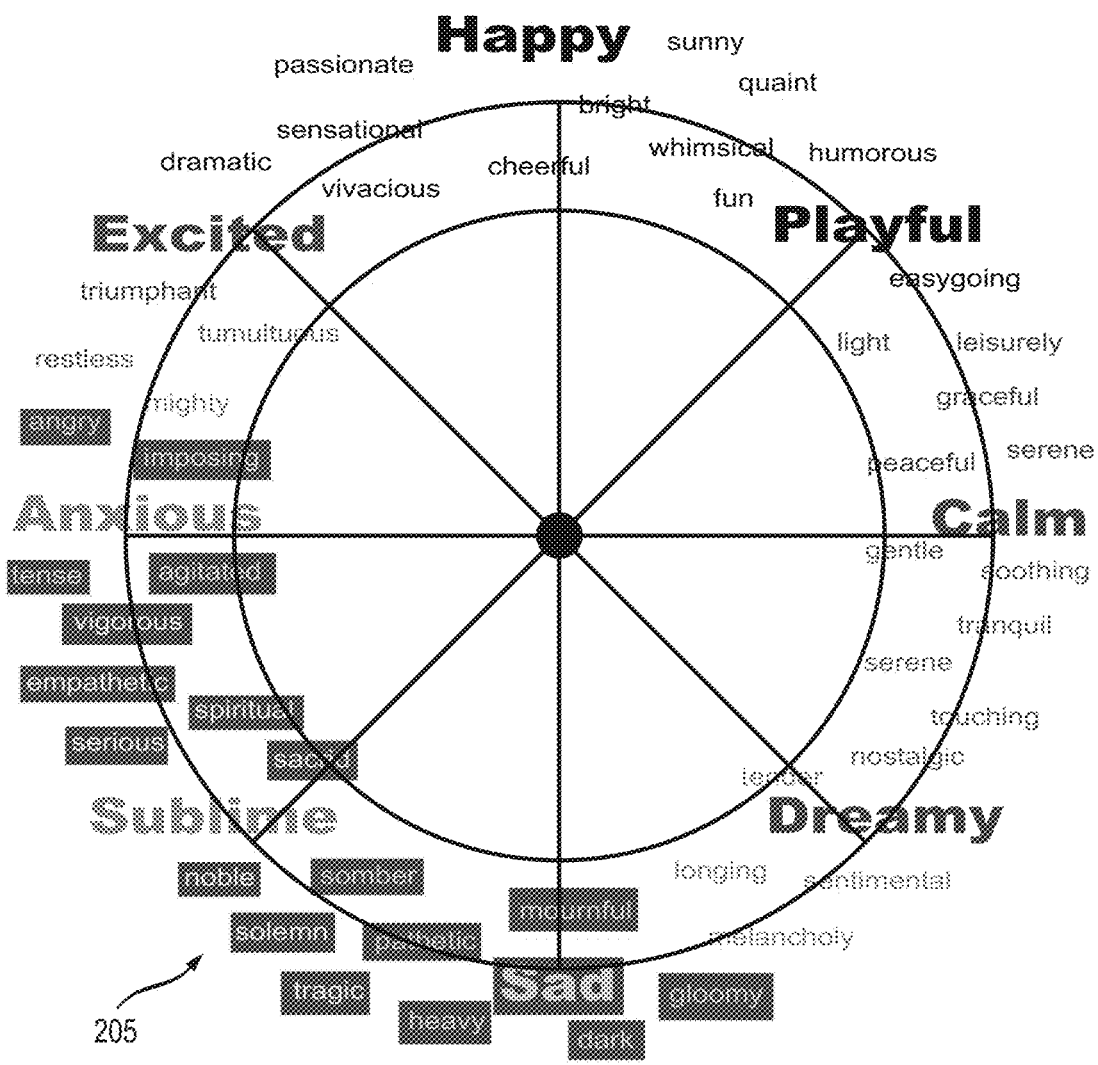
Figure 2C:
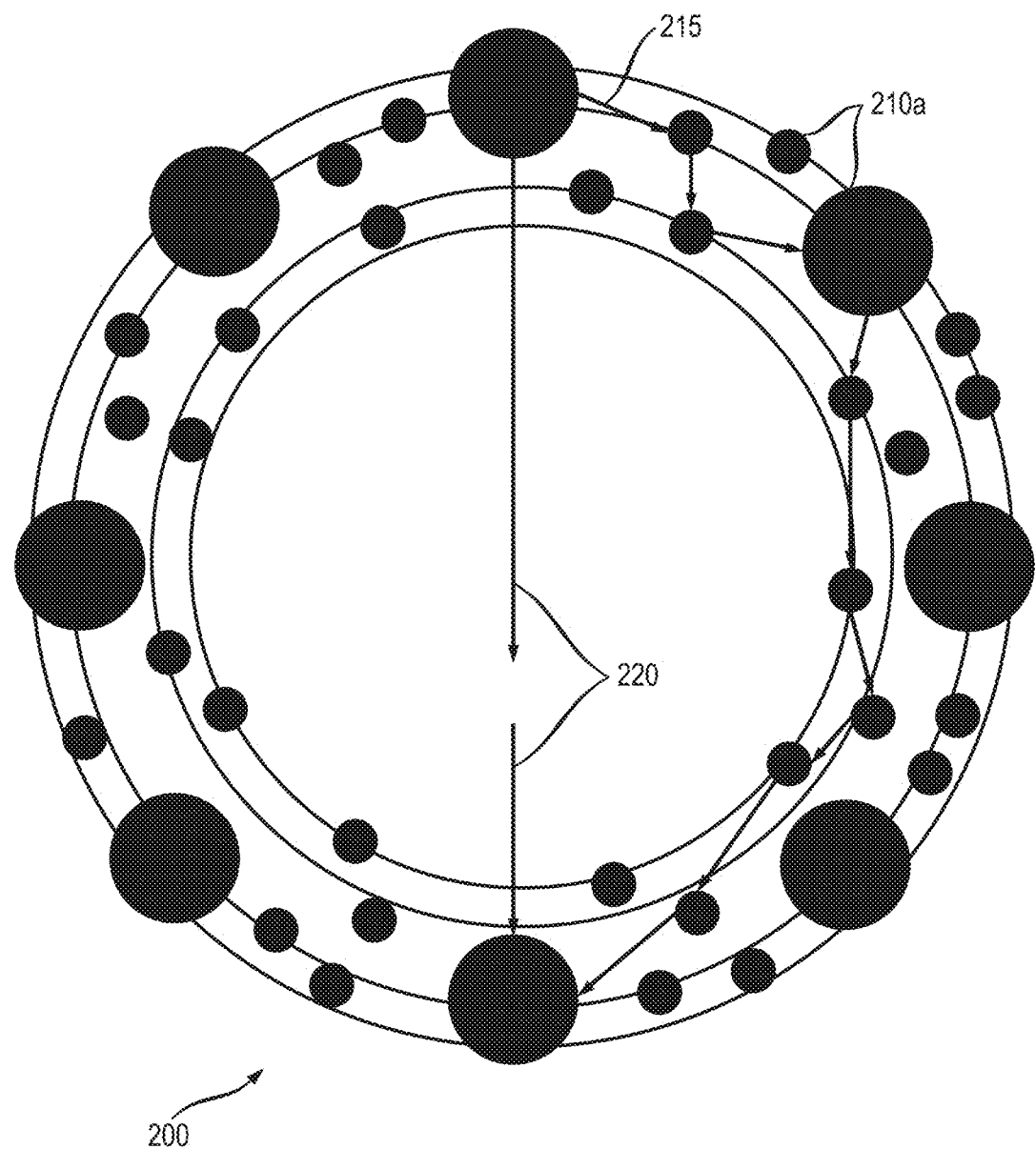

Each state may be associated with an icon (e.g., a text icon and/or emoji icon) and each icon may be mapped to a circular pattern/wheel 205, shown in FIG. 2. Additionally and/or alternatively, instead of icons, each state may be mapped to a position on a circular pattern/wheel 205. FIGS. 2A-2C (collectively, FIG. 2) illustrate user interface designs 200 (also referred to as user interface 200) for interacting with the music generation system (as described with respect to FIGS. 1 and 3-9), in accordance with various embodiments.

The circular pattern/wheel 205 is not limited to only being a circle. The circular pattern could be any pattern (e.g., an oval, triangle, square, rectangle, a two-dimensional graph (e.g., an XY graph, etc.) on a two-dimensional plane. Additionally and/or alternatively, the circular pattern/wheel 205 may be a three-dimensional shape or graph. A person of ordinary skill in the art would understand that any pattern may act in a similar manner as the circular pattern 205 described below. A two-dimensional graph is described in more detail below with respect to FIG. 9D. The two-dimensional graph 900d shown in FIG. 9D may be used in a similar manner as user interface 200.

According to some embodiments, the user interface 200 may display states detected from a communication. A user may then determine from the displayed states what type of music is being generated. The user interface 200 may display only those states detected in the communication. Alternatively, the user interface 200 may display, a plurality of icons 210 and/or positions associated with particular states mapped to a circular pattern 205 and the icons and/or positions associated with the states detected in the communication may be highlighted or bolded to stand out from the rest of the icons/positions on the circular pattern 205.

Additionally and/or alternatively, the circular pattern 205 may display icons associated with elements/concepts other than states. For example, the icons 210 may be associated with scenes (e.g., action scenes, horror scenes, romance scenes, and/or the like) from a movie, book, video game, and/or the like. The music that is generated may then have musical characteristics associated with the scenes (e.g., action scenes, horror scenes, romance scenes, and/or the like). Additionally and/or alternatively, the icons 210 may be associated with an action of the user. For example, different sensors and/or input devices may detect and/or a user may input whether a person is running, walking, biking, sitting down, etc. and the generated sounds may reflect the action of the user. In a non-limiting example, the music that is generated, when the user is sitting down, may be slower than the music that is generated when the user is running.

Additionally and/or alternatively, according to some embodiments (shown in FIG. 2A), a plurality of icons 210 and/or positions associated with particular states and/or other elements/concepts may be mapped to a circular pattern 205 and displayed to a user on user interface 200. The icons may be text icons and/or emojis. Each icon 210 and/or position may be color coded based on the particular state and/or other element/concept it represents. Additionally and/or alternatively, a particular state and/or other element/concept may be represented by an emoji associated with that particular state.

The circular pattern 205 may be displayed to a user on a computing system and/or communication device. The user interface 200 may be hosted on a webpage that is accessible by a user and/or stored in memory of a computing system/communication device. An icon, thumbnail, shortcut, or the like for the user interface 200 may be displayed in a text messaging application, an email application, a video communication application, an e-book, and/or the like. A user may select the icon, thumbnail, shortcut, and/or the like to enable the music generation system/method to determine states contained in communications and/or to display the full user interface 200 to a user.

Additionally and/or alternatively, the computing system and/or communication device may use the circular pattern 205 to determine a location of a particular state represented by an icon/position on the circle without displaying the wheel 205 to the user. An icon, thumbnail, shortcut, or the like for the user interface 200 may be displayed in a text messaging application, an email application, a video communication application, an e-book, and/or the like. A user may select the icon, thumbnail, shortcut, and/or the like to enable the music generation system/method to determine states contained in communications.

The wheel 205 is a circular wheel interface where a range of states and/or other elements/concepts (represented by icons 210) are mapped to different positions. The wheel 205 is the source of control for music parameters and an icon's position on the wheel determines changes in a note pattern, a harmony, a tone, an orchestration, a speed, a rhythm, a volume, and/or the like. The position of each icon on the wheel 205 is the main control over time of the generation of music. Different regions on the wheel 205 map to noticeable differences in the music that is generated by the computing system. A specific intensity and valence score may determine a state region and/or other element region on the circular or X/Y grid (shown in FIG. 9D) interface and each state region and/or other element region may correspond to particular musical parameters in the generated music.

As shown in FIG. 2B, the plurality of icons 210 and/or positions of states may be organized such that similar states and/or other elements/concepts (represented by icons 210) are grouped together in a particular region of the circular wheel 205. Similar states may have similar musical/sound characteristics to aid in smoothly transitioning between states. If a user and/or communication were to traverse around an entire circumference of the circular pattern, a beginning point and an end point would generate audio having similar characteristics because the beginning point and the end point are located in a similar region. States and/or other elements/concepts grouped together in a particular region may sound similar but have some noticeable differences. For example, a position of state on a circumference of the circular pattern or an angle of a position of a state on the circular pattern may correspond to a first subset of characteristics associated with a particular state and/or other element/concept represented by a particular position, while a distance of position of a state from a center of the circular pattern may correspond to a second set of characteristics associated with the particular state. Additionally and/or alternatively, a position of a state on a circumference of the circular pattern or an angle of a position on the circular pattern may correspond to a particular musical arrangement associated with a particular state and/or other element/concept represented by a particular position, while a distance of position of a state from a center of the circular pattern may correspond to an intensity of the particular musical arrangement.

A user may interact with user interface 200 via tactile input and/or mouse input. Additionally and/or alternatively, the user interface 200 may be used by a computing system and/or user device to determine what music to play based on an emotion contained with a communication (e.g., at least one of a sensor communication, an IoT communication, a biometric/health communication, a voice communication, a textual communication, a photographic communication, a video communication, and/or the like). A computing system may determine where a particular position associated with the determined state is on the wheel 205 and access and play the algorithm associated with the particular state based on where the state is located on the wheel 205.

Based on the user interaction with the user interface 200 and/or based on a determined state from a communication, the computing system may determine the position on a circumference of the wheel 205 of an icon 210 and/or position associated with the determined at least one particular state or an angle of the icon 210 and/or position associated with the determined at least one particular state on the circular pattern and the distance of the particular icon 210 and/or position associated with the determined at least one particular state from the center of the wheel 205. Based on the determination of the position or angle and the distance of the icon 210 associated with the determined at least one state the computing system and/or user device may generate music having the musical arrangement and the intensity associated with the determined at least one state of the communication.

Additionally and/or alternatively, the wheel 205 may facilitate transitioning between music associated with a first particular state to music associated with a second particular state. This is shown in FIG. 2C. In FIG. 2C, icons 210 and/or positions associated with a particular state are represented by circles 210a. A user may first indicate the state represented by an icon located at the top of wheel 205 via touch input, mouse input, and/or by indicating a state in a communication.

If the selection is made via touch or a mouse and after a first user indication is made, then a computing system and/or communication device may track a user's interaction with the user interface 200 and wheel 205. A user may continue to drag his or her finger or other device (e.g., mouse, stylus, and/or the like) along a path 215 on the wheel 205 indicating that the music that is generated should transition between music associated with at least two states. The music that is generated may transition in real time or near real time based on the user's interaction with the wheel 205. For example, if the user stops for a period of time on a particular icon associated with a state, then the music associated with that particular state may play for that period of time until the user stops selecting the icon and/or moves on to a different state. Additionally and/or alternatively, each icon that the user selects by dragging his or her finger or other device (e.g., mouse, stylus, and/or the like) along a path 215 may play music associated with that particular icon/state/position for a predetermined amount of time (e.g., until a note is done playing, until a sequence of notes is complete, and/or the like) before transitioning on to the music associated with the next selected icon/state/position. In some cases, the predetermined amount of time may be selected by a user of user interface 200.

The computing system and/or user device may also introduce some lag so that music that is generated by user interaction is not generated in real time. For example, if the user drags his or her finger or device over user interface 200 quickly, the computing system may not be able to transition between music associated with different states smoothly. By introducing lag, the computing system may smoothly transition between music associated with different emotions.

Additionally and/or alternatively, if a user picks up his finger and/or device (220), a computer may determine that a user would like to pause between transitioning between a first selected state and an additional selected state. The music may turn off or continue to play in static position. If the user rests on a particular state, the music can still be continuously generated.

If a selection of more than one state is made via a communication (e.g., at least one of a sensor communication, an IoT communication, a biometric/health communication, a voice communication, a textual communication, a photographic communication, a video communication, and/or the like) and the communication contains at least two states, then a computing device may determine a path 215 between a first selected state and at least one additional state. Using the states between the first selected state and at least one additional state, the computing system may smoothly transition between playing music associated with each of the at least two states contained within the communication by playing music associated with the determined additional states between music associated with the at least two particular states indicated in the communication.

Additionally and/or alternatively, the generated music may transition between music associated with the at least two states indicated in the communication by pausing music associated with a first indicated state before playing music associated with a second indicated state.

The above referenced transition methods may additionally be used to guide a user from a first state to a second desired state. The generated music may continuously guide, based on input from the one or more communications, a user from a first state to a second desired state. In a non-limiting example, a computing device may determine a path 215 between a first state and at least one additional desired state. Using the states between the first selected state and at least one additional state, the computing system may smoothly transition, based on input from the one or more communications, between playing music associated with each of the at least two states contained within the communication by playing music associated with the determined additional states between music associated with the at least two particular states indicated in the communication to guide a user towards the second desired state.

User interface 200, a computing system, and/or a communication device may give a user an option to save music that is generated by user interaction with interface 200 and/or music that is generated by analyzing the communication. A user may then playback the saved music that was previously generated. Additionally and/or alternatively, a user may be given the option to share (via social media site, text, email, phone, and/or the like) the generated music with others. The user may further be able to create a playlist of generated music and/or give the generated music a unique name.

Figure 3:
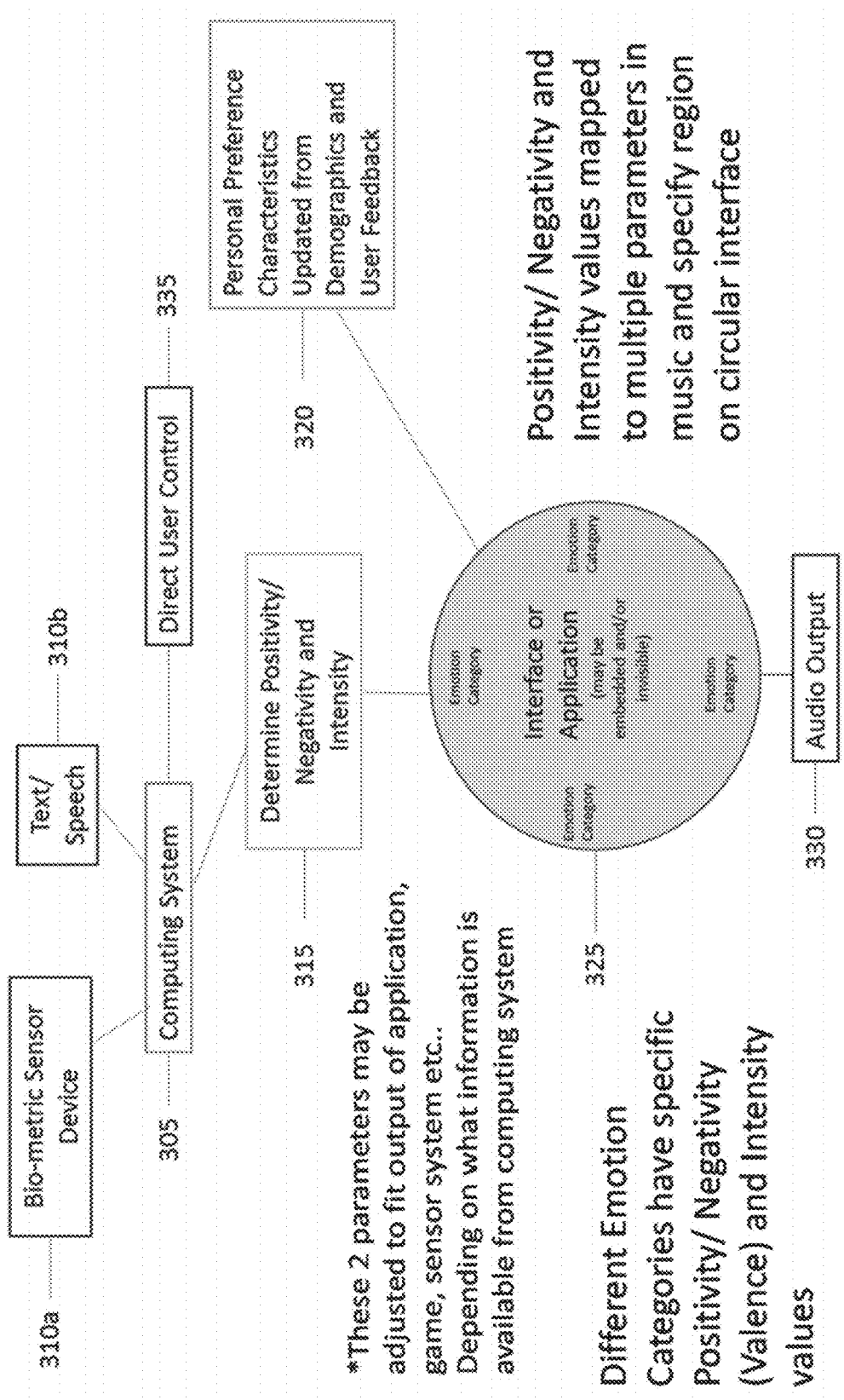
FIG. 3 is a schematic diagram illustrating a system for implementing the generation of music and interactive audio, in accordance with various embodiments.

FIG. 3 is an additional schematic diagram illustrating a system 300 for implementing the generation of music, in accordance with various embodiments. System 300 may be similar to system 100 of FIG. 1 and perform similar functions as system 100 of FIG. 1. Additionally and/or alternatively, system 300 may be used in conjunction with user interface 200 of FIG. 2.

System 300 may comprise computing system 305 (which may correspond to computing system 105 of FIG. 1). Computing system 305 may run applications such as text, voice, and/or video applications and/or receive input from input devices 310. Input devices 310 may include one or more sensor devices including one or more IoT sensors, one or more biometric/health sensor devices 310, text/speech device 310b, VR/AR devices, fitness tracker devices, smart watches, EEG devices, one or more cameras, one or more facial recognition devices, and/or the like. Computing system 305 may also receive direct user input (control) 335 via touch, mouse, video game context and/or the like.

Computing system 305, based on the input received from input devices 310 and/or direct user input 335, may determine a state contained within the input received from input devices 310 and/or user input 335. Based on the determined state, the user interface may determine a positivity/negativity (valence) and/or intensity of music associated with the determined state (block 315). The positivity/negativity and/or intensity of the music are discussed further with respect to FIG. 4. Additionally and/or alternatively, computing system 305 may determine a position of a determined state on the circular pattern 325 or X/Y plane to determine the positivity/negativity and/or intensity of music associated with the determined state. Different combinations of positivity/negativity and/or intensity characterize different state and map to various regions around the circular pattern's circumference or position on an X/Y plane.

In addition to determining a state contained within input devices 310 and/or indicated by user input 335, the computing system may further determine user preferences, demographics, and/or the like when determining what music to generate (block 320). A user may directly enter user preferences, demographics, and/or the like. The computing system 305 may also indirectly determine user preferences, demographics, and/or the like. For example, computing system 305 may determine user habits (i.e. what types of music a user typically listens to and/or buys).

Additionally and/or alternatively, music generation parameters/characteristics may be adjusted to fit output of the application, game, sensor system, and/or the like. For example, if the music generation system is being used to supplement a voice conversation, then the music that is generated may contain lower tones/volumes. If the music generation system is being used to supplement information received from a fitness tracker, then the music that is generated may contain higher tones/volumes.

Figure 9D:
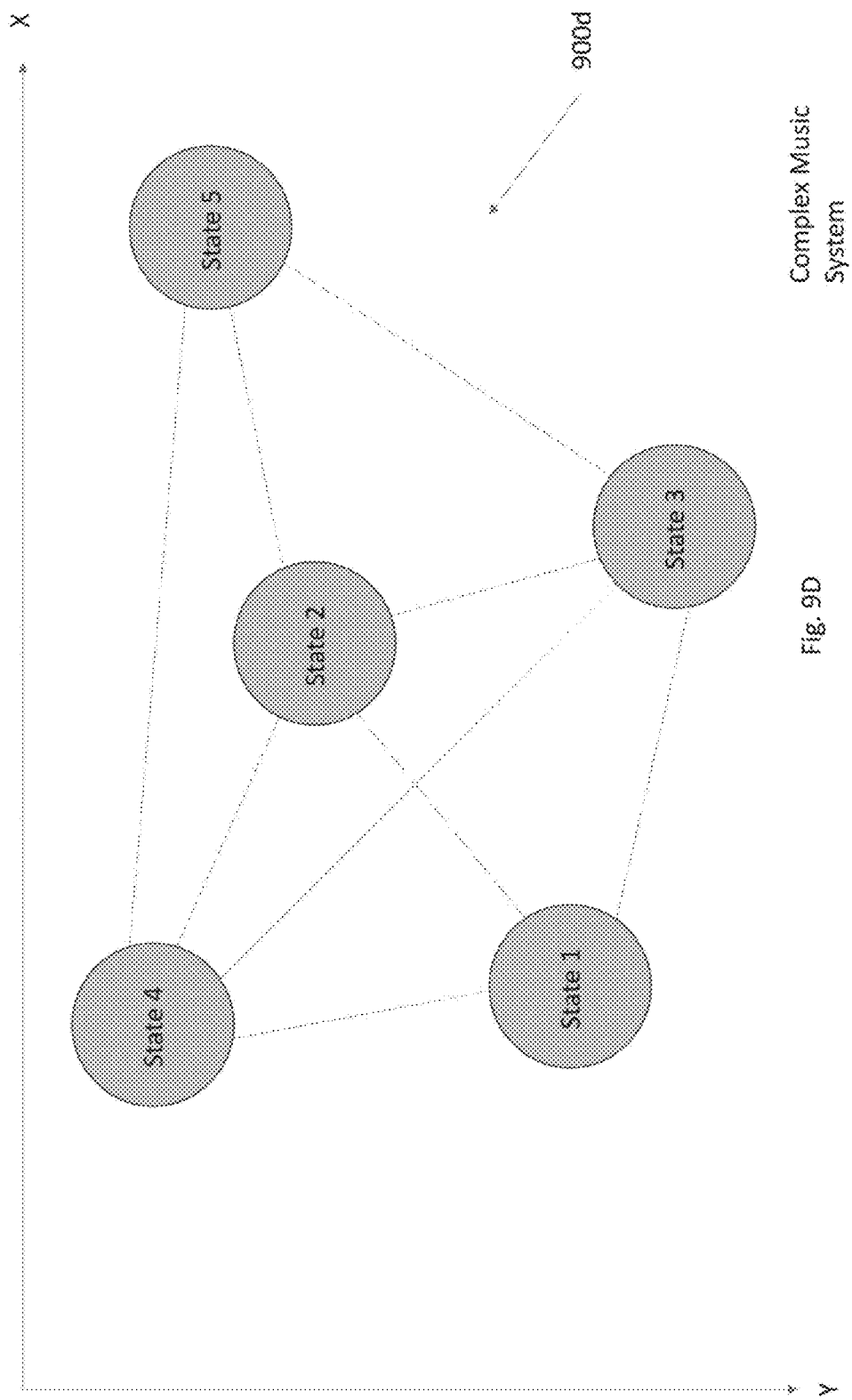

The determined positivity/negativity and/or intensity of the state may be mapped to a circular pattern 325 (which may correspond to user interface 200 of FIG. 2) and/or an XY graph (which may correspond to XY graph 900d of FIG. 9D). States having similar positivity/negativity and/or intensity music may be located in a similar region of the circular pattern 325 and/or graph. Additionally, different state categories may have specific positivity/negativity and/or intensity values.

User interface 325 may be displayed to a user and/or invisible to a user depending on the application of the music generation system 300. For example, if computing system 305 is analyzing text and/or voice input, then the interface 325 may be invisible. If the computing system 305 is receiving user input via touch or mouse, then the interface 325 may be displayed to a user.

After determining the positivity/negativity and/or intensity of music, the generated music may be outputted via audio output 330 (which may correspond to playback devices 120 of FIG. 1). In some embodiments, the audio output 330 might each include, without limitation, one or more speakers external to but communicatively coupled to the computing system 305 and/or input device 310, one of one or more speakers integrated within the computing system 305 and/or input device 310, one or more headphones, one or more earbuds, one or more sound bars, one or more wireless speakers, or one or more stereo speakers, and/or the like.

Figure 4C:
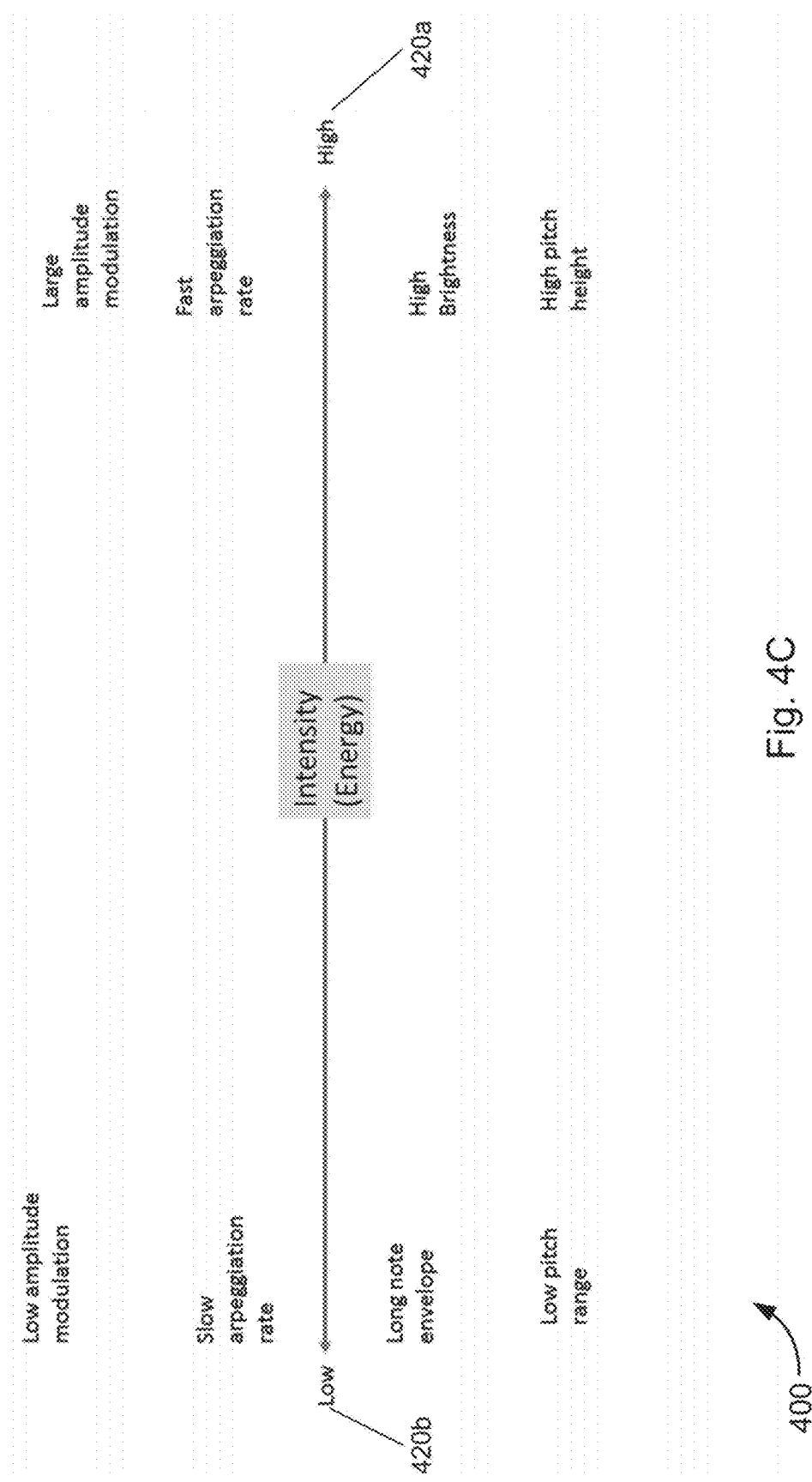

FIGS. 4A-4C (collectively, FIG. 4) represents a system 400 for mapping music to states, in accordance with various embodiments. FIG. 4A includes a table 405 for mapping music to different state categories 410. FIG. 4A has two mapping parameters positivity 415a/negativity 415b and/or intensity 420. The negativity scale 415b is the same as positivity scale 415a, except it is reversed (i.e. on the positivity scale "Happy" is given a 10 while on the negativity scale "Happy" is given a 0). The positivity/negativity parameters may be collectively referred to as positivity/negativity parameters 415. Although only two mapping parameters are shown (positivity/negativity parameters 415 and/or intensity parameter 420) in FIG. 4A, more than two parameters may be used to map music to different states. Additionally and/or alternatively, only one parameter, such as positivity 415a, may be used to map music to states.

Positivity/negativity parameters 415 are rated on a scale of 1-10 while intensity 420 is rated on a scale of 1-100. These values are rescaled between 0-1 then rescaled to control various musical parameters. State categories 410 having a similar positivity/negativity parameter 415 and/or a similar intensity rating 420 may be grouped together on a circular interface and/or a graph (which may correspond to circular pattern 205 of FIG. 2, circular pattern 325 of FIG. 3, graphs of FIGS. 4B and 4C, graph 900d of FIG. 9D, and/or the like). Thus, the state categories 410 that are grouped together will generate similar music with subtle differences.

Positivity/negativity parameters 415 may correspond to a note pattern, a note probability, an envelope, a harmony, a tone, a filter cut-off, pitch, contour, arpeggiation rate, arpeggiation step size, vocal-like inflections, elements of surprise, note envelopes, envelope control signals, randomization, consistency, an orchestration, a speed, a rhythm, a volume, and/or the like associated with a state. Intensity parameters 420 may correspond to a note pattern, a harmony, a tone, crescendo, decrescendo, vocal formant-like filtering or expressive attribute (e.g., inflection), an orchestration, a speed, a volume, and/or the like associated with a state.

Each value that is given to a particular state may be used to generate music that is unique to each particular state. The music that is generated is represented by music attributes column 425. For example, if the computing system determines that a communication contains the state "Happy" and/or a user has selected an icon associated with the state "Happy," the computing system may generate music having a major mode, fast tempo, staccato, quick attack (note onsets), short decay, and bright timbre.

Music attributes column 425 may further vary based on the type of application/communication (e.g., voice, text, speech, fitness tracker, EEG device, smart watch, AR/VR device, user input, and/or the like), the demographics (e.g., age, sex, and/or the like) of the user, the user's preferences, and/or the like.

FIGS. 4B and 4C further represent ways to map different music parameters to states using graphs. FIG. 4B represents mapping positivity/negativity parameters 415 to different musical characteristics. In a non-limiting example, states mapped to positive parameters 415a (e.g., "Happy") may cause the computing system to generate music that has a brighter timbre, a major mode, higher note density, more implied polyphony, steady rhythm, smooth curves, less randomness, larger jumps, and/or the like. While states mapped to negative parameters 415b (e.g. "Sad"), may cause the computing system to generate music that has a darker timber, a minor mode, more chromaticism, higher dissonance, more irregular curves, jagged pitch curves and/or the like.

FIG. 4C represents mapping intensity parameters 420 to different musical characteristics. In a non-limiting example, states mapped to high intensity parameters 420a (e.g. "Excited," "Anxious," and/or the like) may cause the computing system to generate music that has large amplitude modulation, fast arpeggiation rate, high brightness, high pitch height, and/or the like. While states mapped to low intensity parameters 420b (e.g., "Calm," "Dreamy," and/or the like), may cause the computing system to generate music that has low amplitude modulation, slow arpeggiation rate, long note envelope, low pitch range, and/or the like.

Users/communications may interact with graphs of FIGS. 4B and 4C in a similar manner as user interface 200 of FIG. 2 to generate music.

Each of the examples described above, with respect to FIG. 4, is intended to be non-limiting. A variety of parameters (instead of positivity/negativity and/or intensity) may be used to create music associated with each state. Further, positivity/negativity characteristics and/or intensity characteristics are not limited to those described above. Each state could have an almost unlimited number of musical characteristics associated with it and the musical characteristics associated with each emotion are not limited to those mentioned above.

Figure 5:
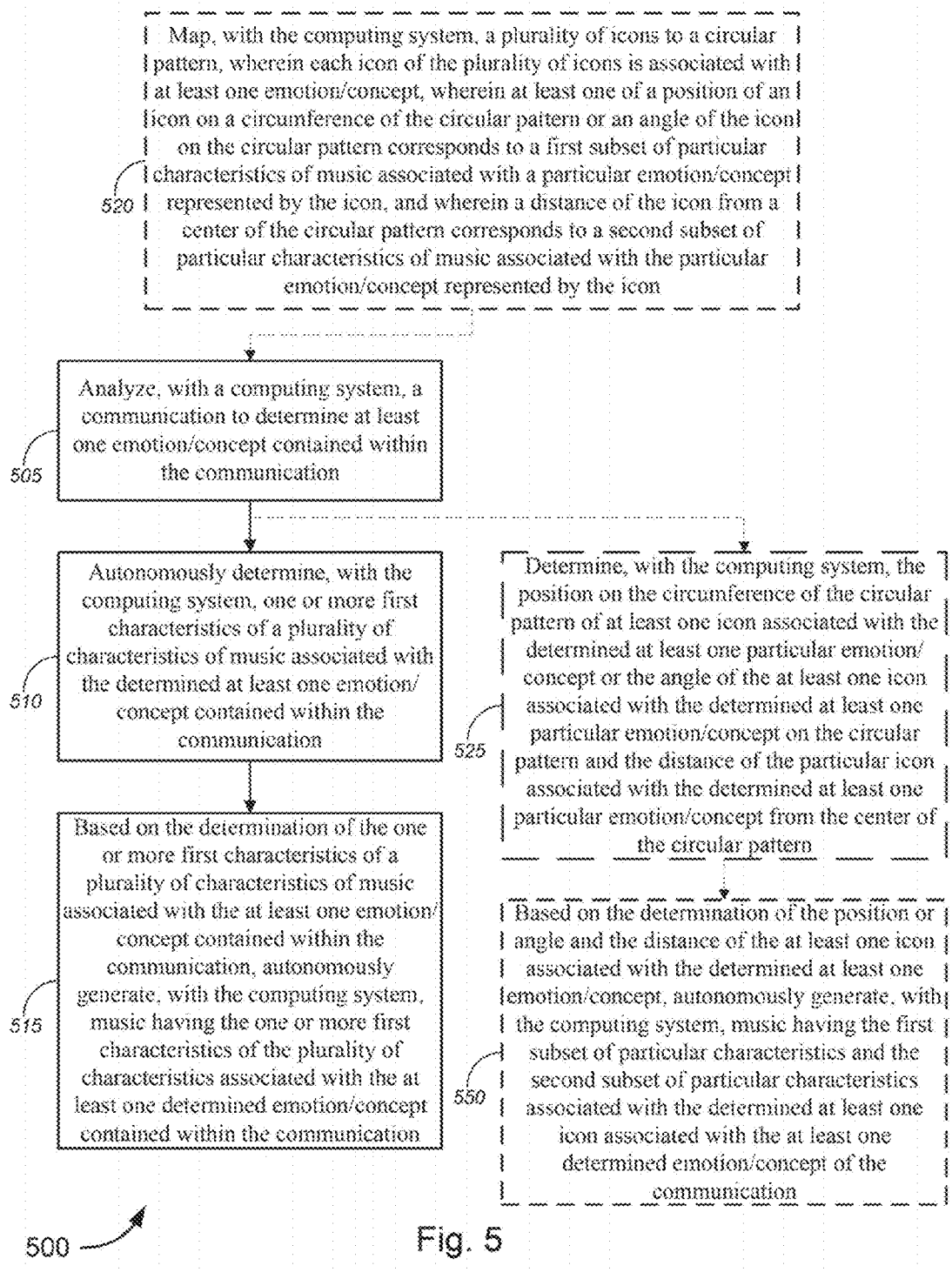
FIG. 5 is a flow diagram illustrating a method for implementing the generation of music/audio, in accordance with various embodiments.

FIG. 5 is a flow diagram illustrating a method 500 for implementing the generation of music, in accordance with various embodiments.

While the techniques and procedures are depicted and/or described in a certain order for purposes of illustration, it should be appreciated that certain procedures may be reordered and/or omitted within the scope of various embodiments. Moreover, while the method 500 illustrated by FIG. 5 can be implemented by or with (and, in some cases, are described below with respect to) the system 100 of FIG. 1 (or components thereof), the user interface 200 of FIG. 2 (or components thereof), the system 300 of FIG. 3 (or components thereof), the mapping system 400 of FIG. 4 (or components thereof), and/or the mapping system of FIG. 9 (or components thereof), such methods may also be implemented using any suitable hardware (or software) implementation. Similarly, while each of the system 100 of FIG. 1 (or components thereof) user interface 200 of FIG. 2 (or components thereof), the system 300 of FIG. 3 (or components thereof), the mapping system 400 of FIG. 4 (or components thereof), and/or the mapping system of FIG. 9 (or components thereof), can operate according to the method 500 illustrated by FIG. 5 (e.g., by executing instructions embodied on a computer readable medium), the system 100 of FIG. 1 user interface 200 of FIG. 2, the system 300 of FIG. 3, the mapping system 400 of FIG. 4, and/or the mapping system of FIG. 9 can each also operate according to other modes of operation and/or perform other suitable procedures.

Although method 500 is described with respect to emotions/concepts, a similar method may be used for different states of an environment or different states of a user which may include at least one of an emotion of a user, a feeling of a user, a location of the user a, a physical position of a user, a level of activity of a user, an action of a user, and/or the like. In the non-limiting embodiment of FIG. 5, method 500, at block 505, might comprise analyzing, with a computing system, a communication to determine at least one emotion (concept or state) contained within the communication. The computing system may be at least one of a desktop computer, a laptop computer, a tablet, a smart phone, an e-reader, and/or the like. Additionally and/or alternatively, in some embodiments, the computer system might be embedded in an exercise machine, physical therapy device, headphone, wristband or headband. Additionally and/or alternatively, in some embodiments, the computing system might include, without limitation, one of a processor of a set-top box, a processor of a digital video recording ("DVR") device, a processor of a user device running a software application ("app"), a processor of an audio playback device, a processor on an input device (e.g., fitness tracker, EEG device, or the like) running an app, a processor of a media player, a processor of a gaming console, a processor in audio equipment, and/or the like. The concept may be at least one of an emotion of a person, a state of a person, an action of a person, or a scene.

The communication may be at least one of a sensor communication, an IoT communication, a biometric/health communication, a voice communication, a textual communication, a photographic communication, a video communication, a VR/AR communication, and/or the like.

The sensor communication may contain feedback from one or more sensors including, but not limited to, one or more distance sensors, one or more motion sensors, one or more movement sensors, one or more speed or velocity sensors, one or more accelerometer sensors, one or more biometric/health sensors, one or more facial recognition sensors, one or more camera sensors, one or more IoT sensors (e.g., thermometers, humidity sensors, etc.) and/or the like. Based on input from the one or more sensors, the computing system 105, input device 115, and/or at least one audio playback device 120 may determine a mental or physical state that a person is experiencing or a state of the environment.

The IoT communication may contain feedback from one or more IoT sensors contained within a home. For example, the one or more IoT sensors might include one of one or more thermometers in one or more rooms, one or more infrared ("IR") thermometers aimed at one or more positions in the one or more rooms, one or more air flow sensors in the one or more rooms, one or more air flow sensors in air ducts directed toward the one or more rooms, one or more indoor solar light sensors, one or more outdoor solar light sensors, one or more outdoor wind sensors, one or more neighborhood weather station sensors, one or more regional weather station sensors, one or more motion detectors detecting presence of people or animals in at least one of the one or more rooms or outside the customer premises, one or more humidity sensors in the one or more rooms, one or more smoke detectors detecting smoke in the one or more rooms, one or more gas detection sensors detecting gas in the one or more rooms, one or more biometric sensors identifying at least one person, or one or more health sensors detecting health information for at least one person, and/or the like. Based on input from the one or more sensors, the computing system, input device, and/or at least one audio playback device may determine a state that a person is experiencing or a state of the environment.

The biometric/health communication may be received from at least one of a fitness tracker or an electroencephalography ("EEG") device and the computing system may determine the at least one emotion of a person and/or concept based on feedback from the at least one of the fitness tracker or the EEG device. In a non-limiting example, the fitness tracker and/or EEG device may provide feedback about a blood pressure of a user, a heart rate of a user, electrical brain waves of a user, and/or the like. Based on the blood pressure, the heart rate, the electrical brain waves and/or the like, the computing system may determine an emotion/concept that a user is experiencing. Merely by way of example, if the user has an elevated blood pressure and a high heart rate the computing system may determine that a user of the fitness tracker and/or EEG device is feeling stressed.

The voice communication may be received via user input or from a phone call between a calling party and a called party. In order to determine the at least one emotion/concept of a person, the computing system may parse the voice communication of the at least one person and/or determine a tone of voice of at least one person. Merely by way of example, if the communication is via phone, the computing system may parse the voice communication between the calling party and the called party to determine how each party is feeling. Additionally and/or alternatively, the computing system may analyze the tone of voice of each party to determine what emotions/state each party is experiencing.

With regard to the textual communications, the computing system may analyze text messages, instant messages, social media posts, emails, books, and/or the like to determine an emotion/concept that a user/person is experiencing. The computing system may parse the text of the textual communication to determine the emotion/concept of a person. Merely by way of example, the computing system may parse the text for key words such as "happy" or "sad" and/or the computing system may parse the textual communication for emojis to determine the mood of a person. Additionally, the computing system may parse the words of a book to determine a scene (e.g., action scene, adventure scene, romance scene, etc.) of a book or an action/state of a person in the book.

The photographic communication may be a photograph taken with a camera. The computing system may then use facial recognition tools to determine a displayed emotion/concept of at least one person in the photograph. The video communication may be taken with a video camera. The video communication may also be a video phone call between at least two parties. The computing system may then use facial recognition tools to determine a displayed emotion/concept of the at least one person in the video. The computing system may also use tools to analyze body language of the at least one person in the video communication to determine an emotion/concept that the at least one person is experiencing. The computing system may further parse the dialogue of the at least one person in the video or analyze the tone of voice of at least one person in the video communication to determine an emotion/concept that the at least one person in the video is experiencing. Additionally and/or alternatively, the computing system may use facial recognition tools, analyze body language, parse dialogue, analyze tone of voice to determine a state/action (e.g., running, walking, and/or the like) of a person and/or a scene (e.g., action scene, adventure scene, romance scene, and/or the like) of the video/picture.

A VR communication and/or AR communication may be obtained from VR/AR devices (e.g., cell phones, tablets, headsets, glasses, goggles, lenses, and/or the like). The computing system 105, input device 115, and/or at least one audio playback device 120 may analyze the facial expression, body language, and/or the like of the user of the AR/VR device and/or one or more persons interacting/communicating with the user of the AR/VR device. The computing system 105, input device 115, and/or at least one audio playback device 120 may also parse the dialogue or determine a tone of voice of the user and/or one or more persons interacting with the user of the AR/VR device. The facial expression, body language, dialogue, and/or tone of voice may then be used to determine a concept/emotion of a user and/or person. A state of a virtual concept defined within the game metrics may also be used to drive the state of the music system.

The method 500, at block 510, may further comprise autonomously determining, with the computing system, one or more first characteristics of a plurality of characteristics of music associated with the determined at least one emotion/concept/state contained within the communication. The one or more first characteristics of the plurality of characteristics of music include at least one of a note pattern, a harmony, a tone, an orchestration, a speed, a rhythm, a volume, and/or the like associated with the first emotion/concept indicated by the communication.

At block 515, method 500 may further comprise, based on the determination of the one or more first characteristics of a plurality of characteristics of music associated with the at least one emotion/concept/state contained within the communication, autonomously generating, with the computing system, music having the one or more first characteristics of the plurality of characteristics associated with the at least one determined emotion/concept contained within the communication.

Additionally and/or alternatively, the communication may further indicate at least one of an age and/or sex of a person. The one or more first characteristics of a plurality of characteristics of music may further be associated with the at least one of the age or the sex indicated by the communication. The music that is generated further has the one or more first characteristics of the plurality of characteristics associated with the at least one of the age or the sex indicated by the communication.

The generated music may further have human-like embellishments. The human-like embellishments may be created from at least one of timing jitter, frequency jitter, timbral jitter, and/or the like. These allow for the music to continuously evolve even when stuck in one state.

Human performers have a natural imprecision which must be explicitly accounted for in computer generated music. To do this, irregular micro-fluctuations may be added to the timing of note onsets. This kind of small random signal bias is often referred to as "timing jitter." As a result, quantized notes are gently un-quantized to provide a more pleasing and human-sounding musical aesthetic. Timing jitter provides subtle rhythmic variation that may add nuance to the static note patterns.

Similar to jittered timing offsets ("timing jitter"), "frequency jitter" may be utilized to modulate the frequency (pitch) of the generated music. Depending on the duration and articulation of the note, frequency jitter parameters will change. For instance, long sustained notes will be subject to more evolved jitter (gradual drift), a technique to add warmth; while shorter, more percussive notes will have little to no jitter.

Jitter may also be mapped to a number of other parameters in charge of producing timbre or the sound qualities of the notes. This is referred to as "timbral jitter." These parameters exist due in part to the real-time audio synthesis engine, which allow dynamic control of a sound over time via digital signal processing.

Additional embodiments of method 500 may further comprise an initial step of mapping, with the computing system, a plurality of icons to a circular pattern, wherein each icon of the plurality of icons is associated with at least one emotion/concept/state, wherein at least one of a position of an icon on a circumference of the circular pattern or an angle of the icon on the circular pattern corresponds to a first subset of particular characteristics of music associated with a particular emotion/concept/state represented by the icon, and wherein a distance of the icon from a center of the circular pattern corresponds to a second subset of particular characteristics of music associated with the particular emotion/concept/state represented by the icon (block 520). This map of the plurality of icons may be displayed to the user or the circular pattern may merely be used by the computer to map particular emotions/concepts to a particular musical generation algorithm.

After determining at least one emotion/concept/state contained within the communication (block 505), the method may further determine the position on the circumference of the circular pattern of at least one icon associated with the determined at least one particular emotion/concept/state or the angle of the at least one icon associated with the determined at least one particular emotion/concept/state on the circular pattern and the distance of the particular icon associated with the determined at least one particular emotion/concept/state/adjective from the center of the circular pattern (block 525). Based on the determination of the position or angle and the distance of the at least one icon associated with the determined at least one emotion/concept/state, the method, at block 550, may autonomously generate music having the first subset of particular characteristics and the second subset of particular characteristics associated with the determined at least one icon associated with the at least one determined emotion/concept/state of the communication.

Figure 6:
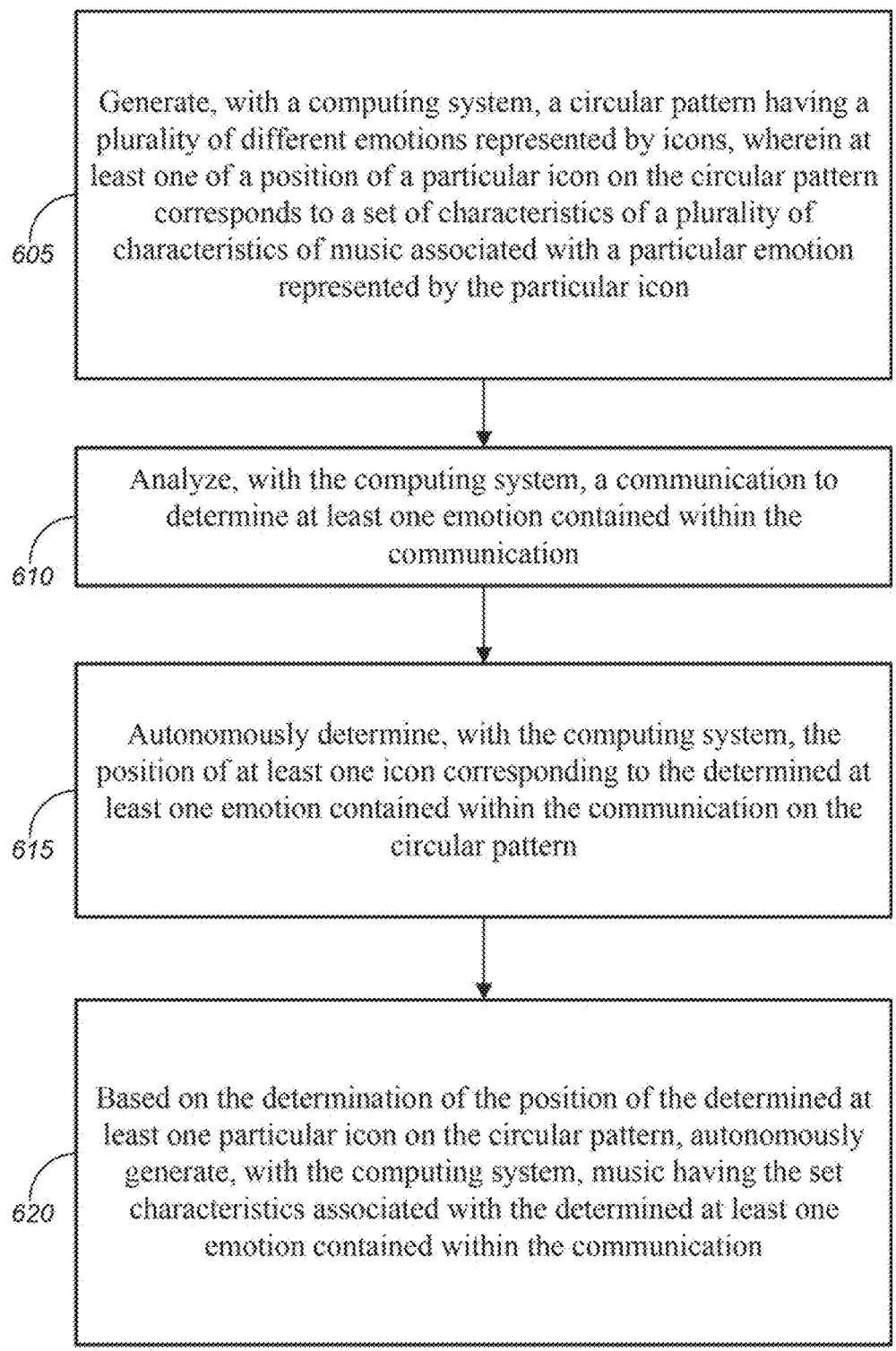
FIG. 6 is a flow diagram illustrating a method for implementing a user interface for the generation of music/audio, in accordance with various embodiments.

FIG. 6 is a flow diagram illustrating a method 600 for implementing a user interface for the generation of music, in accordance with various embodiments.

While the techniques and procedures are depicted and/or described in a certain order for purposes of illustration, it should be appreciated that certain procedures may be reordered and/or omitted within the scope of various embodiments. Moreover, while the method 600 illustrated by FIG. 6 can be implemented by or with (and, in some cases, are described below with respect to) the system 100 of FIG. 1 (or components thereof), the user interface 200 of FIG. 2 (or components thereof), the system 300 of FIG. 3 (or components thereof), the mapping system 400 of FIG. 4 (or components thereof), and/or the mapping system of FIG. 9 (or components thereof), such methods may also be implemented using any suitable hardware (or software) implementation. Similarly, while each of the system 100 of FIG. 1 (or components thereof) user interface 200 of FIG. 2 (or components thereof), the system 300 of FIG. 3 (or components thereof), the mapping system 400 of FIG. 4 (or components thereof), and/or the mapping system of FIG. 9 (or components thereof), can operate according to the method 600 illustrated by FIG. 6 (e.g., by executing instructions embodied on a computer readable medium), the system 100 of FIG. 1 user interface 200 of FIG. 2, the system 300 of FIG. 3, the mapping system 400 of FIG. 4, and/or the mapping system of FIG. 9 can each also operate according to other modes of operation and/or perform other suitable procedures.

Although method 600 is described with respect to emotions/concepts, a similar method may be used for different states of an environment or different states of a user which may include at least one of an emotion of a user, a mental state of a user, a feeling of a user, a physical state of a user, a location of the user a, a physical position of a user, a level of activity of a user, an action of a user, or different states of an environment, and/or the like. In the non-limiting embodiment of FIG. 6, method 600, at block 605, might comprise generating with a computing system, a circular pattern having a plurality of different emotions represented by icons, wherein at least one of a position of a particular icon on the circular pattern corresponds to a set of characteristics of a plurality of characteristics of music associated with a particular emotion represented by the particular icon. The set of characteristics may correspond to positivity/negativity and/or intensity described with respect to FIGS. 3 and 4 and/or any other characteristics of music. At block 610, method 600 may further analyze, with a computing system, a communication to determine at least one emotion contained within the communication.

Additionally and/or alternative, the method 600, at block 615 may autonomously determine, with the computing system, the position of at least one icon corresponding to the determined at least one emotion contained within the communication on the circular pattern. The method 600 may then, based on the determination of the position of the determined at least one particular icon on the circular pattern, autonomously generate, with the computing system, music having the set characteristics associated with the determined at least one emotion contained within the communication (block 620).

Figure 7A:
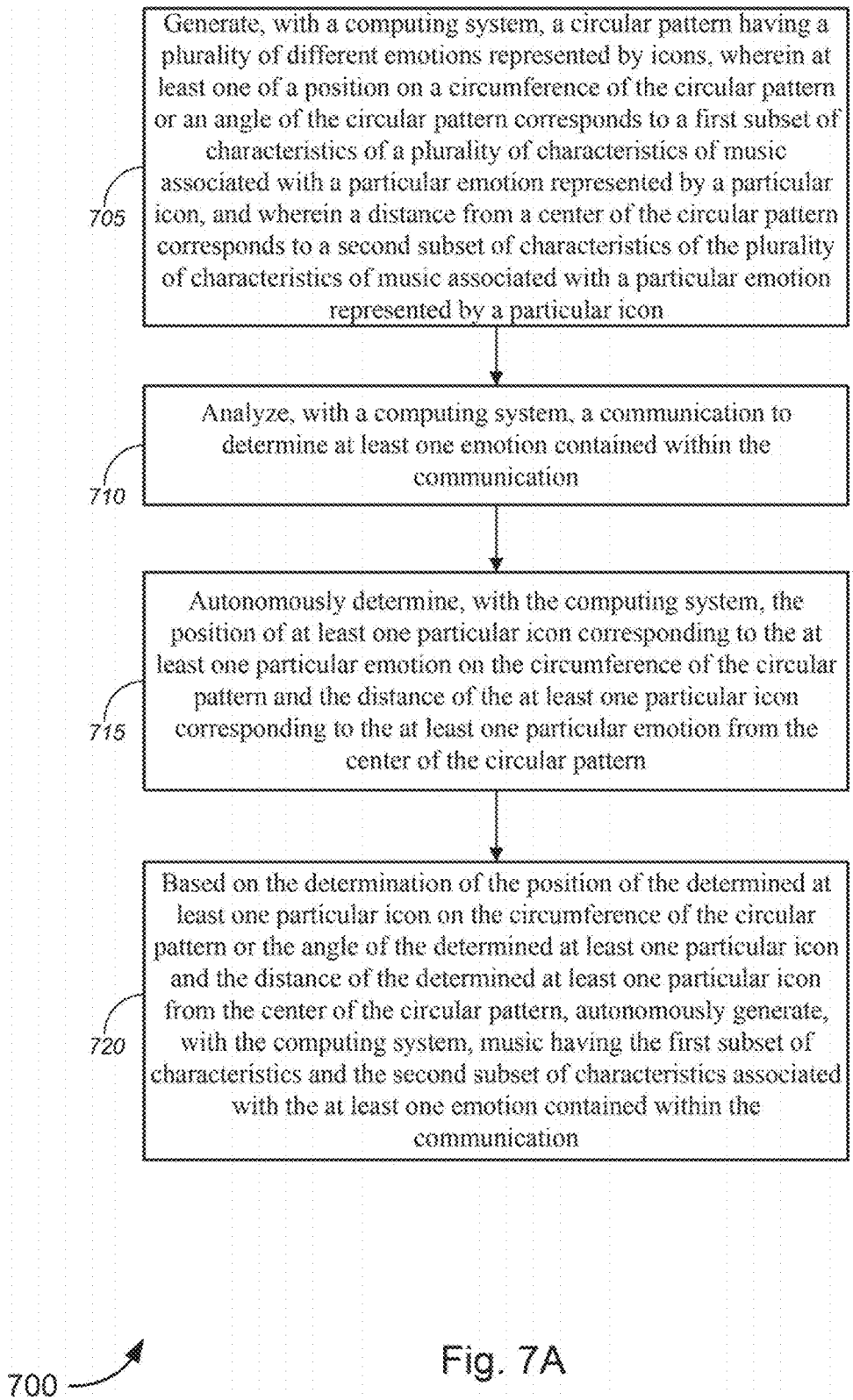
FIGS. 7A-7C are flow diagrams illustrating a method for implementing a user interface for the generation of music/audio, in accordance with various embodiments.
Figure 7B:
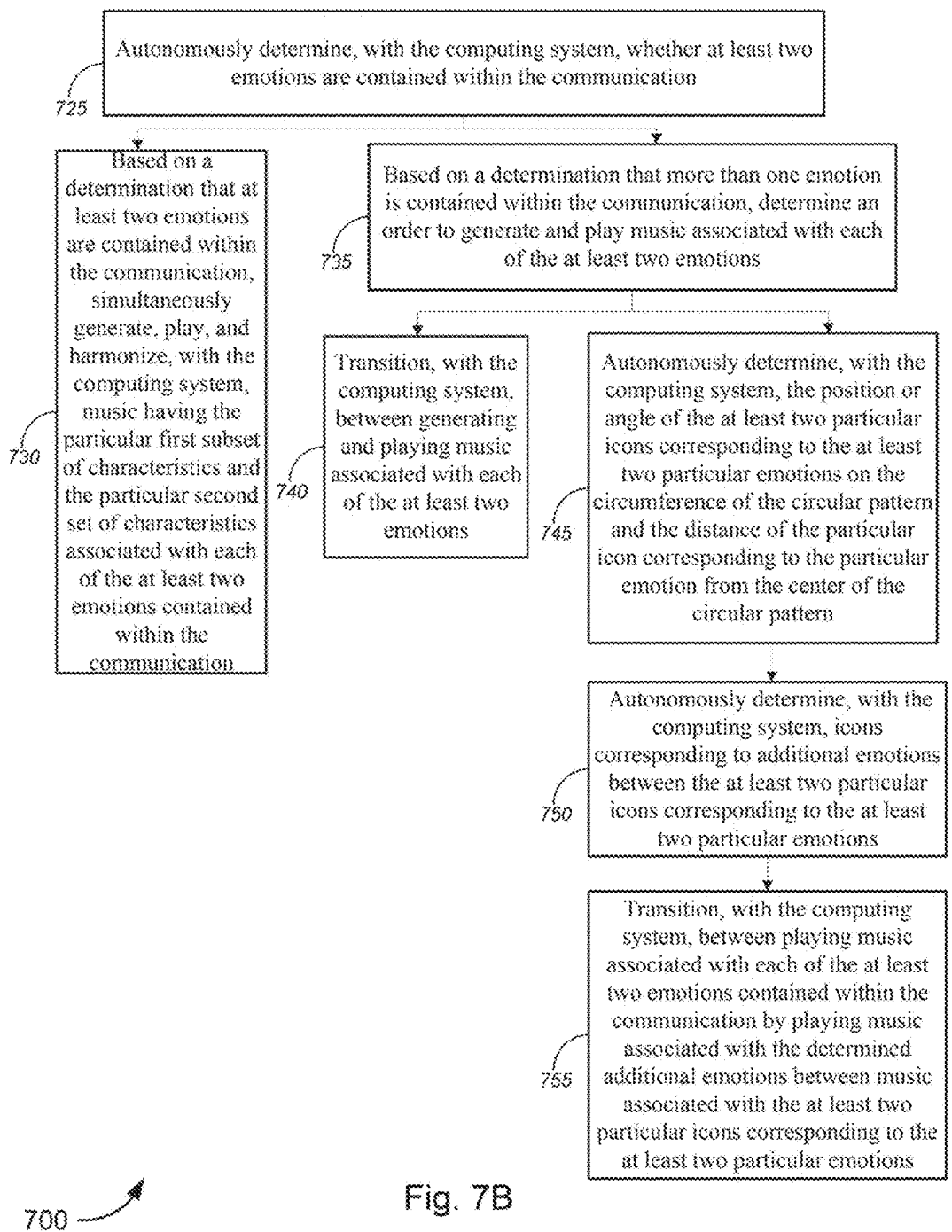
Figure 7C:
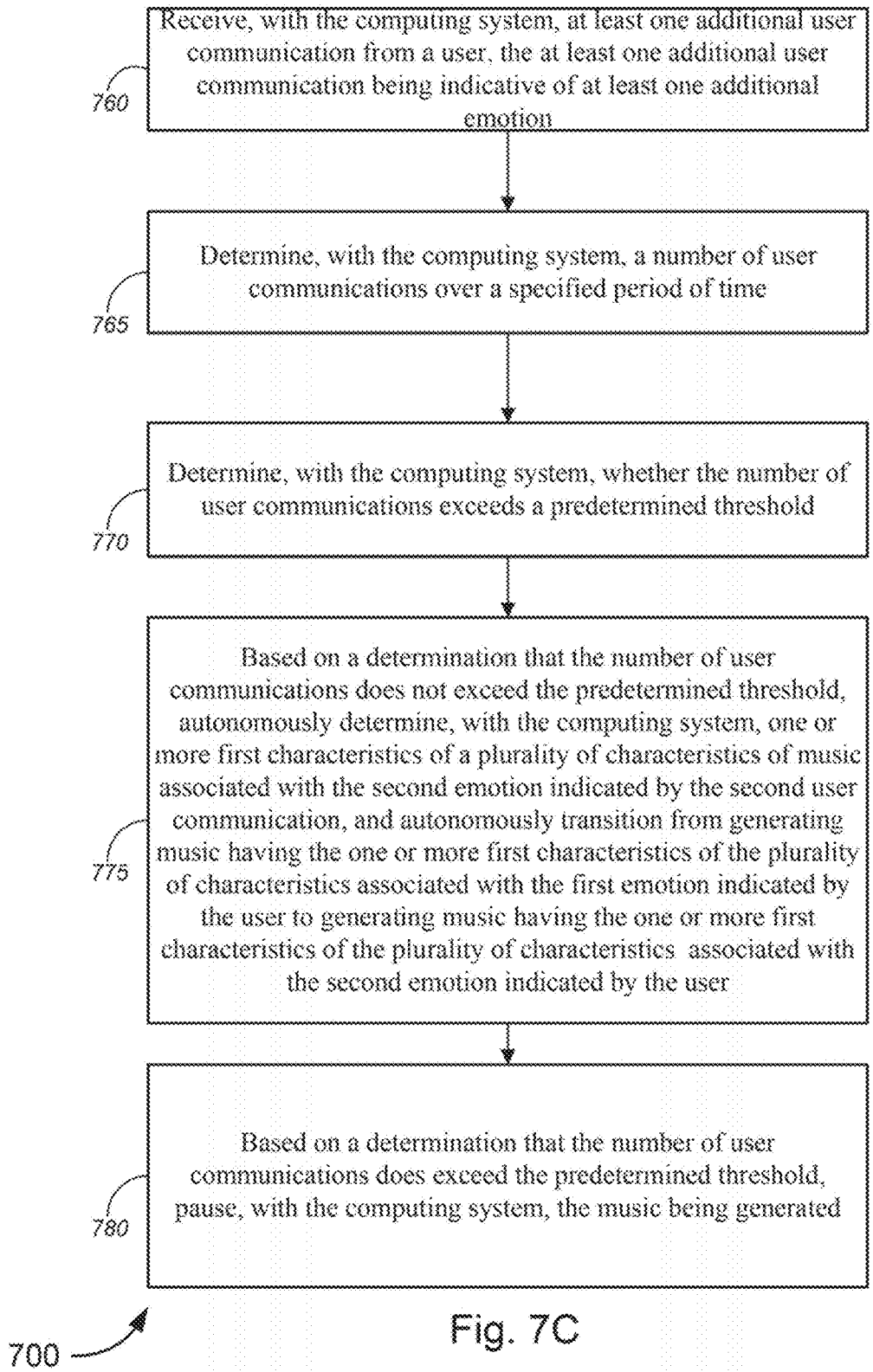

FIGS. 7A-7C (collectively, FIG. 7) are flow diagrams illustrating a method 700 for implementing a user interface for the generation of music, in accordance with various embodiments.

While the techniques and procedures are depicted and/or described in a certain order for purposes of illustration, it should be appreciated that certain procedures may be reordered and/or omitted within the scope of various embodiments. Moreover, while the method 700 illustrated by FIG. 7 can be implemented by or with (and, in some cases, are described below with respect to) the system 100 of FIG. 1 (or components thereof) the user interface 200 of FIG. 2 (or components thereof), the system 300 of FIG. 3 (or components thereof), the mapping system 400 of FIG. 4 (or components thereof), and/or the mapping system of FIG. 9 (or components thereof), such methods may also be implemented using any suitable hardware (or software) implementation. Similarly, while each of the system 100 of FIG. 1 (or components thereof) user interface 200 of FIG. 2 (or components thereof), the system 300 of FIG. 3 (or components thereof), the mapping system 400 of FIG. 4 (or components thereof), and/or the mapping system of FIG. 9 (or components thereof), can operate according to the method 700 illustrated by FIG. 7 (e.g., by executing instructions embodied on a computer readable medium), the system 100 of FIG. 1, user interface 200 of FIG. 2, the system 300 of FIG. 3, the mapping system 400, and/or the mapping system of FIG. 9 can each also operate according to other modes of operation and/or perform other suitable procedures.

Although method 700 is described with respect to emotions/concepts, a similar method may be used for different environmental states or different states of a user which may include at least one of an emotion of a user, a feeling of a user, a location of the user a, a physical position of a user, a level of activity of a user, an action of a user, and/or the like. In the non-limiting embodiment of FIG. 7, method 700, at block 705, may comprise generating, with a computing system, a circular pattern having a plurality of different emotions represented by icons (or a position on the circular pattern), wherein at least one of a position on a circumference of the circular pattern or an angle of the circular pattern corresponds to a first subset of characteristics of a plurality of characteristics of music associated with a particular emotion represented by a particular icon (or position), and wherein a distance from a center of the circular pattern corresponds to a second subset of characteristics of the plurality of characteristics of music associated with a particular emotion represented by a particular icon.

Although icons are used in the method described below, states or emotions may also be mapped to particular regions/positions and the regions/positions may be used instead of icons to generate music.

Instead of a circular pattern, a graph may also be used. The method 700 might alternatively include generating, with a computing system, a graph having a plurality of different states mapped to different positions on the graph. An x-axis might correspond to a first subset of characteristics of a plurality of characteristics of music while a y-axis might correspond to a second subset of characteristics of the plurality of characteristics of music. In this way each axis serves as a separate input into the generative music system. Moving along the X-axis and/or Y axis might cause the first or second parameters of music to change. Based on a determination of the position of a first state, the computing system may synthesize the one or more first subset of characteristics of music together with the one or more second characteristics of music.

In a non-limiting example, the angle of an icon/position of a state and/or the position of an icon on the circumference of the circular pattern may correspond to a positivity/negativity parameter of music (described with respect to FIGS. 3 and 4) while the distance of the icon from the center of the circle may correspond to an intensity parameter of music (described with respect to FIGS. 3 and 4). Additionally and/or alternatively, the angle of an icon and/or the position of an icon on the circumference of the circular pattern may correspond to an intensity parameter of music (described with respect to FIGS. 3, 4, and 9) while the distance of the icon from the center of the circle may correspond to a positivity/negativity parameter of music (described with respect to FIGS. 3, 4, and 9).

The music associated with the emotions is not limited to only positivity/negativity and/or intensity parameters. A variety of parameters (instead of positivity/negativity and/or intensity) may be used to create music associated with each emotion. There is virtually an unlimited number of ways to position icons associated with emotions on the circular pattern and group icons associated with emotions together in a particular region on the circular pattern.

The computing system may be at least one of a desktop computer, a laptop computer, a tablet, a smart phone, an e-reader, and/or the like. Additionally and/or alternatively, in some embodiments, the computing system might include, without limitation, one of a processor of a set-top box, a processor of a digital video recording ("DVR") device, a processor of a user device running a software application ("app"), a processor of an audio playback device, a processor on an input device (e.g., fitness tracker, EEG device, or the like) running an app, a processor of a media player, a processor of a gaming console, a processor in audio equipment, and/or the like.

The icons used to represent the different emotions may be at least one of a text icon that represents the particular emotion (e.g., "HAPPY," "SAD," or the like) and/or an emoji (e.g., C)) that represents a particular emotion. Additionally and/or alternatively, states may be mapped to particular regions of a circular pattern or graph without the use of icons and music may be generated based on the position of the state within the circular pattern or graph.

The first subset of characteristics of music may include at least one of a note pattern, a harmony, a tone, an orchestration, a speed, a volume, and/or the like associated with the first emotion indicated by the user communication. The second subset of characteristics may include at least one of a note pattern, a harmony, a tone, an orchestration, a speed, a volume, and/or the like associated with the first emotion indicated by the user communication. In a non-limiting example, the position of an icon on the circumference of the circle and/or an angle of the icon may correspond to a particular musical/note arrangement and/or musical algorithm and all emotions that are located in a position/angle may have the same or similar musical/note arrangement and/or musical algorithm. A distance from center may correspond to a particular volume or speed of the same or similar musical/note arrangement and/or musical algorithm. Thus, each icon on the circular pattern will be different (if only slightly) from every other icon on the circular pattern.

Method 700, at block 710, may further comprise analyzing, with a computing system, a communication to determine at least one emotion contained within the communication. The communication may be at least one of an IoT communication, biometric/health communication, a voice communication, a textual communication, a photographic communication, a video communication, a tactile communication, and/or the like.

The biometric/health communication may be received from at least one of a fitness tracker or an electroencephalography ("EEG") device and the computing system may determine the at least one mental state of a person based on feedback from the at least one of the fitness tracker or the EEG device. In a non-limiting example, the fitness tracker and/or EEG device may provide feedback about the attention level, relaxation level, a blood pressure of a user, a heart rate of a user, electrical brain waves of a user, and/or the like. Based on the mental state, blood pressure, the heart rate, the electrical brain waves and/or the like, the computing system may determine a mental state that a user is experiencing. Merely by way of example, if the user has an elevated blood pressure and a high heart rate the computing system may determine that a user of the fitness tracker and/or EEG device is feeling stressed.

The voice communication may be received via user input or from a phone call between a calling party and a called party. In order to determine the at least one emotion of a person, the computing system may parse the voice communication of the at least one person and/or determine a tone of voice of at least one person. Merely by way of example, if the communication is via phone, the computing system may parse the voice communication between the calling party and the called party to determine how each party is feeling. Additionally and/or alternatively, the computing system may analyze the tone of voice of each party to determine what emotions each party is experiencing.

With regard to the textual communications, the computing system may analyze text messages, instant messages, social media posts, emails, books, and/or the like to determine an emotion that a user is experiencing. The computing system may parse the text of the textual communication to determine the emotion of a person. Merely by way of example, the computing system may parse the text for key words such as "happy" or "sad" and/or the computing system may parse the textual communication for emojis to determine the mood of a person.

The photographic communication may be a photograph taken with a camera. The computing system may then use facial recognition tools to determine a displayed emotion of at least one person in the photograph. The video communication may be taken with a video camera. The video communication may also be a video phone call between at least two parties. The computing system may then use facial recognition tools to determine a displayed emotion of the at least one person in the video. The computing system may also use tools to analyze body language or gestures of the at least one person in the video communication to determine an emotion that the at least one person is experiencing. The computing system may further parse the dialogue of the at least one person in the video or analyze the tone of voice of at least one person in the video communication to determine an emotion that the at least one person in the video is experiencing.

The tactile communication may be received via user input from a touch screen and/or a mouse. The user may select one or more icons representing an emotion on a display that is displaying the circular pattern of emotions to generate music associated with that emotion. The computing system may determine whether the user selected at least two icons by tracking the tactile communication of the user with the display device. Based on a determination that at least two icons have been selected, the computing system may determine whether the tactile input, when selecting the at least two icons, was continuous input. In other words, continuous input would occur when a user remains in constant tactile contact with the display device and/or if the user holds down the left button of the mouse. Non-continuous input would occur if the user lifts his or her finger/hand from the display device and/or lets go of the left mouse button. Based on a determination that the tactile input was not continuous, the method 700 may pause the generated music between each user selection of an icon. Based on a determination that the tactile input was continuous, the method 700 may transition between playing music associated with each of the at least two emotions selected by the tactile input. Touching the interface may turn on the sound, while lifting the finger turns it off. The position of the finger, velocity, direction finger is moving may be used to control the sound that is generated. In other cases, the sound is always on and the finger input can be used to influence the sound.

If the computing system cannot keep up with the tactile communication of the user (via tactile, mouse, or the like), then the computing system may create a time lag between the selection of each icon and the generation of music associated with each icon. Additionally and/or alternatively, the computing system may play the generated music for each selected icon for a predetermined amount of time before transitioning to music associated with a subsequent selected icon.

Interpolation, both smooth and quantized, may also be used to allow for the gradual transitioning between music associated with at least two emotions. In other words, once the computing system determines that a new emotion has been included in a communication and/or selected by a user, different aspects of the music will the transition between the states associated between the at least two emotions. Unusually jumpy rapid, jumpy movements in the communication, signal noise, and/or indicated by user selection (unexpectedly rapid signals) will be handled via standard smoothing filters for control signals.

Depending on the type of communication the computing system receives, the circular pattern may be displayed to the user on a user interface and/or the circular pattern may merely be used by the computing system to create differences between music associated with a particular emotion. For example, if the computing system is receiving a tactile communication, then the tactile input may be received on a user interface that is displaying the communication. However, if the computing system is receiving a voice communication, then the computing system may determine where the emotion is on the circular pattern to determine what type of music to generate, without displaying the circular pattern to the user.

Merely by way of example, method 700, at block 715 may further comprise autonomously determining, with the computing system, the position of at least one particular icon corresponding to the at least one particular emotion on the circumference of the circular pattern and the distance of the at least one particular icon corresponding to the at least one particular emotion from the center of the circular pattern. Based on the determination of the position of the determined at least one particular icon on the circumference of the circular pattern or the angle of the determined at least one particular icon and the distance of the determined at least one particular icon from the center of the circular pattern, the computing system may autonomously generate music having the first subset of characteristics and the second subset of characteristics associated with the at least one emotion contained within the communication (block 720).

Additionally and/or alternatively, the communication may further indicate at least one of an age and/or sex of a person. The one or more first characteristics of a plurality of characteristics of music may further be associated with the at least one of the age or the sex indicated by the communication. The music that is generated further has the one or more first characteristics of the plurality of characteristics associated with the at least one of the age or the sex indicated by the communication.

The generated music may further have human-like embellishments. The human-like embellishments may be created from at least one of timing jitter, frequency jitter, timbral jitter, and/or the like.

Human performers have a natural imprecision which must be explicitly accounted for in computer generated music. To do this, irregular micro-fluctuations are added to the timing of note onsets. This kind of small random signal bias is often referred to as "timing jitter." As a result, quantized notes are gently un-quantized to provide a more pleasing and human-sounding musical aesthetic. Timing jitter provides subtle rhythmic variation that add nuance to the static note patterns.

Similar to jittered timing offsets ("timing jitter"), "frequency jitter" is utilized to modulate the frequency (pitch) of the generated music. Depending on the duration and articulation of the note, frequency jitter parameters will change. For instance, long sustained notes will be subject to more evolved jitter (gradual drift), a technique to add warmth to the timbre; while shorter, more percussive notes will have little to no jitter.

Jitter may also be mapped to a number of other parameters in charge of producing timbre or the sound qualities of the notes. This is referred to as "timbral jitter." These parameters exist due in part to the real-time audio synthesis engine, which allow dynamic control of a sound over time via digital signal processing.

Additionally and/or alternatively, a non-limiting embodiment of method 700, at block 725, may comprise autonomously determining, with the computing system, whether at least two emotions are contained within the communication. Based on a determination that at least two emotions are contained within the communication, method 700 may simultaneously generate, play, and harmonize music associated with each emotion (block 730) and/or transition between music associated with each emotion (blocks 735-760).

Merely by way of example, method 700 at block 730 may comprise, based on a determination that at least two emotions are contained within the communication, simultaneously generating, playing, and shaping music having the particular first subset of characteristics and the particular second set of characteristics associated with each of the at least two emotions contained within the communication. In other words, if more than one emotion is present in the communication, the music associated with each determined emotion may be generated and played at the same time. The music associated with each emotion may further be harmonized to ensure that the sound that is generated is pleasing to hear.

Additionally and/or alternatively, method 700, at block 735, may further comprise, based on a determination that more than one emotion is contained within the communication, determining an order to generate and play music associated with each of the at least two emotions. The order may be determined based on the order that the emotions appear in a text, video, and/or voice communication or the order may be based on who is speaking in a voice or video communication. At block 740, the method 700 may transition, with the computing system, between generating and playing music associated with each of the at least two emotions. In other words, the method 700 may play music associated with each emotion separately. Music associated with a particular emotion may be played for a predetermined period of time before transitioning to music associated with the next determined emotion.

Additionally and/or alternatively, method 700 may smoothly transition between music associated with each emotion. In order to do this, after determining an order to generate and play music (block 735), method 700, at block 745, may further comprise autonomously determining, with the computing system, the position and/or angle of the at least two particular icons corresponding to the at least two particular emotions on the circumference of the circular pattern and the distance of the particular icon corresponding to the particular emotion from the center of the circular pattern. Method 700 may further autonomously determine, with the computing system, icons corresponding to additional emotions between the at least two particular icons corresponding to the at least two particular emotions (block 750). Method 700, at block 755, may then transition, with the computing system, between playing music associated with each of the at least two emotions contained within the communication by playing music associated with the determined additional emotions between music associated with the at least two particular icons corresponding to the at least two particular emotions. By playing music associated with the determined additional emotions between music associated with the at least two particular icons corresponding to the at least two particular emotions, the transition between music may be smoother and less dissonant.

Additionally and/or alternatively, method 700 may synchronize music associated with a subset of emotions while transitioning between music associated with another subset of emotions.

Method 700 may additionally comprise steps to ensure that the user interface and music generation system can effectively transition between music associated each determined emotion. In some situations, a user may select icons associated with particular emotions or send communication containing text or emojis representing emotions quicker than the computer can generate and output the music, in order to address those situations, method 700, at block 760 may comprise receiving, with the computing system, at least one additional user communication from a user, the at least one additional user communication being indicative of at least one additional emotion. Next, the computing system may determine a number of user communications over a specified period of time (block 765) and determine whether the number of user communications exceeds a predetermined threshold (block 770).

Based on a determination that the number of user communications does not exceed the predetermined threshold, method 700, at block 775, may further comprise autonomously determining, with the computing system, one or more first characteristics of a plurality of characteristics of music associated with the second emotion indicated by the second user communication, and autonomously transitioning from generating music having the one or more first characteristics of the plurality of characteristics associated with the first emotion indicated by the user to generating music having the one or more first characteristics of the plurality of characteristics associated with the second emotion indicated by the user. Based on a determination that the number of user communications does exceed the predetermined threshold, method 700, at block 780, may comprise pausing, with the computing system, the music being generated.

FIG. 8 is a flow diagram illustrating a method 800 for generating music associated with an emotion, in accordance with various embodiments.

While the techniques and procedures are depicted and/or described in a certain order for purposes of illustration, it should be appreciated that certain procedures may be reordered and/or omitted within the scope of various embodiments. Moreover, while the method 800 illustrated by FIG. 8 can be implemented by or with (and, in some cases, are described below with respect to) the system 100 of FIG. 1 (or components thereof) the user interface 200 of FIG. 2 (or components thereof), the system 300 of FIG. 3 (or components thereof), the mapping system 400 of FIG. 4 (or components thereof), and/or the mapping system of FIG. 9 (or components thereof), such methods may also be implemented using any suitable hardware (or software) implementation. Similarly, while each of the system 100 of FIG. 1 (or components thereof) user interface 200 of FIG. 2 (or components thereof), the system 300 of FIG. 3 (or components thereof), the mapping system 400 of FIG. 4 (or components thereof), and/or the mapping system of FIG. 9 (or components thereof), can operate according to the method 800 illustrated by FIG. 8 (e.g., by executing instructions embodied on a computer readable medium), the system 100 of FIG. 1 user interface 200 of FIG. 2, the system 300 of FIG. 3, the mapping system 400 of FIG. 4, and/or the mapping system of FIG. 9 can each also operate according to other modes of operation and/or perform other suitable procedures.

Although method 800 is described with respect to emotions/concepts, a similar method may be used for different states of a user which may include at least one of an emotion of a user, a feeling of a user, a location of the user a, a physical position of a user, a level of activity of a user, an action of a user, and/or the like. In a non-limiting embodiment, method 800, at block 805 may comprise defining, with a computing system, a predetermined set of notes. Next, method 800, at block 810 may comprise defining, with the computing system, at least one of a note pattern, a note range, a harmony, a tone, an orchestration, a speed, or a volume associated with a particular emotion. At block 815, method 800 may comprise generating, with the computing system, music associated with the at least one of the note pattern, the note range, the harmony, the frequencies, the orchestration, the speed, note amplitude envelope or the output amplitude associated with the particular emotion. At block 820, method 800, may comprise adding, with the computing system, human-like embellishments to the generated music.

Figure 9E:
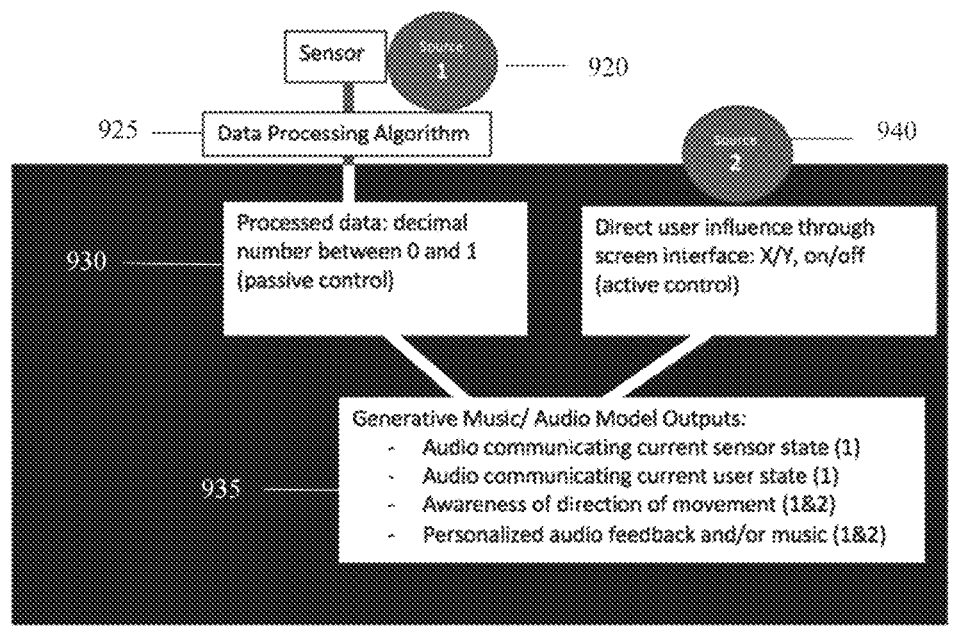
Figure 10:
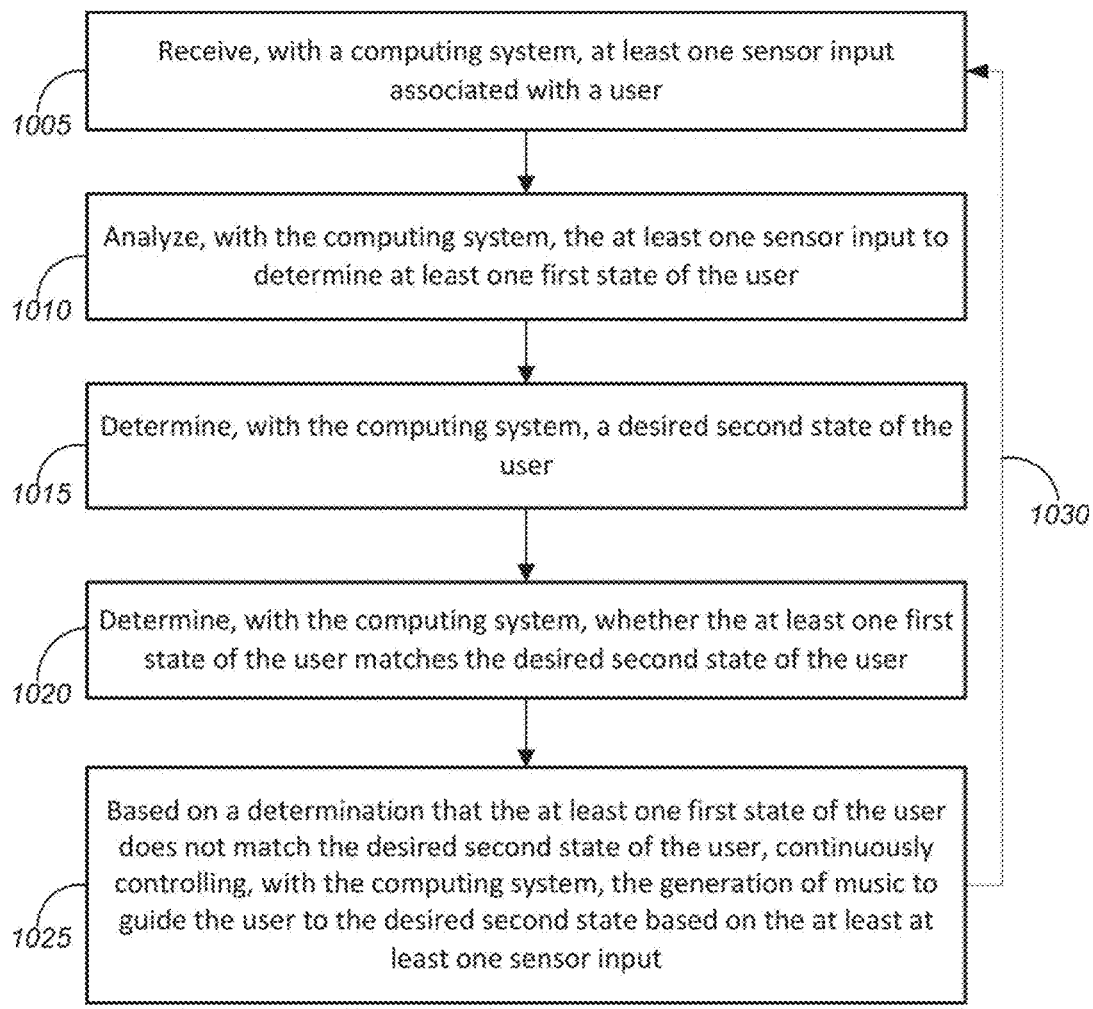
FIG. 10 is a flow diagram illustrating a method for continuously controlling the generation of the music to guide a user toward a goal, in accordance with various embodiments.

FIGS. 9 and 10 represent methods, systems, and apparatuses for exercising continuous control over music generation to guide a user toward a desired state or goal. Each of the methods, systems, and apparatuses described with respect to FIGS. 9 and 10 may be incorporated into the different embodiments described with respect to FIGS. 1-8. Additionally, each of the different embodiments described with respect to FIGS. 1-8 may be incorporated into the different embodiments described with respect to FIGS. 9 and 10. In a non-limiting example, user interface 200 may be used to implement different embodiments described in FIGS. 9 and 10. Additionally, graphical interface 900*d* may be used in place of user interface 200 and function in a similar manner as user interface 200. Other patterns/shapes may be used as an interface (e.g., a three-dimensional graph, a triangle, a square, an oval, etc.).

FIGS. 9A-9E are schematic diagrams illustrating systems 900 for continuously controlling the generation of music/audio/sound to guide a user toward a desired state, in accordance with various embodiments. FIGS. 9A and 9B are directed towards guiding a user from a first location or first position to a second location or position. FIG. 9A represents a system 900*a* using one parameter (distance to goal) 905 to continuously control the one or more parameters of music/audio/sound. FIG. 9B represents a system 900*b* using two parameters (distance to goal and movement direction) 905 and 910 to continuously control one or more parameters of music/audio/sound. FIG. 9C represents a system 900*c* using three parameters to continuously control the generation of music/audio/sound. FIG. 9D represents a XY coordinate system 900*d* for mapping different states to music/audio/sound and for transitioning between music/audio/sound associated with different states.

FIGS. 9A and 9B include systems 900*a* and 900*b* for mapping music/audio/sound to different parameters to guide a user toward a desired goal. The different parameters may correspond to a state of a user and may include, but are not limited to, at least one of a distance to goal, a direction of movement, an amount of movement, a breathing pattern, a heart rate, a state in a video game, a step rate, an exercise rate or pattern, an amount of perspiration, a brainwave pattern, and/or the like. FIG. 9A has one mapping parameter 905—distance to goal. FIG. 9B has two mapping parameters 905 and 910 which (for this model) represent distance to goal and movement direction with respect to goal and previous point, respectively. Although only two mapping parameters are shown in FIG. 9B, more than two parameters may be used to map music to different states and control the generation of music as shown in FIG. 9C. Additionally, one mapping parameter may control one or more musical/audio/sound elements.

Mapping parameters 905 and 910 may correspond or map to one or more musical/audio/sound characteristics 915a-915n. The different musical characteristics might correspond to a note pattern, a harmony, a tone, pitch, a density, vocal-like qualities, elements of surprise, randomization, consistency, an orchestration, a speed, a rhythm, a volume, note envelope, control signal envelope, rate, amplitude on part of signal, and/or the like designed to guide a user toward a desired state.

Each value that is given to a particular state may be used to generate and continuously control music to guide a user toward a desired state (e.g., from a first location to a second location). The music may be continuously controlled based on one or more sensor inputs. For example, one or more sensors may be used to detect user movement/motion. As a user moves, the sensors may detect whether the user is moving closer to a desired second location or away from a desired second location. Based on the input from the sensors, the computing system may then generate music indicating that the user is moving closer to or away from the desired second location. The computing system may continuously control and/or change the generated music based on input from the one or more sensors to guide the user toward the desired location.

Additionally and/or alternatively, in a two-parameter model, one or more sensors may be used to detect a user's position relative to a desired location and a user's direction of movement. As a user moves, the sensors may detect (1) whether the user is moving closer to a desired second location or away from a desired second location and (2) the direction (angle relative to the desired location) the user is moving. Based on the input from the sensors, the computing system may then generate music indicating (1) that the user is moving closer to or away from the desired second location and/or (2) the direction the user is moving relative to the object. In a non-limiting example, the rhythm of the music/audio/sound may increase as the user gets closer to the desired location while the music/audio/sound becomes more random if the user is heading in the wrong direction. The computing system may continuously control and/or change the generated music/audio/sound based on input from the one or more sensors to guide the user toward the desired location.

Music attributes 915a-915n may further vary based on the type of application/communication (e.g., voice, text, speech, fitness tracker, EEG device, smart watch, AR/VR device, facial recognition device, camera, user input, and/or the like), the demographics (e.g., age, sex, and/or the like) of the user, the user's preferences, input from a user, and/or the like.

FIG. 9C represents a sysyem 900c having three musical/sound/audio characteristics: (1) amplitude (volume of music/audio/sound), (2) attack rate (rhythm, arpeggiation), and (3) note probabilities (how likely a particular note will be played). State 1 (current state) has three corresponding values for amplitude, attack rate, and note probabilities and state 2 (goal state) has three different corresponding values for amplitude, attack rate, and note probabilities. One or more sensors may be used to measure where a user is i.e. state 1, state 2, or between states 1 and 2. Based on the measured state of the user, music/audio/sound may be continuously generated and controlled to lead a user from state 1 to state 2. In a non-limiting example, movement direction may control attack rate and note probabilities while distance from goal may control amplitude.

FIG. 9D represents an XY coordinate system 900d for mapping different states to a region on an XY coordinate system. This XY coordinate system 900d may be used in place of or in addition to user interface 200 shown in FIG. 2 and function in a similar way as user interface 200 to control one or more musical parameters. The position on a two or more-dimensional graph can be used as coordinates to drive a multi-input music system where different axes control different musical attributes. The X-axis might correspond to one or more characteristics of music/audio/sound while the Y-axis might correspond to one or more different characteristics of music/audio/sound. In a non-limiting example, The X-axis might correspond to a valence of music/audio/sound, i.e. positive/minor notes, randomness/synchronicity of notes, and/or the like, while the Y-axis might correspond to intensity of music/audio/sound, i.e. loudness, number of beats per minute, and/or the like.

Each state may be mapped to a region on the XY coordinate system shown in FIG. 9D. The XY coordinate system is not limited to only being a XY plane. The XY plane could be any pattern/shape (e.g., an oval, circle, triangle, square, rectangle, grid, XYZ coordinate system, 2-D model, 3-D model, etc.). A person of ordinary skill in the art would understand that any pattern may act in a similar manner as the XY plane described below.

The XY plane 900d may be displayed to a user on a computing system and/or communication device. Additionally and/or alternatively, the computing system and/or communication device may use the XY plane to determine one or more musical parameters corresponding to a user's determined state.

A user may interact with XY plane 900d via tactile input and/or mouse input. Additionally and/or alternatively, the XY plane 900d may be used by a computing system and/or user device to determine what music to play based on a state contained within a communication (e.g., at least one of a sensor communication, an IoT communication, a biometric/health communication, a voice communication, a textual communication, a photographic communication, a video communication, and/or the like). A computing system may determine where a particular state is mapped on XY plane 900d and access and play the algorithm associated with the particular state based on where the state is positioned on the XY plane 900d.

Based on the user interaction with the XY plane 900d and/or based on a determined state from a communication, the computing system may determine the distance from an x-axis on the XY plane 900d associated with the determined at least one particular state and/or a distance from a y-axis on the XY plane 900d. Based on the determination of the position (distance from x-axis and/or y-axis) associated with the determined at least one state, the computing system and/or user device may generate music having the valence and the intensity associated with the determined at least one state of the communication.

Additionally and/or alternatively, the XY plane 900d may facilitate transitioning between music associated with a first particular state to music associated with a second particular state. In FIG. 9D, states located in different regions of XY plane 900d. A user may first indicate a first state (state 1) via touch input, mouse input, and/or by indicating a state in a communication.

If the selection is made via touch or a mouse and after a first user indication is made, then a computing system and/or communication device may track a user's interaction with the XY plane 900d. A user may continue to drag his or her finger or other device (e.g., mouse, stylus, and/or the like) along a path on the XY plane 900d indicating that the music that is generated should transition between music associated with at least two states. The music that is generated may transition in real time or near real time based on the user's interaction with the XY plane 900d. For example, if the user stops for a period of time on a particular region associated with a state, then the music associated with that particular state may play for that period of time until the user stops selecting the region and/or moves on to a different region associated with a different state. Additionally and/or alternatively, each state that the user selects by dragging his or her finger or other device (e.g., mouse, stylus, and/or the like) along a XY plane 900d may play music associated with that particular state for a predetermined amount of time (e.g., until a note is finished playing, until a sequence is complete, and/or the like) before transitioning on to the music associated with the next selected state/region. In some cases, the predetermined amount of time may be selected by a user of XY plane 900d.

The computing system and/or user device may also introduce some lag so that music that is generated by user interaction is not generated in real time. For example, if the user drags his or her finger or device over XY plane 900d quickly, the computing system may not be able to transition between music associated with different states smoothly. By introducing lag, the computing system may smoothly transition between music associated with different emotions.

Additionally and/or alternatively, if a user picks up his finger and/or device, a computer may determine that a user would like to pause between transitioning between a first selected state and an additional selected state. The music may turn off or continue to play in static position. If the user rests on a particular state, the music can still be continuously generated.

If a selection of more than one state is made via a communication (e.g., at least one of a sensor communication, an IoT communication, a biometric/health communication, a voice communication, a textual communication, a photographic communication, a video communication, and/or the like) and the communication contains at least two states, then a computing device may determine a path on XY plane 900d between a first selected state and at least one additional state. Using the states between the first selected state and at least one additional state, the computing system may smoothly transition between playing music associated with each of the at least two states contained within the communication by playing music associated with the determined additional states between music associated with the at least two particular states indicated in the communication.

Additionally and/or alternatively, the generated music may transition between music associated with the at least two states indicated in the communication by pausing music associated with a first indicated state before playing music associated with a second indicated state.

In a non-limiting example, a computing system may determine that the user's goal state is state 2. In order to determine a user's goal state, a user may select an option for a desired state (e.g., work-out option, navigation option, etc.) on a user interface (e.g., user interface 200, interface 900d, or other interface, etc.). Additionally and/or alternatively, a computing system may receive feedback from one or more sensors (e.g., an indication of a high stress state, etc.) and determine a user's goal state (e.g., calm, relaxed, etc.) based on the feedback from the one or more sensors. In some cases, a user may also select a length of time or a distance (e.g., a mile, a kilometer, etc.) to run the music generation application.

Based on one or more sensor inputs, the computing system may determine that the user is currently at state 1, between state 1 and 2, how close a user is to state 2, and/or the like. The computing system might continuously control synthesized music/audio/sound to guide the user to state 2 based on the one or more sensor inputs and/or indicate to a user how far away or close the user is to state 2. As the user gets closer to state 2, the music will adapt to incorporate more elements of state 2. As the user gets further from state 2 the music will adapt to incorporate more elements of state 1. Thus, a user may receive continuous feedback about how close he or she is to state 1 or state 2.

FIG. 9E represents a schematic diagram 900e for receiving multiple inputs from different sources to generate music associated with one or more states, in accordance with various embodiments. The music that is generated may be influenced by a passive control (e.g., sensor/communication input) and/or an active control (e.g., a user interface). Additionally and/or alternatively, the music that is generated may be based on input from two passive controls (e.g., two sensors, etc.) and/or two active controls (e.g., two user interfaces, two inputs via a user interface, etc.) and the music/sound that is generated from the two passive controls and/or two active controls may be generated based on a similar method described below.

In various embodiments, a first source 920 might be received from one or more passive source(s) (e.g., one or more sensors and/or communications (e.g., an IoT communication, a biometric/health communication, a voice communication, a textual communication, a picture communication, a video communication, a haptic communication, etc.)). Data received from the passive source 920 may be continuously received, received periodically (e.g., every second, every minute, every hour, and/or the like), and/or received once. Data received from the passive source 920 may be processed through a data processing algorithm 925 to determine a state of a user and/or an environment. The determined state of the user and/or environment may be mapped to a location as shown in FIG. 9D and/or FIG. 2, given a binary value, and/or given a number between 0 and 1 (930). The location, binary value, and/or number may control one or more musical parameters and cause a computing system to generate music based on the one or more audio feature parameter values (935). The music that is generated may be continuously updated/controlled by the continuous one or more active or passive inputs, regularly updated/controlled based on inputs received periodically, updated only when a discrete message is received, and/or the like.

In some cases, a second source 940 may be added to control the generation of music. The second source 940 may be an active source which receives direct user input via a user interface (e.g., user interface 200, user interface 900d), a touch screen, one or more actuated buttons, and/or the like. A user may control one or more of turning the music off and on, a genre of music created, one or more musical instruments being played, transitioning between different types of music, selecting different states, selecting a goal state, and/or the like.

The music generated from the inputs (e.g., first source 920 and second source 940) may be harmonized, layered, cross-faded, and/or the like. For example, the music may start out generating a user's current state based on sensor input and based on a selection from a user via a user interface of a goal state, the music that is generated may then transition/change to guide a user from a first state to a second state. Additionally and/or alternatively, in another non-limiting example, the music that is generated based on sensor input may have one or more musical attributes and a user selection of age, genre, etc. may cause the music to adapt or change based on the selections. Additionally and/or alternatively, the music generated based on one or more sensors may adapt or change as a user drags his or her finger over a user interface (e.g., user interface 200 and/or 900*d*).

In another non-limiting example, sensor input may be received from two passive sources e.g., two biometric inputs, a biometric input and a camera, etc. The sensor input may be associated with two different users and/or participants in a race or competitive activity. The music that is generated may be used to reflect a user's position in the race or competitive activity. The music may speed up or slow down to reflect if the user is ahead or behind other participants in the race or competitive activity.

These are only some examples of the different ways music may be generated using two different input sources.

Although FIGS. 9A-9E are directed toward guiding a user from a first state to a second state, similar methods may be used to exercise continuous control over music generation to guide a user toward other particular desired states or goals. Additionally and/or alternatively, similar methods may be used to transition between environmental states (e.g., transitioning from sunny to rainy weather, transitioning from one temperature to another temperature, and/or the like). Additionally and/or alternatively, the user interface described with respect to FIGS. 2-4 may be used to exercise continuous control music generation to guide a user from a first state to a second desired state.

For example, systems similar to those described in FIGS. 2-4 and 9 may be used to continuously control the generation of music to guide a user from a stressful/aroused state to a relaxed/calm state, from a non-meditative state to a meditative state, from an unfocused state to a focused state, from a negative state to a positive state, from a state of inactivity to a state of activity, from a slow breathing pattern to a fast breathing pattern, from a fast breathing pattern to a slow breathing pattern, from a slow heartbeat to a fast heartbeat, from a slow heartbeat to a fast heartbeat, from bad posture to good posture, from less movement to more movement and vice versa, from a bad body position to a good body position, and/or the like. Additionally and/or alternatively, systems similar to those described in FIGS. 2-4 and 9 may be used to continuously control the generation of music to guide a user through a workout (warm-up, exercise, cool-down, etc.).

Additionally and/or alternatively, systems similar to those described in FIGS. 2-4 and 9 may be used to continuously control the generation of music to sync to at least one of a running speed of the user, a heartbeat of the user, a breathing pattern of the user, a brainwave pattern of the user, and/or the like. In this manner, a user may receive instant feedback about his or her current state.

In various embodiments, these systems and methods may be used to continuously generate music that reflects a user's current state and may be constantly adapted/changed in real-time as the user's state changes.

FIG. 10 is a flow diagram illustrating a method for continuously controlling the generation of the music to guide a user toward a goal, in accordance with various embodiments.

While the techniques and procedures are depicted and/or described in a certain order for purposes of illustration, it should be appreciated that certain procedures may be reordered and/or omitted within the scope of various embodiments. Moreover, while the method illustrated by FIG. 10 can be implemented by or with (and, in some cases, are described below with respect to) the system 100 of FIG. 1 (or components thereof) the user interface 200 of FIG. 2 (or components thereof), the system 300 of FIG. 3 (or components thereof), the mapping system 400 of FIG. 4 (or components thereof), and/or the mapping system of FIG. 9 (or components thereof), such methods may also be implemented using any suitable hardware (or software) implementation. Similarly, while each of the system 100 of FIG. 1 (or components thereof) user interface 200 of FIG. 2 (or components thereof), the system 300 of FIG. 3 (or components thereof), the mapping system 400 of FIG. 4 (or components thereof), and/or the mapping system of FIG. 9 (or components thereof), can operate according to the method illustrated by FIG. 10 (e.g., by executing instructions embodied on a computer readable medium), the system 100 of FIG. 1 user interface 200 of FIG. 2, the system 300 of FIG. 3, the mapping system 400 of FIG. 4, and/or the mapping system of FIG. 9 can each also operate according to other modes of operation and/or perform other suitable procedures.

In the non-limiting embodiment of FIG. 10, the method, at block 1005, might comprise receiving, with a computing system, at least one sensor input associated with a user and/or an environment.

The computing system may be at least one of a desktop computer, a laptop computer, a tablet, a smart phone, an e-reader, and/or the like. Additionally and/or alternatively, in some embodiments, the computing system might include, without limitation, one of a processor of a set-top box, a processor of a digital video recording ("DVR") device, a processor of a user device running a software application ("app"), a processor of an audio playback device, a processor on an input device (e.g., fitness tracker, EEG device, or the like) running an app, a processor of a media player, a processor of a gaming console, a processor in audio equipment, and/or the like.

The sensor input may contain feedback from one or more sensors including, but not limited to, one or more GPS sensors, one or more distance sensors, one or more motion sensors, one or more movement sensors, one or more speed or velocity sensors, one or more accelerometer sensors, one or more eye tracking sensors, one or more biometric/health sensors, one or more facial recognition sensors, one or more camera sensors, and/or the like.

The biometric/health sensor input may be received from at least one of a fitness tracker, a smart watch, a smart phone, an electroencephalography ("EEG") device, a virtual reality ("VR") device, an augmented reality ("AR") device, and/or the like. The feedback from the one or more biometric/health sensors might include, but is not limited to, at least one of a heart rate, a blood pressure, a stress level, a measure of electrical activity within a brain, pupil dilation, skin conductivity, a level of activity, number of steps, and/or the like.

The method of FIG. 10, at block 1010, may further comprise analyzing, with the computing system, the at least one sensor input to determine at least one first state of the user. The state of the user may correspond to at least one of an emotion of a user, a feeling of a user, a location of the user, a physical position (e.g., a posture of a user, a body position of a user, etc.) of a user, a level of activity of a user, a direction of an action of a user, an action (e.g., walking, running, biking, etc.) of a user, and/or the like.

In various embodiments, the method of FIG. 10, at block 1015, may additionally include determining, with the computing system, a desired second state of the user. The desired second state of a user may correspond to at least one of an emotion of a user, a feeling of a user, a location of the user, a physical position (e.g., a posture of a user, a body position of a user, etc.) of a user, a level of activity of a user, an action (e.g., walking, running, biking, etc.) of a user, and/or the like.

A user may manually enter a desired second state. Additionally and/or alternatively, the computing system may determine a desired second state. In a non-limiting example, the computing system, using the one or more sensors, may detect that a user is feeling stressed or anxious. Based on the determination that a user is stressed or anxious, the computing system may determine that the desired second state is calm or relaxed.

At block 1020, the method of FIG. 10 may determine whether the at least one first state of the user matches the desired second state of the user. Based on a determination that the at least one first state of the user does not match the desired second state of the user, the method 1000, at block 1025 may continuously control, with the computing system, the generation of music having one or more characteristics to guide the user to the desired second state based on the at least at least one sensor input. This process may continue as indicated by arrow 1030 until the computing system determines that the user has achieved the desired second state.

The computing system may be configured to autonomously determine and continuously generate one or more characteristics of music to guide a user toward a desired second state based on the sensor feedback. The generated music may be designed to gradually lead a user in a step-by-step process toward the desired second state. In other words, the generated music may continuously adapt and/or evolve based on feedback received from the one or more sensors to lead a user toward a desired second state.

In order to guide the user toward a desired second state, the computing system may control, adapt, and/or evolve one or more characteristics of music based on input from the one or more sensors. The one or more characteristics of music might, include, but are not limited to, a note pattern, a harmony, a tone, vocal-like qualities, elements of surprise, randomization, consistency, crescendo, decrescendo an orchestration, a speed, a rhythm, a beat, or a volume. The one or more characteristics of music might be associated with guiding a user toward a desired state. In a non-limiting example, a beat or rhythm might be designed to help a user control his or her breathing. The one or more first characteristics of a plurality of characteristics of music may further be associated with the at least one of the age, the sex or other demographic of a user.

The following examples represent ways the generated music may be used to guide a user from a first state to a desired second. These are examples only and they are not intended to limit the scope of the invention.

In a first non-limiting example, the generated music may be designed to guide the user from a first stressful state to a second more relaxed state based on the at least one sensor input. The computing system may determine that a user is stressed based on input from the sensor and generate music to soothe and relax the user. The music that is generated may be designed to gradually lead the user to a more relaxed state. Initially, the music may start out louder and faster and as the computing system determines that the user is calming down (based on sensor input) the music may become softer and slower until the desired second state is reached. Once the desired second state is reached the computing system may generate music that is consistent with the desired second state.

In a second non-limiting example, the generated music may be designed to guide the user from a first non-meditative state or stressed to a second meditative or relaxed state based on the at least one sensor input. The music that is generated may be designed to gradually lead the user to a meditative or relaxed state. Initially, the music may start out louder and brighter in timbre and as the computing system determines that the user is entering a meditative or relaxed state (based on the sensor input) the music may become darker in timbre and slower until the desired second state is reached. Once the desired second state is reached the computing system may generate music that is consistent with the meditative or relaxed state.

In a third non-limiting example, the generated music might be designed to guide the user from a first unfocused state to a second focused state based on the at least one sensor input.

In a fourth non-limiting example, the generated music might be designed to guide the user from a first negative emotion to a second positive emotion.

In a fifth non-limiting example, the generated music might be designed to guide the user through a periodic activity (e.g., a desired number of steps per minute, a desired number of repetitions per minute, and/or the like) based on input from the one or more sensors. The music that is generated may be designed to gradually lead the user through the periodic activity (e.g., toward a desired number of steps per minute, toward a desired number of repetitions per minute, and/or the like). Initially, the music may start out with a slower beat. Once the computing system determines that the user's periodic activity matches the slower beat (based on input from the sensor), the computing system might increase the beat until the user is at the desired periodic activity. Once the desired periodic activity is reached the computing system may generate music that is consistent with maintaining the desired periodic activity.

In a sixth non-limiting example, the generated music might be designed to sync to at least one of a running speed of the user, a heartbeat of the user, a breathing pattern of the user, a brainwave pattern of the user, and/or the like based on input from the one or more sensors.

In a seventh non-limiting example, the generated music might be designed to guide the user to at least one of a slower breathing pattern, a slower heartbeat, a faster breathing pattern, a faster heartrate, and/or the like based on input from the one or more sensors.

In an eighth non-limiting example, the generated music may be designed to lead a user through a workout routine. The music may start out slow and gradually speed up (based on input from the one or more sensors) to lead a user through a warm-up routine. The computing system may determine, based on biometric/health feedback from the user, when the user is ready to move on to the next stage of a workout routine and provide cues to the user that it is time to move on through the generated music. Additionally and/or alternatively, a user may indicate that he or she would like to exercise for an hour. The computing system may then lead a user through an hour exercise routine (warm-up, cool-down, etc.) using the generated music and the input from the one or more sensors.

In a ninth non-limiting example, the generated music may be designed to guide the user from a first location to a second desired location. This feature may be used by a user who is visually impaired to guide to a desired second location. For example, a user may indicate that he or she would like to go to the kitchen. Using sensor input, the computing system may generate music to guide the user towards the kitchen. The music may become faster as the user gets closer to the kitchen or the music may become slower as the user moves away from the kitchen. The sensor input may be used to continuously update and control the generated music.

In a tenth non-limiting example, the generated music may be designed to guide the user to at least one of a better posture, a better body position, and/or through a physical therapy routine. Sensor input may be used to provide information about a user's posture or body information and different musical characteristics may be designed to guide the user to better posture, body position, or toward a correct position for physical therapy.

In an eleventh non-limiting example, the generated music may be designed to alleviate pain and/or reflect a user's current state of pain. Sensor input may be used to detect a user's current level of pain and different musical attributes may be used to guide a user to a less painful state, distract a user from a painful state, and/or provide a doctor with feedback about a patient's current state of pain.

In a twelfth non-limiting example, the generated music might be designed to help a user win a race or determine where a user is within a race. Sensor input may be received from one or more passive sources e.g., two biometric inputs, a biometric input and a camera, etc. The sensor input may be associated with two different users and/or participants in a race. The music that is generated may be used to reflect a user's position in a race. The music may speed up or slow down to reflect if the user is ahead or behind other participants in a race.

The examples above of guiding a user toward a desired second state are intended to be non-limiting. Generating music using sensors may be used to guide users towards many other states than those listed above.

An exemplary system and hardware implementation will now be described, with reference to FIGS. 11 and 12.

Figure 11:
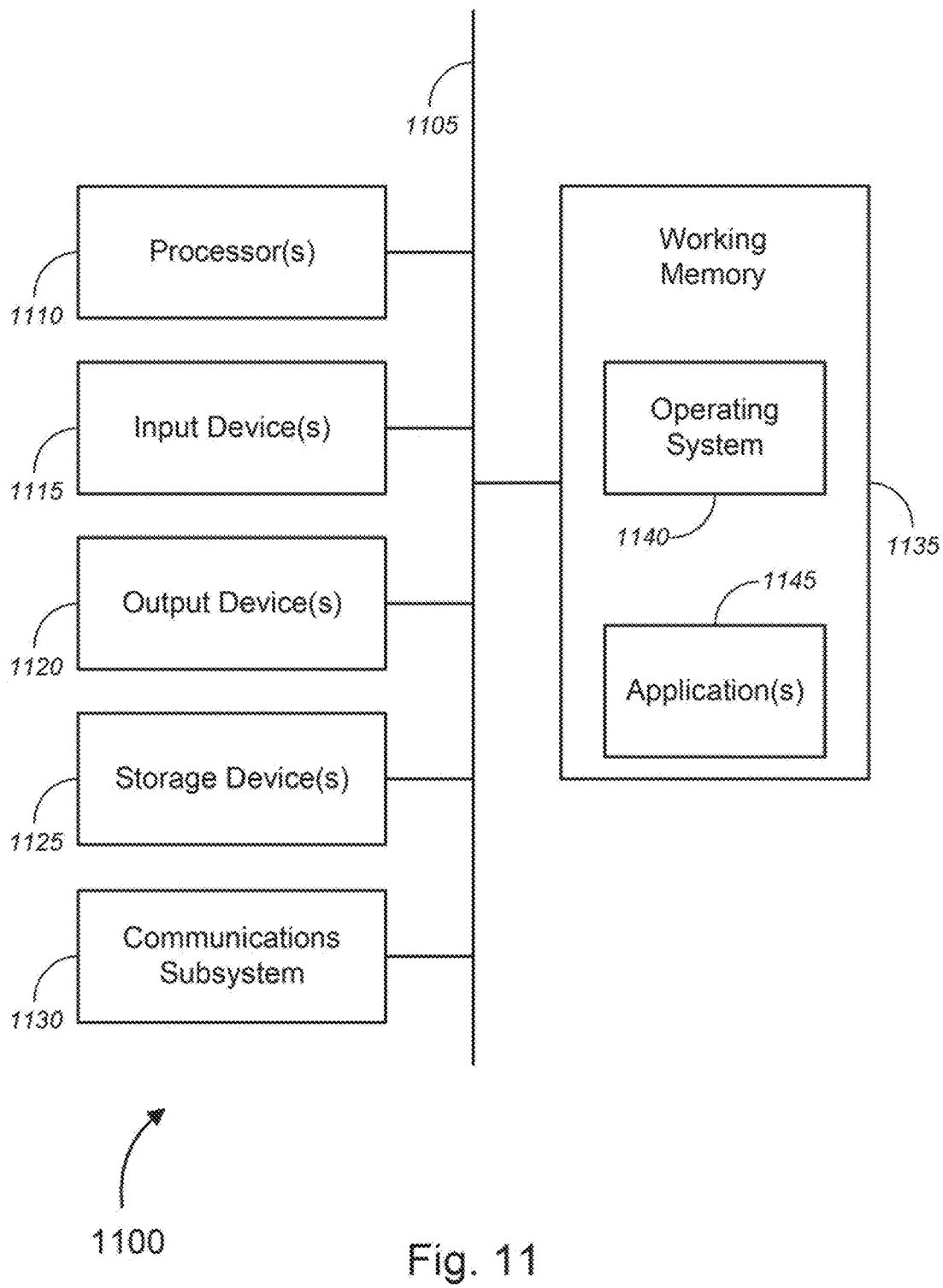
FIG. 11 is a block diagram illustrating an exemplary computer or system hardware architecture, in accordance with various embodiments.

FIG. 11 is a block diagram illustrating an exemplary computer or system hardware architecture, in accordance with various embodiments. FIG. 11 provides a schematic illustration of one embodiment of a computer system 1100 of the service provider system hardware that can perform the methods provided by various other embodiments, as described herein, and/or can perform the functions of computer or hardware system (i.e., computing systems/user device 105, input devices 115, audio playback devices 120a-120n, music sources (or servers) 125, user interface 200, computing system 305, input devices 310, XY interface 900d, etc.), as described above. It should be noted that FIG. 11 is meant only to provide a generalized illustration of various components, of which one or more (or none) of each may be utilized as appropriate. FIG. 11, therefore, broadly illustrates how individual system elements may be implemented in a relatively separated or relatively more integrated manner.

The computer or hardware system 1100—which might represent an embodiment of the computer or hardware system (i.e., computing systems/user devices 105, input devices 115, audio playback devices 120a-120n, music sources (or servers) 125, user interface 200, computing system 305, input devices 310, XY interface 900d, etc.), described above with respect to FIGS. 1-10—is shown comprising hardware elements that can be electrically coupled via a bus 1105 (or may otherwise be in communication, as appropriate). The hardware elements may include one or more processors 1110, including, without limitation, one or more general-purpose processors and/or one or more special-purpose processors (such as microprocessors, digital signal processing chips, graphics acceleration processors, and/or the like); one or more input devices 1115 (i.e., input devices 115, input devices 310, etc.), which can include, without limitation, a mouse, a keyboard, fitness trackers, smart watches, EEG devices, and/or the like; and one or more output devices 1120, which can include, without limitation, a display device, a printer, and/or the like.

The computer or hardware system 1100 may further include (and/or be in communication with) one or more storage devices 1125, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable and/or the like. Such storage devices may be configured to implement any appropriate data stores, including, without limitation, various file systems, database structures, musical algorithms associated with different emotions, and/or the like.

The computer or hardware system 1100 might also include a communications subsystem 1130, which can include, without limitation, a modem, a network card (wireless or wired), an infra-red communication device, a wireless communication device and/or chipset (such as a Bluetooth™ device, an 802.11 device, a WiFi device, a WiMax device, a WWAN device, cellular communication facilities, etc.), and/or the like. The communications subsystem 1130 may permit data to be exchanged with a network (such as the network described below, to name one example), with other computer or hardware systems, and/or with any other devices described herein. In many embodiments, the computer or hardware system 1100 will further comprise a working memory 1135, which can include a RAM or ROM device, as described above.

The computer or hardware system 1100 also may comprise software elements, shown as being currently located within the working memory 1135, including an operating system 1140, device drivers, executable libraries, and/or other code, such as one or more application programs 1145, which may comprise computer programs provided by various embodiments (including, without limitation, hypervisors, VMs, and the like), and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 1125 described above. In some cases, the storage medium might be incorporated within a computer system, such as the system 1100. In other embodiments, the storage medium might be separate from a computer system (i.e., a removable medium, such as a compact disc, etc.), and/or provided in an installation package, such that the storage medium can be used to program, configure and/or adapt a general purpose computer with the instructions/code stored thereon. These instructions might take the form of executable code, which is executable by the computer or hardware system 1100 and/or might take the form of source and/or installable code, which, upon compilation and/or installation on the computer or hardware system 1100 (e.g., using any of a variety of generally available compilers, installation programs, compression/decompression utilities, etc.) then takes the form of executable code.

It will be apparent to those skilled in the art that substantial variations may be made in accordance with specific requirements. For example, customized hardware (such as programmable logic controllers, field-programmable gate arrays, application-specific integrated circuits, and/or the like) might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer or hardware system (such as the computer or hardware system 1100) to perform methods in accordance with various embodiments of the invention. According to a set of embodiments, some or all of the procedures of such methods are performed by the computer or hardware system 1100 in response to processor 1110 executing one or more sequences of one or more instructions (which might be incorporated into the operating system 1140 and/or other code, such as an application program 1145) contained in the working memory 1135. Such instructions may be read into the working memory 1135 from another computer readable medium, such as one or more of the storage device(s) 1125. Merely by way of example, execution of the sequences of instructions contained in the working memory 1135 might cause the processor(s) 1110 to perform one or more procedures of the methods described herein.

The terms "machine readable medium" and "computer readable medium," as used herein, refer to any medium that participates in providing data that causes a machine to operate in a specific fashion. In an embodiment implemented using the computer or hardware system 1100, various computer readable media might be involved in providing instructions/code to processor(s) 1110 for execution and/or might be used to store and/or carry such instructions/code (e.g., as signals). In many implementations, a computer readable medium is a non-transitory, physical, and/or tangible storage medium. In some embodiments, a computer readable medium may take many forms, including, but not limited to, non-volatile media, volatile media, or the like. Non-volatile media includes, for example, optical and/or magnetic disks, such as the storage device(s) 1125. Volatile media includes, without limitation, dynamic memory, such as the working memory 1135. In some alternative embodiments, a computer readable medium may take the form of transmission media, which includes, without limitation, coaxial cables, copper wire and fiber optics, including the wires that comprise the bus 1105, as well as the various components of the communication subsystem 1130 (and/or the media by which the communications subsystem 1130 provides communication with other devices). In an alternative set of embodiments, transmission media can also take the form of waves (including without limitation radio, acoustic and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 1110 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer or hardware system 1100. These signals, which might be in the form of electromagnetic signals, acoustic signals, optical signals, and/or the like, are all examples of carrier waves on which instructions can be encoded, in accordance with various embodiments of the invention.

The communications subsystem 1130 (and/or components thereof) generally will receive the signals, and the bus 1105 then might carry the signals (and/or the data, instructions, etc. carried by the signals) to the working memory 1135, from which the processor(s) 1110 retrieves and executes the instructions. The instructions received by the working memory 1135 may optionally be stored on a storage device 1125 either before or after execution by the processor(s) 1110.

Additionally and/or alternatively, system 1100 may utilize neural networks (e.g., convolutional, recurrent, spiking, or other statistical learning mode) to classify an emotional state, determine emotion state from incoming sensor data, control position in the user interface, etc.

As noted above, a set of embodiments comprises methods, systems, and apparatuses for generating music, and, more particularly, to methods, systems, and apparatuses for generating music associated with a state or an emotion contained within a communication, for a user interface for generating music associated with a state or an emotion, and for generating music to guide a user toward a desired state or goal.

Figure 12:
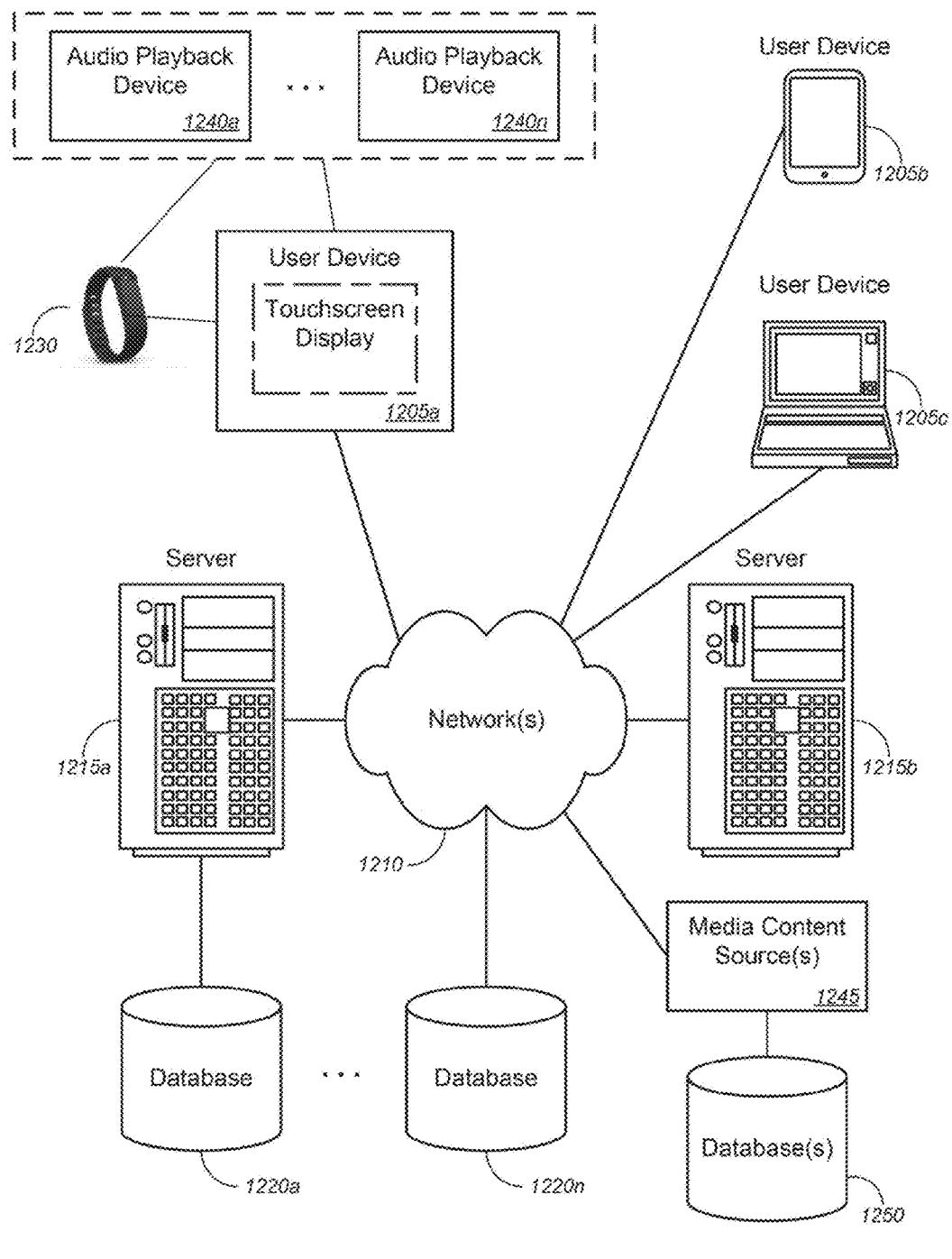
FIG. 12 is a block diagram illustrating a networked system of computers, computing systems, or system hardware architecture, which can be used in accordance with various embodiments.

FIG. 12 illustrates a schematic diagram of a system 1200 that can be used in accordance with one set of embodiments. The system 1200 can include one or more user computers, user devices, or customer devices 1205 (similar to computing systems/user devices 105, input devices 115, etc.). A user computer, user device, or customer device 1205 can be a general purpose personal computer (including, merely by way of example, desktop computers, tablet computers, laptop computers, handheld computers, and the like, running any appropriate operating system, several of which are available from vendors such as Apple, Microsoft Corp., and the like), cloud computing devices, a server(s), and/or a workstation computer(s) running any of a variety of commercially-available UNIX™ or UNIX-like operating systems. A user computer, user device, or customer device 1205 can also have any of a variety of applications, including one or more applications configured to perform methods provided by various embodiments (as described above, for example), as well as one or more office applications, database client and/or server applications, and/or web browser applications. Alternatively, a user computer, user device, or customer device 1205 can be any other electronic device, such as a thin-client computer, Internet-enabled mobile telephone, and/or personal digital assistant, capable of communicating via a network (e.g., the network(s) 1210 described below) and/or of displaying and navigating web pages or other types of electronic documents. Although the exemplary system 1200 is shown with three user computers, user devices, or customer devices 1205, any number of user computers, user devices, or customer devices can be supported.

Certain embodiments operate in a networked environment, which can include a network(s) 1210. The network(s) 1210 can be any type of network familiar to those skilled in the art that can support data communications using any of a variety of commercially-available (and/or free or proprietary) protocols, including, without limitation, TCP/IP, SNA™, IPX™, AppleTalk™, and the like. Merely by way of example, the network(s) 1210 (similar to network(s) 140 FIG. 1, or the like) can each include a local area network ("LAN"), including, without limitation, a fiber network, an Ethernet network, a Token-Ring™ network and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including, without limitation, a network operating under any of the IEEE 702.11 suite of protocols, the Bluetooth™ protocol known in the art, and/or any other wireless protocol; and/or any combination of these and/or other networks. In a particular embodiment, the network might include an access network of the service provider (e.g., an Internet service provider ("ISP")). In another embodiment, the network might include a core network of the service provider, and/or the Internet.

Embodiments can also include one or more server computers 1215. Each of the server computers 1215 may be configured with an operating system, including, without limitation, any of those discussed above, as well as any commercially (or freely) available server operating systems. Each of the servers 1215 may also be running one or more applications, which can be configured to provide services to one or more clients 1205 and/or other servers 1215.

Merely by way of example, one of the servers 1215 might be a data server, a web server, a cloud computing device(s), or the like, as described above. The data server might include (or be in communication with) a web server, which can be used, merely by way of example, to process requests for web pages or other electronic documents from user computers 1205. The web server can also run a variety of server applications, including HTTP servers, FTP servers, CGI servers, database servers, Java servers, and the like. In some embodiments of the invention, the web server may be configured to serve web pages that can be operated within a web browser on one or more of the user computers 1205 to perform methods of the invention. A user interface (similar to user interface 200) may be featured on a webpage hosted by one of the servers 1215.

The server computers 1215, in some embodiments, might include one or more application servers, which can be configured with one or more applications accessible by a client running on one or more of the user computers 1205 and/or other servers 1215. In a non-limiting example, a user interface (similar to user interface 200) may be run as an application by a client running on one or more of the user computers 1205 and/or other servers 1215. Merely by way of example, the server(s) 1215 can be one or more general purpose computers capable of executing programs or scripts in response to the user computers 1205 and/or other servers 1215, including, without limitation, web applications (which might, in some cases, be configured to perform methods provided by various embodiments). Merely by way of example, a web application can be implemented as one or more scripts or programs written in any suitable programming language, such as Java™, C, C#™ or C++, and/or any scripting language, such as Perl, Python, or TCL, as well as combinations of any programming and/or scripting languages. The application server(s) can also include database servers, including, without limitation, those commercially available from Oracle™, Microsoft™, Sybase™ IBM™, and the like, which can process requests from clients (including, depending on the configuration, dedicated database clients, API clients, web browsers, etc.) running on a user computer, user device, or customer device 1205 and/or another server 1215. In some embodiments, an application server can perform one or more of the processes for generating music, and, more particularly, for generating music associated with a state or an emotion contained within a communication and for a user interface for generating music associated with a state or an emotion. Data provided by an application server may be formatted as one or more web pages (comprising HTML, JavaScript, etc., for example) and/or may be forwarded to a user computer 1205 via a web server (as described above, for example). Similarly, a web server might receive web page requests and/or input data from a user computer 1205 and/or forward the web page requests and/or input data to an application server. In some cases, a web server may be integrated with an application server.

Additionally and/or alternatively, user computer 1205 may utilize neural networks (e.g., convolutional, recurrent, spiking, or other statistical learning mode) to classify a state or an emotional state, determine a state or an emotional state from incoming sensor data, control position in the user interface, etc.

In accordance with further embodiments, one or more servers 1215 can function as a file server and/or can include one or more of the files (e.g., application code, data files, etc.) necessary to implement various disclosed methods, incorporated by an application running on a user computer 1205 and/or another server 1215. Alternatively, as those skilled in the art will appreciate, a file server can include all necessary files, allowing such an application to be invoked remotely by a user computer, user device, or customer device 1205 and/or server 1215.

It should be noted that the functions described with respect to various servers herein (e.g., application server, database server, web server, file server, etc.) can be performed by a single server and/or a plurality of specialized servers, depending on implementation-specific needs and parameters.

In certain embodiments, the system can include one or more databases 1220a-1220n (collectively, "databases 1220"). The location of each of the databases 1220 is discretionary: merely by way of example, a database 1220a might reside on a storage medium local to (and/or resident in) a server 1215a (and/or a user computer, user device, or customer device 1205). Alternatively, a database 1220n can be remote from any or all of the computers 1205, 1215, so long as it can be in communication (e.g., via the network 1210) with one or more of these. In a particular set of embodiments, a database 1220 can reside in a storage-area network ("SAN") familiar to those skilled in the art. (Likewise, any necessary files for performing the functions attributed to the computers 1205, 1215 can be stored locally on the respective computer and/or remotely, as appropriate.) In one set of embodiments, the database 1220 can be a relational database, such as an Oracle database, that is adapted to store, update, and retrieve data in response to SQLformatted commands. The database might be controlled and/or maintained by a database server, as described above, for example.

According to some embodiments, system 1200 might further comprise one or more input devices 1230 (similar to input devices 115 of FIG. 1, or the like), one or more audio playback devices 1240a-1240n (similar to audio playback devices 120a-120n of FIG. 1, or the like), one or more music (e.g., video) content sources 1245 (similar to music sources (or servers) 125, or the like) and corresponding database(s) 1250 (similar databases 130 of FIG. 1, or the like), and/or the like. In some embodiments, the computing system 1200 might be communicatively coupled to one or more input device, one or more a playback device(s), or the like (i.e., one or more of input devices 115 or 1230 and/or audio playback device(s) 120a-120n or 1240a-1240n, or the like). In some cases, the input device might comprise one of a fitness tracker, EEG device, smart watch, and/or the like.

These and other functions of the system 1200 (and its components) are described in greater detail above with respect to FIGS. 1-11.

In one aspect, a method for creating generative music might be characterized by the following numbered paragraphs:

1. A method, comprising: analyzing, with a computing system, a communication to determine at least one state contained within the communication; autonomously determining, with the computing system, one or more first characteristics of a plurality of characteristics of music associated with the determined at least one state contained within the communication; and based on the determination of the one or more first characteristics of a plurality of characteristics of music associated with the at least one state contained within the communication, autonomously generating, with the computing system, music having the one or more first characteristics of the plurality of characteristics associated with the at least one determined state contained within the communication.

2. The method of paragraph 1, wherein the computing system comprises at least one of a desktop computer, a laptop computer, a tablet, an embedded processing unit, or a smart phone.

3. The method of paragraph 1, wherein the one or more first characteristics of the plurality of characteristics of music include at least one of a pitch, note pattern, note envelope or shape, a control signal, a harmony, a grouping, vocal-like filtering and inflections, elements of surprise, randomization, consistency, crescendo, decrescendo an orchestration, a rate, a tempo, a rhythm, a timbre or an amplitude associated with the first state indicated by the communication.

4. The method of paragraph 1, wherein the music that is generated is generated in real-time based on feedback from the communication.

5. The method of paragraph 1, wherein the at least one state includes at least one of a first state associated with a person, a second state associated with an environment, a third state associated with a user interface involving at least one of an interactive touch screen, phone, tablet, digital book, a video game, or a virtual reality or augmented reality system.

6. The method of paragraph 5, wherein the first state associated with the person includes at least one of a physical state of a person, a mental state of a person, an emotion, a feeling, a biometric, a location, an activity, a rate of activity, a level of activity or an action of a user, wherein the second state associated with the environment includes at least one of a weather situation, a temperature, an amount of humidity, an amount of light, a time of day, or a time of year, wherein the third state associated with the state determined by a text, image, video, video or audio game, or virtual, augmented or mixed reality technology includes at least one of a sixth state associated with the state of one or more characters, scenes, or quantifiable attribute.

7. The method of paragraph 1, wherein the communication comprises at least one of a sensor communication, an Internet of Things ("IoT") communication, a biometric communication, a voice communication, a textual communication, a photographic communication, or a video communication.

8. The method of paragraph 7, wherein the sensor communication is received from one or more sensors including at least one of one or more GPS sensors, one or more distance sensors, one or more motion sensors, one or more movement sensors, one or more speed or velocity sensors, one or more accelerometer sensors, one or more gyroscope sensors, one or more biometric/health sensors, one or more facial recognition sensors, one or more cameras, one or more weather sensors, one or more temperature sensors, one or more ambient light sensors, one or more humidity sensors, one or more touch sensors, one or more movement sensors, one or more rotation sensors, or one or more microphones or audio sensors, and wherein the at least one state is determined based on feedback from the one or more sensors.

9. The method of paragraph 7, wherein the IoT communication is received from one or more devices comprising at least one of a smart home device, one or more thermometers in one or more rooms, one or more infrared ("IR") thermometers aimed at one or more positions in the one or more rooms, one or more air flow sensors in the one or more rooms, one or more air flow sensors in air ducts directed toward the one or more rooms, one or more indoor solar light sensors, one or more outdoor solar light sensors, one or more outdoor wind sensors, one or more neighborhood weather station sensors, one or more regional weather station sensors, one or more motion detectors detecting presence of people or animals in at least one of the one or more rooms or outside the customer premises, one or more humidity sensors in the one or more rooms, one or more smoke detectors detecting smoke in the one or more rooms, one or more gas detection sensors detecting gas in the one or more rooms, one or more biometric sensors identifying at least one person, or one or more health sensors detecting health information for at least one person, and wherein the at least one state is determined based on feedback from the one or more devices.

10. The method of paragraph 7, wherein the biometric communication is received from at least one of a fitness tracker or an electroencephalography ("EEG") device and wherein the computing system determines the at least one state based on feedback from the at least one of the fitness tracker or the EEG device.

11. The method of paragraph 7, wherein the computing system determines the at least one state by at least one of parsing the voice communication of at least one person or determining a tone of voice of the voice communication of the at least one person.

12. The method of paragraph 7, wherein the computing system determines the at least one state by parsing the textual communication or detecting at least one emoji used in the textual communication.

13. The method of paragraph 7, wherein the computing system determines the at least one state by determining a displayed state of at least one person in the photographic communication.

14. The method of paragraph 7, wherein the computing system determines the at least one state by at least one of determining a displayed state of at least one person in the video communication, analyzing body language of the at least one person in the video communication, parsing dialogue of the at least one person in the video, or determining a tone of voice of the at least one person in the video.

15. The method of paragraph 1, wherein the communication is further indicative of at least one of an age, a sex or location of a person, wherein the one or more first characteristics of a plurality of characteristics of music are further associated with the at least one of the age or the sex or the location indicated by the communication, and wherein the music that is generated further has the one or more first characteristics of the plurality of characteristics associated with the at least one of the age or the sex indicated by the communication.

16. The method of paragraph 1, wherein the music that is generated contains human-like embellishments.

17. The method of paragraph 16, wherein the human-like embellishments are created from at least one of timing jitter, frequency jitter, or timbral jitter.

18. The method of paragraph 1, further comprising: mapping, with the computing system, a plurality of states to a circular pattern, wherein at least one of a position of a state of the plurality of states on a circumference of the circular pattern or an angle of the state on the circular pattern corresponds to a first subset of characteristics of music associated with the state, and wherein a distance of the state from a center of the circular pattern corresponds to a second subset of characteristics of music associated with the state; determining, with the computing system, the position on the circumference of the circular pattern of at least one state contained within the communication or the angle of the at least one state contained within the communication and the distance of state contained within the communication from the center of the circular pattern; and based on the determination of the position or angle and the distance of the at least one state contained within the communication, autonomously generating, with the computing system, music having the first subset of particular characteristics and the second subset of particular characteristics associated with the determined at least one state contained within the communication.

19. The method of paragraph 1, further comprising: mapping, with the computing system, a plurality of states to a plurality of positions on a two-dimensional graph, wherein at least one of a first distance of a position from a first axis corresponds to an input mapped to a first subset of characteristics of music, and wherein a second distance of the position from a second axis corresponds to an input controlling a second subset of characteristics of music; determining, with the computing system, a state position associated with the determined at least one state contained within the communication and having a first particular distance from the first axis and a second particular distance from the second axis; based on the determination of the state position having the first particular distance from the first axis and a second particular distance from the second axis, autonomously generating, with the computing system, music having the first subset of characteristics and the second subset of characteristics corresponding to the state position associated with the at least one state contained within the communication.

In another aspect, a method for generating music might be characterized by the following sample numbered paragraphs:

20. A method for generating music, said method comprising: generating, with a computing system, a circular pattern having a plurality of different states mapped to different regions on the circular pattern, wherein at least one of a position of a region on a circumference of the circular pattern or an angle of the region on the circular pattern corresponds to a first subset of characteristics of a plurality of characteristics of music, and wherein a distance of the region from a center of the circular pattern corresponds to a second subset of characteristics of the plurality of characteristics of music; analyzing, with a computing system, a communication to determine at least one state contained within the communication; autonomously determining, with the computing system, the position of at least one particular region corresponding to the at least one particular state on the circumference of the circular pattern or the angle of the region on the circular pattern corresponding to the at least one particular state and the distance of the at least one particular region corresponding to the at least one particular emotion from the center of the circular pattern; based on the determination of the position of the determined at least one particular region on the circumference of the circular pattern or the angle of the determined at least one particular region and the distance of the determined at least one particular region from the center of the circular pattern, autonomously generating, with the computing system, music having the first subset of characteristics and the second subset of characteristics associated with the at least one state contained within the communication.

21. The method of paragraph 20, wherein the computing system comprises at least one of a desktop computer, a laptop computer, a tablet, embedded processing unit or a cellular phone.

22. The method of paragraph 20, wherein the different regions are represented by icons, and wherein the icons are at least one of a textual icon representing the at least one emotion or an emoji representing the at least one of the emotion.

23. The method of paragraph 20, wherein the first subset of characteristics includes at least one of a pitch, a note envelope, a note pattern, a filter, a harmony, a tone, a density, vocal-like quality, a grouping, an orchestration, a timbre, a rate, a tempo, or an amplitude associated with the first state indicated by the user communication.

24. The method of paragraph 20, wherein the second subset of characteristics includes at least one of a pitch, a note pattern, a filter, a harmony, a tone, a density, vocal-like quality, an orchestration, a speed, a timbre, or an amplitude associated with the first state indicated by the user communication.

25. The method of paragraph 20, further comprising: autonomously determining, with the computing system, whether at least two states are contained within the communication; based on a determination that at least two states are contained within the communication, simultaneously generating, playing, and harmonizing music having the particular first subset of characteristics and the particular second set of characteristics associated with each of the at least two states contained within the communication.

26. The method of paragraph 20, further comprising: autonomously determining, with the computing system, whether at least two states are contained within the communication; based on a determination that more than one states is contained within the communication, determining an order to generate and play music associated with each of the at least two states; transitioning, with the computing system, between generating and playing music associated with each of the at least two states.

27. The method of paragraph 26, wherein transitioning between playing music associated with each of the at least two states contained within the communication further comprises: autonomously determining, with the computing system, the position or angle of the at least two particular regions corresponding to the at least two particular states on the circumference of the circular pattern and the distance of two particular regions corresponding to the particular states from the center of the circular pattern; autonomously determining, with the computing system, regions corresponding to additional states between the at least two particular regions corresponding to the at least two particular states; transitioning, with the computing system, between playing music associated with each of the at least two states contained within the communication by playing music associated with the determined additional states between music associated with the at least two particular regions corresponding to the at least two particular states.

28. The method of paragraph 20, wherein the user communication comprises at least one of a tactile communication, a sensor communication, an Internet of Things "IoT" communication, a biometric communication, a voice communication, a textual communication, a picture communication, or a video communication.

29. The method of paragraph 28, further comprising: displaying the circular pattern having the plurality of different states represented by regions to a user on a user interface, wherein the tactile communication is received from the user selecting at least one regions associated with at least one particular state on the circular pattern displayed on the user interface.

30. The method of paragraph 28, further comprising: displaying the circular pattern having the plurality of different states represented by regions to a user on a user interface, wherein the tactile communication includes the user selecting at least two regions.

31. The method of paragraph 30, further comprising: tracking, with the computing system, the tactile communication of a user; determining, with the computing system, whether at least one region has been selected; based on a determination that at least two regions have been selected, determining, with the computing system, whether the tactile input, when selecting the at least two regions, was continuous input; based on a determination that the tactile input was not continuous, pausing, with the computing system, the generated music between each user selection of a region; based on a determination that the tactile input was continuous, smoothly transitioning between playing music associated with each of the at least two states selected by the tactile input.

32. The method of paragraph 31, wherein smoothly transitioning between playing music, further comprises: creating, with the computing system, a time lag between the selection of each region and the generation of music associated with each region. 33. The method of paragraph 32, wherein in the time lag further comprises playing the generated music for each selected region for a predetermined amount of time before transitioning to a subsequent selected region.

34. The method of paragraph 28, wherein the biometric communication is received from at least one of a fitness tracker or an electroencephalography ("EEG") device and wherein the computing system determines the first state of the user based on feedback from the at least one of the fitness tracker or the EEG device.

35. The method of paragraph 28, wherein the computing system determines the first state of the user by at least one of parsing the voice communication of the user or determining a tone of the voice communication of the user.

36. The method of paragraph 28, wherein the computing system determines the first state of the user by parsing the textual communication of the user.

37. The method of paragraph 28, wherein the computing system determines the first state of the user by determining a displayed state of a person in the picture communication.

38. The method of paragraph 28, wherein the computing system determines the first state of the user by at least one of determining a displayed state of a person in the video communication, parsing dialogue of the person in the video, or determining a tone of voice of the person in the video.

39. The method of paragraph 20, wherein the user communication is further indicative of at least one of a demographic such as age, sex or location of a user, wherein the intensity or character of the music is further associated with the at least one of the demographics indicated by the user communication, and wherein the music that is generated further has the intensity associated with the at least one of the demographics indicated by the user.

40. The method of paragraph 20, wherein the music that is generated contains variation and human-like embellishments.

41. The method of paragraph 20, wherein the human-like embellishments are created from at least one of timing jitter, frequency jitter, or timbre jitter, wherein a random signal may influence parameter values.

42. The method of paragraph 20, further comprising: receiving, with the computing system, at least one additional user communication from a user, the at least one additional user communication being indicative of at least one additional state; determining, with the computing system, a number of user communications over a specified period of time; determining, with the computing system, whether the number of user communications exceeds a predetermined threshold; based on a determination that the number of user communications does not exceed the predetermined threshold, autonomously determining, with the computing system, one or more first characteristics of a plurality of characteristics of music associated with the second state indicated by the second user communication, and autonomously transitioning from generating music having the one or more first characteristics of the plurality of characteristics associated with the first state indicated by the user to generating music having the one or more first characteristics of the plurality of characteristics associated with the second state indicated by the user; and based on a determination that the number of user communications does exceed the predetermined threshold, pausing, with the computing system, the music being generated.

In yet another aspect, a method for generating music might be characterized by the following sample numbered paragraphs:

43. A method for generating music, said method comprising: generating, with a computing system, a two-dimensional graph having a plurality of different states mapped to different regions on the two-dimensional graph, wherein at least one of a first distance of a region from a first axis on the two-dimensional graph corresponds to an input mapped to a first subset of characteristics of a plurality of characteristics of music, and wherein a second distance of the region from a second of the two-dimensional graph corresponds to an input mapped to second subset of characteristics of the plurality of characteristics of music; analyzing, with a computing system, a communication to determine at least one state contained within the communication; autonomously determining, with the computing system, a position of at least one particular region corresponding to the at least one state contained within the communication and having a first particular distance from the first axis and a second particular distance from the second axis; based on the determination of the position of the determined at least one particular region corresponding to the at least one state contained within the communication, autonomously generating, with the computing system, music having the first subset of characteristics and the second subset of characteristics associated with the position of the at least one state contained within the communication.

In a further aspect, a method for generating music might be characterized by the following sample numbered paragraphs:

44. A method for generating new music, the method comprising: defining, with a computing system, a predetermined set of notes; defining, with the computing system, at least one of a frequency, note pattern, a note envelope, a note range, a melody, a harmony, a probability of a note event, a tone, an orchestration, a timbre, a rate, a tempo, a rhythmic structure, a density, a grouping of audio components, a filter, a musical gesture, or an amplitude associated with a particular state; generating, with the computing system, music associated with the at least one of a note pattern, a note range, a harmony, a tone, a orchestration, a timbre, a speed, a rhythmic structure, a grouping, a gesture or the amplitude associated with the particular state; and adding, with the computing system, human-like embellishments to the generated music.

In another aspect, an apparatus for generating music might be characterized by the following sample numbered paragraphs:

45. An apparatus, comprising: at least one processor; and a non-transitory computer readable medium communicatively coupled to the at least one processor, the non-transitory computer readable medium having stored thereon computer software comprising a set of instructions that, when executed by the at least one processor, causes the apparatus to: analyze a communication to determine at least one emotion or state contained within the communication; autonomously determine one or more first characteristics of a plurality of characteristics of music associated with the determined at least one emotion or state contained within the communication; and based on the determination of the one or more first characteristics of a plurality of characteristics of music associated with the at least one emotion or state contained within the communication, autonomously generate music having the one or more first characteristics of the plurality of characteristics associated with the at least one determined emotion or state contained within the communication.

In an additional aspect, a system for generating music might be characterized by the following sample numbered paragraphs:

46. A system, comprising: a computing system, comprising: at least one first processor; and a first non-transitory computer readable medium communicatively coupled to the at least one first processor, the first non-transitory computer readable medium having stored thereon computer software comprising a first set of instructions that, when executed by the at least one first processor causes the computing system to: analyze a communication to determine at least one emotion or state contained within the communication; autonomously determine one or more first characteristics of a plurality of characteristics of music associated with the determined at least one emotion or state contained within the communication; and based on the determination of the one or more first characteristics of a plurality of characteristics of music associated with the at least one emotion or state contained within the communication, autonomously generate music having the one or more first characteristics of the plurality of characteristics associated with the at least one determined emotion or state contained within the communication.

In another aspect, an apparatus for generating music might be characterized by the following sample numbered paragraphs:

47. An apparatus, comprising: at least one processor; and a non-transitory computer readable medium communicatively coupled to the at least one processor, the non-transitory computer readable medium having stored thereon computer software comprising a set of instructions that, when executed by the at least one processor, causes the apparatus to: generate a circular pattern having a plurality of different emotions or states represented by icons, wherein at least one of a position on a circumference of the circular pattern or an angle of the circular pattern corresponds to a first subset of characteristics of a plurality of characteristics of music associated with a particular emotion or states represented by a particular icon, and wherein a distance from a center of the circular pattern corresponds to a second subset of characteristics of the plurality of characteristics of music associated with a particular emotion or states represented by a particular icon; analyze a communication to determine at least one emotion or state contained within the communication; autonomously determine the position of at least one particular icon corresponding to the at least one particular emotion or state on the circumference of the circular pattern and the distance of the at least one particular icon corresponding to the at least one particular emotion or state from the center of the circular pattern; and based on the determination of the position of the determined at least one particular icon on the circumference of the circular pattern or the angle of the determined at least one particular icon and the distance of the determined at least one particular icon from the center of the circular pattern, autonomously generate music having the first subset of characteristics and the second subset of characteristics associated with the at least one emotion or state contained within the communication.

In an additional aspect, a system for generating music might be characterized by the following sample numbered paragraphs:

48. A system, comprising: a computing system, comprising: at least one first processor; and a first non-transitory computer readable medium communicatively coupled to the at least one first processor, the first non-transitory computer readable medium having stored thereon computer software comprising a first set of instructions that, when executed by the at least one first processor causes the computing system to: generate a circular pattern having a plurality of different emotions or states represented by icons, wherein at least one of a position on a circumference of the circular pattern or an angle of the circular pattern corresponds to a first subset of characteristics of a plurality of characteristics of music associated with a particular emotion or states represented by a particular icon, and wherein a distance from a center of the circular pattern corresponds to a second subset of characteristics of the plurality of characteristics of music associated with a particular emotion or states represented by a particular icon; analyze a communication to determine at least one emotion or state contained within the communication; autonomously determine the position of at least one particular icon corresponding to the at least one particular emotion or state on the circumference of the circular pattern and the distance of the at least one particular icon corresponding to the at least one particular emotion or state from the center of the circular pattern; and based on the determination of the position of the determined at least one particular icon on the circumference of the circular pattern or the angle of the determined at least one particular icon and the distance of the determined at least one particular icon from the center of the circular pattern, autonomously generate music having the first subset of characteristics and the second subset of characteristics associated with the at least one emotion or state contained within the communication.

In another aspect, an apparatus for generating music might be characterized by the following sample numbered paragraphs:

49. An apparatus, comprising: at least one processor; and a non-transitory computer readable medium communicatively coupled to the at least one processor, the non-transitory computer readable medium having stored thereon computer software comprising a set of instructions that, when executed by the at least one processor, causes the apparatus to: define a predetermined set of notes; define at least one of a note pattern, a note range, a harmony, a tone, a pitch, an envelope, a probability of a note event, an orchestration, a speed, a rate, a timbre, a density, a filter, a contour, a gesture, a density, a grouping of audio components, a group, or an amplitude of an audio feature associated with a particular emotion or state; generate music associated with the at least one of the note pattern, the note range, the harmony, the tone, the orchestration, the speed, a rate, a timbre, a contour, a gesture or an amplitude associated with the particular emotion or state; and add human-like variations to the generated music.

In an additional aspect, a system for generating music might be characterized by the following sample numbered paragraphs:

50. A system, comprising: a computing system, comprising: at least one first processor; and a first non-transitory computer readable medium communicatively coupled to the at least one first processor, the first non-transitory computer readable medium having stored thereon computer software comprising a first set of instructions that, when executed by the at least one first processor causes the computing system to: define a predetermined set of notes; define at least one of a note pattern, a note range, a harmony, a tone, a pitch, an envelope, a probability of a note event, an orchestration, a speed, a rate, a timbre, a density, a filter, a contour, a gesture, a density, a grouping of audio components, a group, or an amplitude of an audio feature associated with a particular emotion or state; generate music associated with the at least one of the note pattern, the note range, the harmony, the tone, the orchestration, the speed, a rate, a timbre, a contour, a gesture or an amplitude associated with the particular emotion or state; and add human-like variations to the generated music.

In a further aspect, a method might be characterized by the following sample numbered paragraphs:

51. A method for generating music, said method comprising: generating, with a computing system, a circular pattern having a plurality of different emotions or states represented by icons, wherein at least one of a position of a particular icon on the circular pattern corresponds to a set of characteristics of a plurality of characteristics of music associated with a particular emotion or state represented by the particular icon or position; analyzing, with the computing system, a communication to determine at least one emotion or state contained within the communication; autonomously determining, with the computing system, the position of at least one icon or position corresponding to the determined at least one emotion or state contained within the communication on the circular pattern; based on the determination of the position of the determined at least one particular icon on the circular pattern, autonomously generating, with the computing system, music having the set characteristics associated with the determined at least one emotion or state contained within the communication.

52. The method of paragraph 51, further comprising: autonomously determining, with the computing system, whether at least two emotions or states are contained within the communication; based on a determination that at least two emotions are contained within the communication, simultaneously generating, playing, and harmonizing music having the set of characteristics associated with each of the at least two emotions or states contained within the communication.

53. The method of paragraph 51, further comprising: autonomously determining, with the computing system, whether at least two emotions or states are contained within the communication; based on a determination that more than one emotion or state is contained within the communication, determining an order to generate and play music associated with each of the at least two emotions or states; transitioning, with the computing system, between generating and playing music associated with each of the at least two emotions or states.

54. The method of paragraph 53, wherein transitioning between playing music associated with each of the at least two emotions or states are contained within the communication further comprises: autonomously determining, with the computing system, the position of the at least two particular icons or positions corresponding to the at least two particular emotions or states on the circular pattern; autonomously determining, with the computing system, icons corresponding to additional emotions or states between the at least two particular icons corresponding to the at least two particular emotions or states; transitioning, with the computing system, between playing music associated with each of the at least two emotions or states contained within the communication by playing music associated with the determined additional emotions or states between music associated with the at least two particular icons corresponding to the at least two particular emotions or states.

In an aspect, a method might be characterized by the following sample numbered paragraphs:

55. A method for generating music, said method comprising: generating, with a computing system, a pattern having a plurality of different concepts represented by icons, wherein at least one of a position of a particular icon on the pattern corresponds to a set of characteristics of a plurality of characteristics of music associated with a particular concept represented by the particular icon; analyzing, with the computing system, a communication to determine at least one concept contained within the communication; autonomously determining, with the computing system, the position of at least one icon corresponding to the determined at least one concept contained within the communication on the pattern; based on the determination of the position of the determined at least one particular icon on the pattern, autonomously generating, with the computing system, music having the set characteristics associated with the determined at least one concept contained within the communication.

56. The method of paragraph 55, wherein the at least on concept corresponds to at least one of an emotion, a state of a person, an action of a person, an attribute of a physical or virtual environment, or interaction in a physical or virtual environment.

57. The method of paragraph 55, wherein the pattern is at least one of a circular pattern, a triangular patter, a rectangular pattern, a pentagonal pattern, a hexagonal pattern, an octagonal pattern, a two-dimensional grid, or a three-dimensional grid.

In an additional aspect, a method for generating music might be characterized by the following sample numbered paragraphs:

58. A method, comprising: analyzing, with a computing system, a communication to determine at least one concept contained within the communication; autonomously determining, with the computing system, one or more first characteristics of a plurality of characteristics of music associated with the determined at least one concept contained within the communication; and based on the determination of the one or more first characteristics of a plurality of characteristics of music associated with the at least one concept contained within the communication, autonomously generating, with the computing system, music having the one or more first characteristics of the plurality of characteristics associated with the at least one determined concept contained within the communication.

59. The method of paragraph 58, wherein the at least one concept corresponds to at least one of an emotion of a person, a state of a person, an action of a person, an attribute or interaction in a virtual or physical environment.

60. The method of paragraph 58, wherein the concept corresponds to an emotion of a person or a state of a person, and wherein the one or more first characteristics of a plurality of characteristics of music associated with the determined at least one concept are designed to guide a user from a negative emotion or negative state to a more positive emotion or positive state.

61. The method of paragraph 58, wherein the music that is generated may be used as an assistive aid for musical therapy or assistive technology.

In yet another aspect, a method for generating music might be characterized by the following sample numbered paragraphs:

62. A method, comprising: receiving, with a computing system, at least one sensor input associated with a user; analyzing, with the computing system, the at least one sensor input to determine at least one first state of the user; determining, with the computing system, a desired second state of the user; determining, with the computing system, whether the at least one first state of the user matches the desired second state of the user; based on a determination that the at least one first state of the user does not match the desired second state of the user, continuously controlling, with the computing system, the generation of music to guide the user to the desired second state based on the at least one sensor input.

63. The method of paragraph 62, further comprising: based on a determination that the at least one first state of the user does matches the desired second state of the user, continuously controlling, with the computing system, the generation of music to have one or more characteristics associated with the desired second state.

64. The method of paragraph 62, wherein continuously controlling the generation of music further comprises both fixed evolving aspects and variable changes driven by at least at least one sensor input.

65. The method of paragraph 62, wherein the at least one sensor comprises at least one of a biometric sensor, an electrode, a GPS sensor, a distance sensor, a motion sensor, a movement sensor, a speed or velocity sensor, an accelerometer, a gyroscope, a facial recognition sensor, or a video or still image.

66. The method of paragraph 62, wherein the desired second state of the user corresponds to a desired stress level or amount of arousal of the user, and wherein continuously controlling the generation of the music causes the generated music to guide the user from a first stressful state to a second more relaxed state based on the at least one sensor input.

67. The method of paragraph 62, wherein the desired second state corresponds to state of meditation, and wherein continuously controlling the generation of the music causes the generated music to guide the user from a first non-meditative state to a second meditative state based on the at least one sensor input.

68. The method of paragraph 62, wherein the desired second state corresponds to state of focus, and wherein continuously controlling the generation of the music causes the generated music to guide the user from a first unfocused state to a second focused state based on the at least one sensor input.

69. The method of paragraph 62, wherein the desired second state corresponds to an emotion, and wherein continuously controlling the generation of the music causes the generated music to guide the user from a first negative emotion to a second positive emotion.

70. The method of paragraph 62, wherein the desired second state corresponds to a desired number of steps to take per minute, and wherein continuously controlling the generation of the music causes the generated music to guide the user to take the desired number of steps per minute.

71. The method of paragraph 62, wherein continuously controlling the generation of the music causes the generated music to sync to at least one of a running speed of the user, a heartbeat of the user, a breathing pattern of the user, or a brainwave pattern of the user.

72. The method of paragraph 62, wherein the desired second state corresponds to at least one of a slower breathing pattern, a slower heartbeat, a faster breathing pattern, or a faster heartrate, and wherein continuously controlling the generation of the music causes the generated music to guide the user to at least one of a slower breathing pattern, a slower heartbeat, a faster breathing pattern, or a faster heartrate.

73. The method of paragraph 62, wherein the desired second state corresponds to at least one of a decreasing intensity of a workout or an increasing intensity of a workout, and wherein continuously controlling the generation of the music causes the generated music to guide the user through at least one of the decreasing intensity of a workout or the increasing intensity of a workout.

74. The method of paragraph 62, wherein the desired second state corresponds to at least one of a location or a position of the user, and wherein continuously controlling the generation of the music causes the generated music to guide the user from a first location to a second desired location.

75. The method of paragraph 62, wherein the desired second state corresponds to at least one goal-oriented state, and wherein continuously controlled music allows the sound generated to guide the user to towards the desired goal state.

76. The method of paragraph 75, wherein the desired goal to be maintained corresponds to at least one of maintaining a heart rate, maintaining a breathing pattern, maintaining a running pace, maintaining a step pace, maintaining a rate of periodic activity, or maintaining a velocity or amount of an activity.

77. The method of paragraph 62, wherein the desired second state corresponds to at least one of a posture of the user or a body position of the user, and wherein continuously controlling the generation of the music causes the generated music to guide the user to at least one of an improved posture or improved body position or improved gesture movement.

78. The method of paragraph 62, wherein the at least one sensor input is at least one biometric input, and wherein the at least one biometric input is received from at least one of a biometric input reader comprising at least one of a blood pressure monitor, a heart rate monitor, EKG sensor, PPG sensor, a fitness tracker, CO2 monitor, pulse oximeter, muscle sensor, temperature sensor, respiration sensor, camera, accelerometer, gyroscope or an electroencephalography ("EEG") device and wherein the computing system determines the at least one state of a person based on feedback from the at least one of the biometric input.

79. The method of paragraph 62, wherein the one or more characteristics of music include at least one of a frequency, a note pattern, a note envelope, a filter, a harmony, a tone, vocal-like quality, surprise element, randomization, consistency, crescendo, decrescendo an orchestration, a speed, a rate, a rhythm, or an amplitude associated with the at least first biometric input.

In yet a further aspect, an apparatus for generating music might be characterized by the following sample numbered paragraphs:

80. An apparatus comprising: at least one processor; and a non-transitory computer readable medium communicatively coupled to the at least one processor, the non-transitory computer readable medium having stored thereon computer software comprising a set of instructions that, when executed by the at least one processor, causes the apparatus to: receive at least one sensor input associated with a user; analyze the at least one sensor input to determine at least one first state of the user; determine a desired second state of the user; determine whether the at least one first state of the user matches the desired second state of the user; based on a determination that the at least one first state of the user does not match the desired second state of the user, continuously control the generation of music to guide the user to the desired second state based on the at least at least one sensor input.

In an additional aspect, a system for generating music might be characterized by the following sample numbered paragraphs:

81. A system, comprising: a computing system, comprising: at least one first processor; and a first non-transitory computer readable medium communicatively coupled to the at least one first processor, the first non-transitory computer readable medium having stored thereon computer software comprising a first set of instructions that, when executed by the at least one first processor causes the computing system to: receive at least one sensor input associated with a user; analyze the at least one sensor input to determine at least one first state of the user; determine a desired second state of the user; determine whether the at least one first state of the user matches the desired second state of the user; based on a determination that the at least one first state of the user does not match the desired second state of the user, continuously control the generation of music to guide the user to the desired second state based on the at least at least one sensor input.

In another aspect, a method for generating music might be characterized by the following sample numbered paragraphs:

82. A method, comprising: receiving, with a computing system, a first biometric input associated with a user; analyzing, with the computing system, the first biometric input to determine a first state of the user; autonomously determining, with the computing system, one or more first characteristics of music associated with the determined first state of the user; based on the determination of the one or more first characteristics of music associated with the determined first state of the user, autonomously generating, with the computing system, music having the one or more first characteristics associated with the first state of the user; receiving, with the computing system, at least one second biometric input associated with the user; analyzing, with the computing system, the at least one second biometric input to determine at least one second state of the user; determining, with the computing system, whether the second state of the user is different from the first state of the user; based on a determination that the second state of the user is different from the first state of the user, autonomously determining, with the computing system, one or more second characteristics of music associated with the determined at least one second state of the user; based on a determination of the one or more second characteristics of music associated with the second state of the user, autonomously transitioning between generating music having the one or more first characteristics of music associated with the first state of the user to generating music having the one or more second characteristics of the plurality of characteristics associated with the second state of the user.

In an additional aspect, a method for generating music might be characterized by the following sample numbered paragraphs:

83. A method, comprising: continuously receiving, with a computing system, one or more biometric inputs associated with a user; analyzing, with the computing system, the one or more biometric inputs to determine at least one first state of the user; determining, with the computing system, a desired second state of the user; determining, with the computing system, whether the at least one first state of the user matches the desired second state of the user; based on a determination that the at least one first state of the user does not match the desired second state of the user, continuously generating music having one or more evolving characteristics of music associated with the at least one biometric input, wherein the one or more evolving characteristics of music guide the user to the desired second state based on the at least at least one biometric input.

In an aspect, a method for generating music might be characterized by the following sample numbered paragraphs:

84. A method, comprising: analyzing, with a computing system, a sensor input or a communication to determine at least one state; autonomously determining, with the computing system, one or more first characteristics of a plurality of characteristics of music associated with the determined at least one state; and based on the determination of the one or more first characteristics of a plurality of characteristics of music associated with the at least one state, autonomously generating, with the computing system, music having the one or more first characteristics of the plurality of characteristics associated with the at least one determined state.

85. The method of paragraph 84, wherein the music that is generated is generated in real-time based on feedback from the sensor input or the communication.

86. The method of paragraph 84, wherein the one or more first characteristics of the plurality of characteristics of music reflect an intensity of the determined at least one state.

87. The method of paragraph 84, wherein the one or more first characteristics of the plurality of characteristics of music reflect a valence of the determined at least one state.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above and elsewhere herein, it will be appreciated that the invention is intended to cover all modifications and equivalents within the scope of the appended claims.

Additional illustrative embodiments will now be described herein with reference to exemplary breathing entrainment sonification systems and associated computers and other processing devices, as shown in FIGS. 13 through 24. It is to be appreciated that the embodiments described below, like others described herein, are presented by way of example only, and should not be construed as limiting in any way. Other types of entrainment sonification systems can be implemented using the disclosed techniques. It should also be noted that terms such as "music" and "musical" as used herein are intended to be broadly construed, so as to encompass a wide variety of different sound arrangements.

Although illustrative embodiments are described primarily in the context of breathing entrainment sonification, it will be readily apparent that the disclosed techniques can be adapted for use in entrainment sonification contexts involving a wide variety of other mindfulness related activities.

A breathing entrainment sonification system in some embodiments disclosed herein may be implemented in the form of a musical communication system configured to support a breathing entrainment application. For example, breathing entrainment sonification systems disclosed herein may be implemented in the form of musical communication systems of the type described above, but particularly configured for breathing entrainment sonification.

In some embodiments, a breathing entrainment sonification system comprises a musical communication system particularly configured for an application involving guided breathing exercises.

A breathing entrainment sonification system in some embodiments is configured in accordance with a breathing entrainment model. The system configured in accordance with the breathing entrainment model more particularly comprises a closed-loop system featuring two different types of sound cues, namely, a sound cue of a first type to direct the user's breathing pattern (an "entrainment component") and one or more sound cues of a second type to provide feedback to the user on their current status during the exercise (one or more "auxiliary components").

The two different types of sound cues are designed to overcome many of the challenges in biofeedback systems including negative feedback loops and ambiguity in the function and meaning of the sonification. Additional or alternative sound cues for entrainment and/or auxiliary components may be used in other embodiments.

The entrainment component illustratively relates to a "leader" role of sound as described elsewhere herein, functioning to guide, instruct and/or direct the user's activity. With the exception of a few edge cases including sleep onset detection and external interrupts for real-time ramp generation, the user's performance during the activity generally does not influence this component.

An auxiliary component's function illustratively relates to a "follower" role as described elsewhere herein, responding to and reflecting the user's activity. It is influenced by the user's activity during the exercise, providing feedback on how the user is doing (progress) and what they should do to improve (adjustment).

Other embodiments can be configured to utilize only an entrainment component. The auxiliary components can therefore be eliminated in some embodiments. Additionally or alternatively, some embodiments can be implemented using an open-loop arrangement rather than a closed-loop arrangement. Accordingly, some embodiments disclosed herein are configured to utilize only entrainment components, and such embodiments can be implemented using closed-loop or open-loop arrangements.

Many conventional auditory solutions attempt to assist with activities—such as meditation, relaxation and exercise—by providing a conducive soundtrack, but none offer intuitive feedback through sound that guides the user towards their goal. Illustrative embodiments of the breathing entrainment sonification systems disclosed herein address this need by offering users the ability to increase bodily awareness through real-time auditory response to sensor input. Such breathing entrainment sonification systems are flexible enough to sonify any datastream through synthesis techniques, without using bulky audio clips.

Mindfulness, the practice of being aware of the present moment through mental focus, is an example of an activity that can benefit from sonifying sensor input, in this case taking a breath. Sound cues in illustrative embodiments can help users follow a programmed breathing exercise (entrainment, guide or leader signal), understand how well they are doing at the activity (response, feedback or follower signal), and experience heightened awareness of the breath, thus encouraging a state of mindfulness.

By presenting users with access to breath-by-breath guide and auditory feedback, illustrative embodiments overcome the drawbacks of conventional use of a soundtrack conducive to the activity. The breathing entrainment sonification techniques disclosed herein assist users in working toward a goal.

For example, sound cues as disclosed herein are intuitive from the first listen, and associations are strengthened through practice. The temporal dimension of sound affords both a means to guide transformation over time, as well as to induce regularity through rhythmic and pattern repetition. Research has shown music's power in regulating respiration, improving gait control, and other therapeutic and restorative goals.

Illustrative embodiments utilize a generative sound model for guided breathing that harnesses sound's ability to calm the mind, and focus the listener on their breath.

The breathing entrainment model described is an assistive application consisting of multiple sound cues which simultaneously guide the user's breathing patterns and reflect how they are doing during the exercise.

Figure 13:
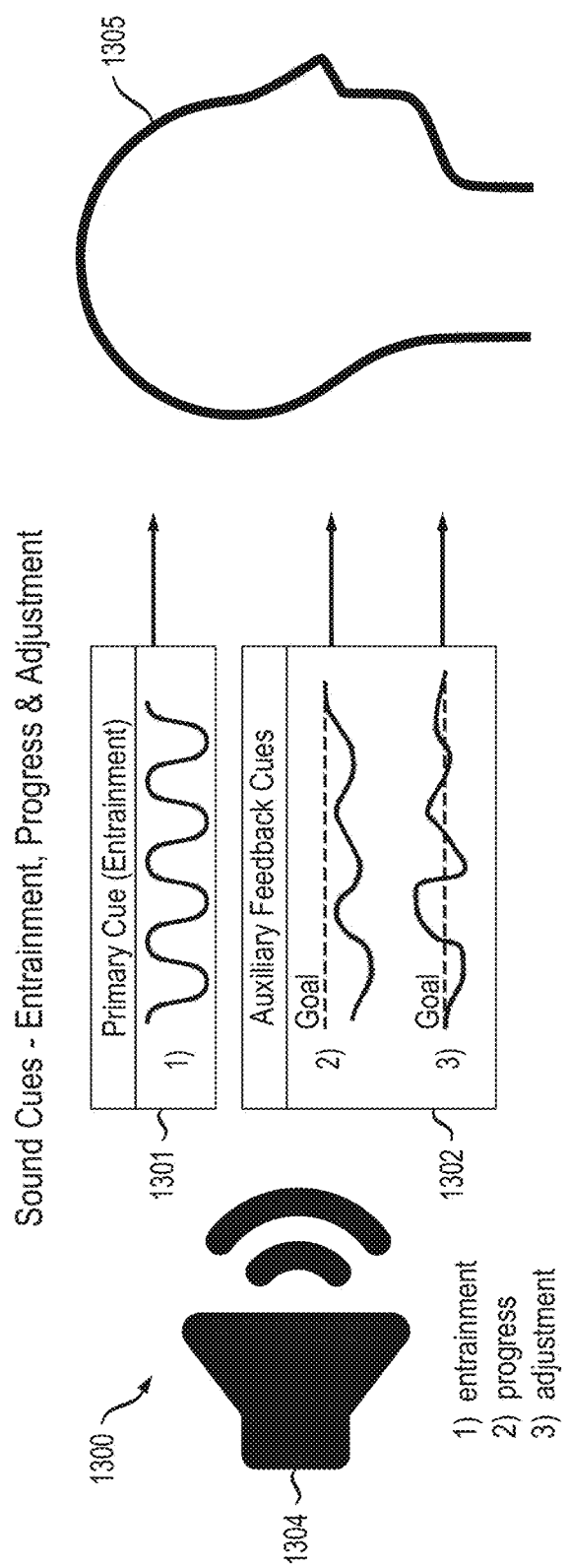
FIGS. 13 through 24 show aspects of breathing entrainment sonification techniques in illustrative embodiments.

FIG. 13 shows a breathing entrainment sonification system 1300 that utilizes an example arrangement of sound cues configured to provide entrainment, progress and adjustment in an illustrative embodiment. In this embodiment, there are two types of auditory cues heard by the user: a primary cue 1301 for entrainment (e.g., leader, guide) and multiple auxiliary cues 1302 (e.g., follower, feedback). The primary cue 1301 and auxiliary cues 1302 in some embodiments are combined together in a signal combiner with the resulting combined signal driving an audio device 1304 for generation of sound for audible presentation to a user 1305. Other types of signal processing arrangements are possible. The audio device 1304 illustratively comprises at least one speaker, and may be part of a larger processing device that implements at least a portion of the breathing entrainment sonification system, such as a mobile telephone, tablet computer or other type of computer.

The primary cue 1301 is an example of what is more generally referred to herein as a first sound cue of a first type, and illustratively comprises a primary entrainment cue for the breathing entrainment sonification system 1300. The primary breathing entrainment cue illustratively comprises a particular entrainment signal configured to direct a breathing pattern of the user 1305 towards a desired breathing pattern. For example, the particular entrainment signal may comprise a selected one of a plurality of distinct entrainment signals available within the breathing entrainment sonification system 1300. Additionally or alternatively, one or more characteristics of the particular entrainment signal are illustratively adjustable by the user 1305, such as via a touchscreen or other user interface of a mobile telephone or tablet computer that implements at least a portion of the breathing entrainment sonification system 1300.

The auxiliary cues 1302 are examples of what are more generally referred to herein as additional sound cues of a second type, with each such additional sound cue illustratively comprising an auxiliary breathing entrainment cue for the breathing entrainment sonification system 1300. A given auxiliary breathing entrainment cue is illustratively configured to provide an indication to the user 1305 of his or her current status relative to a designated goal and/or guidance of the user 1305 toward the designated goal.

In other embodiments, the auxiliary cues 1302 may be eliminated, and the system 1300 can operate to provide entrainment sonification using only the primary cue 1301.

Figure 14:
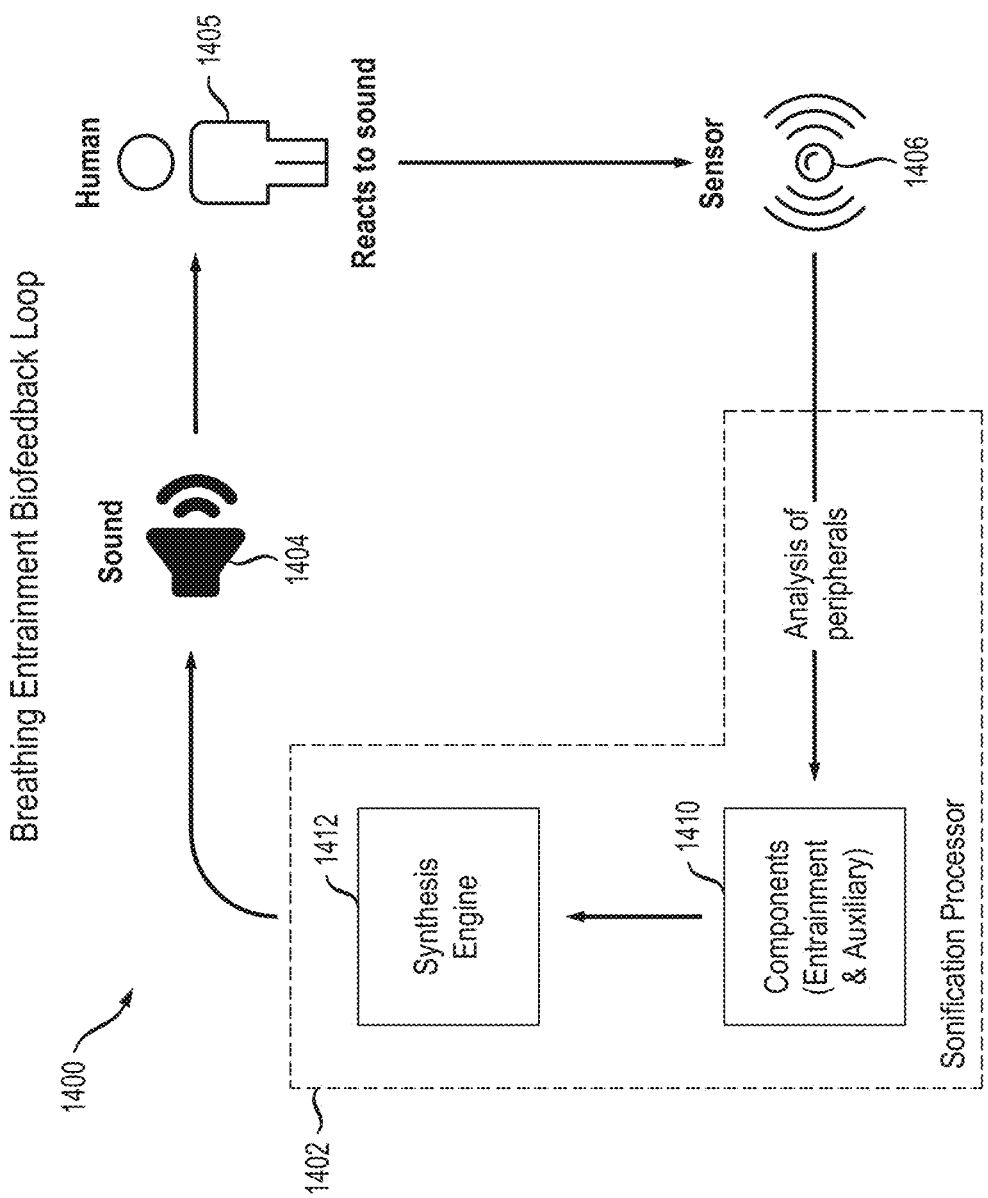

In some implementations of the breathing entrainment sonification system 1300 of FIG. 13, the primary cue 1301 and the auxiliary cues 1302 are provided via the audio device 1304 to the user 1305, and one or more feedback signals are received from one or more sensors of the breathing entrainment sonification system 1300. The system 1300 can then adjust one or more characteristics of one or both of the auxiliary cues 1302, and additionally or alternatively one or more characteristics of the primary cue 1301, based at least in part on the one or more feedback signals received from the one or more sensors. Such sensors are not explicitly shown in the embodiment as illustrated in FIG. 13, but an example of such a sensor is shown in the embodiment of FIG. 14 to be described below. Open-loop implementations of system 1300 and other systems herein are possible in other embodiments.

FIG. 14 shows a breathing entrainment sonification system 1400 that implements a breathing entrainment biofeedback loop in an illustrative embodiment. This diagram depicts an overall breathing entrainment sonification system configuration based on a breathing entrainment model, such as, for example, a valence/intensity model in which a primary entrainment cue is mapped to an intensity parameter, and an auxiliary entrainment cue is mapped to a valence parameter. It is to be appreciated, however, that numerous other types of entrainment sonification models can be used in other embodiments.

The breathing entrainment sonification system 1400 comprises a sonification processor 1402 coupled to an audio device 1404 that includes at least one speaker. The sonification processor 1402 is configured to analyze feedback signals received from one or more sensors 1406, each illustratively referred to as a "peripheral," and possibly from one or more other peripherals of other types. The sonification processor 1402 includes an analysis stage 1410 for generating entrainment and auxiliary components of the type previously described in conjunction with FIG. 13. Such components are provided to a synthesis engine 1412 that generates one or more signals for driving the audio device 1404.

In the system 1400, sound is generated by the audio device 1404 and a user 1405 listens to the sound and interprets the primary and auxiliary sound cues contained therein. The user 1405 responds to the sound cues which provide instruction and feedback to the user 1405 on how he or she should perform an activity. The activity of the user 1405 is then measured by the one or more sensors 1406 and possibly other peripherals which provide feedback to the sonification processor 1402 as illustrated in the diagram. The analysis stage 1410 measures activity changes and provides further processing to generate mapping signals for the sound components, including entrainment and auxiliary components. The sound components are fed in as inputs into the synthesis engine 1412 where they are mapped to sonic gestures or other types of sound cues.

A wide variety of different sensors and/or other peripherals can be used in illustrative embodiments, examples of which are provided elsewhere herein. Also, the term "sensor" as used herein is intended to be broadly construed, and accordingly can encompass a wide variety of sensing devices of different types and configurations. As indicated above, an open-loop implementation of system 1400 is possible, in which the one or more sensors 1406 may be eliminated. Some implementations of system 1400 in other embodiments can eliminate the one or more auxiliary components and utilize only an entrainment component.

Figure 15:
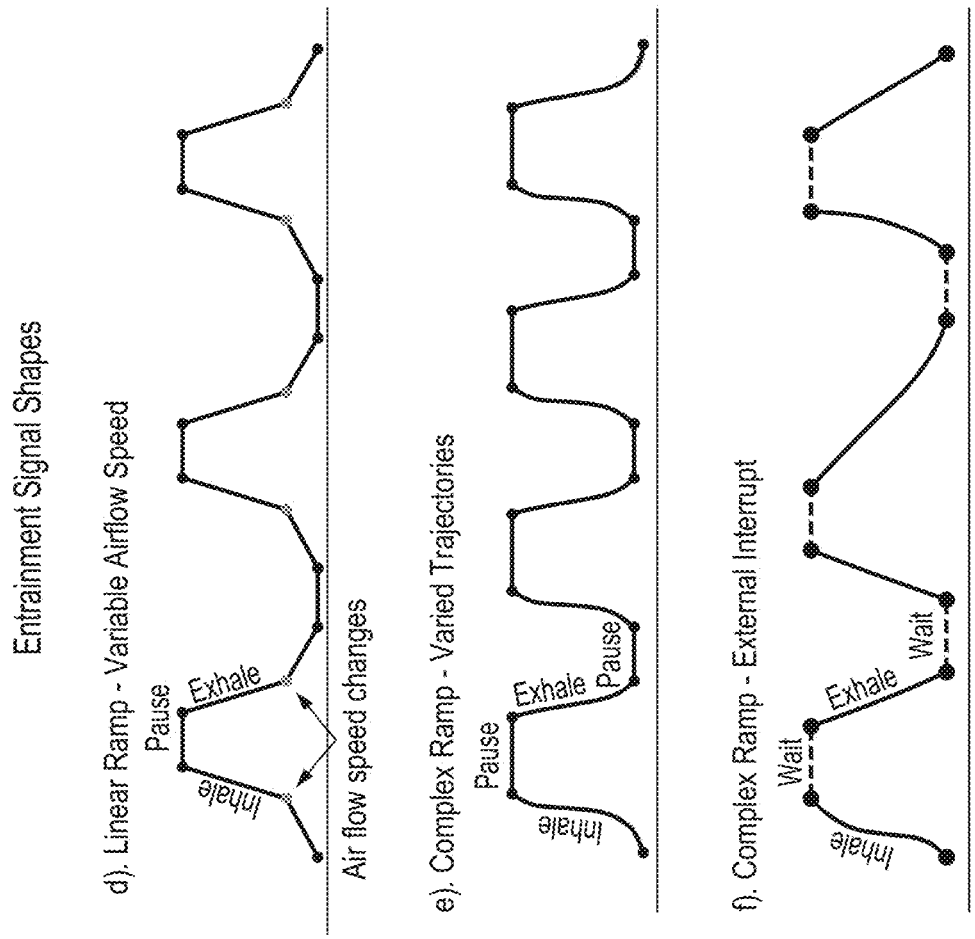
Figure 15:
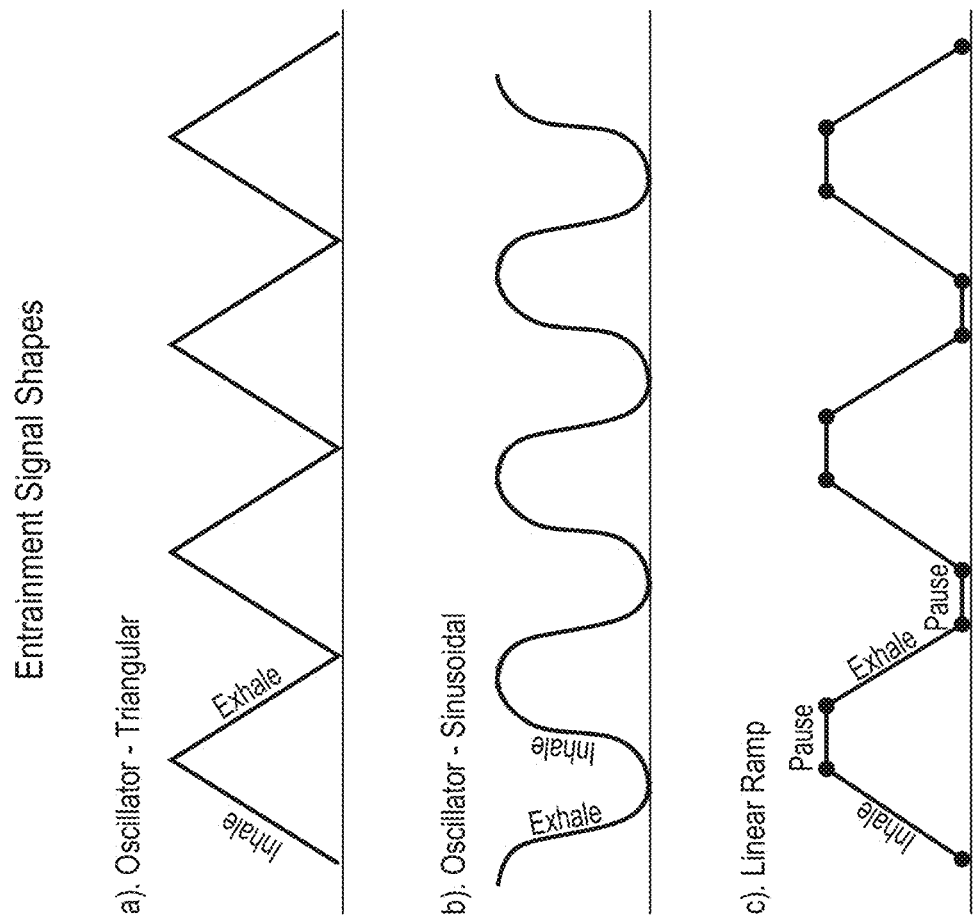

FIG. 15 shows examples of entrainment signal shapes utilized in breathing entrainment systems such as systems 1300 and 1400 in illustrative embodiments. These are various different types of signals which can be used to guide breathing air flow in and out. Such examples include entrainment signals having rising portions corresponding to respective inhale phases of a desired breathing pattern and falling portions corresponding to respective exhale phases of the desired breathing pattern.

A given such entrainment signal of FIG. 15 can comprise a triangular oscillator signal as shown in example (a) or a sinusoidal oscillator signal as shown in example (b). A linear ramp signal with pause phases between adjacent instances of the inhale and exhale phases can be used, as shown in example (c). Another type of linear ramp signal that can be used as an entrainment signal in illustrative embodiments comprises one or more variable air flow speed changes as shown in example (d). Other types of entrainment signals include a complex ramp signal with varied or otherwise variable trajectories as shown in example (e), and a complex ramp signal with one or more external interrupts as shown in example (f). Combinations of these and other entrainment signals can also be used, and the particular examples of FIG. 15 should therefore be considered as non-limiting illustrations only.

Figure 16:
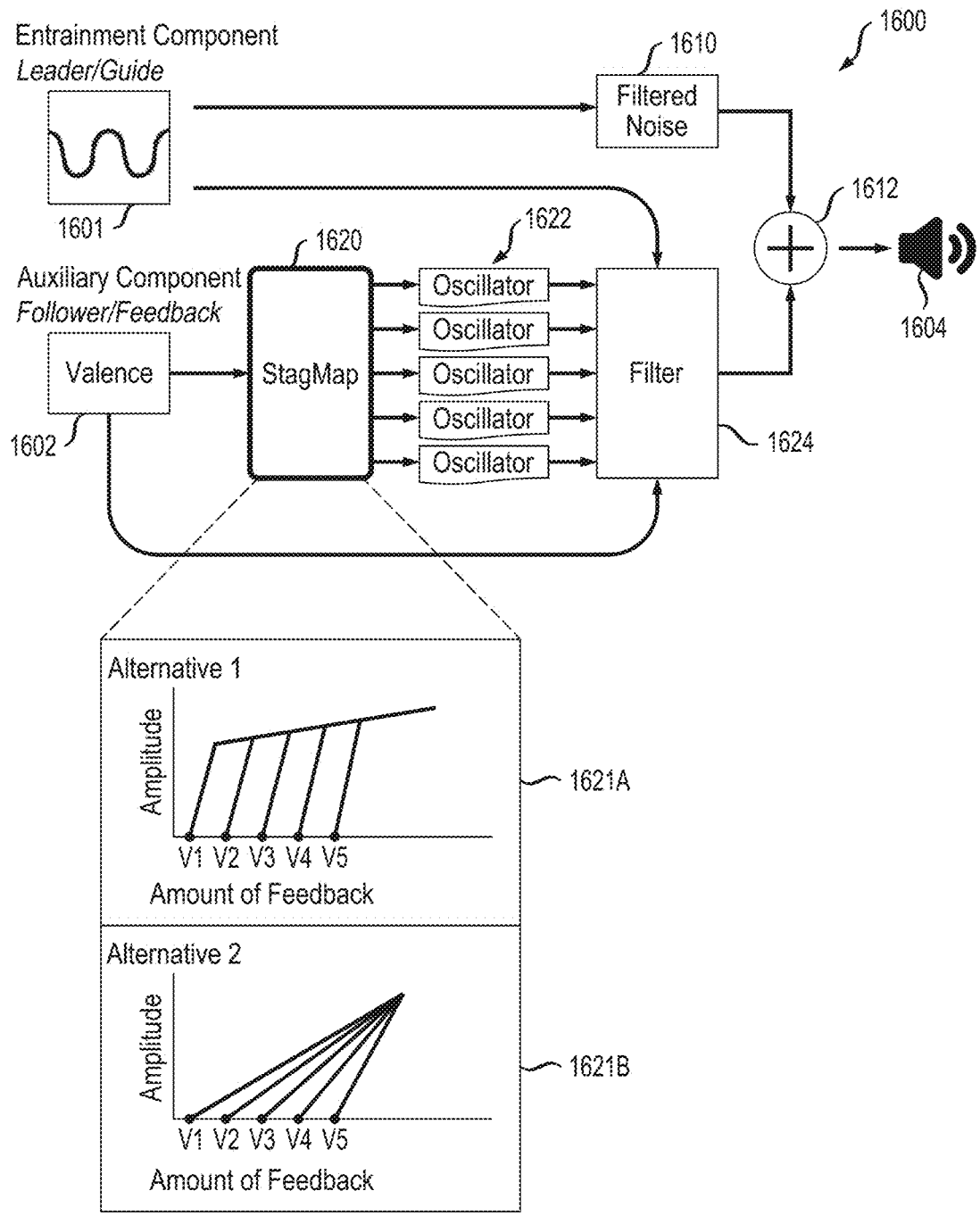

FIG. 16 shows an implementation example of a breathing entrainment sonification system 1600 utilizing a breathing entrainment model in an illustrative embodiment. In this embodiment, system 1600 comprises an entrainment component 1601, illustratively providing a "leader/guide" function, and an auxiliary component 1602, illustratively based at least in part on valance of a valence/intensity model as described elsewhere herein, and providing a "follower/feedback" function. The system 1600 further comprises an audio device 1604 that includes at least one speaker.

The diagram in FIG. 16 illustrates the signal flow of the breathing entrainment model for this particular implementation example. The entrainment component 1601 is applied via a filtered noise component 1610 to a first input of a signal combiner 1612. The auxiliary component 1602 is coupled to a mapping component 1620, illustratively denoted "Stag-Map" in the figure, which drives a bank of oscillators 1622 that have their respective outputs coupled to respective corresponding inputs of a filter 1624. The filter 1624 also receives as its other inputs the entrainment component 1601 and the auxiliary component 1602. An output of the filter 1624 is applied to a second input of the signal combiner 1612, which generates a composite signal for driving the audio device 1604. The mapping component 1620 provides a staggered mapping function that illustratively includes at least two alternative mappings 1621A and 1621B, also referred to as Alternative 1 and Alternative 2, respectively. Each of these alternatives provides multiple different mappings of valence to signal amplitude based at least in part on amount of feedback as illustrated.

Figure 18:
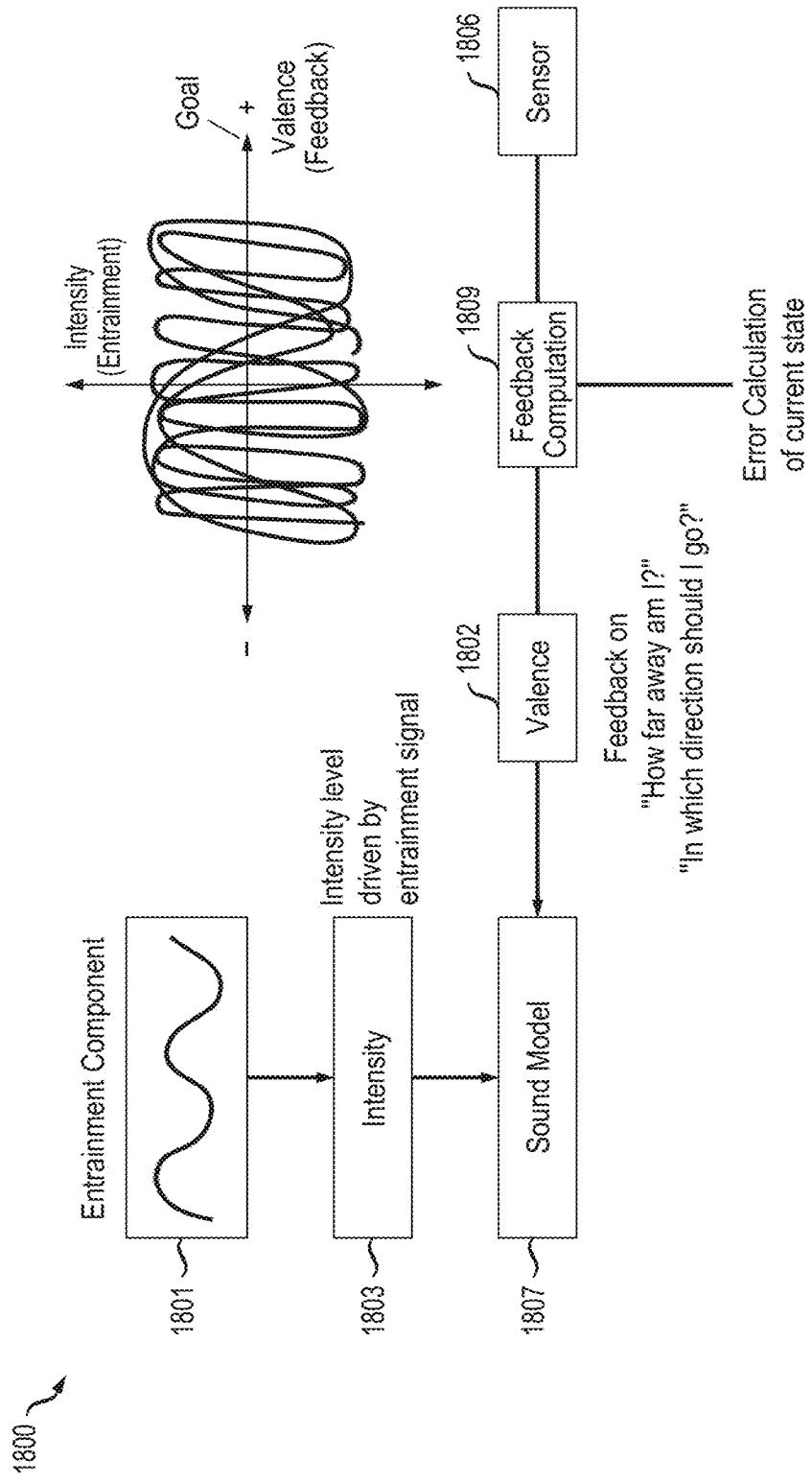
Figure 19:
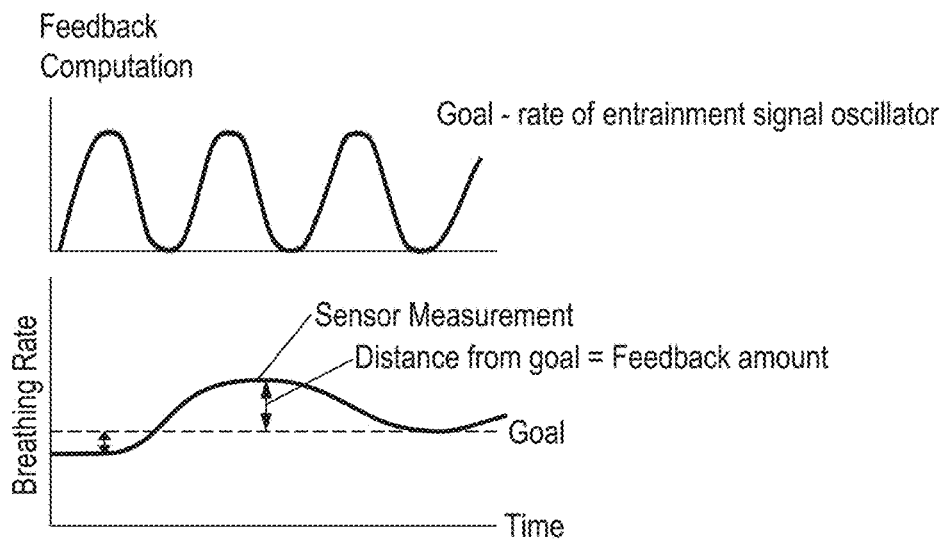

Additional details regarding the operation of system 1600 can be found in FIGS. 18 and 19, which show the entrainment component and auxiliary components mapped to valence/intensity emotion model parameters.

In some embodiments, the different sound cues are constructed by mapping various combinations of sound design techniques to parameters controlled by the entrainment and auxiliary components. Examples of sound design techniques utilized to convey information include timbral density, tonality vs. nosiness, timbre heterogeneity, spectrum morphing, event density, formant filtering and synthesis, high/low pitch, spectrum distribution, rate, tempo, frequency, relative phase, filter sweeps, note length, note distance, randomness, articulation, loudness, pitch height, number of voices, pitch distribution, and spatialization mappings, although numerous other sound characteristics can be used.

The entrainment component and the auxiliary components of illustrative embodiments will now be described in greater detail.

Entrainment Component

An entrainment component (e.g., leader) illustratively comprises a periodic control signal intended to guide breathing activity. The periodic signal illustratively outlines the shape of a breath, and is mapped to continuous parameters in the sound model.

The entrainment component drives a strongly implied gesture in the sound model, outlining the trajectory of an inhale, exhale and pause times in-between breaths. This is achieved by mapping the oscillating leader signal to musical parameters which carve out a trajectory a user can readily perceive in the overall sound.

Musical parameters associated with up and down movement may be related to in and out movement.

The entrainment component in some embodiments is parametric and may be controlled in real-time. These parameters may be set at the beginning of exercise or be dynamically controlled throughout the exercise.

The entrainment component can be configured to adapt to a variety of breathing exercises which are outlined by different signal shapes. An upward slope signals an inhale, a downward slope signals an exhale, while no change in slope relates to a pause or hold time in-between breaths.

Once a breath shape signal for a given exercise has been determined, the waveform may be repeated to create a continuously changing signal.

Different entrainment signal slopes cue different speeds of airflow. See the examples illustrated in FIG. 15, which were introduced above.

These entrainment signal shapes each generally include a repeated signal used to synchronize breathing.

For example, a low frequency oscillator entrainment signal can be based on a table-lookup algorithm with some form of interpolation (e.g., linear, cubic, etc.) The entrainment component may take the shape of common oscillators including triangle and sinusoidal waveforms, as illustrated in respective examples (a) and (b) of FIG. 15. Amplitude can influence how dramatic the breathing gesture cue is. The "dramatic-ness" of the entrainment cue may be reduced if the user does not need to follow the breathing cue anymore to achieve a desired outcome. The amplitude of the entrainment signal being gradually reduced after sleep onset is detected. The frequency of the oscillator can be adjusted during the session to correspond with the intended breathing exercise, e.g., the frequency may gradually decrease over time if the breathing exercise is designed to slow down the user's breathing.

Other examples include ramping entrainment signals, illustratively comprised of calculated line segments, typically with breakpoints in units of time or as a ratio relative to the other segments of a breath cycle. Ramp signals may be generated in real-time by interrupts, messages received by an external protocol with information to shape the inhale and exhale ramps. They can include a wait portion, where the signal waits for input from an external interrupt before it continues with the next line segment or group of segments. This behavior can be used in situations when breathing is correlated with muscle contraction (e.g., exercise equipment). Inhale (ramp up), exhale, (ramp down), and hold times (pauses) may be specified by providing the ratio values for each of the parts of the breath cycle or specifying time for each section of the breathing cycle before beginning exercise. Ramping entrainment signals can include linear ramps, which have linear line segments between points, as in example (c) of FIG. 15. More complex ramps include ramps with varied trajectories, e.g. multiple different slopes (or speeds) for inhaling and/or exhaling (fast to slow air flow), as illustrated in examples (d), (e) and (f) of FIG. 15. These and other complex ramps can be configured utilizing hand drawn curves, exponential curves, Bezier curves, or a wide variety of other curve types.

Although only a single entrainment component is referred to above, it is possible in some embodiments to use multiple such components.

Auxiliary Components

An auxiliary component (e.g., follower) illustratively comprises a second continuous sound cue influenced by an external input, functioning to provide feedback to the user about their progress or current status. For example, an auxiliary component can be used to provide an indicator of the degree which the user is doing the breathing exercise correctly, thereby conveying progress and/or adjustment information. Progress and/or adjustment can be based at least in part on physiological state determined from a biosensor, or can be time-based if there is no biosensor input available. As mentioned previously, numerous other types of sensors can used, including, for example, RF sensors.

An auxiliary component does not overpower or cloud the entrainment component in the sound model but modifies the overall sound so that the user is aware that something has changed.

Figure 17:
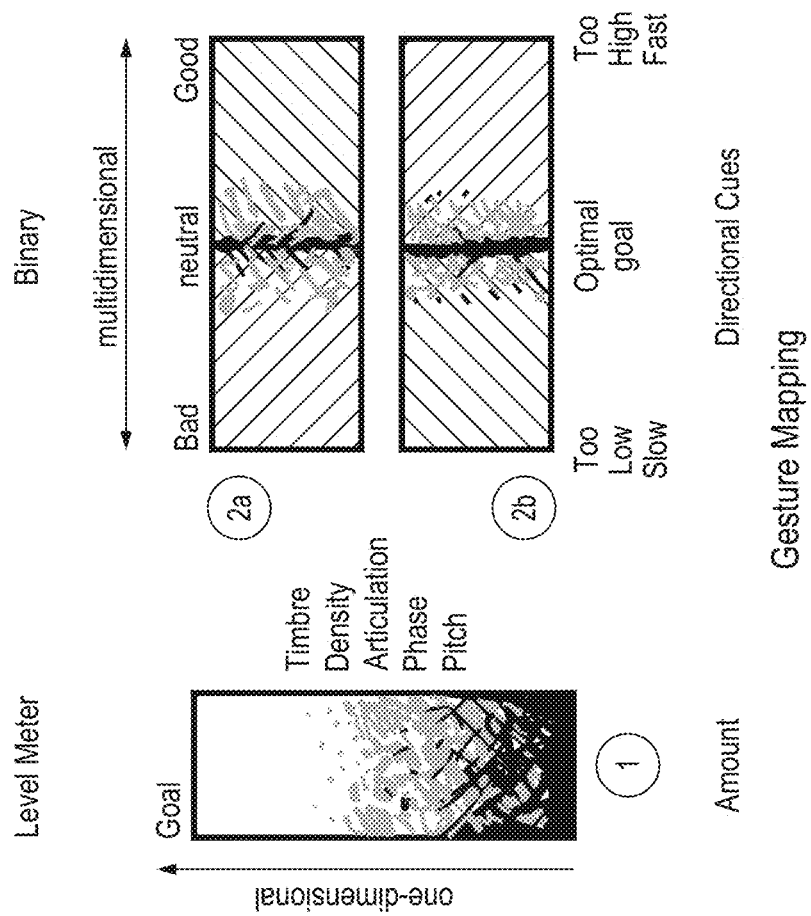

FIG. 17 illustrates examples of two major ways in which the user can interpret the information conveyed by a continuous auxiliary component: progress and adjustment. See (1) vs (2a) and (2b) in FIG. 17.

There can be multiple auxiliary components in a single model. For example, two separate auxiliary components are utilized in some embodiments, such as the illustrative embodiment of FIG. 13.

Different types of progress can be conveyed, as illustrated in FIG. 17. For example, auxiliary components may be perceived as unidirectional or bidirectional to provide information to the user about progress and adjustment instruction. FIG. 17 shows different ways in which the listener can perceive the feedback sound cues. Amount in (1) can be related to progress, while directional cues in (2a) and (2b) can be related to adjustment.

With regard to progress, the general magnitude of an auxiliary component can answer questions relating to progress of the user. Such questions are implicitly posed by the user as he or she participates in an activity.

For example, one question of interest to a given user is "How am I doing?" The magnitude of the sound cue can depict if a user is doing good or bad. Noticeably different regions on the progress meter can signal if the user is close to or far away from the goal. The user can hear from the progress meter if their activity is being done correctly or close to correctly.

Another example of a question of interest to a user is "How far away am I from my target goal?" The continuous auxiliary component offers more resolution on quantitative information. The continuous control signal allows for users to hear the distance they are away from the goal to provide awareness the sense of how far away they are from the goal or optimal state. Duration can be set as a target goal to convey to the user how much time is left in the activity.

With regard to adjustment, the position on a multi-state auxiliary component can provide instructional information to the user about how they should adjust their activity, as illustrated in FIG. 17.

Figure 20:
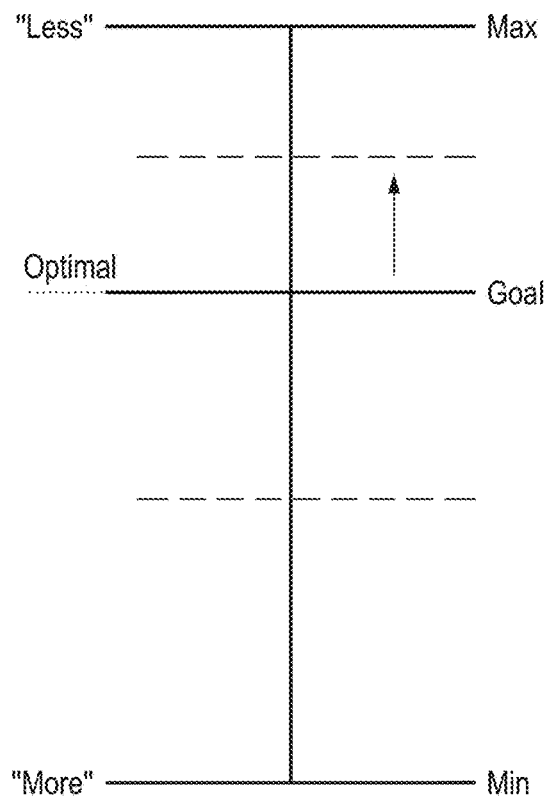

An example of a question in this area is "How should I adjust my breathing?" Interpolated different regions controlled by continuous auxiliary component can provide feedback cues to indicate whether breathing is faster or slower than it should be. A bi-directional feedback component can signal to the user that they need to go faster or slower (and how much faster or slower). The directional cues portion of FIG. 17 shows an example of bi-directional sound cues where the goal lies somewhere in the middle (~0.5) so a user can tell if he or she is are breathing too fast (<0.5) or too slow (>0.5). The position of goal on a slider from 0-1 may not be exactly at 0.5, and there may be a bias to the left or right. Another example shown in FIG. 20 illustrates a custom goal positions diagram. This diagram illustrates other situations where the position of the goal state on a feedback meter may be customized to some other location between the minimum and maximum values.

As noted above, various types of external inputs can be applied to the auxiliary components. Examples of external inputs into the auxiliary components include data streams that encapsulate information about the current status or progress of the user during the exercise. Inputs relate to the intended outcome or goal of the breathing exercise, or any other mindfulness related activity. There may be different breathing exercises for different situations which require different combinations of peripherals to convey progress. Different intended outcomes (goals) from the breathing exercise may include synchronization (entrainment), relaxation, energizing, focus, or meditation, arousal or simply doing the activity for a given amount of time. A wide variety of different inputs can be used, including by way of example various measurable parameters that relate to intended outcome of the breathing activity.

Various metrics can additionally or alternatively be used, including by way of example one or more of:

1. Relaxation, stress and sleep onset and stage (derived from one or more of the following: EEG, GSR, EMG, PPG, EKG, other heart sensor).

2. Entrainment amount as reflected in breathing rate (derived from one or more of the following: EKG, conductive or resistive respiration belt, accelerometer, gyroscope, RF sensor, camera, pressure sensor); walking rate (derived from same sensors above); and other movement rate(s).

3. Time (timers, passage of time, etc.) if goals are time-based.

4. Focus and meditation amount (via EEG).

5. Movement amount.

6. Increased heart rate variability (HRV).

7. Lower blood pressure.

8. Reduced muscle tension.

9. Any other metric which relates to an intended outcome of the breathing exercise.

Again, the foregoing and other listings herein are examples only, and other arrangements can be used.

Although multiple auxiliary components are referred to above, it is possible in some embodiments to use only a single such component.

FIGS. 18 and 19 illustrate an implementation example based on mapping using a valence/intensity emotion model as described elsewhere herein. A two-component breathing entrainment sonification system in an illustrative embodiment can use such a valence/intensity emotion model. In such an embodiment, the entrainment component can be mapped to global intensity parameter, while the auxiliary or feedback component can be mapped to valence. The diagrams of FIGS. 18 and 19 illustrate the signal flow for this two-component breathing entrainment sonification system using the valence/intensity emotion model. Other types of models can be used in other embodiments.

Referring initially to FIG. 18, a breathing entrainment sonification system 1800 in this embodiment comprises an entrainment component 1801 and an auxiliary component 1802 based at least in part on valence using the above-noted valence/intensity emotion model. The model as illustrated by the graph in the upper right portion of the figure is configure to map the entrainment component 1801 to an intensity parameter, and to map the auxiliary component 1802 to a valence parameter.

In the system 1800 utilizing the valence/intensity emotion model, an intensity level 1803 is driven by an entrainment signal of the entrainment component 1801, with the result being input to a sound model 1807. A sensor 1806 provides input to a feedback computation module 1809 that is configured to perform an error calculation for a current state, and also to drive auxiliary component 1802 to generate feedback as indicated. Such feedback is also provided to the sound model 1807, which is utilized to adjust one or more characteristics of at least one of the entrainment component 1801 and the auxiliary component 1802.

As indicated previously, entrainment sonification systems such as system 1600 and system 1800 described above can alternatively be configured in other embodiments to utilize only entrainment components, and/or to utilize an open-loop arrangement rather than a closed-loop arrangement.

Turning now to FIG. 19, an example of the feedback computation is illustrated. The upper portion of the figure shows the goal as a desired breathing pattern characterized by a rate of entrainment signal oscillator. Actual breathing rate as determined from sensing data provided by sensor 1806, and an amount of feedback is determined as the distance between a sensor measurement and a horizontal dashed line corresponding to the goal. The absolute value ("Abs") of the rescaled distance conveys an indication to the user as to how far off from the goal that user is based on the sensor measurement. The rescaled distance itself can be positive or negative relative to the goal and indicates to the user a direction in which the user should move with its breathing (e.g., faster or slower) order to get closer to the goal.

FIG. 20 illustrates custom goal positions that may be used in some embodiments. This diagram shows how the position of the goal state on a feedback meter may be varied. For situations where the goal is not at the maximum, minimum or midpoint of a feedback slider, the goal region may be customized to be an arbitrary point between the maximum and minimum. The horizontal goal arrow in this embodiment may therefore be implemented as a slider or other control mechanism in a user interface of a mobile telephone, tablet computer or other type of computer that implements at least a portion of the breathing entrainment sonification system.

Figure 21:
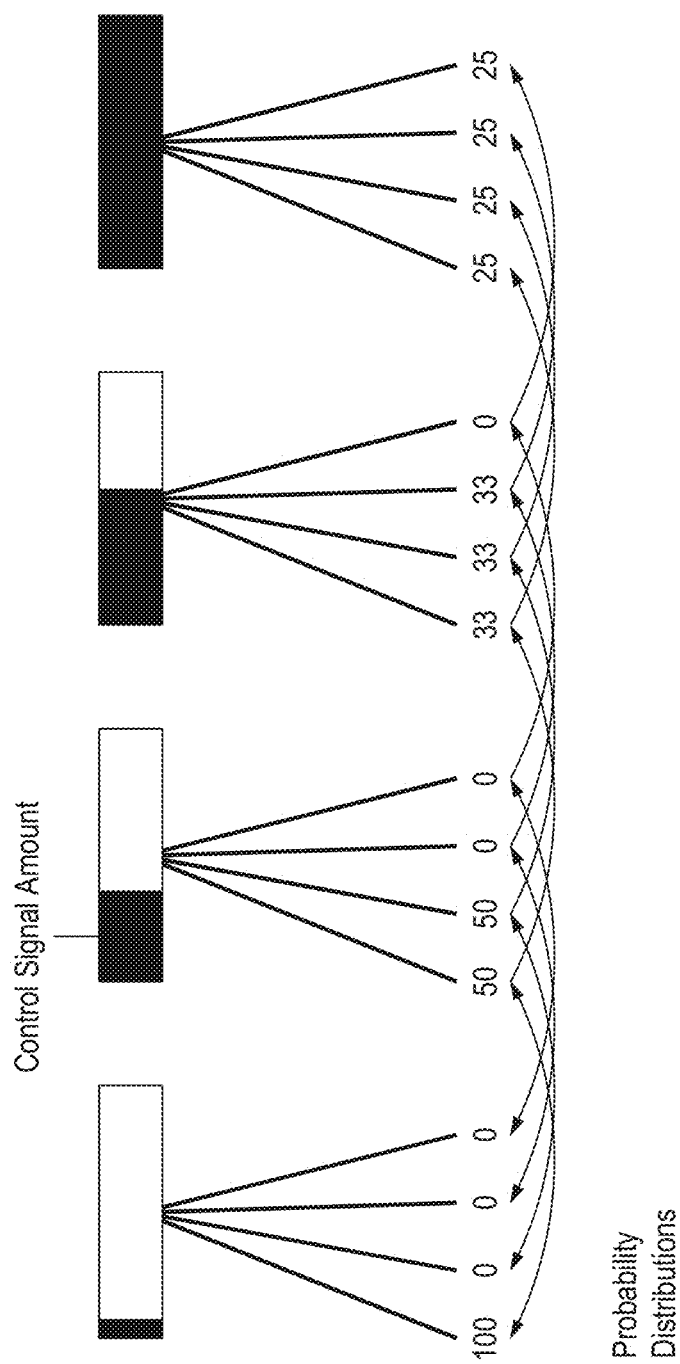

FIG. 21 shows an example of state interpolation that may be used in illustrative embodiments. This diagram shows density distribution mappings which illustratively correspond to an example implementation of a mapping component, such as the StagMap of FIG. 16. Different states are associated with regions having values which always add up to 1. It is possible to interpolate between different states to create different regions with noticeably different characteristics.

Figure 22A:
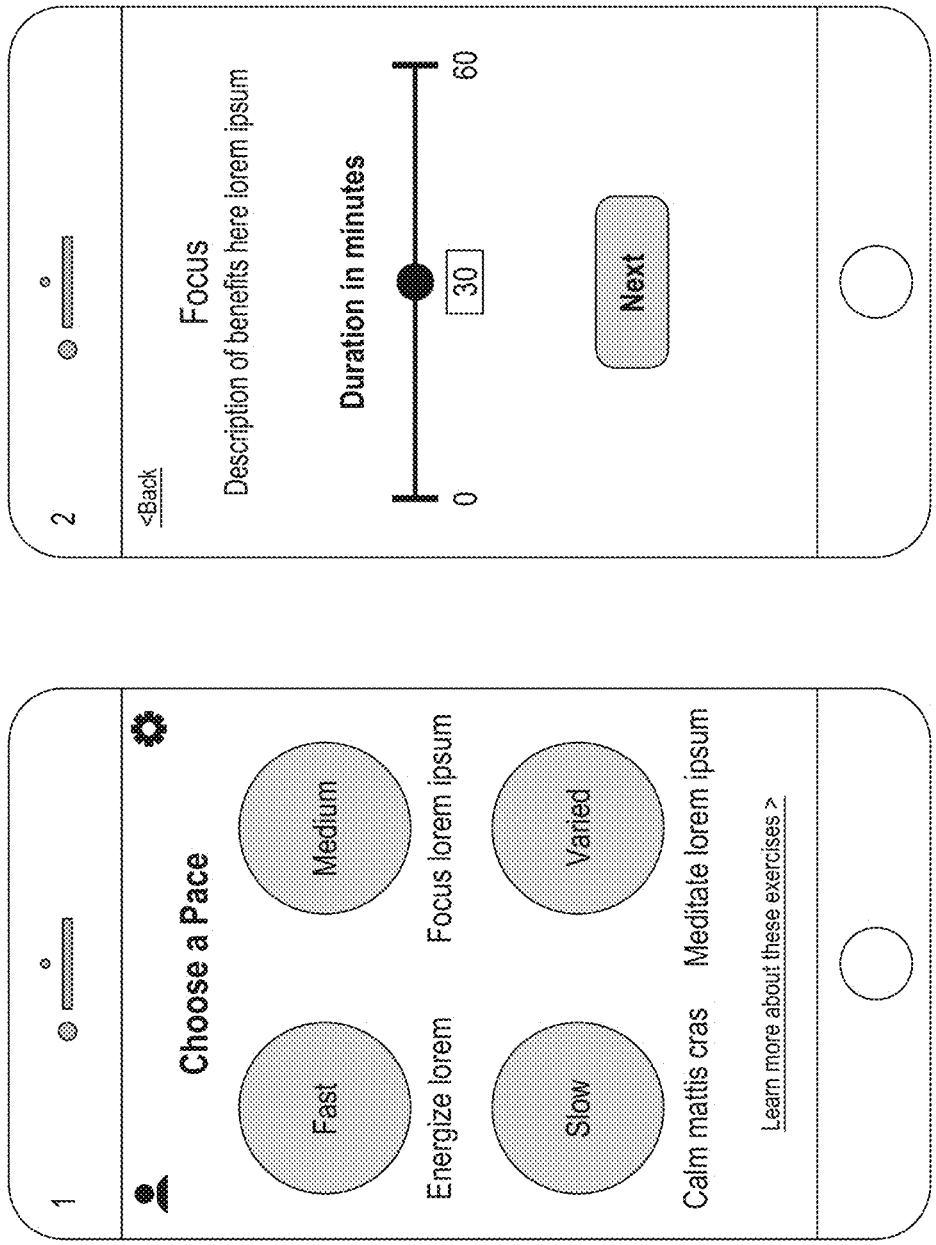
Figure 22B:
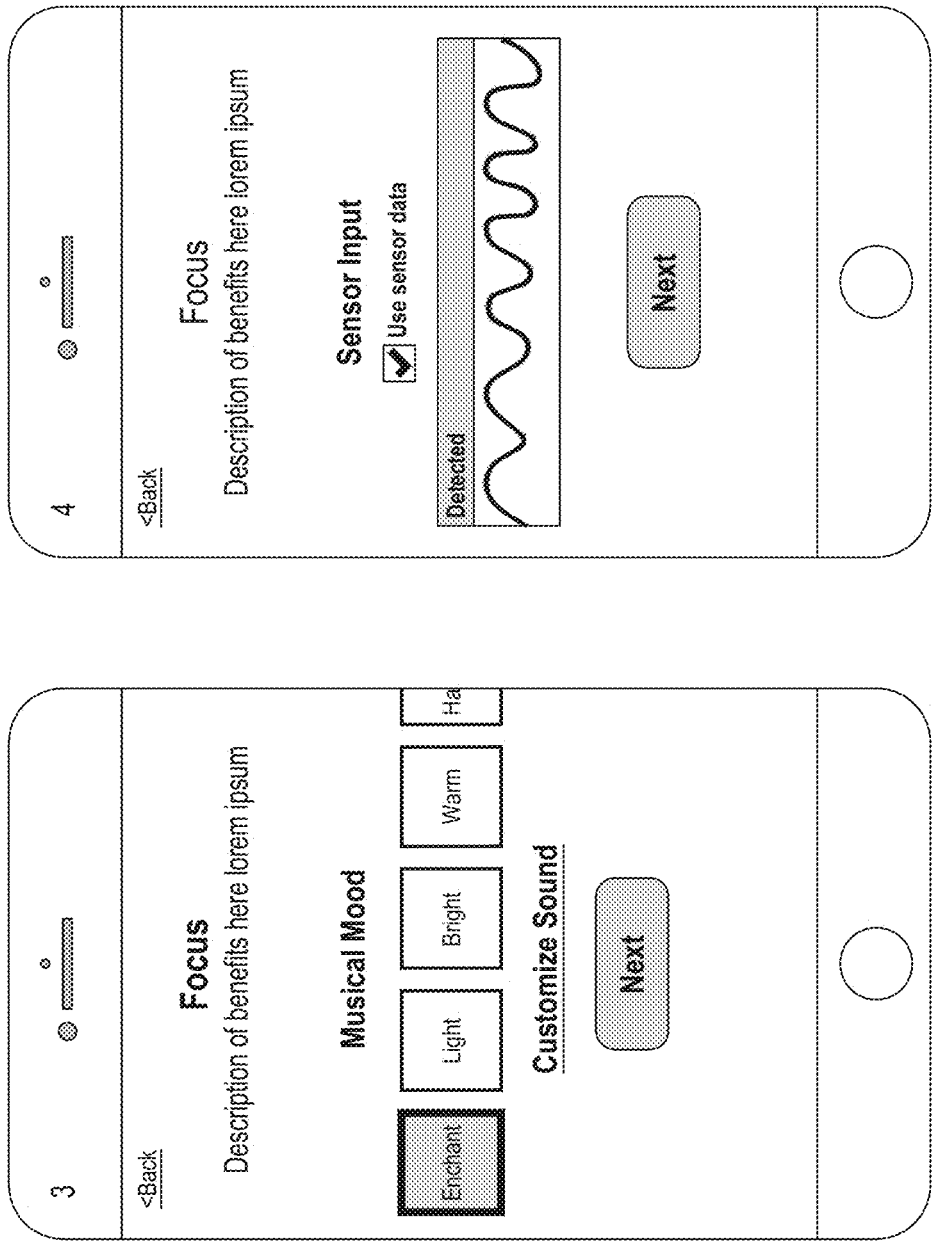

FIG. 22 shows customized interface examples in illustrative embodiments in which the interface is on a mobile phone, although a wide variety of other types of user devices with different interfaces can be utilized in other embodiments. The baseline entrainment sound and feedback components' sonic attributes can be customized to fit different musical preferences. FIG. 22 more particularly comprises four distinct screenshots, two in FIG. 22A and two in FIG. 22B. Screenshot #1 of FIG. 22A shows a portion of an interface allowing a user to choose a pace, and screenshot #2 of FIG. 22A shows a portion of an interface allowing a user to adjust focus in terms of duration. Screenshots #3 and #4 of FIG. 22B show portions of an interface allowing a user to adjust focus in terms of musical mood and sensor input, respectively.

Numerous alternative arrangements are possible. For example, simple customization may involve selecting different presets which modify the mood of the overall sound heard (see #3 in FIG. 22B).

It is also possible to morph preset customization. For example, customization may involve gesture-based control over default entrainment sound (without influence by a follower component).

There are a wide variety of different ways in which one may customize the sound. For example, some embodiments utilize a single model with different presets that can be mixed by interpolating values of parameters defining presets. A single model can load in many presets that alter musical parameters different from those being controlled by the leader and follower components. In such an arrangement, users can select and mix up to a particular number (e.g., 4) different presets of the same model. This can be achieved by loading different presets from the same model into a two-dimensional interface where they can explore different combinations of the presets by moving the X/Y coordinate position on a touch screen.

Figure 23:
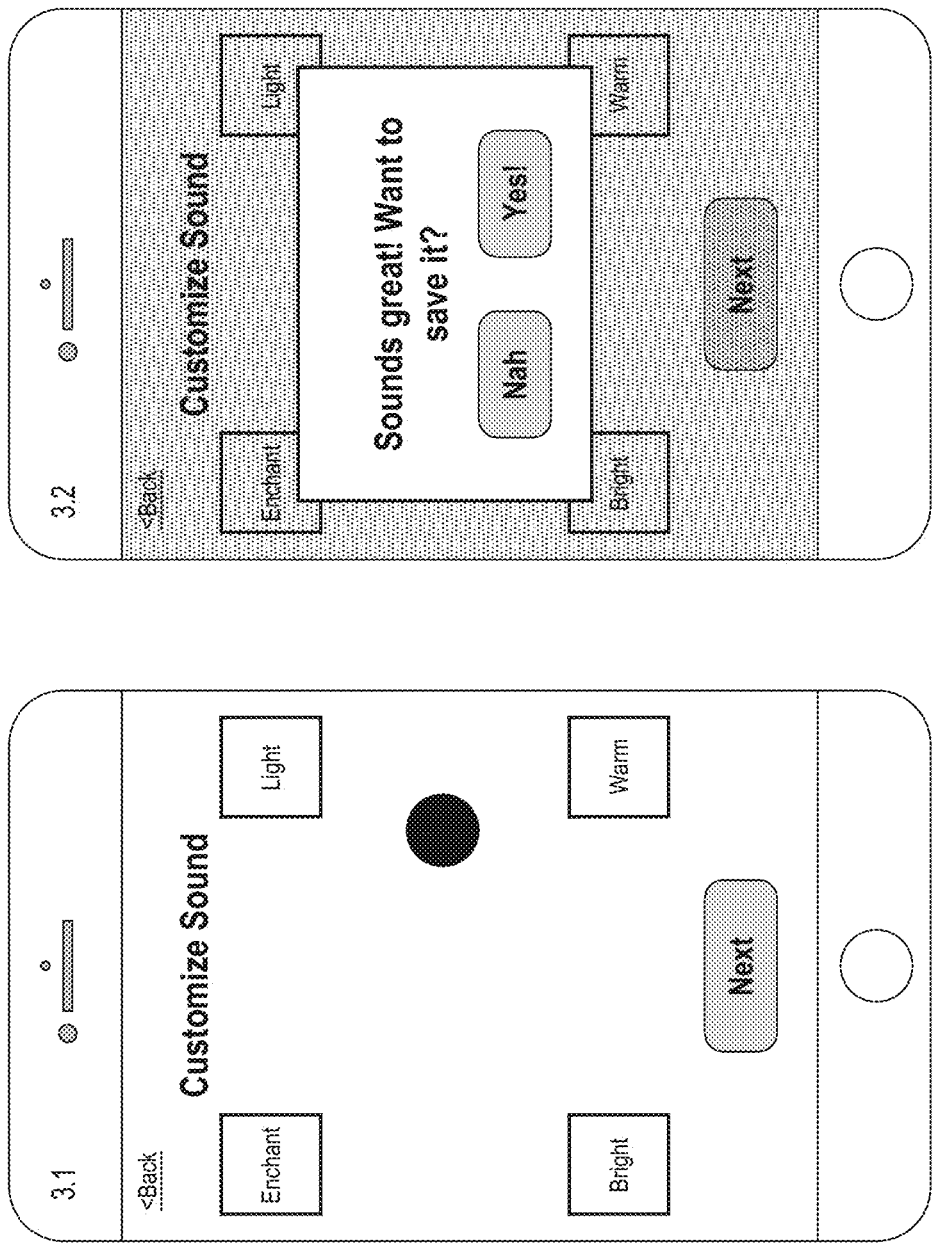

FIG. 23 includes a screenshot #3.1 illustrating an example interface to allow for mixing different combinations of 4 presets where each corner in a customization view can load a different preset. Once the desired mix is achieved, the user can save the configuration using the portion of the interface shown in screenshot #3.2.

It is also possible to utilize multiple models. For example, different models can be used that all feature two high-level parameters. In such an arrangement, each preset has two parameters which user can modify on X/Y.

Figure 24:
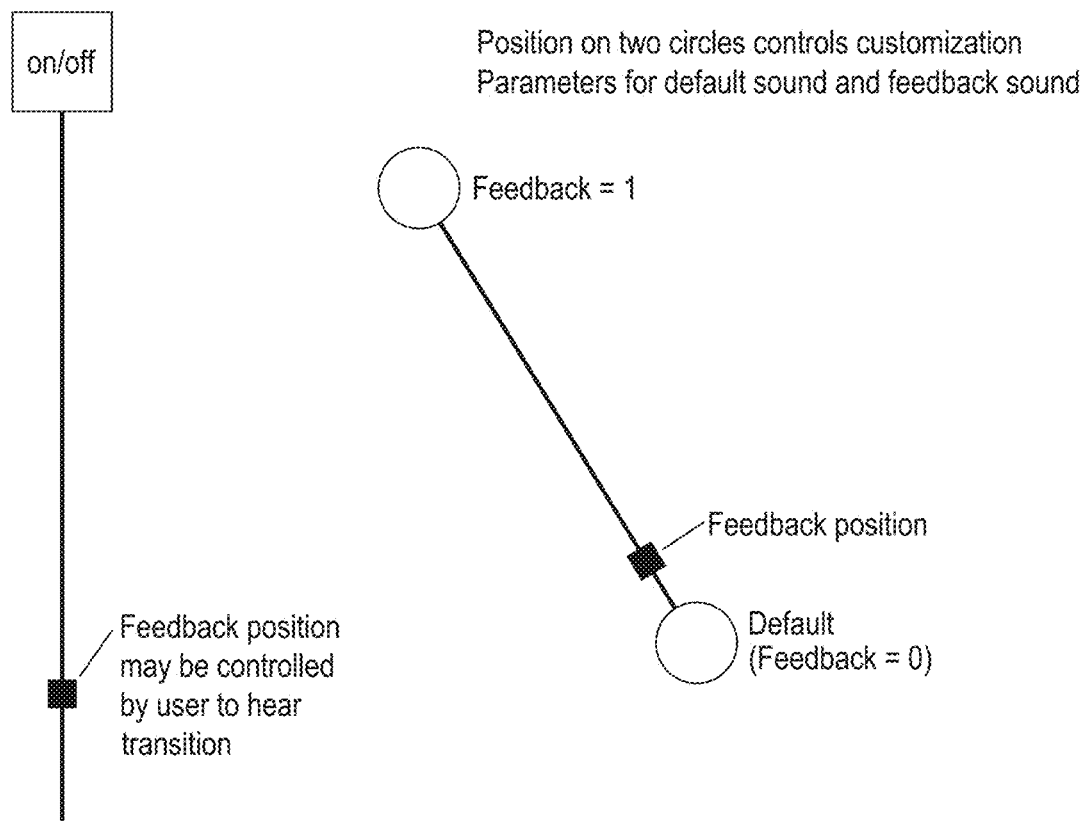

FIG. 24 shows an example of a two-dimensional interface where a user can control a feedback amount to preview sound, so as to allow the user to customize the baseline and reward sounds separately. On the left side of the figure, a feedback position associated with a slider relative to an on/off icon can be controlled by a user in order to allow the user to hear various types of transitions in certain sound cues. The right side of the figure illustrates an arrangement in which a position of a slider between two circles controls customization parameters for respective default sound and feedback sound. One of the two circles in this arrangement denotes a default position with a feedback value of 0 (i.e., no feedback) and the other circle denotes a position with a feedback value of 1 (i.e., maximum feedback). Other customized feedback values are achievable by adjusting a position of the slider between the two circles.

As mentioned previously, these and other particular features of illustrative embodiments are presented by way of example only, and should not be viewed as limiting in any way. For example, although some embodiments are described in the context of breathing entrainment sonification, such embodiments can be adapted in a straightforward manner for use in a wide variety of other entrainment sonification contexts. Also, although some embodiments herein are in the form of closed-loop entrainment sonification systems, other embodiments can be implemented as open-loop entrainment sonification systems which do not require feedback from sensors or other peripherals.

Additional illustrative embodiments will now be described herein with reference to FIGS. 25 through 29. These figures show aspects of musical communication systems and associated applications including breathing entrainment sonification.

Illustrative embodiments provide methods, apparatus, systems and computer program products for musical communication and associated applications. Such embodiments include musical communication systems that are configured to support at least one of a plurality of distinct applications, including, for example, self-regulation of biometrics and biofeedback training applications, with information conveyed through abstract sound providing assistance in relaxation, focus, meditation, fitness and posture; physical therapy and gesture training applications, with sound providing continuous feedback to performing a gesture with minimal error; entrainment applications in which sound is used to synchronize activity to a rate; and navigation applications, with sound providing an awareness of position and directionality of movement in a multi-dimensional space.

These embodiments can be illustratively configured to provide a user with an awareness of a current state and a guide towards an optimal or target state, illustratively through the use of appropriate feedback to adjust user behavior. These and other embodiments can additionally or alternatively provide rewards for achieving and/or maintaining the optimal or target state, and can provide additional or alternative functionality.

Many other musical communication systems and associated applications are supported in other embodiments, including, without limitation, screenless interfaces for augmented reality systems, and environmental monitoring systems.

Figure 25:
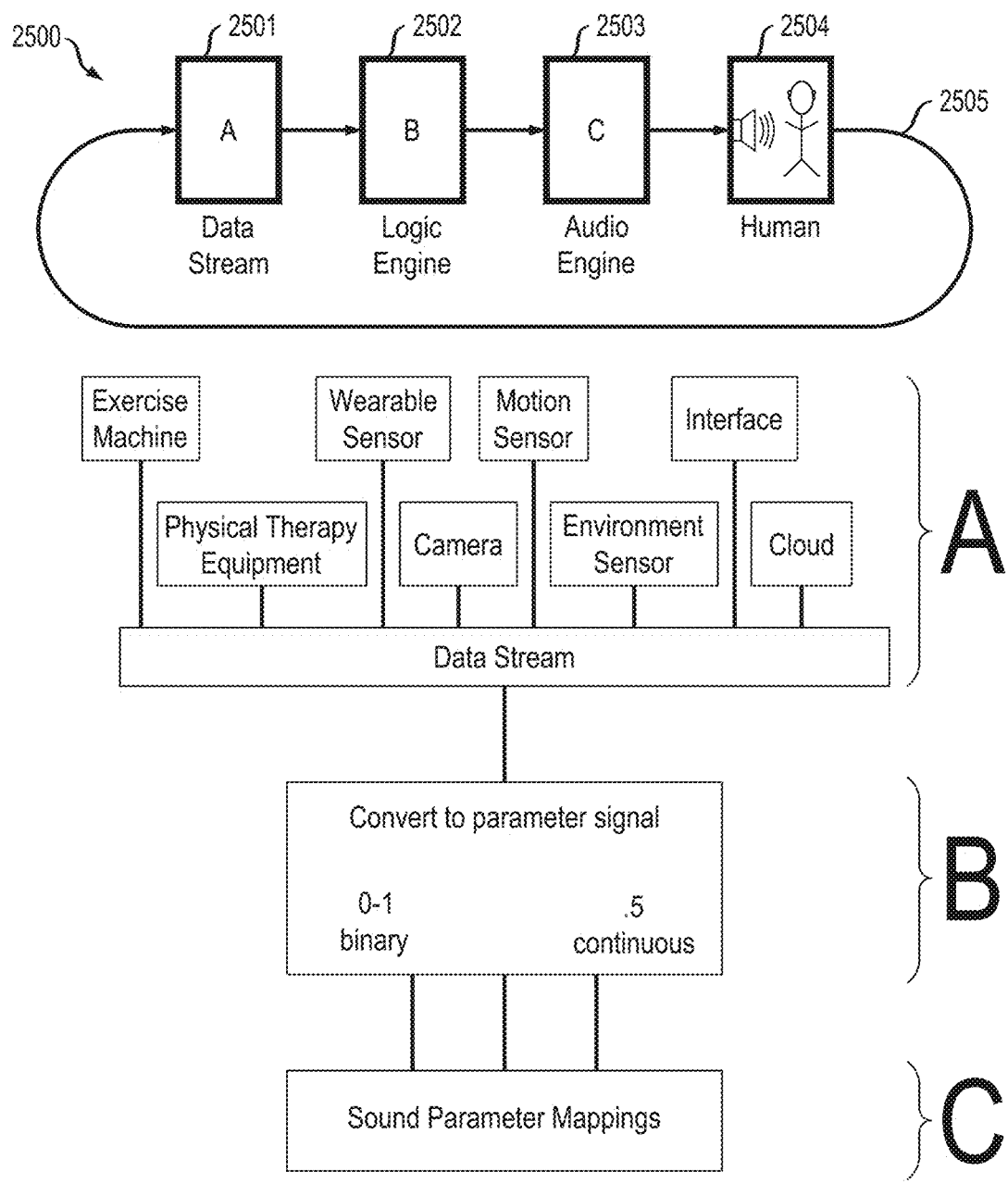
FIGS. 25 through 29 show aspects of musical communication systems and associated applications including breathing entrainment sonification in illustrative embodiments.

FIG. 25 shows an example of a musical communication system 2500 in one embodiment. The musical communication system 2500 in this embodiment comprises a data stream 2501 ("A"), a logic engine 2502 ("B"), an audio engine 2503 ("C") and a human 2504. The human in this system is an example of what is more generally referred to herein as a "user," and accordingly will be referred to as user 2504 below. The user 2504 is assumed to be associated with a processing device, such as a mobile telephone, a tablet computer or another type of computer, including an audio device comprising at least one speaker. Feedback 2505 based at least in part on activity of the user 2504 becomes part of the data stream 2501. The various components of the FIG. 25 system are described in more detail below.

The data stream 2501 is illustratively defined as including a signal comprising at least one numerical value that updates over a reasonably regular period of time. The signal is assumed to be received in real-time. For example, the data may be currently streaming from a real-time data source. Multiple signals of different types can be included in the data stream 2501, such as different signals from different ones of a plurality of sources, such as an exercise machine, physical therapy equipment, a wearable sensor, a camera, a motion sensor, an environment sensor, and interface, and the cloud.

A given signal of the data stream 2501 can also include combinations of signals from these and additional or alternative data sources. Also, there may be multiple distinct instances of data stream 2501 in some embodiments, such as different data streams from respective different ones of the above-noted sources.

The logic engine 2502 performs stream processing. For example, it takes in the data stream 2501 or multiple such data streams and outputs streams of data mappable to parameters in a sound synthesis improvisation model. It can perform functions such as signal filtering, scaling, statistics generation and analysis, and long term analysis. Output signals are mostly continuous in nature, but can also include discrete events sent to the audio engine 2503.

The audio engine 2503 implements at least one procedural sound model involving sound parameter mappings. For example, built-in structures are illustratively improvised on, and streams of improvisations are shaped by inputs coming into the model. Algorithms implemented by the audio engine 2503 are illustratively configured to produce sound cues that listeners can take meaning from. The audio engine 2503 is illustratively configured to provide smooth or seamless transitions between sound states (e.g., from a user experience point of view). For example, audio output sounds can update in sub-milliseconds in some embodiments because the sounds are being synthesized rather than sampled, thereby providing a better user experience that is customizable on a nuanced level.

The ears and brain of user 2504 represents a human audience component of the system 2500. In some embodiments, the user 2504 can have active control over the sound through an interface, but such control is an optional feature. Sounds from the audio engine 2503 produce cues audible to the human ear. The user 2504 interprets these cues and is thereby informed about the current state. For example, state could be used to describe the state of the processed data stream and/or the state of the musical communication system. State in some embodiments could be defined as the state of the data stream in the context of what it is trying to convey, although numerous other state definitions can be used in other embodiments.

Additional details regarding the FIG. 25 embodiment and other illustrative embodiments will be described below.

Figure 26:
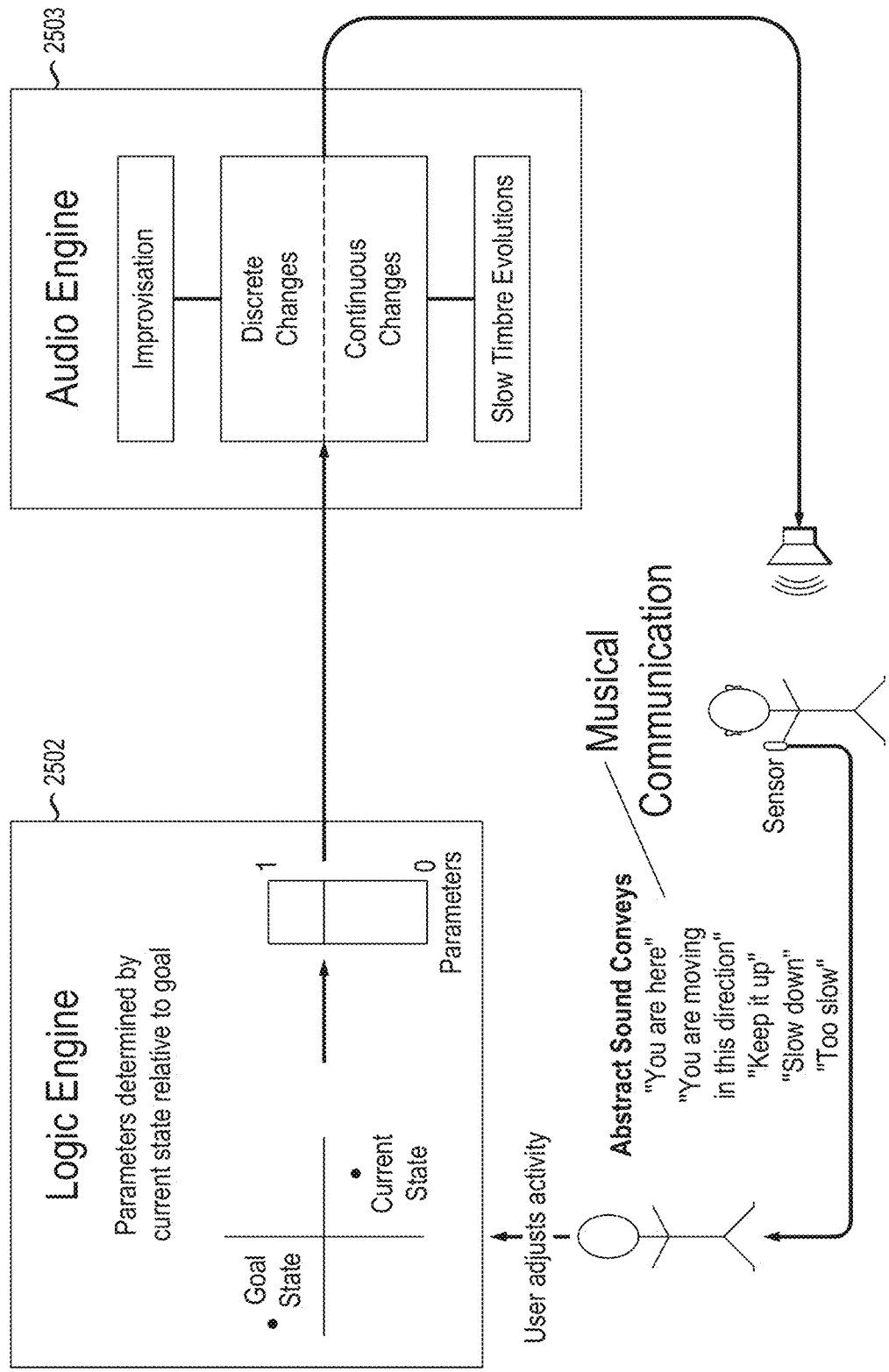

FIG. 26 illustrates example interactions between the logic engine 2502, the audio engine 2503 and the user 2504 within the musical communication system 2500. The audio engine 2503 in some embodiments is implemented in the form of a computer system that synthesizes electronic sound in a procedural way. For example, instead of reading from a pre-determined musical score, a computer generates and improvises new sound and music based on an underlying set of inputs, rules and constraints. The procedural music used in this on context is engineered to bring an intuitive understanding to what the data stream 2501 is conveying.

Streams of music/sound are illustratively modulated in real-time by the input data processed via the logic engine 2502. For example, the logic engine 2502 in this embodiment is configured to generate one or more parameter signals based at least in part on a current state relative to a goal state. A given parameter signal can indicate a distance between the current state and the goal state, or other similar parameter, possibly scaled to fall within a predetermined parameter range such as the 0 . . . 1 range illustrated for one or more example parameters in the figure. The corresponding parameter signals in this embodiment are provided by the logic engine 2502 to the audio engine 2503, which illustratively implements discrete changes and continuous changes, possibly based at least in part on respective improvisation and slow timbre evolutions as indicated in the figure.

Such changes are made audibly apparent to the user 2504 via an audio device comprising at least one speaker, and the resulting abstract sound conveys various types of information to the user 2504, examples of which are shown in the figure. The user 2504 in response to such sound cues adjusts his or her activity in a manner that attempts to drive an updated current state closer to the goal state for that activity.

In some embodiments, the system 2500 is configured to differentiate large gestures consisting of more obvious or noticeable sound cues and musical events, illustratively comprising examples of what are more generally referred to herein as "communications," from smaller, less noticeable changes, illustratively referred to herein as "embellishments," which employ more subtle changes to the sound, and which may involve randomness and jitter used to generate variation in the sound and music. Gesture illustratively refers to a more macro level control in which cues are designed to have clear communicative functions, which could provide a sound guide to follow, such as, for example, "sync with" or "entrain to," or provide feedback to convey the current state of the user or to prompt the user to make an adjustment. The amount of change in such an arrangement may be encoded into one or more corresponding sound cues.

It should be noted that a wide variety of different types of feedback can be provided in illustrative embodiments herein. For example, in some embodiments, feedback in may be driven at least in part by a timer. The timer in some embodiments of this type can be configured by incrementing a slider value mapped to continuous gesture and/or discrete sound cues. Similar to notifications when certain goals are met, the timer may trigger discrete musical events at various subdivisions. As a more particular example, illustrative embodiments can implement musical timers that could be applied to technology such as a microwave or food delivery service when there is a countdown featured. The music can serve to provide a sense of how much time is left in a given task. This timer concept may also be employed in numerous other applications, including, for example, the running, breathing and masking applications described in conjunction with FIG. 29 below.

The logic engine represents the data pre-processing which is done to massage the data into a simple format so that the audio engine can take in as a high-level parameter.

Improvisational aspects relate to variation in the musical notes or score. These features include statistical models, randomness, grammars, etc. that affect the discrete note events in the audio engine. The improvisational components may be used as communication to provide information to the listener or embellishments to promote long term listenability, for example, allowing for the sound/music to play for a long time without ever repeating. Probabilities may be changed dynamically to increase or decrease the likelihood of a note event to occur. These features can be thought of as embellishments or ornaments within predefined structures if they do not inhibit the main communication sound cues so drastically that it clouds the meaning or sense of directionality of the overarching gesture. The structure of meaning embedded in the sounds remain even with the generative components.

Slow evolutions similarly provide constant variation but on a continuous time frame. These slow evolutions can be employed as embellishments if the musical parameters they are mapped to subtly influence the musical system, e.g. changes to them are barely noticeable by the listener. Gradual changes in timbre can occur over time so that the texture is constantly evolving. These can be achieved by having slowly changing control signals influence different continuous parameters. Randomness and jitter signals which change on as faster time frame may be similarity be applied to different parameters to insure that there is not a static timbre. Like the improvisational features which create variation on the note level, the amount of influence of these signals can be minimized so that it does not overpower the overall gesture controlled by changes in the input data stream in order to maintain the communication.

Sound gesture refers to a type of continuous sound cue where the overall perceived change of the sound provides a sense of position and directionality. This illustratively comprises changes of musical events happening in time as well as other features, such as timbre, which are changing continuously. Typically, a single gesture is defined by a control signal which is then mapped to multiple musical parameters. The combined effect of all the musical features moving together, changing as a result from changes in the data stream, create the sense of a gesture. Gesture can provide an awareness of state movement directionality.

The musical communication system in some embodiments shapes sound in a way that can be broken down into two distinct time scales or components, namely, discrete time scales or components and continuous time scales or components, also referred to as respective discrete and continuous layers.

The discrete layer refers to the musical abstraction of a "note," the foundational building block in music theory. This layer concerns itself with things like chords, musical scales, and counterpoint. For example, the discrete layer illustratively denotes "what is played," comprises musical symbolic encoding of a score at the note level, and conveys large changes.

The continuous layer can be largely interpreted as a (perceptually) continuous signal underneath the discrete time layer. Continuous time parameters of the continuous layer map to features like timbral brightness of an instrument playing a note. The continuous layer outlines the gesture of a particular discrete phrase, and can be used to signal a change in state faster than the discrete layer. For example, the continuous layer illustratively denotes "how it is played," comprises fine tune control over sound attributes, and conveys small, nuanced state changes.

Features are controlled in both discrete and continuous time to convey states.

States refer to what that the music or sound generated is intended to convey. There is usually an optimal goal state and the sound generated is intended to convey the users current state with respect to the goal state.

States may be single or multi-dimensional. Logic may be applied to data streams to get it into the right format to be inputted into the musical communication system. A single input may determine the goal, or alternatively a combination of multiple inputs may determine single or multiple goals.

Examples of states that may be utilized in illustrative embodiments include mental state (e.g., emotional state, relaxation level, focus level, stress level); physical state (e.g., activity rate, posture, gesture, amount (amplitude) of movement or change in state, velocity of movement or change in state, angle (gyroscope/accelerometer), GPS location, elevation); virtual position (e.g., position in interface, such as angle/rotation of movement (with respect to previous location), screen area location or location of game element, three or more dimensional location in virtual space); and level meter (e.g., quantifiable data stream, level of something computed, environment condition such as temperature, humidity, light, etc.) Sound features that convey information in some embodiments may be similar to features present in the emotion models described elsewhere herein.

For example, an emotion model can have two high level input parameters: valence and intensity. Most emotions can be depicted with these two parameters: Happy=high valence & high intensity, Sad=low valence, low intensity, Angry=low valence, high intensity, Calm=high valence, low intensity, etc.

Valence can be positive and negative, and related to a goal state.

Intensity is similar to energy.

Both valence and intensity can provide an awareness of current state and movement between states.

Particular examples of sound features include timbre e.g. brightness, harshness, spectral density, articulation; rate/density e.g. tempo, note onset events, number of instrument voices; pitch, e.g. melody, harmonization; and randomization/jitter.

This is only one way in which musical mappings can be constructed to convey meaning. Numerous other models can be used in other embodiments for conveying meaning in contexts outside of emotion that are focused on goal-based activities.

Some embodiments make use of leader and/or follower roles. In such arrangements, sound generated in a musical communication system as disclosed herein can play different functions in goal-oriented tasks.

In the case of a follower, the sound symbolically reflects user state. Sound is intended to mirror a given state, acting like a direct translation of the data into sound and music. Sound provides what is referred to herein as "informative entertainment," where abstract communication of information regarding current state(s) is conveyed to the listener(s) through an entertaining medium. The follower role is mainly for less directed and free-form settings. A goal or optimal state (if featured) likely indirectly relates to input state and may likely involve additional logic algorithms. If applicable, sound may reward user for maintaining goal over time.

In the case of a leader, sound is intended to guide the user towards an optimal state. Sound informs the user how close the current state is to the goal state, and informs the user about a change in state. Sound rewards the user for maintaining goal state over time. The goal/optimal state are more likely to directly relate to input state.

In some embodiments, musical communication technique are classified into the following two categories which are based off of perception of auditory cues: absolute sounds and relative sounds.

Absolute sounds are distinct sound characteristics we can immediately hear and classify. Such sounds facilitate categorical association (instinctive or easily learned intuitive association). For example, sound at given position can provide information about current state without the need for movement, and no reference sounds are needed. Examples include recognizable harmonic, melodic and rhythmic motifs, etc. Absolute sounds may consist of short bursts of sounds with characteristics that symbolize the event or action that has occurred.

Relative sounds are distinct audible changes in sound from a moving state. Movement between states provides information about current state and direction of movement. Relative changes may reflect changes in state with respect to previous state, and/or changes in state with respect to goal state. Relative sounds provide responsiveness and fluid evolutions to a sound driven by a continuous input data stream. Relative sounds provide a sense of gesture that would be more difficult to convey with an absolute sound. Examples include amplitude, pitch, filter cut-off, tempo, rate, articulation, etc. Unlike an absolute sound, a relative sound cue requires some sort of reference to quantify amount of change.

Additional details regarding exemplary applications that may be supported by a musical communication system in illustrative embodiments will now be described. Aspects of these applications involve configuration of the logic engine and/or audio engine. These particular applications and their respective features and functionality are presented as examples and should not be viewed as limiting in any way.

In a valence/intensity application of the type described elsewhere herein, a two input parameter model is designed to convey positivity or negativity of a state and the intensity of the state. For example, in a graphical representation in which an x-axis intersects with a y-axis at an origin point, an x-axis can be used to represent valence, with positive values to the right of the origin point and negative values to the left of the origin point, and a y-axis can be used to represent intensity, with higher intensity values above the origin point and lower intensity values below the origin point. More detailed examples of two parameter emotion models and associated mappings are described elsewhere herein.

In some embodiments of this type, intensity (y-axis) controls pitch height, rate of note onsets, tempo, timbre or brightness. Valence (x-axis) controls amount of randomness of pitch, note envelope or articulation, harshness of timbre, detuning amount, amplitude of certain voices, e.g., bass.

Another example relates to guided entrainment for periodic activities, for a single user. In this application, the system mechanics are configured such that the music/sound/stimulus features a rhythmic element that plays at optimal "goal" rate. The musical communication system detects what rate the activity is actually being performed at and compares it to a goal rate. Sound attributes (e.g., apart from rate) provide cues to the listener about their current rate with respect to the goal.

The function of sound in this embodiment is to guide a single user to perform cyclic activity at an optimal rate (e.g., cycles per minute).

The goal state is illustratively an optimal rate that may be influenced by the activity performed.

For example, the optimal state may be predetermined and not influenced directly by activity being performed. Leader examples in this case include goal determined by fixed state or position, predefined curve outlines changing goal state over time, goal determined by user profile, e.g. sensor calibration or demographic information inputted.

Alternatively, the optimal state may be influenced in real-time by activity performed. A leader/follower example in this case includes one in which the rate of music/sound/stimulus speeds up or slows down with user's activity. The goal is to maintain any rate consistently for a certain amount of time with minimal fluctuation.

Figure 27:
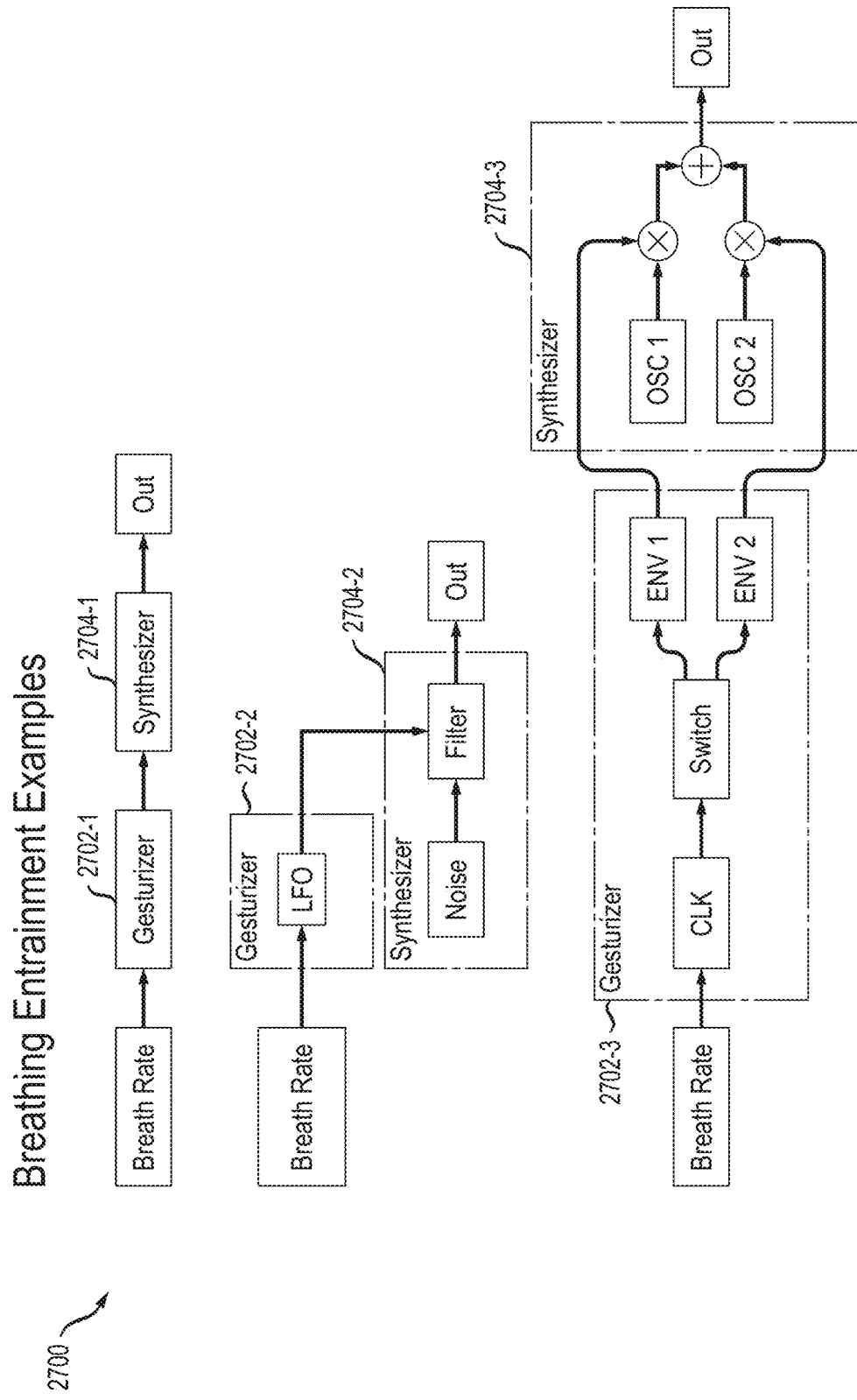

FIG. 27 shows a number of different breathing entrainment examples collectively denoted as breathing entrainment modules 2700. Three different modules are shown, each of which includes a gesture generator ("gesturizer") 2702 coupled to a synthesizer 2704, with the input to the gesturizer 2702 in each module being a "breath rate" signal that illustratively corresponds to a desired breathing pattern.

The first module at the top of the figure is a general implementation comprising a gesturizer 2702-1 coupled to a synthesizer 2704-1. A signal generated by the gesturizer 2702-1 outlines a breathing gesture and controls the synthesizer 2704-1 to guide and/or reflect breathing (sound could play both leader and follower roles). The pattern of inhale and exhale at the input breath rate is mirrored by the gesturizer 2702-1 which produces a variable signal to control the synthesizer 2704-1. Multiple synthesizers may be used in place of a single synthesizer in other embodiments. The gesturizer 2702-1 takes in the breath rate signal and produces a control signal. The control signal generated by the gesturizer 2702-1 may be an oscillator signal, illustratively having a sinusoidal, triangular or custom shape that reflects the ratio of inhales, exhale and hold time in-between breaths, various examples of which were previously described in conjunction with FIG. 15. The ratio between inhales and exhale times may change depending on rate and can be looked up in a table or determined using other techniques.

Each of the other modules in FIG. 27 generally operates in a manner similar to that described above for the first module. However, the second module is more particularly configured with a gesturizer 2702-2 that include a low frequency oscillator (LFO), and a synthesizer 2704-2 that includes a noise source and a filter, with the filter being driven by an output of the LFO of the gesturizer 2702-2, in order to generate an output of the type described above.

In the third module at the bottom of FIG. 27, a gesturizer 2702-3 includes a clock signal source driven by the breath rate signal as shown. The resulting clock signal is fed into a switch which alternates between two parallel envelope signals ENV 1 and ENV 2 that are applied to respective inputs of a synthesizer 2704-3. The two envelope signals are more particularly applied to respective first inputs of two different mixers of the synthesizer 2704-3. Those mixers also receive at their respective second inputs two different oscillator signals from respective oscillators denoted OSC 1 and OSC 2. The outputs of the mixers are combined in a signal combiner to provide the output of the synthesizer 2704-3.

Signals from the gesturizers 2702 in the various example breathing entrainment modules described above may be used to modulate amplitude, timbral spectrum, filter parameters and other sound attributes of the synthesizers 2704.

Another example embodiment provides a running companion, in which music is intended to guide running rate (e.g., steps per minute) while motivating the user to maintain goal rate. The goal rate may be determined by one or more the following: rate(s) may be set by user at start of work out, as a single steady rate or a fluctuating rate determined by a predefined curve. Predefined trajectories of different work out types, e.g. steady rise and fall, rapid increases and decreases etc. can be used.

Figure 28:
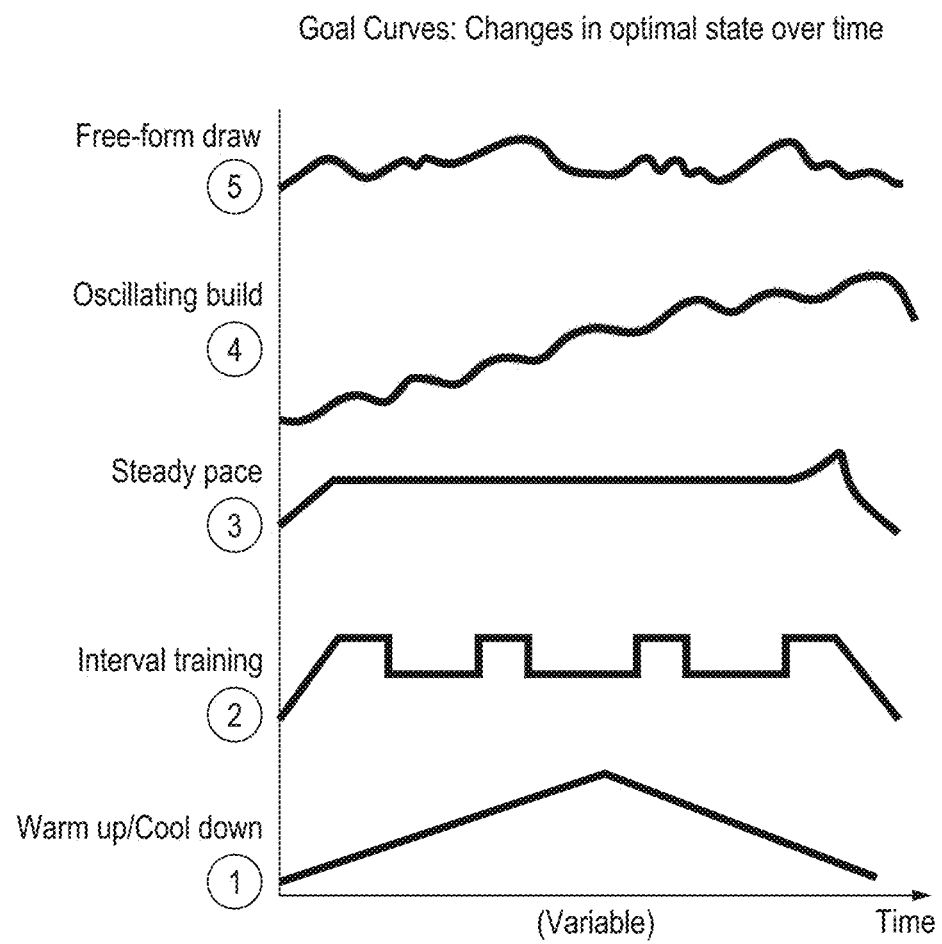

FIG. 28 shows a number of example goal curves, each indicating changes in optimal state over time. The example goal curves illustrated in this figure include a warm-up/cool-down curve, an interval training curve, a steady page curve, an oscillating build curve, and a free-form drawing curve, with these curves being denoted in the figure as respective example 1 through 5. Accordingly, illustrative embodiments can be configured to utilize goal curves determined by preset workout curves with variable time lengths which can be set by the user (examples 1-4). It is also possible to use free-form drawing of an ideal trajectory over time in interface (example 5). Rate(s) may be dynamically adjusted during work out. External logic involving additional input can include heart-rate. For example, optimal heart rate during work out may be determined by sensor calibration, age/demographics and workout time. The aim is keep heart rate in a given range by speeding up and slowing down running. If the detected heart rate is too high at a given point in time, the music signals the user to slow down and vice versa. Third party direct influence, e.g., from trainer or competitor, can also be used.

The generated sounds in this embodiment are intended to convey, for example, how fast you are going (raw steps per minute or speed categories), the need to speed up, slow down (signed deviation from target running speed), rewards, motivation (that you are doing a good job for extended period of time), and completing running milestones (e.g., hitting thresholds for specific running targets).

A given musical communication system in an embodiment of this type provides entrainment functionality, illustratively through rhythmic or cyclic main pulse/beat of music/sound/stimuli at optimal rate e.g. overall tempo. It can utilize directional cues such as absolute sound to give the user a sense of position, and relative sound to instruct the user with features other than tempo, to move faster or slower to reach optimal rate (see 2b. in Gesture Mapping diagram of FIG. 17). In addition, sounds rewards can be provided to the user for performing activity successfully at optimal rate. The particular amount of reward sound/effect may be a separate continuous parameter (See 1. Level Meter example in Gesture Mapping diagram of FIG. 17.)

The goal state may also simply be reflected by the middle state of a binary parameter.

Synthesis techniques to convey meaning may involve various combinations of mapping density, pitch, rate/tempo, frequency, tonality, formants, pitch, randomness, articulation, loudness, phase, timbre morphing, voice multiplicity (number of instrument voices), and spatialization parameters.

Another implementation example utilizes movement rate cues and is referred to herein as "RunFast." In this embodiment, sound and music conveys a message to "speed up" or "slow down" through sonic cues other than tempo. A combination of discrete and continuous controls over sounds cue the listener to speed up, slow down or maintain a rate of movement.

In one possible instrument example of this type, three main rhythmic profiles with three distinctly different densities act as readily apparent cues about current state. The rhythmic profiles have built-in generative aspects to create variation. Such an embodiment can utilize bi-directional timbre with two contrasting states (with high and low pitch profiles) of a designated lead instrument, thereby allowing for continuous morphing of instrument voice spectrum depending on position of input state.

In other embodiments, pitch, timbre and density of notes may be mapped to single input parameter, or drum pitch, density and envelope can be continuously controlled by an input parameter. Additional instrument examples can be configured using variations on the above examples.

An example instrument signal flow for such an implementation of RunFast can illustratively include multiple distinct "steppers" comprising respective signal generators that control respective instruments (e.g., bass lead, gated pad, hi-hat, claps, kick, etc.) Each of the signal generators is illustratively driven by a common clock signal, generated by a tempo component, and receives other control signals from a director component. Instrument outputs are illustratively combined in a signal combiner, and then subject to a limiting operation in a limiter component.

A breathing entrainment gesture may sonify the airflow speed or volume of a breath. Both sonifications may also be employed simultaneously, where the airflow speed cues the user on how fast to inhale or exhale, while the volume displays imagery of how full the lungs are of air. A second gesture, independent of the entrainment cue, may provide feedback to the user on their activities performed. The second gesture may be viewed as a type of auxiliary component as disclosed herein.

Similar to the breathing entraining application, a custom movement trajectory can be mapped to a musical gesture to guide body form during strength training exercises involving movement and contractions back and forth. A custom curve outlining the oscillating trajectory of movement is mapped to a musical gesture which the user is intended to follow or entrain to. This musical gesture can outline the trajectory of movement or muscle contractions. Feedback can be provided if the activity is detected to let the user know how close he or she is to the goal trajectory, and instruct the user to make adjustments. Exercises where this application may be used include, for example, weight lifting, squats, push-ups, presses, or activities where form is critical such as circuit training exercise on machines such as pull-downs.

In some embodiments, functionality for customizing entrainment signals is provided. For example, individuals can adjust the shape of the entrainment signal mapped onto the musical gesture manually or automatically. If manual, the system can be adjusted through a touch interface. If a breath or movement detection system is available to track different sections on the breath or movement cycle, this signal may be used to automatically adjust the length or ratio of each section to match that of the user. This may be used to calibrate the system to fit each user optimally. Numerous other customization arrangements are possible in these and other embodiments disclosed herein.

Yet another application relates to guided entrainment for multiple users. The goal in this application is to guide multiple people to move to an optimal rate together and convey the degree to which the multiple people are in sync. Like the single user example, the optimal rate may be determined and/or influenced by activity measured. If the optimal rate is set by activity measured, it may reflect the activity of one or more users. For example, the optimal rate may be set by a single user's activity who assumes a leader role, and the other users must follow the rate set by the single leader. Alternatively, the optimal rate may be determined by multiple users' activity, possibly based on collected statistics. It is also possible that the optimal rate may not be influenced by user activity and is instead determined by a predefined value or a trajectory over time.

A more particular example is a "Breathing Together" application in which sound is utilized to guide multiple people to breathe together at an optimal rate. The goal/optimal rate may be set by predefined curves or trajectories (sound plays leader role similar to running example), or may be influenced by the actual breathing rates of the participants. For example, if the majority of participants are breathing much faster than the goal rate, the rate may speed up (rate feature takes follower role). A group reward may be provided. For example, as more people breathe at the correct rate, the sound will be more rewarding, e.g. the sound becomes more positive and grows in intensity.

In some group entrainment systems disclosed herein, an instructor may control the breathing entrainment sonification system in different ways. For example, an instructor may control the parameters of a predetermined guiding entrainment signal through a touch screen interface. Through such an interface, an instructor may control the speed and shape of the entrainment signal driving the sound cue which the listeners must move and/or breathe to. The instructor may also control the feedback component which may influences the amount of energy in the sound generated. Feedback can also be used to reinforce the instructor if it is driven by the instructor's movements. For example, an instructor may wear sensors detecting movement, such as speed and position, measured by a camera, gyroscope, or accelerometer, and the amount of movement detected would be mapped to the feedback component.

Group activity detected may additionally or alternatively influence the feedback component of the sound. For example, data from individual users can be mapped to particular instruments that make up the sonification, however, the number should be limited (e.g., to about 3) in order to ensure that the sound cue does not get lost in the mix. For larger groups, data from individual users may be averaged or otherwise combined together and then used to drive the entrainment or feedback components.

Examples of user interface (UI) control panels for illustrative embodiments of running, breathing and masking sonification systems are described in more detail below in conjunction with FIG. 29.

Other applications include level meters and monitors, and illustratively involve state monitoring. Sound conveys the current state/position/status of the user or environment. Continuously mappable sound with optimal state (e.g., value somewhere between −1 and 1 or 0 and 1) is used.

As a more particular example, an application is configured to monitor relaxation level as determined by biometric sensor(s) (e.g., EEG, EMG, ECG, PPG, GSR, HRV, breathing rate). The monitored relaxation level is a single parameter that is mapped to potentially many features in sound to convey relaxation level and directionality of change in state.

In one implementation referred to herein as "SonicPull," relaxation level is determined from relative alpha level to other frequency bands in EEG signal and scaled between 0-1. The relaxation level is fed into a model as the main input and is mapped to various sound attributes to convey level of relaxation to the user. The continuous directional nature of sounds pull the user towards maximum relaxation state. Directionality may be conveyed through pitch, with dissonance being resolved into consonance as input level rises. Directionally can additionally or alternatively be conveyed utilizing a filter cutoff on a noise oscillator. Sound becomes denser as more voices fade in at stacked levels relating to input. Such arrangements illustratively use probabilities to control density. For example, discrete time control can be used in a monophonic arrangement, with probabilities (e.g., P=0.1, P=0.5, P=0.9) set by parameter and applied to a rhythmic motif. Additionally or alternatively, layering can be used to control density. For example, continuous time control can be used in a polyphonic arrangement, in which different regions on a slider or other type of scaled parameter map to different voices. Thus, in such an arrangement, a main input parameter can control the amplitude levels of respective ones of a plurality of voices.

One example SonicPull implementation includes four main components (e.g., pads, noise, plucks, arps) with sub-mappings controlled by global relaxation level. A "pad" may comprise a sustained chord or tone generated by a synthesizer, typically used for background. A "pluck" in electronic music illustratively refers to a percussive and melodic category of sound that is widely used. An "arp" or arpeggiator is illustratively a feature, available on some hardware synthesizers and software instruments, allowing conversion of a held note or chord into an arpeggio. Other components may be used in other embodiments.

Outputs of the four main components are combined in a first signal combiner. An output of the first signal combiner is applied to a reverb component, while another output of the signal combiner bypasses the reverb component and is applied to a second signal combiner that also receives an output of the reverb component. An output of the second signal combiner represents the output of this example SonicPull implementation.

Another example involves sonification of risk level, illustratively in the form of a screenless risk monitoring tool for traders who need to be aware of overall risk level while making quick decisions. An optimal range is determined somewhere between maximum threshold and minimum value. (See 2b. in Gesture Mapping diagram of FIG. 17). Different zones convey different amounts of risk, e.g. at low levels far away from threshold, sound encourages upward movement, while sound is most rewarding and positive in mid-range safe zone, and sound gets more intense with growing negative cues at high levels past safe zone threshold.

Yet another example involves a navigation application in which sounds is used to guide a person in a space to reach the goal position.

In one implementation referred to herein as "SoniNav," sound conveys how close a current position is to a goal position while providing feedback on direction and speed of movement. The user listens to two separate sound cues that are changed continuously by position and movement data to be guided towards the goal position. There is illustratively a previous position, a current position and a goal position, with an absolute distance between the current position and the goal position, and an angle between a first line connecting the previous position and the current position, and a second line connecting the previous position and the goal position.

For example, a first cue denoted Cue 1 is the absolute distance from the current position to the goal position, and is one parameter controlling the rate, pitch and envelope of clicks. When the current position is closer to the goal position, intensity of the clicks grows and they are faster, higher in pitch and more articulated. A second cue denoted Cue 2 is the angle or direction of movement with respect to the goal position, and controls a second aspect of the sound which includes a bi-directional tone with two contrasting pitch and timbre profiles. At one end (0 degrees), the sound signifies movement in the correct direction, while at the other end (180 degrees), sound conveys movement in the wrong direction. Interpolation between the two contrasting profiles allows for continuous morphing between the two states to give an awareness of location between states.

The angle between the goal state and the current position with respect to the previous position gets rescaled to determine mix or position between of two contrasting profiles. If the angle is closer to 0 degrees, the sound signifies the correct direction. If the angle is closer to 180 degrees, the sound cue signifying movement in the wrong direction is heard more. Velocity controls loudness of Cue 2, so that is only heard when there is movement.

Another example of a level meter application is an application that guides a user to perform a gesture with minimal error. In this example, continuous sound cues convey whether the gesture is being performed correctly, in real-time as the gesture is being performed by the user. The farther away the movement performed is from the optimal gesture trajectory, the less rewarding the sound generated will be. Similar implementations to those previously described in conjunction with the navigation and running applications may also be applied in this application for shaping sound in continuous and discrete time.

The above-described embodiments and their features and functionality are examples only.

Other embodiments can include alternative implementations of the logic engine and/or the audio engine.

Some embodiments can comprise arrangements such as discrete density implementations and/or pitch height control. Both arrangements are illustratively driven by a clock ("CLK") in these embodiments. The density implementation utilizes a probabilistic trigger element ("may-trig") that controls an instrument (e.g., a hi-hat). The pitch height is also probabilistically-controlled in this embodiment.

In other embodiments, discrete improvisation may be implemented in a musical communication system, to provide selection between note groupings, chords, scales, melodies or counterpoints based on probabilities.

Additionally or alternatively, a cross-fading rhythm approach may be utilized in some embodiments. This approach involves linearly interpolating between rhythms, using a probabilistic model with a continuous probability value. The assumption is that the rhythms can be represented by binary values on a fixed time scale. This cross-fading rhythm approach is in contrast to tree-like probabilistic approaches that are used to generate rhythmic/melodic content that does not necessarily share the same time scale.

Figure 29:
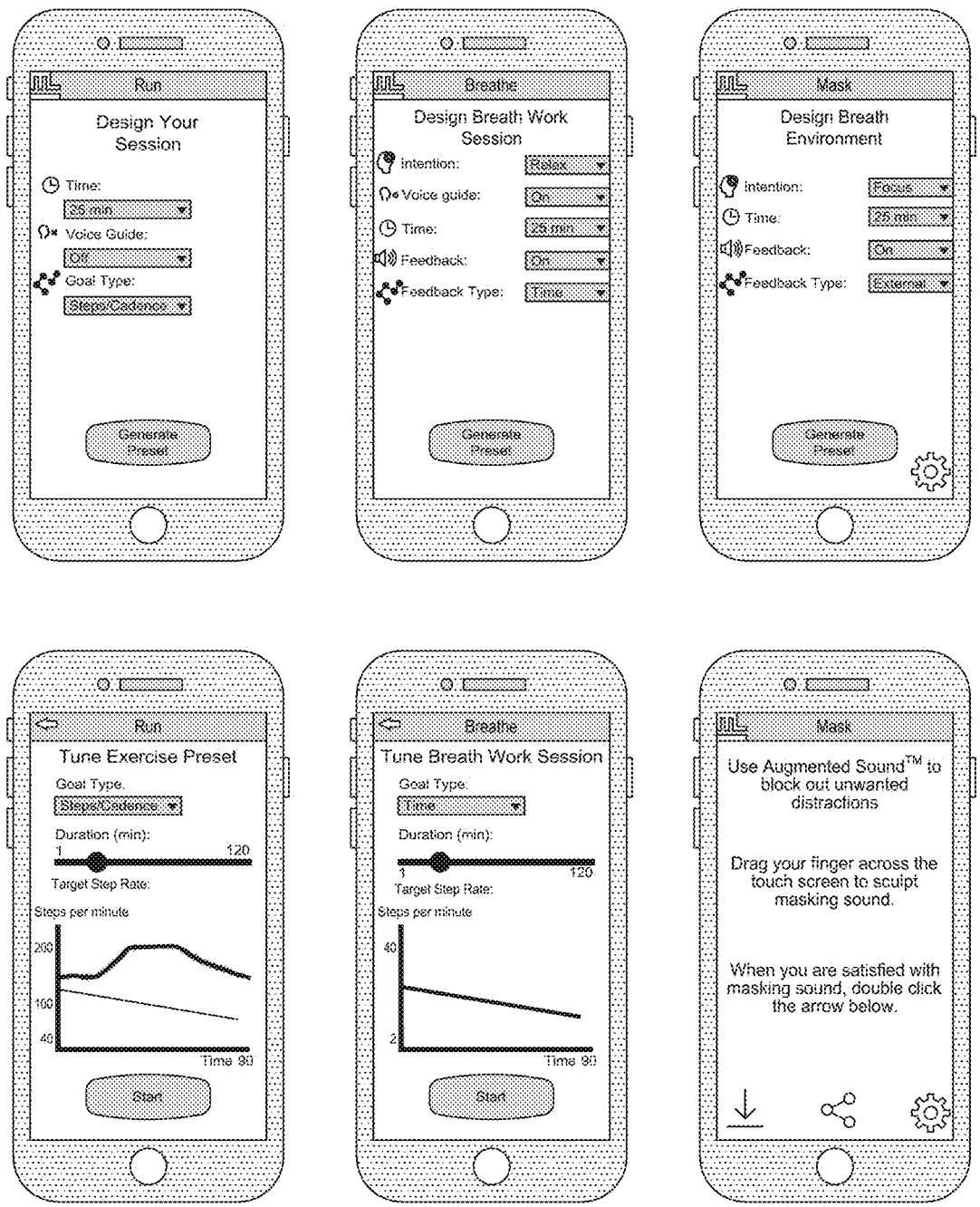

Referring now to FIG. 29, examples of UI control panels are shown for running, breathing and masking sonification systems in illustrative embodiments. The running, breathing and masking sonification systems comprise respective Run, Breathe and Mask applications running on a smart phone as illustrated in the figure. The upper and lower parts of the left side of FIG. 29 show different UI screens of the Run application. Similarly, the upper and lower parts of the middle and right side of the figure show different UI screens of the respective Breathe and Mask applications.

The Run smart phone application UI allows users to generate a musical trainer, which can help pace exercise and keep track of progress through audio feedback. Music builds if activity detected matches a target goal. This example shows the target goal to be a running cadence (steps per minute rate) set by a pre-determined curve. If heart rate detection is available, a different mode allows for heart rate goal trajectory to be set. Music tempo fluctuates with heart rate to help the user match the target heart rate. A logic engine is used to determine the difference between actual heart rate and target heart rate, and to adjust the tempo accordingly. Feedback may be driven by difference in heart rate or steps per minute depending on configuration. Other metrics may be used to set goals including distance and intensity.

The Breathe smart phone application is designed to assist with stress regulation and train focus. The smart phone UI illustrated in this example allows the user to specify breathing rate trajectory over time. In Breathe, compatible sensors used to drive feedback in some implementations can include sensors for respiration, HRV, GSR and relaxation level from EEG, movement, etc. Additional examples are described elsewhere herein.

The Mask smart phone application is designed to block out unwanted distractions. The smart phone UI illustrated in this example allows the user to create and sculpt a masking soundscape to aid with sleep and focus. The user may tune adaptive noise to fit his or her environment and listening preferences. If biometric sensors are available, feedback may be provided by modulating the sound to convey information to the user in a non-obtrusive manner through gradual transformations. Feedback can also be employed to help with mind wandering, or to gently wake you up from slumber. Sensors which may be used as plug-ins include EEG or eye tracker sensors. Masking and personalization features characterizing Mask may be used as a standalone application or be combined with the Breathing application and/or one or more other applications.

These and other illustrative embodiments disclosed herein can include tools for augmented reality which use generative music for abstract communication. For example, some embodiments are in the form of music software configured to intuitively convey information through sound and music from data streams in interactive platforms.

Such embodiments can be configured to interact with wearables, virtual assistants, smart cars and IoT devices, as well as numerous other data sources, in order to leverage available data to improve lives. Audio engines in illustrative embodiments are configured to generate "flexible" music in the form of sound that can be shaped in real-time, so as to provide users with awareness of themselves and their environments.

Illustrative embodiments enhance user experience by providing meaningful communication, in some cases through interactive AI producing engaging sound, state-of-the-art algorithmic models and real-time sonic attribute mapping.

Some embodiments provide highly personalized listening, including generative audio with infinite variation, dynamic sound and music shaped while playing, and intuitive control through simple interfaces.

These and other embodiments are illustratively implemented in a highly flexible manner, possibly utilizing a software development kit (SDK) that is highly portable and cross-platform, and provides easy mapping to sensor inputs and efficient DSP algorithms.

Some embodiments can be configured to avoid the need for sample loops or pre-rendered musical material. Examples of embodiments of this type include musical communication systems that generate material using probabilities to continuously create variation. In such an arrangement, the musical communication system is illustratively synthesis-based using signal processing algorithms to shape the sound in real-time.

Examples of features of the sound that can be controlled to provide an awareness of state include tempo, pitch, density, filter cut-off, rate, frequency, tonality, formants, randomness, articulation, loudness, phase, timbre morphing, voice multiplicity, and spatialization parameters, each potentially involving utilization of a distinct generation algorithm. Different combinations of attributes can be mapped to convey information. Also, different algorithms to manipulate these perceived attributes can be used in different contexts.

In illustrative embodiments, a musical communication system is configured to map different synthesis techniques to parameters that define models for specific use cases. A wide variety of different synthesis techniques can be used to convey information (e.g., current state with respect to goal state, amount of change and direction of change) through sound in illustrative embodiments disclosed herein include the following:

1. Density. Density can refer to the implied number of things happening in a particular soundscape. A particular value could be mapped to how dense a perceived sound is. This falls into the category of a relative sound cue. Density can be a very effective musical tactic, as listeners we get very excited by a sound that gets increasingly dense because it implies growth and success.

2. High/low notes. This is a very specific system utilized in some sonic navigation embodiments. For example, we can have two sounds: a high note or complex sound in high range, and a low note or complex sound in a noticeably lower range. This is used to map a bidirectional sound, such as "warm/cold" or "good/bad" or "left/right". We use this in some navigation and gesture models.

3. Rate/Tempo. Rate can be formally explained as a perception based on hearing the distance between a rapid succession of note onsets. Tempo is an often used subset of rate. We will often perceive rate as a kind of speed, such as fast or slow. Rate can also be used locally in things like clickers as a kind of continuous control. Vibrato can be a certain form of rate.

4. Frequency mapping. This specifically refers to taking data and directly mapping it to frequency in an oscillator.

5. Tonal/Noise. This is a subset of timbral morphing that involves going between something perceived as pitched/tonal, to something that is more in the category of broadband noise. These two extremes provide very clear morphing between states.

6. Formant filters/synthesis. Formants are a primary example of sounds that are "absolute": without any prior introduction, a listener could easily differentiate major vowel sounds such as "a", "e", "i", "o", and "u". We emphasize different formants using filters and cross fade parameters (filter cut-off, Q, band-width) to morph between vowels.

7. Filter Sweeps. Subtractive synthesis techniques that usually involves shaping the timbre of a harmonically rich sound with a filter. Filters provide a very intuitive form of relative sound control, and work especially well to communicate signals with regular dynamic movement.

8. Pitch Height. Pitch height refers to the relative distances between notes and refers to the range between the highest and lowest notes played during a given amount of time. This can be done sequentially for melodies, or in parallel for harmony.

9. Randomness. Randomness is a relative concept that refers to the amount of perceivable chaos in a system: Steady to unsteady, regular to irregular, predictable to unpredictable. This concept can be mapped to many musical concepts like note duration and frequency/pitch selection.

10. Articulation. Articulation refers to the amplitude characteristics of the beginning, middle, and end of a note envelope. This also extends to note duration as well. Articulation is often nuanced.

11. Perceptual loudness. This includes amplitude modulation and direct mapping to loudness. This one is also relative since sound systems have volume control.

12. Phase Alignment. This refers to our ability to hear things out of sync. For example, there may be two pulsating sound sources: one moving at a constant rate, and one that is controlled. The idea is it can be tuned it to match the rate of the reference. This can work at sub audio rate signals with clicks/pulses, but also with tones.

13. Discrete Alerts. We define an alert as being an abrupt or new sound that appears in the soundscape. The very presence of the sound is the core means of conveying information. This is indeed an absolute sound, and a very clear one at that. Because of its binary nature, it is a very limited mechanic.

14. Timbre Morphing. This is a broad category that includes interpolation or crossfading between two or more distinct spectrums. Several techniques described above implement subsets of this approach. Timbral states are absolute sounds, and morphing between them is a relative sound.

15. Spatialization. Spatialization includes anything built to leverage the ability of our ears to localize sound objects in a space. Primarily this includes panning (left/right), object position using head-related transfer functions (HRTFs), and/or reverberation. An HRTF, which can include an anatomical transfer function, is illustratively a response that characterizes how an ear receives a sound from a point in space.

16. Timbral Heterogeneity. This is a parameter that makes multiple perceived voices sound like a single source. An example algorithm using this parameter maps multiple voices to a parameter value which controls the timbre. At one extreme, all the voices share the same timbre with the same spectrum, while at the other extreme they all have different contrasting timbral spectrums.

As mentioned previously, these and other particular features of illustrative embodiments are presented by way of example only, and should not be viewed as limiting in any way.

The above-described logic engine and audio engine of a musical communication system as disclosed herein are illustratively implemented utilizing at least one corresponding processing device comprising a processor coupled to a memory. The processor executes software program code stored in the memory in order to control the performance of processing operations and other functionality. The processing device also comprises a network interface that supports communication over one or more networks.

Still further illustrative embodiments will now be described with reference to FIGS. 30 through 32, which show aspects of goal-driven auditory display techniques for use in breathing entrainment sonification and other contexts involving musical communication and/or sonification as disclosed herein.

It is a common practice in exercise machines, wearables and other fitness applications to employ goal-driven exercises to help a user quantify his or her progress over time to get a sense of how well he or she is doing. Common exercise goals in conventional practice involve a time duration, exercise intensity, calories burned, distance traveled, heart rate, exercise cadence, or some combination of these.

The illustrative embodiments to be described include methods, apparatus, systems and computer program products for goal-driven auditory display techniques. The disclosed techniques are particularly well-suited for use in enhancing user experience and performance in contexts such as cardio fitness, aerobic activity, and numerous others.

We have found that conventional approaches of the type mentioned previously are deficient in many important respects. For example, existing motivational systems for cardio fitness include DJ applications consisting of precomposed content launched at different points in time. Such systems may function by matching a given running rate to song tempo. The systems either choose songs, or parts of songs in the form of loops, which match the tempo of the music to the cadence of the exercise, i.e. steps per minute, or cycles per minute. These systems may guide the user to perform the exercise at a certain rate, or match to the rate of the exercise. As mentioned, these systems rely on precomposed content that is launched at different points in time and do not generate or adapt content while it is playing, to the environment.

The music featured in these systems does not accurately and realistically convey sufficient information about the user's progress or current status with respect to a given exercise goal. For example, the information is not embedded into musical structures. If progress is conveyed acoustically, the cues are restricted to voice samples, i.e. where a recorded voice tells the user how he or she is doing, or a marker is triggered to signify to the user that he or she has passed some check hold or reached some threshold.

Accordingly, while conventional systems exist to help users pace their exercises using tempo, illustrative embodiments disclosed herein provide significant improvements which overcome the above-noted drawbacks of these and other conventional systems.

For example, some embodiments disclosed herein are illustratively configured to use music to intuitively convey to a user, through continuous sound cues embedded into parametric musical structures, controlled in real-time, how close he or she is to a fitness goal.

These and other illustrative embodiments disclosed herein are in some cases implemented in the form of an application that employs multiple auditory display and gamification techniques (e.g., levels) to enhance perception, awareness of technique and motivation during cardio exercise or other aerobic activity. The application can run on a mobile telephone, computer, fitness equipment or other processing device.

Although the following illustrative embodiments are described primarily in the contexts of cardio fitness and aerobic activity, it will be readily apparent that the disclosed techniques can be adapted for use in other contexts involving a wide variety of other types of activities.

A goal-driven auditory display system in some embodiments disclosed herein may comprise one or more components, features or functionalities of an entrainment sonification system and/or a musical communication system of the type described elsewhere herein.

In some embodiments, a goal-driven auditory display technique utilizes a mixed approach with sonification, layering and "earcons" (e.g., sound cues) to help users meet exercise goals in cardio fitness, aerobic activity and other contexts. For example, a goal-driven auditory display system in such an embodiment is configured to adapt real-time audio to input data to perform the following functions:

1. Convey to a user the current status of his or her progress with respect to an exercise goal.

2. Motivate the user to perform a movement-based activity a certain way to reach goal.

3. Guide user to perform activity at a certain rate (pace user). Rate can influence the intensity of exercise.

4. Break long-term goal into shorter sub-goal sections which may be perceived as levels.

5. Parametrically reward a user for doing an activity correctly by incrementing a global parameter to provide a continuous control signal mapping to pitch, frequency, timbre, note probabilities, timing and amount of sound objects introduced into the system.

6. Create an illusion to a user that his or her activity (and energy exerted) is building the song and driving its progression forward.

Figure 30:
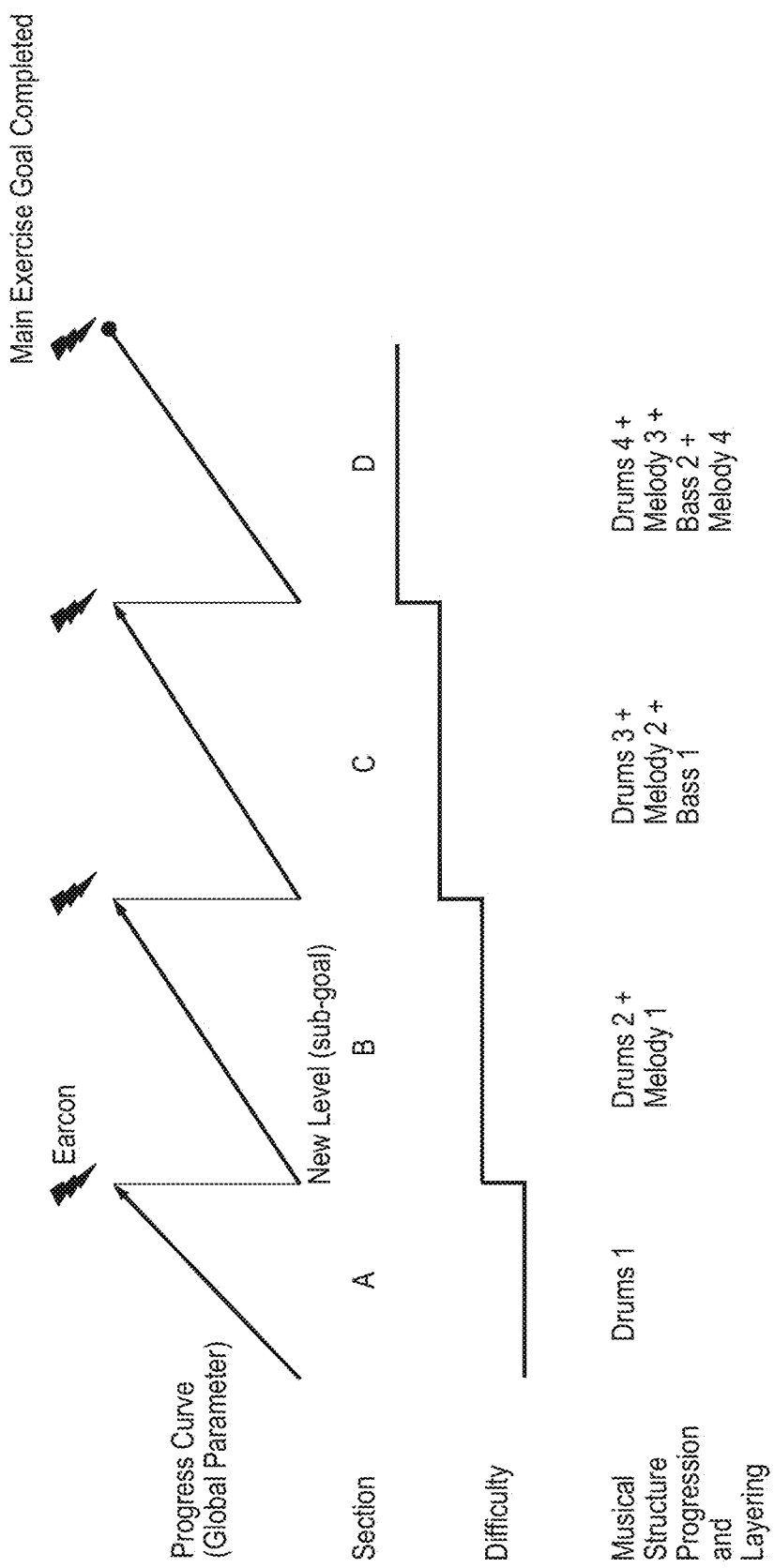
FIGS. 30 through 32 show aspects of goal-driven auditory display techniques in illustrative embodiments.

FIG. 30 shows an example of ramp-up behavior in an illustrative embodiment. If an activity detected satisfies necessary conditions, the global control parameter increments as shown by the upward diagonal arrows in the figure. An upward trajectory of a global control parameter drives the musical progression forward, to signal to the user to keep doing what he or she is doing. At the endpoint of each such upward trajectory, an earcon is generated as shown. Other than in the case of the final upward trajectory, a new level is then started from the endpoint, with a new upward trajectory, corresponding to a different sub-goal of a main exercise goal. The different levels of increasing difficulty in this example include levels A, B, C and D, each associated with a different instance of musical structure, progression and layering as shown. Upon completion of the upward trajectory of the last level D, a final earcon is generated to indicate completion of the main exercise goal.

It is apparent from the FIG. 30 embodiment that the musical structure progression and layering change from level to level, as the user progresses through the levels, which are of increasingly higher difficulty. This is an example of what is more generally referred to herein as "goal-driven auditory display," where auditory display in this embodiment illustratively refers to varying the presentation of audio to a user in accordance with a progress curve and associated global parameter values. The audio can be presented via a mobile telephone, tablet computer, fitness equipment, or other type of processing device, illustratively through associated speakers, earphones, wireless earbuds, etc.

Figure 31:
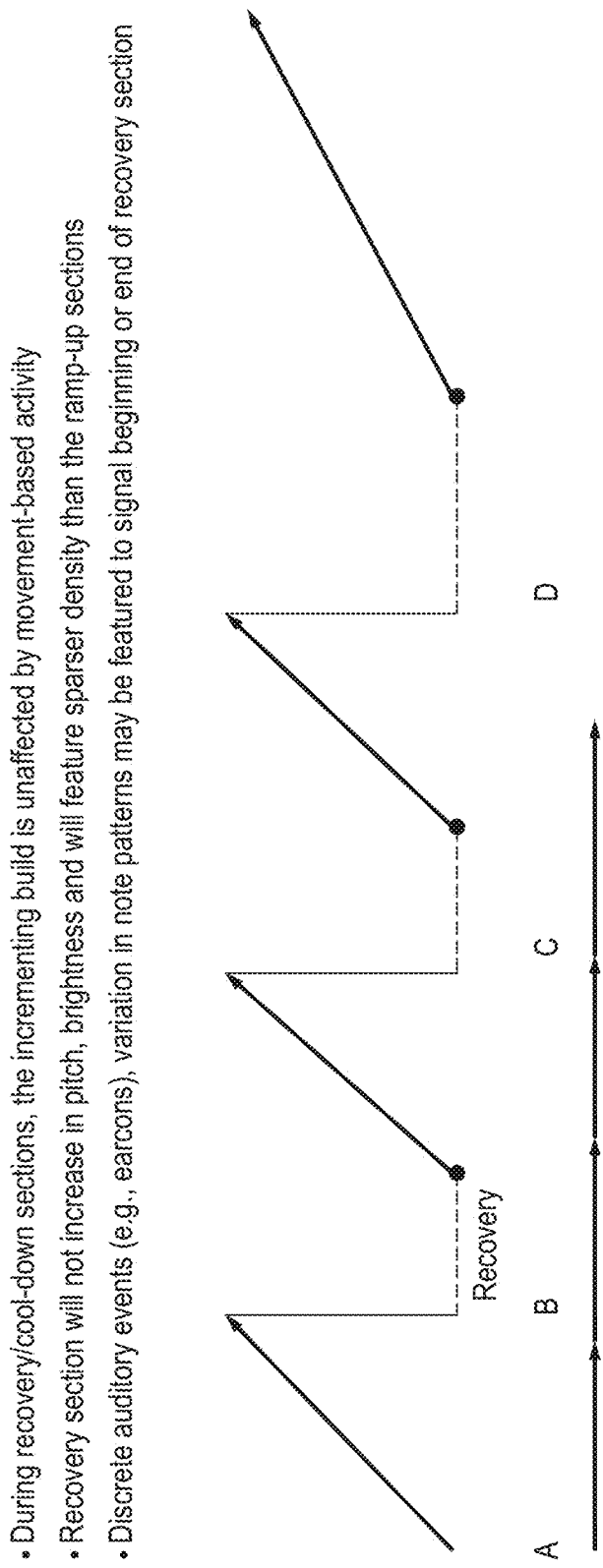

FIG. 31 shows another illustrative embodiment, in this case utilizing a ramp-up model with optional recovery sections. Such recovery sections in some embodiments illustratively include "cool-down" sections.

Recovery sections in illustrative embodiments are characterized by sparse orchestration (e.g., characterized by the beginning of a level before global control parameter has been incremented) and a lack of responsiveness of the global control parameter to activity. Lack of responsive behavior and sparse orchestration signals to the user that he or she should take a break from intense exertion.

During recovery/cool-down sections, the incrementing build is unaffected by movement-based activity. In addition, the recovery section will not increase in pitch and brightness and will feature sparser density than the ramp-up sections. Finally, discrete auditory events (e.g., earcons) and/or variations in note patterns may be featured to signal the beginning or the end of a recovery section.

The particular ramp arrangements used in the embodiments of FIGS. 30 and 31 are presented by way of illustrative example only, and alternative global parameter progress curve shapes can be used in other embodiments.

Figure 32:
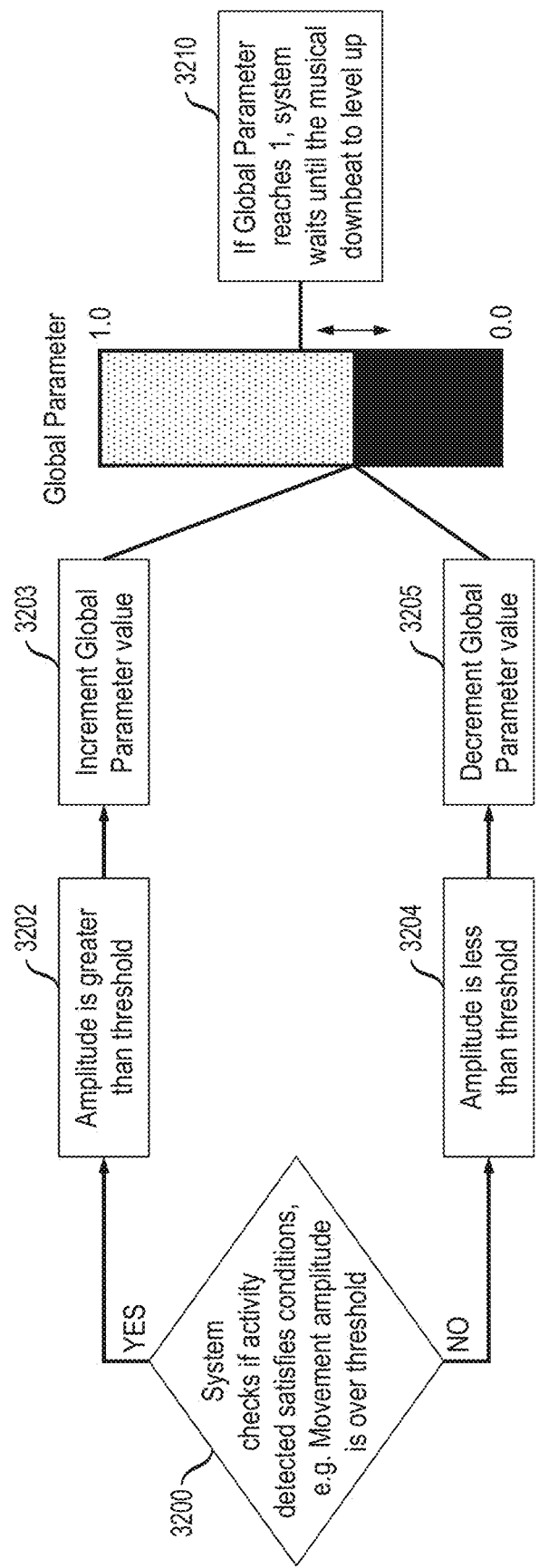

FIG. 32 illustrates global parameter behavior in an illustrative embodiment. In this embodiment, an example global parameter has a value that ranges between 0.0 and 1.0, and that increments or decrements based on the conditions of the activity detected. User levels up on the first down beat after reaching the maximum value (e.g., beat quantization is featured to preserve musicality).

The process flow in this example includes blocks 3200 through 3210 as shown. In block 3200, the system checks if the activity detected satisfies one or more conditions. For example, the system may determine if movement amplitude is above a specified threshold. If the amplitude is greater than the threshold, as indicated in block 3202, the system increments the global parameter value in block 3203. If the amplitude is less than the threshold, as indicated in block 3204, or otherwise not greater than the threshold (i.e., equal to the threshold) the system decrements the global parameter value in block 3205. In block 3210, if the global parameter reaches 1.0, the system waits until the musical downbeat to level up.

Additional examples of goal-driven auditory display techniques of illustrative embodiments will now be described in further detail.

Some embodiments utilize entrainment (e.g., tempo pacing). A feature in such embodiments illustratively comprises a tempo controlled rhythmic component. For example, overall clock signal rate controls the timing of rhythmic patterns featuring probabilistic structures which may be influenced by a substantially continuous ramp. Other types of ramp shapes or arrangements can be used.

1. Exercises, such as interval training, often feature consecutive segments that vary in intensity. Lower intensity is usually correlated with slower speeds and longer cycles or strides.

2. Intensity of a movement-based exercise is correlated with speed.

3. Users naturally entrain to repeating rhythmic structures, therefore, speeding up and slowing down the rate of clock guides users to adjust the exercise intensity.

4. Entrainment via a tempo pacing feature helps users train better, perform better and have shorter recovery times.

Some embodiments utilize levels (e.g., for motivation). For example, gamification tactics can be employed with an auditory display technique to reward a user for performing an activity (correctly) over a duration of time. When activity is detected, a global parameter value from 0-1 increments. Incrementing behavior speeds up if the activity detected is more correct, i.e., closer to an optimal state.

A long term goal is split up into smaller goals which can perceived as levels, to mark progress of the user and allow the user to have a more clear sense of where he or she is with respect to goal. Shorter goals allow for changes in sound to happen fast enough for the user to perceive the effect of his or her energy exertion in real-time.

The number of levels (e.g., sections) that a long term goal is split up into can vary in different exercises.

Some embodiments utilize continuous controls, in which, for example, each level features continuous ramping up behavior (parametric reward), which is the sonification of current position relative to goal. This is a type of "progress" auxiliary sound cue of the type described elsewhere herein, and provides a sense of magnitude.

Continuous parameters answer questions the user may have such as "How am I doing?" and "How close am I from my target goal?"

Sonification techniques are selected in these embodiments to evoke imagery of a device "charging or powering up," to give the user the feeling that his or her activity is paying off. Sound parameter mappings include rhythmic density, pitch and timbre. The progress information is converted to a continuous audio-rate signal, where it is then duplicated, scaled, and mapped to various components in the sound model.

Rhythmic density may be controlled via probabilistic sequences in order to build up anticipation and motivation.

Pitch or frequency mappings, such as to filter cutoff of a resonant or peaky filter, or to an oscillator, can be used to map out overall trajectory.

Uniquely identifiable target spectra, such as vowel formants, characterize the beginning and end of ramp-ups which are interpolated between.

Mappings to levels of auxiliary time-based effects such as delay lines or reverbs can provide a sensation of positive growth.

Additionally or alternatively, some embodiments utilize discrete controls, as will now be described.

For example, a layering approach can be implemented in which, after a user completes a level, a new instrument, or sound component, is introduced to increase the spectrum density and create a sense of reward. This reward metric, provides a clear sound cue for the user to distinguish a higher level from a lower level.

As another example, a note pattern played by an existing instrument can be varied from level to level, for example, the same instrument in level one may play a different melodic sequence in level two. This is a less obvious level distinguishing cue.

Another example of discrete controls involves the use of earcons. An "earcon" as the term is broadly used herein is intended to encompass any of a wide variety of different types of brief, distinctive sounds that are used to represent a specific event or to convey other information. For example, an earcon can comprise a discrete reward sound triggered at the start of each level, as illustrated in FIG. 30, signaling to the user that he or she has just completed a segment. The earcon can be implemented as an audio file sample or a DSP sub-component. It may act as a placeholder for a sonic logo for branding purposes, e.g. once a level is completed, a user hears a particular company's signature sound. Earcons in illustrative embodiments can therefore be customized for different fitness companies or other providers.

Goal-driven exercise examples will now be described.

Different goal-driven exercises involve various inputs that define a goal, and thus goals can be defined by different actions where a system measures the state of an activity and compares it to a set of rules defining a goal.

1. Time duration

Goal=perform an activity in a certain about of time.

Example 1: Global parameter is incremented by the simple passing of time.

Example 2: Global parameter is incremented if any activity is detected.

2. Distance

Goal=traveling across a real or virtual distance.

Global parameter increments if the user gets closer to the distance goal.

3. Calorie

Goal=perform exercise to burn certain number of calories.

Global parameter increments if calories count rises.

4. Activity Intensity (e.g., one or more of resistance, incline, speed or other metric associated with exercise intensity)

Goal=Maintaining a certain intensity over a duration of time, e.g. maintaining an amount of movement amplitude.

Global parameter increments if an intensity (movement amplitude) detected matches or is above a certain intensity threshold.

Global parameter decrements if activity detected is below a certain intensity threshold.

Target intensity may be varied throughout exercise.

5. Heart Rate

Goal=Maintaining a heart rate in a target zone over a duration of time.

Global parameter increments if heart rate is in the target zone.

Global parameter decrements if heart rate is outside of target zone.

Entrainment component is be manipulated to modify exercise intensity to help user reach goal.

Additional adjustment cues may be employed to indicate to the uses if he or she is above or below the target zone.

Target heart rate may vary throughout the exercise.

6. Activity Rate

Goal=Maintaining a target rate, amplitude or speed of movement over a duration of time.

Goal=Entrain to the beat.

Global parameter increments if a rate of movement detected matches the target rate.

Target rate is indicated by entrainment component rate/speed.

Target intensity may vary throughout the exercise.

Additional adjustment cues may be employed to indicate to the user if he or she is above or below the target zone.

7. Running Technique Metrics (e.g., may include one or more of impact, asymmetry, bounce, ground contact time, stride length, gait, striking discrepancy, GCT, flight time, contact time, step time and other running or aerobic exercise technique metrics)

Goal=keep technique metric in optimal zone.

Global parameter increments if metric is in the target zone.

Global parameter decrements if metric is outside of target zone.

The foregoing are only examples, and numerous alternative arrangements are possible. For example, a more complex exercise goal may feature combinations of multiple goals which in sum to act as a normalized macro goal, like an "exercise score," consisting of multiple weighted metrics combined to influence the global parameter.

As indicated previously, the above-described entrainment sonification system and/or musical communication system components, features and functionalities can be implemented in goal-driven auditory display systems in a wide variety of different contexts.

Some of the embodiments described herein implement closed-loop systems that feed physiological state data back to the user. Other embodiments are implemented as open-loop systems that are configured to guide breathing or other activities without feeding physiological state data back to the user.

In some breathing entrainment systems disclosed herein, breath may be guided using sound and music with features that synchronize with a target breathing rate and indicate respiration phases. It may also include a breath signal customized by the user.

Open-loop entrainment may be achieved in some embodiments by mapping target breathing trajectory to sonic gestures. Such a system can utilize one or more static files of audio/visual/haptic content. Closed-loop systems present information about a user's physiological state, which may be a measurement of a stress-related physiological marker, in addition implementing certain functionality associated with open-loop entrainment. The feedback may communicate to the user information about his or her performance during an exercise, and provide additional cues to guide the user to a specified goal.

Some embodiments are configured to provide non-verbal sonic cues, possibly in combination with haptic cues or other types of cues. Such cues can enhance breathing exercise instruction without interfering with visual attention. Abstract sounds used to guide the breath cycle complement vocal instruction, through audio cues which provide more resolution to vocal instruction. Practicing exercises using an entrainment sonification system as disclosed herein can enhance long-term memory of pace, because temporal sequences are learned more efficiently through sound than visuals. In this way, breathing exercises, guided by abstract sound and music, can encode breathing patterns into musical memory.

In some embodiments, a breathing exercise makes use of a ratio which characterizes the shape of the entrainment signal. The entrainment signal in such an embodiment may be generated by a measurement of the user's natural breath cycle, or may be generated by a computer. The parameters given below can be used to configure the entrainment content. An interface is used to allow the user to define these parameters at different points in the exercise and automate the state to change gradually during a section. An example basic set of parameters illustratively includes the following:

1. Breathing Rate: The speed of the breathing entrainment signal. May be compared to tempo.
2. Ratio: The respiration signal shape defining the inner mechanics of each section of the breath cycle, e.g., the inhale, exhale and pause times. An inhale or exhale may have different subsections as well, for example, an inhale may have two parts, where the user must first breathe into the belly, then into the upper chest.
3. Duration: The length of the exercise or section of exercise.
4. Depth: How deep the breath is, from shallow, to deep. May be viewed as an amplitude of the breathing entrainment component.

In other embodiments, additional parameters are added to further customize the breathing guidance provided by a breathing entrainment sonification system. These additional parameters illustratively include the following:

1. Timer: Musical mappings denoting the passing of time. They may be discrete, such as transient sounds which mark different time durations. The timer may also automate the slow evolution of a parameter, for example, slowly change the coefficients of a filter for an ambient sound which is slowly modulating from one state to another. The timer may be used to aid time management tasks, and is in particular useful for an application of this technology for increasing productivity in the work place.
2. Voice guide/vocals: The abstract breathing guide sound to be coupled with a recorded or artificially generated voice giving verbal instructions of mental imagery or further defining the breathing technique. This illustratively includes vocals sparsity, a probabilistic metric controlling how often voice is heard, and voice timing and placement randomization, in which different sections of voice recordings may be tagged and assigned to different sections, where different options may be selected based at least in part on a probability. With such a system, many variations can be created on an exercise.
3. User Listening preferences: Other sound customizations which allow the user to choose a style, generate a preset, or design a preset.
4. Masking: Type of user listening preference adding noise to block out unwanted background noise.
5. Mood or Intensity: This illustratively allows intensity or mood to be varied dynamically through automation. Examples include pulsing beat, brightness, tonality, etc.

A backend portion of a given system as disclosed herein can be configured to generate audio files embodying a particular breathing exercise for a specific intention, through various combinations of the features specified above, and possibly utilizing additional or alternative features. In such embodiments, an entrainment component may be featured without an auxiliary component. Accordingly, it is to be appreciated that although some embodiments herein utilize both an entrainment component and one or more auxiliary components, other embodiments can be configured to utilize only an entrainment component. As indicated above, an embodiment of the latter type can be configured to map the entrainment component to abstract sound and/or music which guides breathing for user.

In some embodiments, an adaptive system may be configured using an interactive software application on a mobile telephone or computer. Such an embodiment can include various entrainment features disclosed herein, including one or more of the following:

1. Biofeedback: An auxiliary component providing secondary cues back to a user to provide a sense of progress during the exercise.
2. Microphone Augmentation: A voice or breath recording may be used to customize the sounds featured in the breathing entrainment system. For example, a personalized breath sound may be used, in which the user records the sound of their breath sections, and the system captures the spectrum characterizing different points of the breath, and generates a unique filter which can capture some unique characteristics of that person's voice. This filter then would be used in the sound characterizing the breath guide. As another example, the user may sing into the microphone of a desktop, phone, tablet, or wearable device, which is then augmented with audio effects. The audio effects may modulate the singing in different ways including: pitch shifting (to harmonize the singing), doubling (to make sound richer), distorting to add overtones, reverb, delay, equalization, etc.
3. Interactive musical instruments: Casual interactivity with the sound for further personalization.

Accordingly, some embodiments herein can be configured to provide basic breathing entrainment solutions without auxiliary components, while others can provide more complex solutions incorporating one or more auxiliary components, all in accordance with the techniques disclosed herein. For example, a basic solution can comprise static files created using a system backend in the manner described above, while a more advanced solution can feature an embedded augmented sound engine in interactive software. The interactivity illustratively allows for the sound to be shaped while it is playing.

The above-noted basic solution can be implemented using packages of audio/video files featuring breathing entrainment content. A feedback track may be generated or created to complement each different breathing exercise, and corresponding signals can be mixed in real-time to facilitate a limited bio-feedback system.

Figure 33:
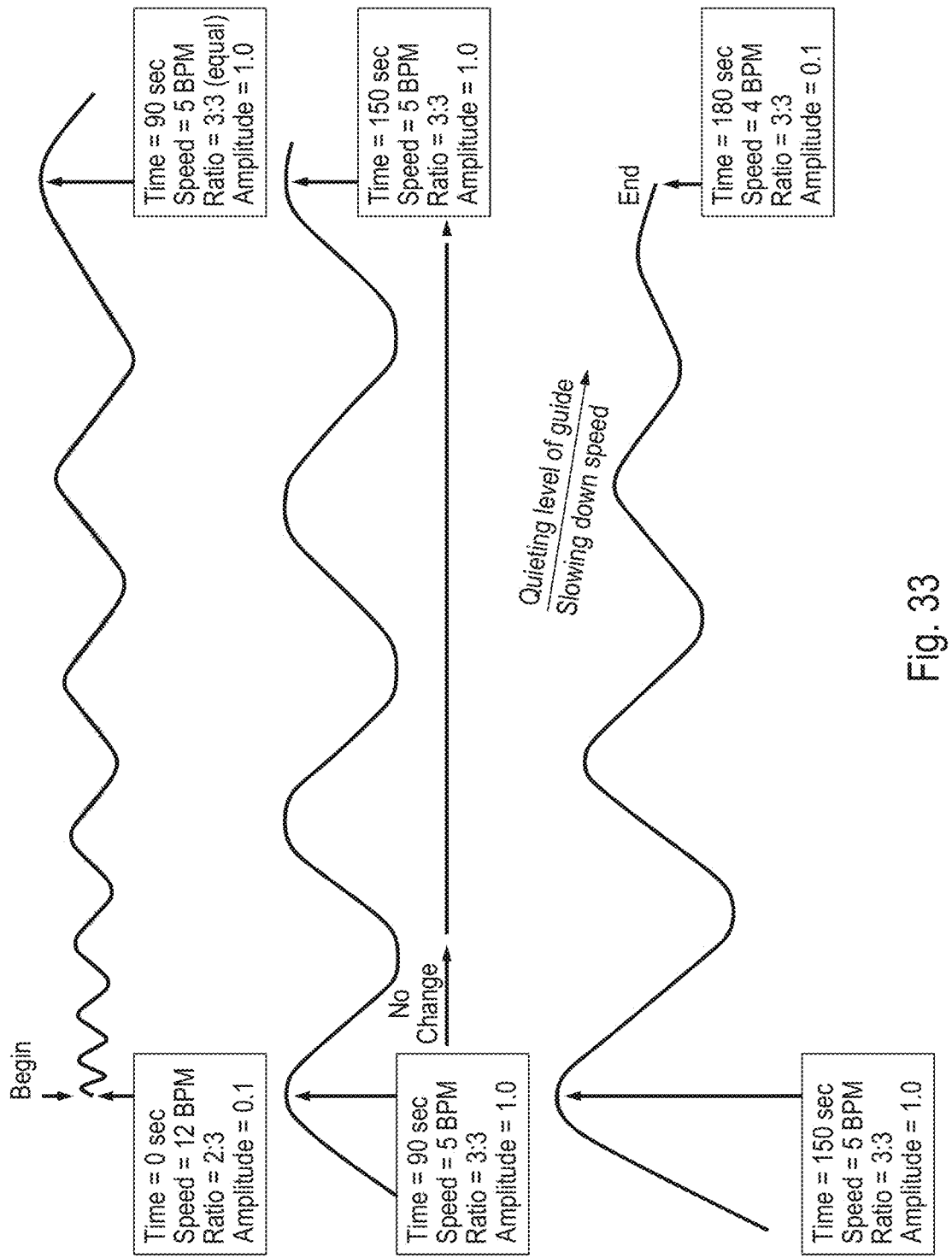
FIG. 33 shows an example of an entrainment signal utilized in a breathing entrainment sonification system in an illustrative embodiment.

Additional illustrative embodiments will now be described with reference to FIG. 33. These embodiments provide example breathing exercises that are implemented using breathing entrainment sonification systems of the type disclosed herein. These examples include breathing exercises denoted as Exercise 1 through Exercise 9, each of which is illustratively guided by a breathing entrainment sonification system as disclosed herein. FIG. 33 illustrates Exercise 1 as described below.

Exercise 1: Simple Breath
Intention=Calming
Duration=180 sec
Level of Expertise=Beginner FIG. 33 shows the exercise timeline with parameters characterizing different sections. The curves illustrate an entrainment signal over time, guiding the breathing process of a user. Different sections are characterized by parameters at the beginning and end of each section, which are interpolated between throughout the exercise. The x-axis in the diagrams of FIG. 33 illustratively depicts breathing rate in seconds, while the y-axis depicts volume/amplitude. In the first 90 seconds the intention is to have the breather gradually shift from an initial baseline of 12 breaths per minute (2 second inhale, 3 second exhale) to a rate of 5 breaths per minute (6 second inhale, 6 second exhale), with the volume also gradually increasing. For the next 60 seconds, there is a sustained breathing rate of 5 breaths per minute (6 second inhale, 6 second exhale), with a maximal volume of breath. For the last 30 seconds, the breather releases the technique and resumes natural breath, which would very gradually taper down in its speed and volume, but still remain slower and deeper than at baseline.

Exercise 2: Clearing Breath
Intention=Calming
Duration<1 minute
Level of Expertise=Beginner The timeline, progression and sections in this example are as follows:

0-60 seconds: Take a big inhalation through the nose and exhale slowly through the mouth. Repeat two times.

Exercise 3: Intro to Paced Breathing (1:1 Ratio)
Intention=Calming & Focusing, also the foundational exercise upon which the subsequent examples are built.
Duration=3 minutes
Level of Expertise=Beginner The timeline, progression and sections in this example are as follows:

0-60 seconds: Gradually shift from an initial baseline of 12 breaths per minute (2 second inhale, 3 second exhale, a typical involuntary breathing pattern) to a rate of 5 breaths per minute (6 second inhale, 6 second exhale), with the volume also gradually increasing.

60-150 seconds: Sustain breathing rate of 5 breaths per minute (6 second inhale, 6 second exhale), with a maximal volume of breath.

150-180 seconds: Release the technique and resume natural breath which, over time, would gradually taper down in volume and increase in speed, yet still remain slower and deeper than at baseline. This period of time at the end of each breathing exercise is intended for the practitioner to cultivate self-awareness by noticing the effects of the technique. It is also intended to allow space for integration before practitioner moves on to the next task.

Exercise 4: Paced Breathing with Longer Exhalation (1:2 Ratio)
Intention=Calming
Duration=4 minutes
Level of Expertise=Intermediate The timeline, progression and sections in this example are as follows:

0-60 seconds: Breather gradually shifts from an initial baseline of 12 breaths per minute (2 second inhale, 3 second exhale—a typical involuntary breathing pattern) to an even breathing 1:1 breathing ratio. Begin with 2 second inhale/2 second exhale, increasing to 3 second inhale/3 second exhale, 4 second inhale/4 second exhale etc., up to 6 second inhale/6 second exhale (5 breaths per minute). Volume will increase as the breath lengthens.

60-90 seconds: Sustain a steady rate of 5 breaths per minute (6 second inhale, 6 second exhale).

90-150 seconds: Gradually shift from a 1:1 ratio to a 1:2 ratio.

150-210 seconds: Sustain 1:2 ratio.

210-240 seconds: Release technique and return to involuntary breathing. Over time breath will gradually taper down in volume and increase in speed.

Exercise 5: Intro to Resistance Breathing (for this exercise the focus is on learning the technique of resistance breathing. Other exercises can combine resistance breathing with paced breathing.)
Intention=Calming
Duration=3 minutes
Level of Expertise=Beginner The timeline, progression and sections in this example are as follows:

0-30 seconds: From involuntary, natural breathing gradually slow and deepen the breath.

30-60 seconds: Verbal guidance to create a soft "ocean sound" on the exhalation by contracting the glottis (the swallowing muscle).

60-90 seconds: Verbal guidance to create the "ocean sound" on the inhalations as well.

90-150 seconds: Sustain the technique of creating a comfortable and steady "ocean sound" on the inhalation and exhalation.

150-180 seconds: Release the contraction in the glottis, resume natural breath and observe the effects.

Exercise 6: Tactical Combat Breathing (1:1:1 Ratio)
Intention=Calming & Focusing
Duration=1 minute
Level of Expertise=Advanced Beginner The timeline, progression and sections in this example are as follows:

0-4 seconds: Breathe in for 4 seconds.

4-8 seconds: Hold breath in for 4 seconds, staying relaxed in belly, shoulders, jaw, and throat.

8-12 seconds: Exhale for 4 seconds.

Repeat sequence 3-5 times.

Exercise 7: Alternate Nostril Breathing Prep
Intention=Focusing
Duration=4 minutes
Level of Expertise=Beginner The timeline, progression and sections in this example are as follows:

0-30 seconds: From involuntary breathing, gradually transition to slow and deep nasal breathing.

60-210 seconds: Instruction given to seal one nostril and breathe through only 1 nostril at a time, as follows:

Block off the right nostril with thumb or finger.

Inhale and exhale through the left nostril focusing on maintaining a comfortable breathing rate & volume.

Repeat breathing in and out of left nostril 5 times total.

Release the right nostril and switch sides, using finger or thumb to block of left nostril.

Inhale and exhale through the right nostril 5 times, maintaining a comfortable breathing rate and volume.

Release the left nostril.

Take 5 breaths through both nostrils, maintaining a comfortable breathing rate and volume.

210-240 seconds: Release the technique, resume natural breath and observe the effects.

Exercise 8: Paced Breathing with Longer Inhalation (2:1 Ratio)

Intention=Energizing, but note that energizing breathing techniques may specify various contraindications and should be brief, typically no more than 2-5 minutes. General contraindications include heart conditions, seizure disorders, pregnancy, recent surgery, hernia, bipolar disorder, etc.

Duration=4 minutes
Level of Expertise=Intermediate

The timeline, progression and sections in this example are as follows:

0-60 seconds: Breather gradually shifts from an initial baseline of 12 breaths per minute (2 second inhale, 3 second exhale, a typical involuntary breathing pattern) to an even breathing 1:1 breathing ratio. Begin with 2 second inhale/2 second exhale.

60-80 seconds: From baseline of 2 second inhale and 2 second exhale, gradually shift from a 1:1 ratio to a 2:1 ratio, inhaling for 4 and exhaling for 2.

80-120 seconds: Slowly increase the volume and duration of the breath, keeping the 2:1 ratio.

120-210 seconds: Sustain maximal 2:1 ratio.

210-240 seconds: Release technique and return to involuntary breathing. Over time breath will gradually taper down in volume and increase in speed.

Exercise 9: Breathing with Segmented Inhalations
Intention=Energizing
Duration=1.5 minutes
Level of Expertise=Intermediate The timeline, progression and sections in this example are as follows:

0-30 seconds: From involuntary breathing, gradually transition to slow and deep nasal breathing.

30-60 seconds: Verbal instruction to segment the inhalation into 3 parts, each followed by a brief pause, then a continuous exhalation:

Inhale into lower lobes of lungs and pause.
Inhale into mid lobes of lungs and pause.
Inhale into upper third of lungs and pause.
Exhale naturally.
Repeat 5-10 rounds.

60-90 seconds: Release the technique, resume natural breath and observe the effects.

Illustrative breathing entrainment sonification systems as disclosed herein are configured to generate entrainment signals and possibly one or more associated auxiliary signals for guiding a user through the particular breathing patterns described above, in a manner that moves the user toward the optimal pattern for each exercise over time. Such systems are therefore configured to translate the above-described breathing exercises into signals that are audibly presented to the user in order to achieve the desired entrainment functionality. Numerous other signal arrangements and exercise types can be used.

In some embodiments, additional information is provided to the user in conjunction with an entrainment component and possibly one or more auxiliary components. For example, an audio configuration interface can be configured to generate visuals mapping the entrainment component to synchronized but evolving graphics which are either rendered into a video, or ported to a game engine where they can be dynamically controlled.

Different embodiments can incorporate different features and functionality based at least in part upon the particular user setting in which the system is deployed.

For example, some embodiments implement entrainment sonification systems on airplanes, illustratively as part of an inflight entertainment system, or on a mobile telephone or tablet computer for use in that setting. Such embodiments can utilize static audio/video content or an embedded engine of the type disclosed herein, and may feature feedback from heart sensor or EEG. Integrated content on embedded seats may be used.

In a corporate setting, users at desks can be equipped with an online, desktop or mobile telephone application, illustratively with features for time management (e.g., timers) and masking. Meditation rooms or wellness pods may also be equipped with entrainment sonification systems of the type disclosed herein.

It is also possible to implement entrainment sonification systems of the type disclosed herein in yoga studios or other types of exercise settings. For example, some embodiments can provide a real-time DJ app for mixing breath music in user classes to enhance practice. Tracks used in these embodiments may be generated beforehand or dynamically controlled throughout class. Such a real-time DJ app can allow a class to breathe together in accordance with a desired pattern while providing vocal instruction simultaneously, and can be used in a wide variety of different exercise contexts, including, for example, flowing vinyasa (movement) and pranayama (still). Arrangements of this type can aid the instructor by taking some strain off otherwise continuously having to conduct both breath and movement for the class. Breathing synced cues in music support better communication during practice and help foster a sense of unity by keeping the class in rhythm.

In some embodiments, a mobile telephone application for at-home use provides an interface for personalized meditation content creation, allowing an instructor to design individualized content to share practice with their followers, students or other clients. This is a tool that will help them to generate perfect background tracks to fit guided breathing exercises, and to generate variations on recorded vocal instruction. This meditation content creation tool allows instructors to customize practice for their clients. Content may be configured through an application interface, allowing the instructor to define exercise parameters, trajectory, and stylistic features making exercise unique. Content may be generated locally on the device, and/or on a cloud server, then sent to individual users. Feedback may be an optional feature, if biometric data is available.

These and other embodiments can be deployed in spas, hotels, wellness centers, gyms, art galleries, airports, and a wide variety of other venues. Some embodiments feature audio/visual content and optional feedback. Large quantities of tagged content can be stored in a database and looked up by metadata (e.g. intention, duration, etc.). Other embodiments can use advanced adaptive integrated systems (e.g., real-time training games). A wide variety of other implementations using numerous different platforms are possible, given the techniques of the present disclosure.

Entrainment sonification systems and other types of systems as disclosed herein, including by way of example musical communication systems and/or goal-driven auditory display systems, are illustratively implemented at least in part utilizing at least one corresponding processing device comprising a processor coupled to a memory. The processor is configured to execute software program code stored in the memory in order to control the performance of processing operations and other functionality. The processing device also comprises a network interface that supports communication over one or more networks.

The processor may comprise, for example, a microprocessor, a microcontroller, an application-specific integrated circuit (ASIC), a field-programmable gate array (FPGA), a central processing unit (CPU), an arithmetic logic unit (ALU), a digital signal processor (DSP), a graphics processing unit (GPU) or other similar processing device component, as well as other types and arrangements of processing circuitry, in any combination.

The memory stores software program code for execution by the processor in implementing portions of the functionality of the processing device. A given such memory that stores such program code for execution by a corresponding processor is an example of what is more generally referred to herein as a processor-readable storage medium having program code embodied therein, and may comprise, for example, electronic memory such as SRAM, DRAM or other types of random access memory, read-only memory (ROM), flash memory, magnetic memory, optical memory, or other types of storage devices in any combination.

Articles of manufacture comprising such processor-readable storage media are considered embodiments of the invention. The term "article of manufacture" as used herein should be understood to exclude transitory, propagating signals.

Other types of computer program products comprising processor-readable storage media can be implemented in other embodiments.

In addition, embodiments of the invention may be implemented in the form of integrated circuits comprising processing circuitry configured to implement processing operations associated with the embodiments described herein.

Processing devices in a given embodiment can include, for example, laptop, tablet or desktop personal computers, mobile telephones, or other types of computers or communication devices, in any combination.

Communications between the various elements of an entrainment sonification system comprising processing devices associated with respective parties or other system entities may take place over one or more networks. Such networks can illustratively include, for example, a global computer network such as the Internet, a wide area network (WAN), a local area network (LAN), a satellite network, a telephone or cable network, a cellular network, a wireless network implemented using a wireless protocol such as WiFi or WiMAX, or various portions or combinations of these and other types of communication networks.

An entrainment sonification system as disclosed herein may be implemented using one or more processing platforms, or portions thereof.

For example, one illustrative embodiment of a processing platform that may be used to implement at least a portion of an entrainment sonification system comprises cloud infrastructure including virtual machines implemented using a hypervisor that runs on physical infrastructure. Such virtual machines may comprise respective processing devices that communicate with one another over one or more networks.

The cloud infrastructure in such an embodiment may further comprise one or more sets of applications running on respective ones of the virtual machines under the control of the hypervisor. It is also possible to use multiple hypervisors each providing a set of virtual machines using at least one underlying physical machine. Different sets of virtual machines provided by one or more hypervisors may be utilized in configuring multiple instances of various components of the entrainment sonification system.

Another illustrative embodiment of a processing platform that may be used to implement at least a portion of an entrainment sonification system as disclosed herein comprises a plurality of processing devices which communicate with one another over at least one network. As indicated previously, the network may comprise any type of network, including by way of example a global computer network such as the Internet, a WAN, a LAN, a satellite network, a telephone or cable network, a cellular network, a wireless network such as a WiFi or WiMAX network, or various portions or combinations of these and other types of networks.

Each processing device of the processing platform comprises a processor coupled to a memory. As indicated above, the processor may comprise a microprocessor, a microcontroller, an ASIC, an FPGA, a CPU, an ALU, a DSP, a GPU or other type of processing circuitry, as well as portions or combinations of such circuitry elements. The memory may comprise RAM, ROM, flash memory or other types of memory, in any combination.

Again, the memory and other memories disclosed herein should be viewed as illustrative examples of what are more generally referred to as "processor-readable storage media" storing program code of one or more software programs.

As mentioned previously, articles of manufacture comprising such processor-readable storage media are considered embodiments of the present invention. A given such article of manufacture may comprise, for example, a storage array, a storage disk, an integrated circuit containing RAM, ROM, flash memory or other electronic memory, or any of a wide variety of other types of computer program products.

Also included in the processing device is network interface circuitry, which is used to interface the processing device with the network and other system components, and may comprise conventional transceivers.

Again, these particular processing platforms are presented by way of example only, and an entrainment sonification system, or other type of system implementing musical communication and/or sonification techniques as disclosed herein, may include additional or alternative processing platforms, as well as numerous distinct processing platforms in any combination, with each such platform comprising one or more computers, servers, storage devices or other processing devices. It is possible in some embodiments that system components can run at least in part in cloud infrastructure or other types of virtualization infrastructure.

It should therefore be understood that in other embodiments different arrangements of additional or alternative elements may be used. At least a subset of these elements may be collectively implemented on a common processing platform, or each such element may be implemented on a separate processing platform.

Also, numerous other arrangements of computers, servers, storage devices or other components are possible in an entrainment sonification system. Such components can communicate with other elements of the entrainment sonification system over any type of network or other communication media.

As indicated previously, components or functionality of the system as disclosed herein can be implemented at least in part in the form of one or more software programs stored in memory and executed by a processor of a processing device.

Accordingly, a given component of an entrainment sonification system implementing functionality as described herein is illustratively configured utilizing a corresponding processing device comprising a processor coupled to a memory. The processor executes program code stored in the memory in order to control the performance of processing operations and other functionality. The processing device also comprises a network interface that supports communication over one or more networks.

The particular configurations of entrainment sonification systems and other systems as described herein are exemplary only, and a given such system in other embodiments may include other elements in addition to or in place of those specifically shown, including one or more elements of a type commonly found in a conventional implementation of such a system.

For example, in some embodiments, an entrainment sonification system may be configured to utilize the disclosed techniques to provide additional or alternative functionality in other contexts. The disclosed techniques can be similarly adapted for use in a wide variety of other types of entrainment sonification systems.

It is also to be appreciated that the particular process steps used in the embodiments described above are exemplary only, and other embodiments can utilize different types and arrangements of processing operations. For example, certain process steps described as being performed serially in the illustrative embodiments can in other embodiments be performed at least in part in parallel with one another.

It should again be emphasized that the embodiments of the invention as described herein are intended to be illustrative only. Other embodiments of the invention can be implemented utilizing a wide variety of different types and arrangements of musical communication systems, entrainment sonification systems, or other information processing systems, and associated networks and processing devices, than those utilized in the particular illustrative embodiments described herein, and in numerous alternative musical communication and/or sonification related processing contexts. Also, the particular types and configurations of system entities, processing devices and process operations can be varied in other embodiments. In addition, the particular assumptions made herein in the context of describing aspects of certain illustrative embodiments need not apply in other embodiments. These and numerous other alternative embodiments will be readily apparent to those skilled in the art.

What is claimed is:

1. An apparatus comprising:
    at least one processing device comprising a processor coupled to a memory;
    said at least one processing device being configured:
    to generate a first sound cue of a first type, the first sound cue comprising a primary entrainment cue for an entrainment sonification system;
    to generate one or more additional sound cues of a second type, each of the one or more additional sound cues comprising an auxiliary entrainment cue for the entrainment sonification system;
    to provide the first sound cue and the one or more additional sound cues to one or more audio devices of the entrainment sonification system for generation of sound for audible presentation to a user;
    to receive from one or more sensors of the entrainment sonification system one or more feedback signals; and
    to adjust one or more characteristics of at least one of the first sound cue and the one or more additional sound cues based at least in part on the one or more received feedback signals;
    wherein the entrainment sonification system comprises a breathing entrainment sonification system, and the first sound cue comprises a primary breathing entrainment cue for the breathing entrainment sonification system, the primary breathing entrainment cue comprising a particular entrainment signal configured to direct a breathing pattern of the user toward a desired breathing pattern.

2. The apparatus of claim 1 wherein at least one of the one or more additional sound cues comprises an auxiliary breathing entrainment cue for the breathing entrainment sonification system, the auxiliary breathing entrainment cue being configured to provide an indication to the user of at least one of current status relative to a designated goal and guidance toward the designated goal.

3. The apparatus of claim 1 wherein the particular entrainment signal comprises a selected one of a plurality of distinct entrainment signals available within the breathing entrainment sonification system.

4. The apparatus of claim 1 wherein one or more characteristics of the particular entrainment signal are adjustable by a user.

5. The apparatus of claim 1 wherein the particular entrainment signal comprises an entrainment signal having rising portions corresponding to respective inhale phases of the desired breathing pattern and falling portions corresponding to respective exhale phases of the desired breathing pattern.

6. The apparatus of claim 1 wherein the particular entrainment signal comprises one of a triangular oscillator signal and a sinusoidal oscillator signal.

7. The apparatus of claim 1 wherein the particular entrainment signal comprises a linear ramp signal with pause phases between adjacent instances of respective inhale and exhale phases.

8. The apparatus of claim 7 wherein the linear ramp signal comprises one or more variable air flow speed changes.

9. The apparatus of claim 1 wherein the particular entrainment signal comprises a complex ramp signal with at least one of one or more variable trajectories and one or more external interrupts.

10. The apparatus of claim 1 wherein providing the first sound cue and the one or more additional sound cues to one or more audio devices of the entrainment sonification system for generation of sound for audible presentation to a user comprises:
    combining respective signals associated with the first sound cue and the one or more additional sound cues in a signal combiner; and
    providing the resulting combined signal to an audio device.

11. An apparatus comprising:
    at least one processing device comprising a processor coupled to a memory;
    said at least one processing device being configured:
    to generate a first sound cue of a first type, the first sound cue comprising a primary entrainment cue for an entrainment sonification system;
    to generate one or more additional sound cues of a second type, each of the one or more additional sound cues comprising an auxiliary entrainment cue for the entrainment sonification system;
    to provide the first sound cue and the one or more additional sound cues to one or more audio devices of the entrainment sonification system for generation of sound for audible presentation to a user;
    to receive from one or more sensors of the entrainment sonification system one or more feedback signals; and
    to adjust one or more characteristics of at least one of the first sound cue and the one or more additional sound cues based at least in part on the one or more received feedback signals;
    wherein the entrainment sonification system is configured to implement an entrainment sonification valence/intensity model in which the primary entrainment cue is mapped to an intensity parameter, and the auxiliary entrainment cue is mapped to a valence parameter.

12. A method comprising:
    generating a first sound cue of a first type, the first sound cue comprising a primary entrainment cue for an entrainment sonification system;
    generating one or more additional sound cues of a second type, each of the one or more additional sound cues comprising an auxiliary entrainment cue for the entrainment sonification system;
    providing the first sound cue and the one or more additional sound cues to one or more audio devices of the entrainment sonification system for generation of sound for audible presentation to a user;
    receiving from one or more sensors of the entrainment sonification system one or more feedback signals; and adjusting one or more characteristics of at least one of the first sound cue and the one or more additional sound cues based at least in part on the one or more received feedback signals;

wherein the entrainment sonification system comprises a breathing entrainment sonification system, and the first sound cue comprises a primary breathing entrainment cue for the breathing entrainment sonification system, the primary breathing entrainment cue comprising a particular entrainment signal configured to direct a breathing pattern of the user toward a desired breathing pattern; and wherein the method is performed by at least one processing device comprising a processor coupled to a memory.

13. The method of claim 12 wherein at least one of the one or more additional sound cues comprises an auxiliary breathing entrainment cue for the breathing entrainment sonification system, the auxiliary breathing entrainment cue being configured to provide an indication to the user of at least one of current status relative to a designated goal and guidance toward the designated goal.

14. A method comprising:
generating a first sound cue of a first type, the first sound cue comprising a primary entrainment cue for an entrainment sonification system;
generating one or more additional sound cues of a second type, each of the one or more additional sound cues comprising an auxiliary entrainment cue for the entrainment sonification system;
providing the first sound cue and the one or more additional sound cues to one or more audio devices of the entrainment sonification system for generation of sound for audible presentation to a user;
receiving from one or more sensors of the entrainment sonification system one or more feedback signals; and
adjusting one or more characteristics of at least one of the first sound cue and the one or more additional sound cues based at least in part on the one or more received feedback signals;
wherein the entrainment sonification system is configured to implement an entrainment sonification valence/intensity model in which the primary entrainment cue is mapped to an intensity parameter, and the auxiliary entrainment cue is mapped to a valence parameter; and
wherein the method is performed by at least one processing device comprising a processor coupled to a memory.

15. A computer program product comprising a non-transitory processor-readable storage medium having stored therein program code of one or more software programs, wherein the program code when executed by at least one processing device causes said at least one processing device:
to generate a first sound cue of a first type, the first sound cue comprising a primary entrainment cue for an entrainment sonification system;
to generate one or more additional sound cues of a second type, each of the one or more additional sound cues comprising an auxiliary entrainment cue for the entrainment sonification system;
to provide the first sound cue and the one or more additional sound cues to one or more audio devices of the entrainment sonification system for generation of sound for audible presentation to a user;
to receive from one or more sensors of the entrainment sonification system one or more feedback signals; and
to adjust one or more characteristics of at least one of the first sound cue and the one or more additional sound cues based at least in part on the one or more received feedback signals;
wherein the entrainment sonification system comprises a breathing entrainment sonification system, and the first sound cue comprises a primary breathing entrainment cue for the breathing entrainment sonification system, the primary breathing entrainment cue comprising a particular entrainment signal configured to direct a breathing pattern of the user toward a desired breathing pattern.

16. The computer program product of claim 15 wherein at least one of the one or more additional sound cues comprises an auxiliary breathing entrainment cue for the breathing entrainment sonification system, the auxiliary breathing entrainment cue being configured to provide an indication to the user of at least one of current status relative to a designated goal and guidance toward the designated goal.

17. A computer program product comprising a non-transitory processor-readable storage medium having stored therein program code of one or more software programs, wherein the program code when executed by at least one processing device causes said at least one processing device:
to generate a first sound cue of a first type, the first sound cue comprising a primary entrainment cue for an entrainment sonification system;
to generate one or more additional sound cues of a second type, each of the one or more additional sound cues comprising an auxiliary entrainment cue for the entrainment sonification system;
to provide the first sound cue and the one or more additional sound cues to one or more audio devices of the entrainment sonification system for generation of sound for audible presentation to a user;
to receive from one or more sensors of the entrainment sonification system one or more feedback signals; and
to adjust one or more characteristics of at least one of the first sound cue and the one or more additional sound cues based at least in part on the one or more received feedback signals;
wherein the entrainment sonification system is configured to implement an entrainment sonification valence/intensity model in which the primary entrainment cue is mapped to an intensity parameter, and the auxiliary entrainment cue is mapped to a valence parameter.

18. The computer program product of claim 17 wherein the first sound cue comprises a primary entrainment cue for the entrainment sonification system, the primary entrainment cue comprising a particular entrainment signal configured to direct the user toward a desired behavior.

19. The computer program product of claim 18 wherein at least one of the one or more additional sound cues comprises an auxiliary entrainment cue for the entrainment sonification system, the auxiliary entrainment cue being configured to provide an indication to the user of at least one of current status relative to a designated goal and guidance toward the designated goal.

20. The computer program product of claim 18 wherein the particular entrainment signal comprises a selected one of a plurality of distinct entrainment signals available within the entrainment sonification system.

21. The computer program product of claim 18 wherein one or more characteristics of the particular entrainment signal are adjustable by a user.

* * * * *